US012559745B2

(12) United States Patent
Devaraj et al.

(10) Patent No.: US 12,559,745 B2
(45) Date of Patent: Feb. 24, 2026

(54) METHODS AND COMPOSITIONS FOR LINKING RNA STEM LOOPS

(71) Applicant: THE REGENTS OF THE UNIVERSITY OF CALIFORNIA, Oakland, CA (US)

(72) Inventors: Neal Devaraj, La Jolla, CA (US); Dongyang Zhang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 448 days.

(21) Appl. No.: 18/038,190

(22) PCT Filed: Nov. 23, 2021

(86) PCT No.: PCT/US2021/060645
§ 371 (c)(1),
(2) Date: May 22, 2023

(87) PCT Pub. No.: WO2022/109495
PCT Pub. Date: May 27, 2022

(65) Prior Publication Data

US 2024/0254477 A1 Aug. 1, 2024

Related U.S. Application Data

(60) Provisional application No. 63/117,403, filed on Nov. 23, 2020.

(51) Int. Cl.

| | |
|---|---|
| ***C12N 15/11*** | (2006.01) |
| ***C07H 21/02*** | (2006.01) |
| ***C12N 9/10*** | (2006.01) |

(52) U.S. Cl.
CPC ............ *C12N 15/11* (2013.01); *C07H 21/02* (2013.01); *C12N 9/1077* (2013.01); *C12Y 204/02029* (2013.01)

(58) Field of Classification Search
CPC ...................................................... C12N 15/11
See application file for complete search history.

(56) References Cited

U.S. PATENT DOCUMENTS 11,267,842 B2 * 3/2022 Devaraj ............... C07D 487/04

OTHER PUBLICATIONS

Zhang, ACS Chem. Biol. Jun. 2, 2020, vol. 15, pp. 1773 to 1779 (Year: 2020).*
Ehret, Mol Pharmaceutics, 2018, 15, 737-742 (Year: 2018).*
Zhang, Angew. Chem. Int. Ed, 2018, vol. 57, 2822-2826 (Year: 2018).*
Alexander, J. Am. Chem. Soc. 2015, 137, 12756-12759 (Year: 2015).*

* cited by examiner

*Primary Examiner* — Mark L Shibuya
(74) *Attorney, Agent, or Firm* — Mintz, Levin, Cohn, Ferris, Glovsky and Popeo, P.C.

(57) ABSTRACT

Provided herein are, inter alia, methods and compositions for linking RNA stem loops. The methods include linking a first RNA stem loop and a second RNA stem loop by way of a preQ1 linking compound.

20 Claims, 40 Drawing Sheets

Specification includes a Sequence Listing.

preQ1-preQ1 preQ1 DEACM preQ1 preQ1 NB preQ1

RNAse-H digestion of 'clamped' RNA

RNAse-H digestion of linear RNA sgRNA-1 sgRNA-2 sgRNA-3 sgRNA-4 sgRNA-5 sgRNA-6 sgRNA-7 sgRNA-8 sgRNA-9 sgRNA-10 wt-sgRNA preQ1-PEG10-preQ1 preQ1-DEACM-preQ1 preQ1-NB-preQ1 preQ1-PEG10-preQ1

SEQUENCE LISTING

<160> NUMBER OF SEQ ID NOS: 42

<210> SEQ ID NO 1
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 1
gcagacugua aaucugc 17

<210> SEQ ID NO 2
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (8)..(8)
<223> OTHER INFORMATION: n is prequeuosine 1 or a prequeuosine 1 analog
<220> FEATURE:
<221> NAME/KEY: misc_feature
<222> LOCATION: (8)..(8)
<223> OTHER INFORMATION: n is a, c, g, t or u

<400> SEQUENCE: 2
gcagacunua aaucugc 17

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
cctttaatcc acgcgaaccg acc 23

<210> SEQ ID NO 4
<211> LENGTH: 98
<212> TYPE: DNA
<213> ORGANISM: Artificial Sequence
<220> FEATURE:
<223> OTHER INFORMATION: Synthetic polynucleotide

<400> SEQUENCE: 4
ggaaauuagg ugcgcuuggc guuuuagagc uagaaauagc aaguuaaaau aaggcuaguc 60
cguuaucaac uugaaaaagu ggcaccgagu cggugcuu 98

<210> SEQ ID NO 5
<211> LENGTH: 3
<212> TYPE: RNA
<213> ORGANISM: Artificial Sequence
<220> FEATURE:
<223> OTHER INFORMATION: Synthetic polynucleotide

<400> SEQUENCE: 5 ugu 3

<210> SEQ ID NO 6
<211> LENGTH: 74
<212> TYPE: DNA
<213> ORGANISM: Artificial Sequence
<220> FEATURE:
<223> OTHER INFORMATION: Synthetic polynucleotide

<400> SEQUENCE: 6
gcagactgta aatctgccac tagtaacggc cgccagtgtg ctggaattct gcagatagca 60
gactgtaaat ctgc 74

<210> SEQ ID NO 7
<211> LENGTH: 96

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 7
nnnnnnnnnn nnnnnnnnnn gttttagagc tagaaatagc aagttaaaat aaggctagtc 60
cgttatcaac ttgaaaaagt ggcaccgagt cggtgc 96

<210> SEQ ID NO 8
<211> LENGTH: 120
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 8
ctaatacgac tcactatann nnnnnnnnnn nnnnnnnngt tttagagcta gaaatagcaa 60
gttaaaataa ggctagtccg ttatcaactt gaaaaagtgg caccgagtcg gtgctttttt 120

<210> SEQ ID NO 9
<211> LENGTH: 117
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(41)
<223> OTHER INFORMATION: n is a, c, g, t or u

<400> SEQUENCE: 9
gcagactgta aatctgcttt tnnnnnnnnn nnnnnnnnnn ngttttagag ctagaaatag 60
caagttaaaa taaggctagt ccgttatcaa cttgaaaaag tggcaccgag tcggtgc 117

<210> SEQ ID NO 10
<211> LENGTH: 109
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 10
nnnnnnnnnn nnnnnnnnnn gttttagagc tagcagactg taaatctgct agcaagttaa 60
aataaggcta gtccgttatc aacttgaaaa agtggcaccg agtcggtgc 109

<210> SEQ ID NO 11
<211> LENGTH: 111
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)

<223> OTHER INFORMATION: n is a, c, g, t or u

<400> SEQUENCE: 11
nnnnnnnnnn nnnnnnnnnn gttttagagc tagaaatagc aagttaaaat aaggcgcaga 60
ctgtaaatct gcgtccgtta tcaacttgaa aaagtggcac cgagtcggtg c 111

<210> SEQ ID NO 12
<211> LENGTH: 109
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 12
nnnnnnnnnn nnnnnnnnnn gttttagagc tagaaatagc aagttaaaat aaggctagtc 60
cgttatcaac ttgcagactg taaatctgca agtggcaccg agtcggtgc 109

<210> SEQ ID NO 13
<211> LENGTH: 112
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 13
nnnnnnnnnn nnnnnnnnnn gttttagagc tagaaatagc aagttaaaat aaggctagtc 60
cgttatcaac ttgaaaaagt ggcaccgagc agactgtaaa tctgctcggt gc 112

<210> SEQ ID NO 14
<211> LENGTH: 118
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 14
nnnnnnnnnn nnnnnnnnnn gttttagagc tagaaatagc aagttaaaat aaggctagtc 60
cgttatcaac ttgaaaaagt ggcaccgagt cggtgcttat tgcagactgt aaatctgc 118

<210> SEQ ID NO 15
<211> LENGTH: 122
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 15
nnnnnnnnnn nnnnnnnnnn gttttagagc tagcagactg taaatctgct agcaagttaa 60
aataaggcta gtccgttatc aacttgcaga ctgtaaatct gcaagtggca ccgagtcggt 120
gc 122

<210> SEQ ID NO 16
<211> LENGTH: 114
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 16
nnnnnnnnnn nnnnnnnnnn gttttagagc taagactgta aatcttagca agttaaaata 60
aggctagtcc gttatcaact tagactgtaa atctaagtgg caccgagtcg gtgc 114

<210> SEQ ID NO 17
<211> LENGTH: 106
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 17
nnnnnnnnnn nnnnnnnnnn gttttagagc taactgtaaa ttagcaagtt aaaataaggc 60
tagtccgtta tcaacttact gtaaataagt ggcaccgagt cggtgc 106

<210> SEQ ID NO 18
<211> LENGTH: 102
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, t or u

<400> SEQUENCE: 18
nnnnnnnnnn nnnnnnnnnn gttttagagc tactgtaaat agcaagttaa aataaggcta 60
gtccgttatc aacttctgta aaaagtggca ccgagtcggt gc 102

<210> SEQ ID NO 19
<211> LENGTH: 141
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (40)..(59)
<223> OTHER INFORMATION: n is a, c, g, t or u

<400> SEQUENCE: 19
ctaatacgac tcactatagc agactgtaaa tctgcttttn nnnnnnnnnn nnnnnnnnng 60
ttttagagct agaaatagca agttaaaata aggctagtcc gttatcaact tgaaaaagtg 120
gcaccgagtc ggtgcttttt t 141

<210> SEQ ID NO 20

<211> LENGTH: 133
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 20
ctaatacgac tcactatann nnnnnnnnnn nnnnnnnngt tttagagcta gcagactgta 60
aatctgctag caagttaaaa taaggctagt ccgttatcaa cttgaaaaag tggcaccgag 120
tcggtgcttt ttt 133

<210> SEQ ID NO 21
<211> LENGTH: 136
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 21
ctaatacgac tcactatann nnnnnnnnnn nnnnnnnngt tttagagcta gaaatagcaa 60
gttaaaataa ggcgcagact gtaaatctgc gtccgttatc aacttgaaaa agtggcaccg 120
agtcggtgct tttttt 136

<210> SEQ ID NO 22
<211> LENGTH: 133
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 22
ctaatacgac tcactatann nnnnnnnnnn nnnnnnnngt tttagagcta gaaatagcaa 60
gttaaaataa ggctagtccg ttatcaactt gcagactgta aatctgcaag tggcaccgag 120
tcggtgcttt ttt 133

<210> SEQ ID NO 23
<211> LENGTH: 136
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 23
ctaatacgac tcactatann nnnnnnnnnn nnnnnnnngt tttagagcta gaaatagcaa 60
gttaaaataa ggctagtccg ttatcaactt gaaaaagtgg caccgagcag actgtaaatc 120
tgctcggtgc tttttt 136

```
<210> SEQ ID NO 24
<211> LENGTH: 142
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 24

ctaatacgac tcactatann nnnnnnnnnn nnnnnnnngt tttagagcta gaaatagcaa      60

gttaaaataa ggctagtccg ttatcaactt gaaaaagtgg caccgagtcg gtgcttattg     120

cagactgtaa atctgctttt tt                                              142


<210> SEQ ID NO 25
<211> LENGTH: 146
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 25

ctaatacgac tcactatann nnnnnnnnnn nnnnnnnngt tttagagcta gcagactgta      60

aatctgctag caagttaaaa taaggctagt ccgttatcaa cttgcagact gtaaatctgc     120

aagtggcacc gagtcggtgc tttttt                                          146


<210> SEQ ID NO 26
<211> LENGTH: 138
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 26

ctaatacgac tcactatann nnnnnnnnnn nnnnnnnngt tttagagcta agactgtaaa      60

tcttagcaag ttaaaataag gctagtccgt tatcaactta gactgtaaat ctaagtggca     120

ccgagtcggt gctttttt                                                   138


<210> SEQ ID NO 27
<211> LENGTH: 130
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 27

ctaatacgac tcactatann nnnnnnnnnn nnnnnnnngt tttagagcta actgtaaatt      60

agcaagttaa aataaggcta gtccgttatc aacttactgt aaataagtgg caccgagtcg     120

gtgctttttt                                                            130
```

<210> SEQ ID NO 28
<211> LENGTH: 126
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (19)..(38)
<223> OTHER INFORMATION: n is a, c, g, t or u

<400> SEQUENCE: 28
ctaatacgac tcactatann nnnnnnnnnn nnnnnnnngt tttagagcta ctgtaaatag 60
caagttaaaa taaggctagt ccgttatcaa cttctgtaaa aagtggcacc gagtcggtgc 120
tttttt 126

<210> SEQ ID NO 29
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 29
gcagacugua aaucugc 17

<210> SEQ ID NO 30
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 30
agacuguaaa ucu 13

<210> SEQ ID NO 31
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 31 acuguaaau 9

<210> SEQ ID NO 32
<211> LENGTH: 7
<212> TYPE: DNA
<213> ORGANISM: Artificial Sequence
<220> FEATURE:
<223> OTHER INFORMATION: Synthetic polynucleotide

<400> SEQUENCE: 32 cuguaaa 7

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
gctgctggcc ttcagatggc 20

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
ggagaacagc actccgctct 20

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
ggagctggtc tgttggagaa 20

<210> SEQ ID NO 36
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 36
tcccaatcca taatcccacg tt 22

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
caggagggcc aggagatttg 20

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
tgaaatcgag gatctgggcg 20

<210> SEQ ID NO 39
<211> LENGTH: 2212
<212> TYPE: DNA
<213> ORGANISM: Artificial Sequence
<220> FEATURE:
<223> OTHER INFORMATION: Synthetic polynucleotide

<400> SEQUENCE: 39
atggtgagca agggcgagga ggataacatg gccatcatca aggagttcat gcgcttcaag 60
gtgcacatgg agggctccgt gaacggccac gagttcgaga tcgagggcga gggcgagggc 120
cgcccctacg agggcaccca gaccgccaag ctgaaggtga ccaagggtgg ccccctgccc 180
ttcgcctggg acatcctgtc ccctcagttc atgtacggct ccaaggccta cgtgaagcac 240

```
cccgccgaca tccccgacta cttgaagctg tccttccccg agggcttcaa gtgggagcgc    300

gtgatgaact tcgaggacgg cggcgtggtg accgtgaccc aggactcctc cctgcaagac    360

ggcgagttca tctacaaggt gaagctgcgc ggcaccaact tcccctccga cggccccgta    420

atgcagaaga agacgatggg ctgggaggcc tcctccgagc ggatgtaccc cgaggacggc    480

gccctgaagg gcgagatcaa gcagaggctg aagctgaagg acggcggcca ctacgacgct    540

gaggtcaaga ccacctacaa ggccaagaag cccgtgcagc tgcccggcgc ctacaacgtg    600

aacatcaagt tggacatcac ctcccacaac gaggactaca ccatcgtgga acagtacgaa    660

cgcgccgagg gccgccactc caccggcggc atggacgagc tgtacaagga gctagcattg    720

ttcagggctt gaccaacact gggtccctgc aggatccagt gagcaagggc gaggagctgt    780

tcaccggggt ggtgcccatc ctggtcgagc tggacggcga cgtaaacggc cacaagttca    840

gcgtgtccgg cgagggcgag ggcgatgcca cctacggcaa gctgaccctg aagttcatct    900

gcaccaccgg caagctgccc gtgccctggc ccaccctcgt gaccaccctg acctacggcg    960

tgcagtgctt cagccgctac cccgaccaca tgaagcagca cgacttcttc aagtccgcca   1020

tgcccgaagg ctacgtccag gagcgcacca tcttcttcaa ggacgacggc aactacaaga   1080

cccgcgccga ggtgaagttc gagggcgaca ccctggtgaa ccgcatcgag ctgaagggca   1140

tcgacttcaa ggaggacggc aacatcctgg ggcacaagct ggagtacaac tacaacagcc   1200

acaacgtcta tatcatggcc gacaagcaga agaacggcat caaggtgaac ttcaagatcc   1260

gccacaacat cgaggacggc agcgtgcagc tcgccgacca ctaccagcag aacaccccca   1320

tcggcgacgg ccccgtgctg ctgcccgaca accactacct gagcacccag tccgccctga   1380

gcaaagaccc caacgagaag cgcgatcaca tggtcctgct ggagttcgtg accgccgccg   1440

ggatcactct cggcatggac gagctgtaca aggttataac atgggtaacc tctacgtgag   1500

caagggcgag gagctgttca ccggggtggt gcccatcctg gtcgagctgg acggcgacgt   1560

aaacggccac aagttcagcg tgtccggcga gggcgagggc gatgccacct acggcaagct   1620

gaccctgaag ttcatctgca ccaccggcaa gctgcccgtg ccctggccca ccctcgtgac   1680

caccctgacc tacggcgtgc agtgcttcag ccgctacccc gaccacatga agcagcacga   1740

cttcttcaag tccgccatgc ccgaaggcta cgtccaggag cgcaccatct tcttcaagga   1800

cgacggcaac tacaagaccc gcgccgaggt gaagttcgag ggcgacaccc tggtgaaccg   1860

catcgagctg aagggcatcg acttcaagga ggacggcaac atcctggggc acaagctgga   1920

gtacaactac aacagccaca acgtctatat catggccgac aagcagaaga acggcatcaa   1980

ggtgaacttc aagatccgcc acaacatcga ggacggcagc gtgcagctcg ccgaccacta   2040

ccagcagaac acccccatcg gcgacggccc cgtgctgctg cccgacaacc actacctgag   2100

cacccagtcc gccctgagca aagaccccaa cgagaagcgc gatcacatgg tcctgctgga   2160

gttcgtgacc gccgccggga tcactctcgg catggacgag ctgtacaagt aa           2212
```

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40

```
gttcagggct tgaccaacac                                                 20
```

-continued

```
<210> SEQ ID NO 41
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 41

ccagcacact ggcggccg                                                    18


<210> SEQ ID NO 42
<211> LENGTH: 5
<212> TYPE: DNA
<213> ORGANISM: Artificial Sequence
<220> FEATURE:
<223> OTHER INFORMATION: Synthetic polynucleotide

<400> SEQUENCE: 42

uuauc                                                                   5
```

METHODS AND COMPOSITIONS FOR LINKING RNA STEM LOOPS

CROSS-REFERENCE TO RELATED APPLICATIONS

This application is a national stage filing under USC 371 of international application PCT/US2021/060645, filed Nov. 23, 2021, which claims priority to U.S. Provisional Application No. 63/117,403, filed Nov. 23, 2020, which are hereby incorporated by reference in their entirety and for all purposes.

STATEMENT AS TO RIGHTS TO INVENTIONS MADE UNDER FEDERALLY SPONSORED RESEARCH AND DEVELOPMENT

The Sequence Listing written in file 048537-637N01US_ST25.txt, created on Feb. 1, 2024, 16,384 bytes, machine format IBM-PC, MS Windows operating system, is hereby incorporated by reference.

REFERENCE TO A SEQUENCE LISTING, A TABLE OR A COMPUTER PROGRAM LISTING APPENDIX SUBMITTED AS AN ASCII TEXT FILE

The Sequence Listing written in file 048537-637001WO_SequenceListing_ST25.txt, created on Nov. 23, 2021, 16,384 bytes, machine format IBM-PC, MS Windows operating system, is hereby incorporated by reference.

BACKGROUND

RNA is one of the most important biomacromolecules in living systems, manipulating a highly complex collection of functions which are critical to the regulation of numerous cellular pathways and processes. Being the cornerstone of biology's central dogma, numerous approached has been developed to study and manipulate the functions of RNAs. However, compared to the study of proteins and DNAs/chromosomes, our understanding of RNA's cellular function is significantly lacking. This is partially because of the transient nature of RNA molecule.

The half-life of RNA is significantly shorter than DNA and protein. Creative methodologies have been developed in the past few decades to address this challenge, for example, how to label and manipulate cellular RNAs. Apart from non-covalent approaches, covalent RNA-modifying approaches have been challenging because of difficulties in selectively modifying a single RNA of interest among the other RNAs in cellular conditions.

Disclosed herein, inter alia, are solutions to these and other problems in the art.

BRIEF SUMMARY

In an aspect is provided a method of linking a first RNA stem loop oligonucleotide and a second RNA stem loop oligonucleotide, the method including contacting the first RNA stem loop oligonucleotide and the second RNA stem loop oligonucleotide with a PreQ1 linking compound and a tRNA-guanine transglycosylase (TGT) enzyme, wherein the PreQ1 linking compound has the formula:

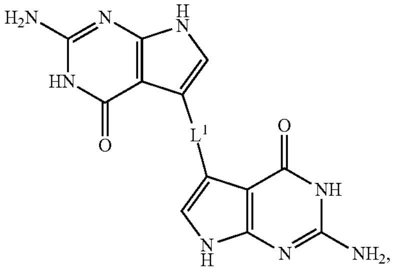

wherein $L^1$ is a covalent linker; wherein the first RNA stem loop oligonucleotide includes a first guanosine in a first RNA loop portion of a first RNA stem loop; and wherein the second RNA stem loop oligonucleotide includes a second guanosine in a second RNA loop portion of a second RNA stem loop.

In an aspect is provided a method of linking a first RNA stem loop of an RNA stem loop oligonucleotide and a second RNA stem loop of the RNA stem loop oligonucleotide, the method including contacting the RNA stem loop oligonucleotide with a PreQ1 linking compound and a tRNA-guanine transglycosylase (TGT) enzyme, wherein the PreQ1 linking compound has the formula:

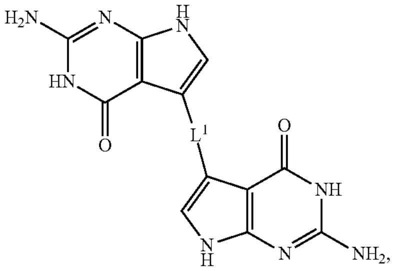

wherein $L^1$ is a covalent linker; and wherein the first RNA stem loop includes a first guanosine in a first RNA loop portion of the first RNA stem loop, and wherein the second RNA stem loop includes a second guanosine in a second RNA loop portion of the second RNA stem loop.

In another aspect is provided an RNA compound having the formula:

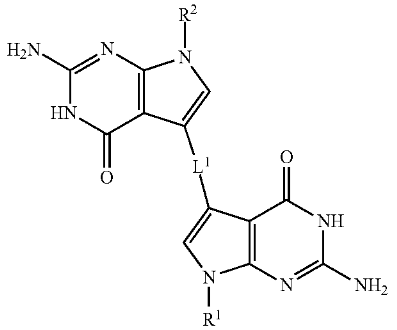

wherein $L^1$ is a covalent linker; $R^1$ is a first RNA loop portion of a first RNA stem loop; and $R^2$ is a second RNA loop portion of a second RNA stem loop.

In an aspect a cell including an RNA compound provided herein including embodiments thereof is provided.

In an aspect is provided a method of modifying an sgRNA molecule including: (a) contacting the sgRNA molecule with a tRNA guanine transglycosylase (TGT) enzyme or functional fragment thereof and 7-(aminomethyl)-7-deazaguanine (preQ1) or a derivative thereof, wherein (i) the sgRNA molecule includes a stem loop including a TGT recognition site; and (ii) wherein the preQ1 is attached to a functional molecule by a chemical linker; and (b) allowing the preQ1 to replace a guanine base in the TGT recognition site.

In another aspect is provided a method of dimerizing two sgRNA molecules including: (a) contacting a first sgRNA molecule and a second sgRNA molecule with a TGT enzyme or functional fragment thereof and a first preQ1 and a second preQ1 or a derivative thereof, wherein (i) the first sgRNA includes a first TGT recognition site; (ii) the second sgRNA includes a second TGT recognition site; and (iii) the first preQ1 and the second preQ1 are attached by a chemical linker; and (b) allowing the first preQ1 to replace a guanine base in the first TGT recognition site and allowing the second preQ1 to replace a guanine base in the second TGT recognition site.

In another aspect is provided a method of cyclizing an sgRNA molecule including: (a) contacting the sgRNA molecule with tRNA guanine transglycosylase (TGT) enzyme or functional fragment thereof and a first preQ1 and a second preQ1 or derivative thereof, wherein (i) the sgRNA molecule includes a first TGT recognition site and a second TGT recognition site; and (ii) wherein the first preQ1 and second preQ1 or derivative thereof are attached by a chemical linker; and (b) allowing the first preQ1 to replace a guanine base in the first TGT recognition site and allowing the second preQ1 to replace a guanine base in the second TGT recognition site.

In an aspect is provided an sgRNA molecule including a first stem loop including a first preQ1 or derivative thereof and a second stem loop including a second preQ1 or derivative thereof, wherein the first preQ1 and second preQ1 are attached by a chemical linker, and wherein the chemical linker includes a cleavable site.

In an aspect is provided a method of modulating expression of a target gene, including (a) delivering to a cell including the target gene an oligonucleotide encoding a CRISPR associated endonuclease and an sgRNA provided herein including embodiments thereof, and (b) cleaving the chemical linker in the sgRNA; thereby modulating expression of the target gene.

BRIEF DESCRIPTION OF THE DRAWINGS

FIG. 8A. The RNA-CLAMP technique. FIG. 8B. Chemical structure of bivalent TGT enzymatic small-molecule substrates preQ1-PEG10-preQ1, preQ1-DEACM-preQ1 and preQ1-NB-preQ1. The preQ1-PEG10-preQ1 substrate is not photo-sensitive. The [7-(diethylamino)coumarin-4-yl]-methyl (DEACM) linker is photo-cleaved by irradiation with 405-456 nm light. The nitrobenzyl based (NB) linker is photo-cleaved by irradiation with 356-390 nm light.

FIG. 10A. Cartoon illustration of the desired 'clamped' RNA product and two by-products (by-products-1 and by-products-2). For RNA by-product-1, each of the two RNA 'Tag' was singly labeled with the preQ1-PEG10-preQ1. For RNA by-product-2, multiple RNA-1 molecules were covalently linked by preQ1-PEG10-preQ1. FIG. 10B. RNAse-H digestion assay. RNAse-H cuts RNA-DNA hybrid. Therefore, the RNAse-H digestion assay can distinguish different RNA products after TGT enzymatic labeling. Only the 'clamped' RNA would result in a single-band product after RNAse-H digestion, whereas other RNA by-products would result in more than one RNA products after RNAse-H digestion.

FIG. 16A. Sequence of the sgRNA (SEQ ID NO:8). The sgRNA has four stem loops, which can be swapped with the Tag sequences to facilitate TGT enzymatic labeling. We replaced the tetra loop and the stem loop 2 of the sgRNA to form sgRNA-7 (SEQ ID NO:15). Modification did not compromise gene editing activity. FIG. 16B. sgRNA with 'Tags' can be intramolecularly crosslinked by RNA- CLAMP. In this example, the preQ1-PEG10-preQ1 small-molecule substrate was used as the cross-linker to form the 'clamped' sgRNA.

FIG. 20A. 12% denaturing PAGE analysis of the RNA-CLAMP reaction on sgRNA-9 using the preQ1-DEACM-preQ1 small-molecule substrate (without purification). The 'clamped' sgRNA conversion rate is 79.4% measured by RNA band intensities. FIG. 20B. In vitro photo-cleavage assay of the unmodified and the 'clamped' sgRNA-9. 3 minutes of irradiation with the 456 nm LED light completely uncaged the 'clamped' sgRNA-9.

FIG. 27A. Experimental design of pre-activation and live-cell photo-activation of the 'clamped' sgRNA. For pre-activation, the clamped sgRNA was uncaged prior to transfection. For live-cell activation, LED light was directly applied to HEK-293 cells 4 hours after the transfection event.

FIG. 27B. Photo-irradiation restored CRISPR-Cas9 gene editing. Pre-activation almost completely restored gene editing activity of 'clamped' sgRNA-9 (97% compared to unmodified sgRNA-9). Live-cell activation also restored gene editing activity of 'clamped' sgRNA (85% compared to unmodified sgRNA-9). FIG. 27C. For multiplexed photo-activation of gene editing, the preQ1-DEACM-preQ1 substrate was used to clamp a sgRNA targeting the DYRK1A genomic site, and the preQ1-NB-preQ1 substrate was used to clamp a sgRNA targeting the GRIN2B genomic site. FIG. 27D. Multiplexed photo-activation of gene editing. Either 456 nm or 390 nm LED light was used to photo-activate gene editing. The 456 nm LED light only cleaved the DEACM photo-sensitive linker, activating the sgRNA targeting the DYRK1A site. The 390 nm LED light cleaved both the DEACM and the NB photo-sensitive linkers, therefore activating gene editing at both genome loci.

FIG. 28B. 18% denaturing PAGE analysis of enzymatic gel. Gel was post-stained with 1× GelRed. The 17-nt RNA 'Tag' oligo starting material was represented as a single RNA band on the 18% denaturing gel. After TGT labeling using preQ1-PEG10-preQ1, two RNA products were formed. The lower band on the left represented unlabeled RNA starting material. The middle band represented singly labeled RNA by product. The upper band represented dimerized RNA 'Tag' oligo.

DETAILED DESCRIPTION

Figure 1:
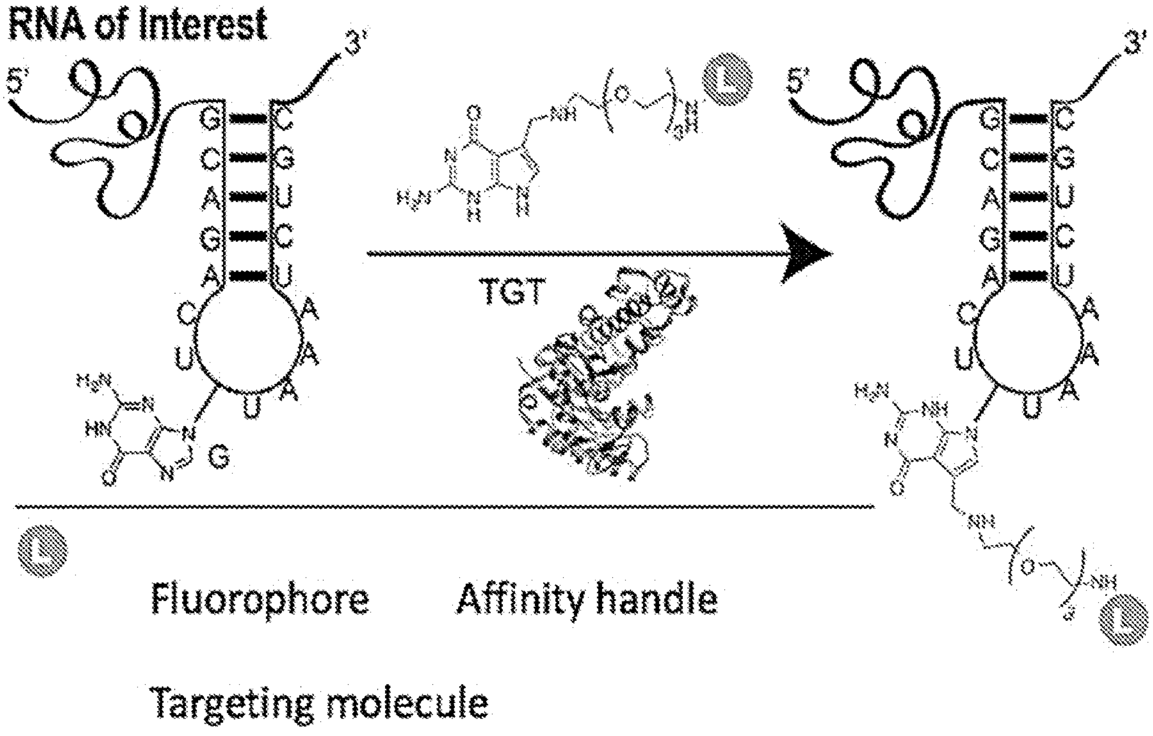
FIG. 1. RNA Transglycosylation at Guanosine (RNA-TAG). TGT-catalyzed transglycosylation of an RNA of interest (SEQ ID NO:1) inserted with an ECY-A1 minihelix with preQ1 derivative nucleobases. Different functional small-molecules, for example, fluorophores, affinity handles and targeting molecules, can be covalently conjugated onto the RNA of interest (SEQ ID NO:2) via the one-step enzymatic labeling.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Definitions

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—S—CH_2—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

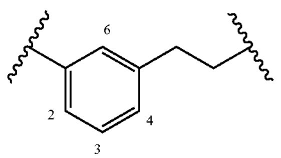

or

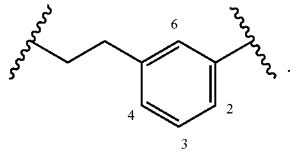

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', halogen, —SiR'R"R'", —OC(O)R', —C(O)R', —$CO_2$R', —CONR'R", —OC(O)NR'R", —NR"C(O)R', —NR'C(O)NR"R'", —NR"C(O)$_2$R', —NRC(NR'R"R'")═NR"", —NRC(NR'R")═NR'", —S(O)R', —S(O)$_2$R', —S(O)$_2$NR'R", —NR$SO_2$R', —NR'NR"R'", —ONR'R", —NR'C(O)NR"NR'"R"", —CN, —$NO_2$, —NR'$SO_2$R", —NR'C(O)R", —NR'C(O)OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —$CO_2$R', —CONR'R", —OC(O)NR'R", —NR"C(O)R', —NR'C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NR$SO_2$R', —NR'NR"R'", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'$SO_2$R", —NR'C(O)R", —NR'C(O)OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X is $-O-$, $-NR'-$, $-S-$, $-S(O)-$, $-S(O)_2-$, or $-S(O)_2NR'-$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), selenium (Se), and silicon (Si). In embodiments, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHC(NH)NH_2$, $-NHSO_2H$, $-NHC(O)H$, $-NHC(O)OH$, $-NHOH$, $-N_3$, $-SF_5$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHC(NH)NH_2$, $-NHSO_2H$, $-NHC(O)H$, $-NHC(O)OH$, $-NHOH$, $-N_3$, $-SF_5$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, —CN, —OH, $-NH_2$, —COOH, $-CONH_2$, $-NO_2$, —SH, $-SO_3H$, $-OSO_3H$, $-SO_2NH_2$, $-NHNH_2$, $-ONH_2$, $-NHC(O)NHNH_2$, $-NHC(O)NH_2$, $-NHC(NH)NH_2$, $-NHSO_2H$, —NHC(O)H, —NHC(O)OH, —NHOH, $-N_3$, $-SF_5$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, —CN, —OH, $-NH_2$, —COOH, $-CONH_2$, $-NO_2$, —SH, $-SO_3H$, $-OSO_3H$, $-SO_2NH_2$, $-NHNH_2$, $-ONH_2$, $-NHC(O)NHNH_2$, $-NHC(O)NH_2$, $-NHC(NH)NH_2$, $-NHSO_2H$, —NHC(O)H, —NHC(O)OH, —NHOH, $-N_3$, $-SF_5$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g., $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

stituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

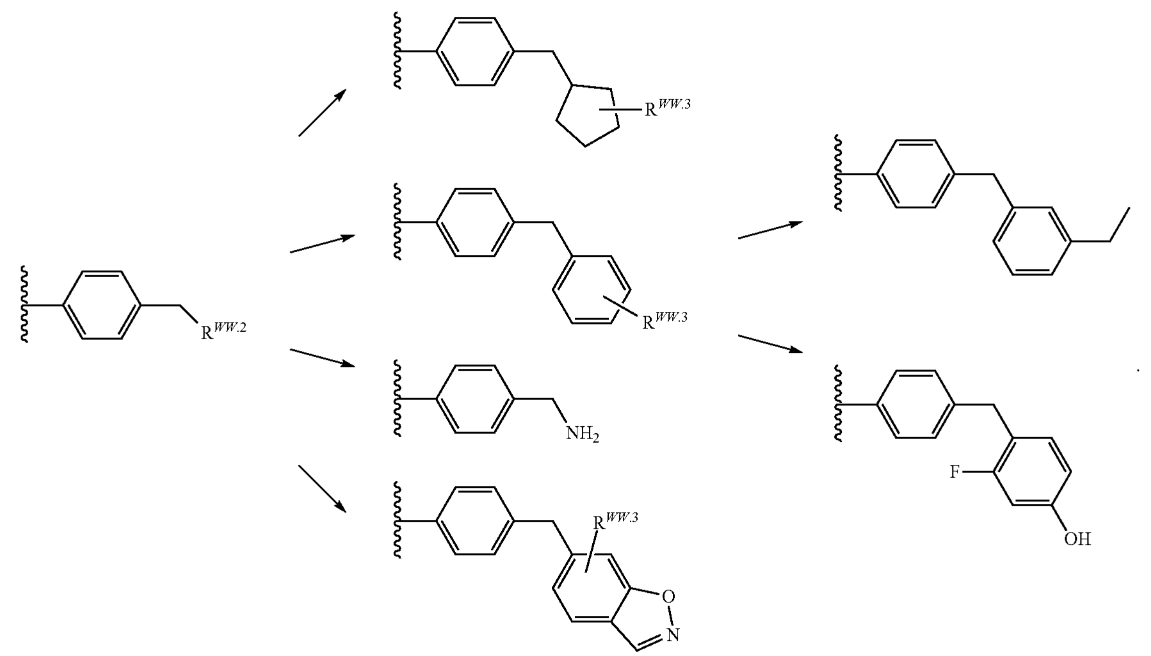

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly sub- $R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, $-SO_3H$, $-OSO_3H$, $-SO_2NH_2$, $-NHNH_2$, $-ONH_2$, $-NHC(O)NHNH_2$, $-NHC(O)NH_2$, $-NHC(NH)NH_2$, $-NHSO_2H$, $-NHC(O)H$, $-NHC(O)$ OH, —NHOH, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —NHC(NH)$NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $—CX^{LWW.2}_3$, $—CHX^{LWW.2}_2$, $—CH_2X^{LWW.2}$, $—OCX^{LWW.2}_3$, $—OCH_2X^{LWW.2}$, $—OCHX^{LWW.2}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, $—CX^{LWW.3}_3$, $—CHX^{LWW.3}_2$, $—CH_2X^{LWW.3}$, $—OCX^{LWW.3}_3$, $—OCH_2X^{LWW.3}$, $—OCHX^{LWW.3}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, $—CX^{WW}_3$, $—CHX^{WW}_2$, $—CH_2X^{WW}$, $—OCX^{WW}_3$, $—OCH_2X^{WW}$, $—OCHX^{WW}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHC(NH)NH_2$, $—NHSO_2H$, —NHC(O)H, —NHC(O)OH, —NHOH, $—N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —NHC(NH)NH—, —C(O)O—, —OC(O)—, —S—, $—SO_2—$, $—SO_2NH—$, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; and (o) biotin conjugate can react with avidin or streptavidin to form an avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an", as used in herein means one or more. In addition, the phrase "substituted with a[n]", as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl", the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pre-queuosine1" or "preQ1", also known as 7-(aminomethyl)-7-deazaguanine, is used according to its common meaning in the art and refers to a precursor in the biosynthesis of queuosine, a bacterial nucleoside incorporated into tRNA by tRNA transglycosylase (TGT). PreQ1 is a natural substrate of bacterial TGT, which catalyzes the exchange of guanine at the wobble position of tRNAs with preQ1, which is typically further converted to queine at the tRNA level.

The structure of PreQ1 follows:

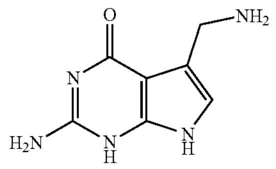 [SMILES: NCc1c[nH]c2[nH]c(N)nc(=O)c12]

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "TGT protein", "TGT enzyme", "TGT", and "tRNA-guanine transglycosylase enzyme" are used interchangeably, and include any of the recombinant or naturally-occurring forms of tRNA-guanine transglycosylase, also known as Queuine tRNA-ribosyltransferase, Guanine insertion enzyme, Queuine tRNA-ribosyltransferase or variants or homologs thereof that maintain TGT activity (e.g. within at least 50%, 80%, 90%, 95%, 96%, 97%, 98%, 99% or 100% activity compared to TGT). In some aspects, the variants or homologs have at least 90%, 95%. 96%, 97%. 98%, 99% or 100% amino acid sequence identity across the whole sequence or a portion of the sequence (e.g. a 50, 100, 150 or 200 continuous amino acid portion) compared to a naturally occurring TGT protein. In embodiments, the TGT protein is substantially identical to the protein identified by the UniProt reference number P0A847 or a variant or homolog having substantial identity thereto. In embodiments, the TGT protein is substantially identical to the protein identified by the UniProt reference number P28720 or a variant or homolog having substantial identity thereto.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

"Nuclease" and "endonuclease" are used interchangeably herein to mean an enzyme which possesses endonucleolytic catalytic activity for nucleic acid (e.g. polynucleotide) cleavage. The term includes site-specific endonucleases such as, designer zinc fingers, transcription activator-like effectors (TALEs), homing meganucleases, and site-specific endonucleases of clustered, regularly interspaced, short palindromic repeat (CRISPR) systems such as, e.g., Cas proteins.

A "ribonucleoprotein complex," or "ribonucleoprotein particle" as provided herein refers to a complex or particle including a nucleoprotein and a ribonucleic acid. A "nucleoprotein" as provided herein refers to a protein capable of binding a nucleic acid (e.g., RNA, DNA). Where the nucleoprotein binds a ribonucleic acid it is referred to as "ribonucleoprotein." The interaction between the ribonucleoprotein and the ribonucleic acid may be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the ribonucleoprotein includes an RNA-binding motif non-covalently bound to the ribonucleic acid. For example, positively charged aromatic amino acid residues (e.g., lysine residues) in the RNA-binding motif may form electrostatic interactions with the negative nucleic acid phosphate backbones of the RNA, thereby forming a ribonucleoprotein complex. Non-limiting examples of ribonucleoproteins include ribosomes, telomerase, RNAseP, hnRNP, CRISPR associated protein 9 (Cas9) and small nuclear RNPs (snRNPs). The ribonucleoprotein may be an enzyme. In embodiments, the ribonucleoprotein is an endonuclease. Thus, in embodiments, the ribonucleoprotein complex includes an endonuclease and a ribonucleic acid. In embodiments, the endonuclease is a CRISPR associated endonuclease.

The term "site-specific modifying enzyme" or "RNA-binding site-specific modifying enzyme" as used herein a polypeptide that binds RNA and is targeted to a specific DNA sequence, such as a Cas9 polypeptide. A site-specific modifying enzyme as described herein is targeted to a specific DNA sequence by the RNA molecule to which it is bound. The RNA molecule includes a sequence that binds, hybridizes to, or is complementary to a target sequence within the target DNA, thus targeting the bound polypeptide to a specific location within the target DNA (the target sequence). This RNA molecule can be a small guide RNA (sgRNA). In some cases, the sgRNAs can be selected to inhibit transcription of target loci (e.g., targeted to optimized human CRISPRi target sites), activate transcription of target loci (e.g., targeted to optimized human CRISPRa target sites. In other instances, the Cas9 protein can be a nuclease deficient sgRNA-mediated nuclease (dCas9) or "catalytically inactive Cas9". This dCas9 can also comprise a dCas9 domain fused to a transcriptional modulator. This transcriptional modulator can be, e.g., a DNA methyltransferase. In embodiments, the target DNA is a gene (target gene) present in the same cell as the Cas9 or dCas9 protein.

The term "RNA-guided DNA endonuclease" and the like refer, in the usual and customary sense, to an enzyme that cleave a phosphodiester bond within a DNA polynucleotide chain, wherein the recognition of the phosphodiester bond is facilitated by a separate RNA sequence (for example, a single guide RNA).

The term "Class II CRISPR endonuclease" refers to endonucleases that have similar endonuclease activity as Cas9 and participate in a Class II CRISPR system. An example Class II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). The Cpf1 enzyme belongs to a putative type V CRISPR-Cas system. Both type II and type V systems are included in Class IL of the CRISPR-Cas system.

Thus, a "CRISPR associated protein 9," "Cas9," "Csn1" or "Cas9 protein" as referred to herein includes any of the recombinant or naturally-occurring forms of the Cas9 endonuclease or variants or homologs thereof that maintain Cas9 endonuclease enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the UniProt reference number Q99ZW2 or a variant or homolog having substantial identity thereto. Cas9 refers to the protein also known in the art as "nickase". In embodiments, Cas9 is an RNA-guided DNA endonuclease enzyme that binds a CRISPR (clustered regularly interspaced short palindromic repeats) nucleic acid sequence. In embodiments, the CRISPR nucleic acid sequence is a prokaryotic nucleic acid sequence. In embodiments, the Cas9 nuclease from *Streptococcus pyogenes* is targeted to genomic DNA by a synthetic guide RNA consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) about 3-base pair upstream of the PAM. In embodiments, the CRISPR nuclease from *Streptococcus aureus* is targeted to genomic DNA by a synthetic guide RNA consisting of a 21-23-nt guide sequence and a scaffold. The guide sequence base-pairs with the DNA target, directly upstream of a requisite 5'-NNGRRT protospacer adjacent motif (PAM), and Cas9 mediates a double-stranded break (DSB) about 3-base pair upstream of the PAM.

The term "gRNA" or "guide RNA" refers to an RNA that includes a sequence that is at least partially complementary to a target nucleic acid sequence of interest. A guide RNA has at least i) a spacer sequence that can hybridize to a target nucleic acid sequence of interest and ii) a CRISPR repeat sequence. In Type II systems, the gRNA also has a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-directed polypeptide such that the guide RNA and site-direct polypeptide form a complex. In embodiments, the gRNA includes at least one stem loop structure.

A "single-guide RNA" or "sgRNA" in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a stem loop structure. The optional tracrRNA extension has one or more stem loops. A single-molecule guide RNA (sgRNA) in a Type V system has, in the 5' to 3' direction, a minimum CRISPR repeat sequence and a spacer sequence.

By "cleavage" it is meant the breakage of a covalent bond (e.g. of a backbone of a DNA molecule, of a peptide bond, of a bond in a chemical linker, etc.). Cleavage can be initiated by a variety of methods including, but not limited to, enzymatic catalysis, photo-cleavage, protease cleavage, modulation of pH, etc. A "cleavage site" as used herein, may refer to a site for cleavage of a portion of a linker (e.g. $L^1$) described herein.

The term "plasmid" or "expression vector" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

An "inhibitor" refers to a compound (e.g. compounds described herein) that reduces activity when compared to a control, such as absence of the compound or a compound with known inactivity.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "activation", "activate", "activating", "activator" and the like in reference to an RNA activity means positively affecting (e.g. increasing) the activity or function of the RNA relative to the activity or function of the RNA in the absence of the activator. In embodiments activation means positively affecting (e.g. increasing) the concentration or levels of a protein encoded by an mRNA relative to the concentration or level of the protein in the absence of the activator. Activation may include, at least in part, partially or totally increasing stimulation, increasing or enabling activation, or activating, sensitizing, or up-regulating signal transduction or activity or the amount of an RNA, for example, a ribozyme, a tRNA, an shRNA, etc. Activation may include, increasing or enabling gene editing activity induced by an RNA, for example a gRNA or an sgRNA.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to an RNA activity means negatively affecting (e.g. decreasing) the activity or function of the RNA relative to the activity or function of the RNA in the absence of the inhibitor. In embodiments inhibition means negatively affecting (e.g. decreasing) the concentration or levels of the protein encoded by an mRNA relative to the concentration or level of the protein in the absence of the inhibitor. In embodiments inhibition refers to reduction of a disease or symptoms of disease. In embodiments, inhibition refers to a reduction in the activity of a particular RNA target. Inhibition includes, at least in part, partially or totally blocking stimulation, decreasing, preventing, or delaying activation, or inactivating, desensitizing, or down-regulating activity of an RNA, for example, an miRNA, tRNA, shRNA, ribozyme, etc. Inhibition may include, decreasing or inhibiting gene editing activity induced by an RNA, for example, a gRNA or an sgRNA.

The terms "inhibitor," "repressor" or "antagonist" or "downregulator" interchangeably refer to a substance capable of detectably decreasing the expression or activity of an RNA (e.g. gRNA, sgRNA, mRNA, etc.). The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule (e.g. an RNA oligonucleotide) or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of an activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the activity or function. As used herein, what is described as being associated with a disease, if a causative agent, could be a target for treatment of the disease.

RNA Compounds

Provided herein, inter alia, are RNA compounds including a preQ1 linking compound (e.g. linking compound), a first RNA stem loop, and a second RNA stem loop, wherein the preQ1 linking compound attaches the first RNA stem loop and the second RNA stem loop. The preQ1 linking compound attaches the loop region of the first RNA stem loop to the loop region of the second RNA stem loop. The terms "RNA stem loop", "RNA hairpin" and "hairpin loop" are interchangeable, are used in accordance to their ordinary meaning in the art, and refer to a region of an RNA oligonucleotide (e.g. RNA stem loop oligonucleotide) that that includes two nucleotide sequences that base pair to form a double-stranded (e.g. RNA double-helix) structure (e.g. the stem) with a non-base paired structure (e.g. the loop) at one end of the double-stranded structure. The double-stranded structure (e.g. stem) in the RNA stem loop may be referred to as an "RNA double-helix". Example RNA stem loops are shown, for example, in FIG. 1 and in FIG. 3A (the tetraloop, stem loop 1, stem loop 2, and stem loop 3). The stem, also referred to as the "stem portion", of the RNA stem loop is typically from about 4 to about 40 base pairs in length. The stem may include internal-loops, also known as "bulges", where the double-stranded RNA separates due to non-base pairing between nucleotides. The loop, also referred to as the "loop portion", forms a non-based paired structure at one end of the RNA stem loop, and must be at least 3 nucleotides in length, and is typically 3 nucleotides to about 10 nucleotides in length. Thus, the "loop" or "loop portion" caps one end of the RNA stem loop. As used herein, an RNA oligonucleotide or RNA stem loop oligonucleotide refers to an RNA nucleic acid with at least one RNA stem loop structure.

In embodiments, the loop (e.g. loop portion) of the RNA stem loop is from about 3 nucleotides to about 10 nucleotides in length. In embodiments, the loop (e.g. loop portion) of the RNA stem loop is from about 4 nucleotides to about 10 nucleotides in length. In embodiments, the loop (e.g. loop portion) of the RNA stem loop is from about 5 nucleotides to about 10 nucleotides in length. In embodiments, the loop (e.g. loop portion) of the RNA stem loop is from about 6 nucleotides to about 10 nucleotides in length. In embodiments, the loop (e.g. loop portion) of the RNA stem loop is from about 7 nucleotides to about 10 nucleotides in length. In embodiments, the loop (e.g. loop portion) of the RNA stem loop is from about 8 nucleotides to about 10 nucleotides in length. In embodiments, the loop (e.g. loop portion) of the RNA stem loop is from about 9 nucleotides to about 10 nucleotides in length.

In embodiments, the loop (e.g. loop portion) of the RNA stem loop is from about 3 nucleotides to about 9 nucleotides in length. In embodiments, the loop (e.g. loop portion) of the RNA stem loop is from about 3 nucleotides to about 8 nucleotides in length. In embodiments, the loop (e.g. loop portion) of the RNA stem loop is from about 3 nucleotides to about 7 nucleotides in length. In embodiments, the loop (e.g. loop portion) of the RNA stem loop is from about 3 nucleotides to about 6 nucleotides in length. In embodiments, the loop (e.g. loop portion) of the RNA stem loop is from about 3 nucleotides to about 5 nucleotides in length. In embodiments, the loop (e.g. loop portion) of the RNA stem loop is from about 3 nucleotides to about 4 nucleotides in length. In embodiments, the loop (e.g. loop portion) of the RNA stem loop is 3 nucleotides, 4 nucleotides, 5 nucleotides, 6 nucleotides, 7 nucleotides, 8 nucleotides, 9 nucleotides, or 10 nucleotides in length. In embodiments, the loop (e.g. loop portion) of the RNA stem loop is 4 nucleotides in length. In embodiments, the loop (e.g. loop portion) of the RNA stem loop is 5 nucleotides in length. In embodiments, the loop (e.g. loop portion) of the RNA stem loop is 6 nucleotides in length. In embodiments, the loop (e.g. loop portion) of the RNA stem loop is 7 nucleotides in length.

In embodiments, the stem (e.g. stem portion) of the RNA stem loop is from about 4 to about 40 base pairs in length. In embodiments, the stem (e.g. stem portion) of the RNA stem loop is from about 8 to about 40 base pairs in length. In embodiments, the stem (e.g. stem portion) of the RNA stem loop is from about 12 to about 40 base pairs in length. In embodiments, the stem (e.g. stem portion) of the RNA stem loop is from about 16 to about 40 base pairs in length. In embodiments, the stem (e.g. stem portion) of the RNA stem loop is from about 20 to about 40 base pairs in length. In embodiments, the stem (e.g. stem portion) of the RNA stem loop is from about 24 to about 40 base pairs in length. In embodiments, the stem (e.g. stem portion) of the RNA stem loop is from about 28 to about 40 base pairs in length. In embodiments, the stem (e.g. stem portion) of the RNA stem loop is from about 32 to about 40 base pairs in length. In embodiments, the stem (e.g. stem portion) of the RNA stem loop is from about 36 to about 40 base pairs in length.

In embodiments, the stem (e.g. stem portion) of the RNA stem loop is from about 4 to about 36 base pairs in length. In embodiments, the stem (e.g. stem portion) of the RNA stem loop is from about 4 to about 32 base pairs in length. In embodiments, the stem (e.g. stem portion) of the RNA stem loop is from about 4 to about 28 base pairs in length. In embodiments, the stem (e.g. stem portion) of the RNA stem loop is from about 4 to about 24 base pairs in length. In embodiments, the stem (e.g. stem portion) of the RNA stem loop is from about 4 to about 20 base pairs in length. In embodiments, the stem (e.g. stem portion) of the RNA stem loop is from about 4 to about 16 base pairs in length. In embodiments, the stem (e.g. stem portion) of the RNA stem loop is from about 4 to about 12 base pairs in length. In embodiments, the stem (e.g. stem portion) of the RNA stem loop is from about 4 to about 8 base pairs in length. In embodiments, the stem (e.g. stem portion) of the RNA stem loop is 4 base pairs, 8 base pairs, 12 base pairs, 16 base pairs, 20 base pairs, 24 base pairs, 28 base pairs, 32 base pairs, 36 base pairs, or 40 base pairs in length. In embodiments, the stem (e.g. stem portion) of the RNA stem loop is 5 base pairs in length. In embodiments, the stem (e.g. stem portion) of the RNA stem loop is 6 base pairs in length. In embodiments, the stem (e.g. stem portion) of the RNA stem loop is 7 base pairs in length. In embodiments, the stem (e.g. stem portion) of the RNA stem loop is 8 base pairs in length. In embodiments, the stem (e.g. stem portion) of the RNA stem loop is 9 base pairs in length. In embodiments, the stem (e.g. stem portion) of the RNA stem loop is 10 base pairs in length. In embodiments, the stem (e.g. stem portion) of the RNA stem loop is 11 base pairs in length.

As used herein, "preQ1 linking compound", also referred to as "linking compound", is a compound including two preQ1 compounds or analogs thereof covalently attached by a linker $L^1$ as provided herein, including embodiments thereof. Thus, in embodiments, the preQ1 linking compound includes two preQ1 compounds covalently attached by a linker $L^1$. In embodiments, the preQ1 linking compound includes two preQ1 analogs covalently attached by a linker $L^1$. The preQ1 compound or preQ1 analog as provided in the preQ1 linking compound may be referred to as the "preQ1 portion".

The structure of the preQ1 linking compound (e.g. linking compound) is as follows:

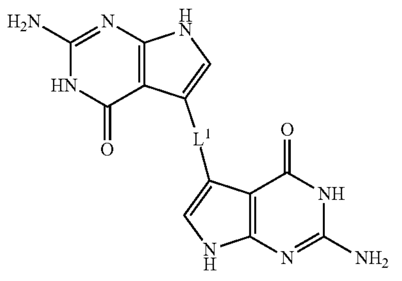

Thus, in an aspect is provided an RNA compound having the formula:

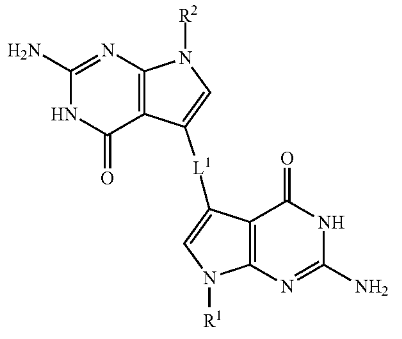

wherein $L^1$ is a covalent linker; $R^1$ is a first RNA loop portion of a first RNA stem loop; and $R^2$ is a second RNA loop portion of a second RNA stem loop.

In embodiments, the first RNA stem loop is in a first RNA oligonucleotide and the second RNA stem loop is in a second RNA oligonucleotide. The term "RNA oligonucleotide" may be used interchangeably with "RNA stem loop oligonucleotide" and refers to an RNA nucleic acid with at least one stem loop structure. In embodiments, the RNA oligonucleotide (e.g. RNA stem loop oligonucleotide) includes 1, 2, 3, 4, 5, 6, 7, 8, 9, or 10 or more RNA stem loops. In embodiments, the RNA oligonucleotide (e.g. RNA stem loop oligonucleotide) includes 1 RNA stem loop. In embodiments, the RNA oligonucleotide (e.g. RNA stem loop oligonucleotide) includes 2 RNA stem loops. In embodiments, the RNA oligonucleotide (e.g. RNA stem loop oligonucleotide) includes 3 RNA stem loops. In embodiments, the RNA oligonucleotide (e.g. RNA stem loop oligonucleotide) includes 4 RNA stem loops.

In embodiments, the first RNA stem loop includes the sequence of SEQ ID NO:29. In embodiments, the first RNA stem loop is the sequence of SEQ ID NO:29. In embodiments, the first RNA stem loop includes the sequence of SEQ ID NO:30. In embodiments, the first RNA stem loop is the sequence of SEQ ID NO:30. In embodiments, the first RNA stem loop includes the sequence of SEQ ID NO:31. In embodiments, the first RNA stem loop is the sequence of SEQ ID NO:31. In embodiments, the first RNA stem loop includes the sequence of SEQ ID NO:32.

In embodiments, the second RNA stem loop includes the sequence of SEQ ID NO:29. In embodiments, the second RNA stem loop is the sequence of SEQ ID NO:29. In embodiments, the second RNA stem loop includes the sequence of SEQ ID NO:30. In embodiments, the second RNA stem loop is the sequence of SEQ ID NO:30. In embodiments, the second RNA stem loop includes the sequence of SEQ ID NO:31. In embodiments, the second RNA stem loop is the sequence of SEQ ID NO:31. In embodiments, the second RNA stem loop includes the sequence of SEQ ID NO:32.

In embodiments, the loop portion of the first RNA stem loop includes the sequence of SEQ ID NO:32. In embodiments, the loop portion of the second RNA stem loop includes the sequence of SEQ ID NO:32. In embodiments, the loop portion of the first RNA stem loop is the sequence of SEQ ID NO:32. In embodiments, the loop portion of the second RNA stem loop is the sequence of SEQ ID NO:32.

In embodiments, the first RNA oligonucleotide (e.g. first RNA stem loop oligonucleotide) and the second RNA oligonucleotide (e.g. second RNA stem loop oligonucleotide) are substantially identical RNA oligonucleotides. In embodiments, the first RNA oligonucleotide and the second RNA oligonucleotide are different RNA oligonucleotides.

In embodiments, the first RNA oligonucleotide (e.g. first RNA stem loop oligonucleotide) and the second RNA oligonucleotide (e.g. second RNA stem loop oligonucleotide) are independently between about 15 nucleotides to about 10,000 nucleotides in length. In embodiments, the first RNA oligonucleotide and the second RNA oligonucleotide are independently between about 200 nucleotides to about 10,000 nucleotides in length. In embodiments, the first RNA oligonucleotide and the second RNA oligonucleotide are independently between about 400 nucleotides to about 10,000 nucleotides in length. In embodiments, the first RNA oligonucleotide and the second RNA oligonucleotide are independently between about 600 nucleotides to about 10,000 nucleotides in length. In embodiments, the first RNA oligonucleotide and the second RNA oligonucleotide are independently between about 800 nucleotides to about 10,000 nucleotides in length. In embodiments, the first RNA oligonucleotide and the second RNA oligonucleotide are independently between about 1,000 nucleotides to about 10,000 nucleotides in length. In embodiments, the first RNA oligonucleotide and the second RNA oligonucleotide are independently between about 1,200 nucleotides to about 10,000 nucleotides in length. In embodiments, the first RNA oligonucleotide and the second RNA oligonucleotide are independently between about 1,400 nucleotides to about 10,000 nucleotides in length. In embodiments, the first RNA oligonucleotide and the second RNA oligonucleotide are independently between about 1,600 nucleotides to about 10,000 nucleotides in length. In embodiments, the first RNA oligonucleotide and the second RNA oligonucleotide are independently between about 1,800 nucleotides to about 10,000 nucleotides in length. In embodiments, the first RNA oligonucleotide and the second RNA oligonucleotide are independently between about 2,000 nucleotides to about 10,000 nucleotides in length. In embodiments, the first RNA oligonucleotide and the second RNA oligonucleotide are independently between about 2,200 nucleotides to about 10,000 nucleotides in length. In embodiments, the first RNA oligonucleotide and the second RNA oligonucleotide are independently between about 2,400 nucleotides to about 10,000 nucleotides in length. In embodiments, the first RNA oligonucleotide and the second RNA oligonucleotide are independently between about 2,600 nucleotides to about 10,000 nucleotides in length. In embodiments, the first RNA oligonucleotide and the second RNA oligonucleotide are independently between about 2,800 nucleotides to about 10,000 nucleotides in length. In embodiments, the first RNA oligonucleotide and the second RNA oligonucleotide are independently between about 3,000 nucleotides to about 10,000 nucleotides in length. In embodiments, the first RNA oligonucleotide and the second RNA oligonucleotide are independently between about 3,200 nucleotides to about 10,000 nucleotides in length. In embodiments, the first RNA oligonucleotide and the second RNA oligonucleotide are independently between about 3,400 nucleotides to about 10,000 nucleotides in length. In embodiments, the first RNA oligonucleotide and the second RNA oligonucleotide are independently between about 3,600 nucleotides to about 10,000 nucleotides in length. In embodiments, the first RNA oligonucleotide and the second RNA oligonucleotide are independently between about 3,800 nucleotides to about 10,000 nucleotides in length. In embodiments, the first RNA oligonucleotide and the second RNA oligonucleotide are independently between about 4,000 nucleotides to about 10,000 nucleotides in length. In embodiments, the first RNA oligonucleotide and the second RNA oligonucleotide are independently between about 4,200 nucleotides to about 10,000 nucleotides in length. In embodiments, the first RNA oligonucleotide and the second RNA oligonucleotide are independently between about 4,400 nucleotides to about 10,000 nucleotides in length. In embodiments, the first RNA oligonucleotide and the second RNA oligonucleotide are independently between about 4,600 nucleotides to about 10,000 nucleotides in length. In embodiments, the first RNA oligonucleotide and the second RNA oligonucleotide are independently between about 4,800 nucleotides to about 10,000 nucleotides in length. In embodiments, the first RNA oligonucleotide and the second RNA oligonucleotide are independently between about 5,000 nucleotides to about 10,000 nucleotides in length. In embodiments, the first RNA oligonucleotide and the second RNA oligonucleotide are independently between about 5,200 nucleotides to about 10,000 nucleotides in length. In embodiments, the first RNA oligonucleotide and the second RNA oligonucleotide are independently between about 5,400 nucleotides to about 10,000 nucleotides in length. In embodiments, the first RNA oligonucleotide and the second RNA oligonucleotide are independently between about 5,600 nucleotides to about 10,000 nucleotides in length. In embodiments, the first RNA oligonucleotide and the second RNA oligonucleotide are independently between about 5,800 nucleotides to about 10,000 nucleotides in length. In embodiments, the first RNA oligonucleotide and the second RNA oligonucleotide are independently between about 6,000 nucleotides to about 10,000 nucleotides in length. In embodiments, the first RNA oligonucleotide and the second RNA oligonucleotide are independently between about 6,200 nucleotides to about 10,000 nucleotides in length. In embodiments, the first RNA oligonucleotide and the second RNA oligonucleotide are independently between about 6,400 nucleotides to about 10,000 nucleotides in length. In embodiments, the first RNA oligonucleotide and the second RNA oligonucleotide are independently between about 6,600 nucleotides to about 10,000 nucleotides in length. In embodiments, the first RNA oligonucleotide and the second RNA oligonucleotide are independently between about 6,800 nucleotides to about 10,000 nucleotides in length. In embodiments, the first RNA oligonucleotide and the second RNA oligonucleotide are independently between about 7,000 nucleotides to about 10,000 nucleotides in length. In embodiments, the first RNA oligonucleotide and the second RNA oligonucleotide are independently between about 7,200 nucleotides to about 10,000 nucleotides in length. In embodiments, the first RNA oligonucleotide and the second RNA oligonucleotide are independently between about 7,400 nucleotides to about 10,000 nucleotides in length. In embodiments, the first RNA oligonucleotide and the second RNA oligonucleotide are independently between about 7,600 nucleotides to about 10,000 nucleotides in length. In embodiments, the first RNA oligonucleotide and the second RNA oligonucleotide are independently between about 7,800 nucleotides to about 10,000 nucleotides in length. In embodiments, the first RNA oligonucleotide and the second RNA oligonucleotide are independently between about 8,000 nucleotides to about 10,000 nucleotides in length. In embodiments, the first RNA oligonucleotide and the second RNA oligonucleotide are independently between about 8,200 nucleotides to about 10,000 nucleotides in length. In embodiments, the first RNA oligonucleotide and the second RNA oligonucleotide are independently between about 8,400 nucleotides to about 10,000 nucleotides in length. In embodiments, the first RNA oligonucleotide and the second RNA oligonucleotide are independently between about 8,600 nucleotides to about 10,000 nucleotides in length. In embodiments, the first RNA oligonucleotide and the second RNA oligonucleotide are independently between about 8,800 nucleotides to about 10,000 nucleotides in length. In embodiments, the first RNA oligonucleotide and the second RNA oligonucleotide are independently between about 9,000 nucleotides to about 10,000 nucleotides in length. In embodiments, the first RNA oligonucleotide and the second RNA oligonucleotide are independently between about 9,200 nucleotides to about 10,000 nucleotides in length. In embodiments, the first RNA oligonucleotide and the second RNA oligonucleotide are independently between about 9,400 nucleotides to about 10,000 nucleotides in length. In embodiments, the first RNA oligonucleotide and the second RNA oligonucleotide are independently between about 9,600 nucleotides to about 10,000 nucleotides in length. In embodiments, the first RNA oligonucleotide and the second RNA oligonucleotide are independently between about 9,800 nucleotides to about 10,000 nucleotides in length.

In embodiments, the first RNA oligonucleotide (e.g. first RNA stem loop oligonucleotide) and the second RNA oligonucleotide (e.g. second RNA stem loop oligonucleotide) are independently between about 15 nucleotides to about 9,800 nucleotides in length. In embodiments, the first RNA oligonucleotide and the second RNA oligonucleotide are independently between about 15 nucleotides to about 9,600 nucleotides in length. In embodiments, the first RNA oligonucleotide and the second RNA oligonucleotide are independently between about 15 nucleotides to about 9,400 nucleotides in length. In embodiments, the first RNA oligonucleotide and the second RNA oligonucleotide are independently between about 15 nucleotides to about 9,200 nucleotides in length. In embodiments, the first RNA oligonucleotide and the second RNA oligonucleotide are independently between about 15 nucleotides to about 9,000 nucleotides in length. In embodiments, the first RNA oligonucleotide and the second RNA oligonucleotide are independently between about 15 nucleotides to about 8,800 nucleotides in length. In embodiments, the first RNA oligonucleotide and the second RNA oligonucleotide are independently between about 15 nucleotides to about 8,600 nucleotides in length. In embodiments, the first RNA oligonucleotide and the second RNA oligonucleotide are independently between about 15 nucleotides to about 8,400 nucleotides in length. In embodiments, the first RNA oligonucleotide and the second RNA oligonucleotide are independently between about 15 nucleotides to about 8,200 nucleotides in length. In embodiments, the first RNA oligonucleotide and the second RNA oligonucleotide are independently between about 15 nucleotides to about 8,000 nucleotides in length. In embodiments, the first RNA oligonucleotide and the second RNA oligonucleotide are independently between about 15 nucleotides to about 7,800 nucleotides in length. In embodiments, the first RNA oligonucleotide and the second RNA oligonucleotide are independently between about 15 nucleotides to about 7,600 nucleotides in length. In embodiments, the first RNA oligonucleotide and the second RNA oligonucleotide are independently between about 15 nucleotides to about 7,400 nucleotides in length. In embodiments, the first RNA oligonucleotide and the second RNA oligonucleotide are independently between about 15 nucleotides to about 7,200 nucleotides in length. In embodiments, the first RNA oligonucleotide and the second RNA oligonucleotide are independently between about 15 nucleotides to about 7,000 nucleotides in length. In embodiments, the first RNA oligonucleotide and the second RNA oligonucleotide are independently between about 15 nucleotides to about 6,800 nucleotides in length. In embodiments, the first RNA oligonucleotide and the second RNA oligonucleotide are independently between about 15 nucleotides to about 6,600 nucleotides in length. In embodiments, the first RNA oligonucleotide and the second RNA oligonucleotide are independently between about 15 nucleotides to about 6,400 nucleotides in length. In embodiments, the first RNA oligonucleotide and the second RNA oligonucleotide are independently between about 15 nucleotides to about 6,200 nucleotides in length. In embodiments, the first RNA oligonucleotide and the second RNA oligonucleotide are independently between about 15 nucleotides to about 6,000 nucleotides in length. In embodiments, the first RNA oligonucleotide and the second RNA oligonucleotide are independently between about 15 nucleotides to about 5,800 nucleotides in length. In embodiments, the first RNA oligonucleotide and the second RNA oligonucleotide are independently between about 15 nucleotides to about 5,600 nucleotides in length. In embodiments, the first RNA oligonucleotide and the second RNA oligonucleotide are independently between about 15 nucleotides to about 5,400 nucleotides in length. In embodiments, the first RNA oligonucleotide and the second RNA oligonucleotide are independently between about 15 nucleotides to about 5,200 nucleotides in length. In embodiments, the first RNA oligonucleotide and the second RNA oligonucleotide are independently between about 15 nucleotides to about 5,000 nucleotides in length. In embodiments, the first RNA oligonucleotide and the second RNA oligonucleotide are independently between about 15 nucleotides to about 4,800 nucleotides in length. In embodiments, the first RNA oligonucleotide and the second RNA oligonucleotide are independently between about 15 nucleotides to about 4,600 nucleotides in length. In embodiments, the first RNA oligonucleotide and the second RNA oligonucleotide are independently between about 15 nucleotides to about 4,400 nucleotides in length. In embodiments, the first RNA oligonucleotide and the second RNA oligonucleotide are independently between about 15 nucleotides to about 4,200 nucleotides in length. In embodiments, the first RNA oligonucleotide and the second RNA oligonucleotide are independently between about 15 nucleotides to about 4,000 nucleotides in length. In embodiments, the first RNA oligonucleotide and the second RNA oligonucleotide are independently between about 15 nucleotides to about 3,800 nucleotides in length. In embodiments, the first RNA oligonucleotide and the second RNA oligonucleotide are independently between about 15 nucleotides to about 3,600 nucleotides in length. In embodiments, the first RNA oligonucleotide and the second RNA oligonucleotide are independently between about 15 nucleotides to about 3,400 nucleotides in length. In embodiments, the first RNA oligonucleotide and the second RNA oligonucleotide are independently between about 15 nucleotides to about 3,200 nucleotides in length. In embodiments, the first RNA oligonucleotide and the second RNA oligonucleotide are independently between about 15 nucleotides to about 2,000 nucleotides in length. In embodiments, the first RNA oligonucleotide and the second RNA oligonucleotide are independently between about 15 nucleotides to about 1,800 nucleotides in length. In embodiments, the first RNA oligonucleotide and the second RNA oligonucleotide are independently between about 15 nucleotides to about 1,600 nucleotides in length. In embodiments, the first RNA oligonucleotide and the second RNA oligonucleotide are independently between about 15 nucleotides to about 1,400 nucleotides in length. In embodiments, the first RNA oligonucleotide and the second RNA oligonucleotide are independently between about 15 nucleotides to about 1,200 nucleotides in length. In embodiments, the first RNA oligonucleotide and the second RNA oligonucleotide are independently between about 15 nucleotides to about 1,000 nucleotides in length. In embodiments, the first RNA oligonucleotide and the second RNA oligonucleotide are independently between about 15 nucleotides to about 800 nucleotides in length. In embodiments, the first RNA oligonucleotide and the second RNA oligonucleotide are independently between about 15 nucleotides to about 600 nucleotides in length. In embodiments, the first RNA oligonucleotide and the second RNA oligonucleotide are independently between about 15 nucleotides to about 400 nucleotides in length. In embodiments, the first RNA oligonucleotide and the second RNA oligonucleotide are independently between about 15 nucleotides to about 200 nucleotides in length. In embodiments, the first RNA oligonucleotide and the second RNA oligonucleotide are independently 15 nucleotides, 200 nucleotides in length, 400 nucleotides in length, 600 nucleotides in length, 800 nucleotides in length, 1,000 nucleotides in length, 1200 nucleotides in length, 1400 nucleotides in length, 1600 nucleotides in length, 1800 nucleotides in length, 2000 nucleotides in length, 2200 nucleotides in length, 2400 nucleotides in length, 2600 nucleotides in length, 2800 nucleotides in length, 3000 nucleotides in length, 3200 nucleotides in length, 3400 nucleotides in length, 3600 nucleotides in length, 3800 nucleotides in length, 4000 nucleotides in length, 4200 nucleotides in length, 4400 nucleotides in length, 4600 nucleotides in length, 4800 nucleotides in length, 5000 nucleotides in length, 5200 nucleotides in length, 5400 nucleotides in length, 5600 nucleotides in length, 5800 nucleotides in length, 6000 nucleotides in length, 6200 nucleotides in length, 6400 nucleotides in length, 6600 nucleotides in length, 6800 nucleotides in length, 7000 nucleotides in length, 7200 nucleotides in length, 7400 nucleotides in length, 7600 nucleotides in length, 7800 nucleotides in length, 8000 nucleotides in length, 8200 nucleotides in length, 8400 nucleotides in length, 8600 nucleotides in length, 8800 nucleotides in length, 9000 nucleotides in length, 9200 nucleotides in length, 9400 nucleotides in length, 9600 nucleotides in length, 9800 nucleotides in length, or 10,000 nucleotides in length.

In embodiments, the first RNA oligonucleotide (e.g. first RNA stem loop oligonucleotide) and the second RNA oligonucleotide (e.g. second RNA stem loop oligonucleotide) are independently between about 20 nucleotides to about 300 nucleotides in length. In embodiments, the first RNA oligonucleotide and the second RNA oligonucleotide are independently between about 40 nucleotides to about 300 nucleotides in length. In embodiments, the first RNA oligonucleotide and the second RNA oligonucleotide are independently between about 60 nucleotides to about 300 nucleotides in length. In embodiments, the first RNA oligonucleotide and the second RNA oligonucleotide are independently between about 80 nucleotides to about 300 nucleotides in length. In embodiments, the first RNA oligonucleotide and the second RNA oligonucleotide are independently between about 100 nucleotides to about 300 nucleotides in length. In embodiments, the first RNA oligonucleotide and the second RNA oligonucleotide are independently between about 120 nucleotides to about 300 nucleotides in length. In embodiments, the first RNA oligonucleotide and the second RNA oligonucleotide are independently between about 140 nucleotides to about 300 nucleotides in length. In embodiments, the first RNA oligonucleotide and the second RNA oligonucleotide are independently between about 160 nucleotides to about 300 nucleotides in length. In embodiments, the first RNA oligonucleotide and the second RNA oligonucleotide are independently between about 180 nucleotides to about 300 nucleotides in length. In embodiments, the first RNA oligonucleotide and the second RNA oligonucleotide are independently between about 200 nucleotides to about 300 nucleotides in length. In embodiments, the first RNA oligonucleotide and the second RNA oligonucleotide are independently between about 220 nucleotides to about 300 nucleotides in length. In embodiments, the first RNA oligonucleotide and the second RNA oligonucleotide are independently between about 240 nucleotides to about 300 nucleotides in length. In embodiments, the first RNA oligonucleotide and the second RNA oligonucleotide are independently between about 260 nucleotides to about 300 nucleotides in length. In embodiments, the first RNA oligonucleotide and the second RNA oligonucleotide are independently between about 280 nucleotides to about 300 nucleotides in length.

In embodiments, the first RNA oligonucleotide (e.g. first RNA stem loop oligonucleotide) and the second RNA oligonucleotide (e.g. second RNA stem loop oligonucleotide) are independently between about 20 nucleotides to about 280 nucleotides in length. In embodiments, the first RNA oligonucleotide and the second RNA oligonucleotide are independently between about 20 nucleotides to about 260 nucleotides in length. In embodiments, the first RNA oligonucleotide and the second RNA oligonucleotide are independently between about 20 nucleotides to about 240 nucleotides in length. In embodiments, the first RNA oligonucleotide and the second RNA oligonucleotide are independently between about 20 nucleotides to about 220 nucleotides in length. In embodiments, the first RNA oligonucleotide and the second RNA oligonucleotide are independently between about 20 nucleotides to about 200 nucleotides in length. In embodiments, the first RNA oligonucleotide and the second RNA oligonucleotide are independently between about 20 nucleotides to about 180 nucleotides in length. In embodiments, the first RNA oligonucleotide and the second RNA oligonucleotide are independently between about 20 nucleotides to about 160 nucleotides in length. In embodiments, the first RNA oligonucleotide and the second RNA oligonucleotide are independently between about 20 nucleotides to about 140 nucleotides in length. In embodiments, the first RNA oligonucleotide and the second RNA oligonucleotide are independently between about 20 nucleotides to about 120 nucleotides in length. In embodiments, the first RNA oligonucleotide and the second RNA oligonucleotide are independently between about 20 nucleotides to about 100 nucleotides in length. In embodiments, the first RNA oligonucleotide and the second RNA oligonucleotide are independently between about 20 nucleotides to about 80 nucleotides in length. In embodiments, the first RNA oligonucleotide and the second RNA oligonucleotide are independently between about 20 nucleotides to about 60 nucleotides in length. In embodiments, the first RNA oligonucleotide and the second RNA oligonucleotide are independently between about 20 nucleotides to about 40 nucleotides in length. In embodiments, the first RNA oligonucleotide and the second RNA oligonucleotide are independently 20 nucleotides, 40 nucleotides, 60 nucleotides, 80 nucleotides, 100 nucleotides, 120 nucleotides, 140 nucleotides, 160 nucleotides, 180 nucleotides, 200 nucleotides, 220 nucleotides, 240 nucleotides, 260 nucleotides, 280 nucleotides, or 300 nucleotides in length.

In embodiments, the first RNA stem loop oligonucleotide and the second RNA stem loop oligonucleotide are independently a pre-miRNA. In embodiments, the first RNA oligonucleotide (e.g. first RNA stem loop oligonucleotide) and the second RNA oligonucleotide (e.g. second RNA stem loop oligonucleotide) are independently an mRNA, a gRNA, an sgRNA, an shRNA, a siRNA, a tRNA, a long non-coding RNA, an rRNA or a ribozyme. In embodiments, the first RNA oligonucleotide and the second RNA oligonucleotide are independently an mRNA. In embodiments, the first RNA oligonucleotide and the second RNA oligonucleotide are independently a gRNA. In embodiments, the first RNA oligonucleotide and the second RNA oligonucleotide are independently an sgRNA. In embodiments, the first RNA oligonucleotide and the second RNA oligonucleotide are independently an shRNA. In embodiments, the first RNA oligonucleotide and the second RNA oligonucleotide are independently a siRNA. In embodiments, the first RNA oligonucleotide and the second RNA oligonucleotide are independently a tRNA. In embodiments, the first RNA oligonucleotide and the second RNA oligonucleotide are independently a long non-coding RNA. In embodiments, the first RNA oligonucleotide and the second RNA oligonucleotide are independently an rRNA. In embodiments, the first RNA oligonucleotide and the second RNA oligonucleotide are independently a ribozyme.

In embodiments, the first RNA oligonucleotide (e.g. first RNA stem loop oligonucleotide) is a first gRNA and the second RNA oligonucleotide (e.g. second RNA stem loop oligonucleotide) is a second gRNA. In embodiments, the first RNA oligonucleotide (e.g. first RNA stem loop oligonucleotide) is a first sgRNA and the second RNA oligonucleotide (e.g. second RNA stem loop oligonucleotide) is a second sgRNA. In embodiments, the first sgRNA includes the sequence of SEQ ID NO:7, 8, 9, 10, 11, 12, 13, 14, 15, 16, 17, 18, 19, 20, 21, 22, 23, 24, 25, 26, 27, or 28. In embodiments, the first sgRNA includes the sequence of SEQ ID NO:7. In embodiments, the first sgRNA includes the sequence of SEQ ID NO:8. In embodiments, the first sgRNA includes the sequence of SEQ ID NO:9. In embodiments, the first sgRNA includes the sequence of SEQ ID NO:10. In embodiments, the first sgRNA includes the sequence of SEQ ID NO:11. In embodiments, the first sgRNA includes the sequence of SEQ ID NO:12. In embodiments, the first sgRNA includes the sequence of SEQ ID NO:13. In embodiments, the first sgRNA includes the sequence of SEQ ID NO:14. In embodiments, the first sgRNA includes the sequence of SEQ ID NO:15. In embodiments, the first sgRNA includes the sequence of SEQ ID NO:16. In embodiments, the first sgRNA includes the sequence of SEQ ID NO:17. In embodiments, the first sgRNA includes the sequence of SEQ ID NO:18. In embodiments, the first sgRNA includes the sequence of SEQ ID NO:19. In embodiments, the first sgRNA includes the sequence of SEQ ID NO:20. In embodiments, the first sgRNA includes the sequence of SEQ ID NO:21. In embodiments, the first sgRNA includes the sequence of SEQ ID NO:22. In embodiments, the first sgRNA includes the sequence of SEQ ID NO:23. In embodiments, the first sgRNA includes the sequence of SEQ ID NO:24. In embodiments, the first sgRNA includes the sequence of SEQ ID NO:25. In embodiments, the first sgRNA includes the sequence of SEQ ID NO:26. In embodiments, the first sgRNA includes the sequence of SEQ ID NO:27. In embodiments, the first sgRNA includes the sequence of SEQ ID NO:28. In embodiments, the first sgRNA is the sequence of SEQ ID NO:7. In embodiments, the first sgRNA is the sequence of SEQ ID NO:8. In embodiments, the first sgRNA is the sequence of SEQ ID NO:9. In embodiments, the first sgRNA is the sequence of SEQ ID NO:10. In embodiments, the first sgRNA is the sequence of SEQ ID NO:11. In embodiments, the first sgRNA is the sequence of SEQ ID NO:12. In embodiments, the first sgRNA is the sequence of SEQ ID NO:13. In embodiments, the first sgRNA is the sequence of SEQ ID NO:14. In embodiments, the first sgRNA is the sequence of SEQ ID NO:15. In embodiments, the first sgRNA is the sequence of SEQ ID NO:16. In embodiments, the first sgRNA is the sequence of SEQ ID NO:17. In embodiments, the first sgRNA is the sequence of SEQ ID NO:18. In embodiments, the first sgRNA is the sequence of SEQ ID NO:19. In embodiments, the first sgRNA is the sequence of SEQ ID NO:20. In embodiments, the first sgRNA is the sequence of SEQ ID NO:21. In embodiments, the first sgRNA is the sequence of SEQ ID NO:22. In embodiments, the first sgRNA is the sequence of SEQ ID NO:23. In embodiments, the first sgRNA is the sequence of SEQ ID NO:24. In embodiments, the first sgRNA is the sequence of SEQ ID NO:25. In embodiments, the first sgRNA is the sequence of SEQ ID NO:26. In embodiments, the first sgRNA is the sequence of SEQ ID NO:27. In embodiments, the first sgRNA is the sequence of SEQ ID NO:28.

In embodiments, the second sgRNA includes the sequence of SEQ ID NO:7, 8, 9, 10, 11, 12, 13, 14, 15, 16, 17, 18, 19, 20, 21, 22, 23, 24, 25, 26, 27, or 28. In embodiments, the second sgRNA includes the sequence of SEQ ID NO:7. In embodiments, the second sgRNA includes the sequence of SEQ ID NO:8. In embodiments, the second sgRNA includes the sequence of SEQ ID NO:9. In embodiments, the second sgRNA includes the sequence of SEQ ID NO:10. In embodiments, the second sgRNA includes the sequence of SEQ ID NO:11. In embodiments, the second sgRNA includes the sequence of SEQ ID NO:12. In embodiments, the second sgRNA includes the sequence of SEQ ID NO:13. In embodiments, the second sgRNA includes the sequence of SEQ ID NO:14. In embodiments, the second sgRNA includes the sequence of SEQ ID NO:15. In embodiments, the second sgRNA includes the sequence of SEQ ID NO:16. In embodiments, the second sgRNA includes the sequence of SEQ ID NO:17. In embodiments, the second sgRNA includes the sequence of SEQ ID NO:18. In embodiments, the second sgRNA includes the sequence of SEQ ID NO:19. In embodiments, the second sgRNA includes the sequence of SEQ ID NO:20. In embodiments, the second sgRNA includes the sequence of SEQ ID NO:21. In embodiments, the second sgRNA includes the sequence of SEQ ID NO:22. In embodiments, the second sgRNA includes the sequence of SEQ ID NO:23. In embodiments, the second sgRNA includes the sequence of SEQ ID NO:24. In embodiments, the second sgRNA includes the sequence of SEQ ID NO:25. In embodiments, the second sgRNA includes the sequence of SEQ ID NO:26. In embodiments, the second sgRNA includes the sequence of SEQ ID NO:27. In embodiments, the second sgRNA includes the sequence of SEQ ID NO:28. In embodiments, the second sgRNA is the sequence of SEQ ID NO:7. In embodiments, the second sgRNA is the sequence of SEQ ID NO:8. In embodiments, the second sgRNA is the sequence of SEQ ID NO:9. In embodiments, the second sgRNA is the sequence of SEQ ID NO:10. In embodiments, the second sgRNA is the sequence of SEQ ID NO:11. In embodiments, the second sgRNA is the sequence of SEQ ID NO:12. In embodiments, the second sgRNA is the sequence of SEQ ID NO:13. In embodiments, the second sgRNA is the sequence of SEQ ID NO:14. In embodiments, the second sgRNA is the sequence of SEQ ID NO:15. In embodiments, the second sgRNA is the sequence of SEQ ID NO:16. In embodiments, the second sgRNA is the sequence of SEQ ID NO:17. In embodiments, the second sgRNA is the sequence of SEQ ID NO:18. In embodiments, the second sgRNA is the sequence of SEQ ID NO:19. In embodiments, the second sgRNA is the sequence of SEQ ID NO:20. In embodiments, the second sgRNA is the sequence of SEQ ID NO:21. In embodiments, the second sgRNA is the sequence of SEQ ID NO:22. In embodiments, the second sgRNA is the sequence of SEQ ID NO:23. In embodiments, the second sgRNA is the sequence of SEQ ID NO:24. In embodiments, the second sgRNA is the sequence of SEQ ID NO:25. In embodiments, the second sgRNA is the sequence of SEQ ID NO:26. In embodiments, the second sgRNA is the sequence of SEQ ID NO:27. In embodiments, the second sgRNA is the sequence of SEQ ID NO:28.

In embodiments, the first RNA stem loop is the stem loop 2 of the first sgRNA and the second RNA stem loop is the tetra-loop of the second sgRNA. In embodiments, the first RNA stem loop is the tetra-loop of the first sgRNA and the second RNA stem loop is the stem loop 2 of the second sgRNA.

For the sgRNA provided herein, in embodiments, the sgRNA includes a tetra-loop including the sequence of SEQ ID NO:29, 30, 31 or 32. In embodiments, the sgRNA includes a tetra-loop including the sequence of SEQ ID NO:29. In embodiments, the sgRNA includes a tetra-loop including the sequence of SEQ ID NO:30. In embodiments, the sgRNA includes a tetra-loop including the sequence of SEQ ID NO:31. In embodiments, the sgRNA includes a tetra-loop including the sequence of SEQ ID NO:32.

For the sgRNA provided herein, in embodiments, the sgRNA includes a stem loop 2 including the sequence of SEQ ID NO:29, 30, 31 or 32. In embodiments, the sgRNA includes a stem loop 2 including the sequence of SEQ ID NO:29. In embodiments, the sgRNA includes a stem loop 2 including the sequence of SEQ ID NO:30. In embodiments, the sgRNA includes a stem loop 2 including the sequence of SEQ ID NO:31. In embodiments, the sgRNA includes a stem loop 2 including the sequence of SEQ ID NO:32.

In embodiments, the first RNA stem loop and the second RNA stem loop are in the same RNA oligonucleotide (e.g. RNA stem loop oligonucleotide). In embodiments, the first RNA stem loop includes the sequence of SEQ ID NO:29. In embodiments, the second RNA stem loop includes the sequence of SEQ ID NO:29. In embodiments, the first RNA stem loop includes the sequence of SEQ ID NO:30. In embodiments, the second RNA stem loop includes the sequence of SEQ ID NO:30. In embodiments, the first RNA stem loop includes the sequence of SEQ ID NO:31. In embodiments, the second RNA stem loop includes the sequence of SEQ ID NO:31. In embodiments, the first RNA stem loop includes the sequence of SEQ ID NO:32. In embodiments, the second RNA stem loop includes the sequence of SEQ ID NO:32.

In embodiments, the first RNA stem loop is the sequence of SEQ ID NO:29. In embodiments, the second RNA stem loop is the sequence of SEQ ID NO:29. In embodiments, the first RNA stem loop is the sequence of SEQ ID NO:30. In embodiments, the second RNA stem loop is the sequence of SEQ ID NO:30. In embodiments, the first RNA stem loop is the sequence of SEQ ID NO:31. In embodiments, the second RNA stem loop is the sequence of SEQ ID NO:31.

In embodiments, the loop portion of the first RNA stem loop includes the sequence of SEQ ID NO:32. In embodiments, the loop portion of the second RNA stem loop includes the sequence of SEQ ID NO:32. In embodiments, the loop portion of the first RNA stem loop is the sequence of SEQ ID NO:32. In embodiments, the loop portion of the second RNA stem loop is the sequence of SEQ ID NO:32.

In embodiments, the RNA oligonucleotide (e.g. RNA stem loop oligonucleotide) is between about 15 nucleotides to about 10,000 nucleotides in length. In embodiments, the RNA oligonucleotide is between about 200 nucleotides to about 10,000 nucleotides in length. In embodiments, the RNA oligonucleotide is between about 400 nucleotides to about 10,000 nucleotides in length. In embodiments, the RNA oligonucleotide is between about 600 nucleotides to about 10,000 nucleotides in length. In embodiments, the RNA oligonucleotide is between about 800 nucleotides to about 10,000 nucleotides in length. In embodiments, the RNA oligonucleotide is between about 1,000 nucleotides to about 10,000 nucleotides in length. In embodiments, the RNA oligonucleotide is between about 1,200 nucleotides to about 10,000 nucleotides in length. In embodiments, the RNA oligonucleotide is between about 1,400 nucleotides to about 10,000 nucleotides in length. In embodiments, the RNA oligonucleotide is between about 1,600 nucleotides to about 10,000 nucleotides in length. In embodiments, the RNA oligonucleotide is between about 1,800 nucleotides to about 10,000 nucleotides in length. In embodiments, the RNA oligonucleotide is between about 2,000 nucleotides to about 10,000 nucleotides in length. In embodiments, the RNA oligonucleotide is between about 2,200 nucleotides to about 10,000 nucleotides in length. In embodiments, the RNA oligonucleotide is between about 2,400 nucleotides to about 10,000 nucleotides in length. In embodiments, the RNA oligonucleotide is between about 2,600 nucleotides to about 10,000 nucleotides in length. In embodiments, the RNA oligonucleotide is between about 2,800 nucleotides to about 10,000 nucleotides in length. In embodiments, the RNA oligonucleotide is between about 3,000 nucleotides to about 10,000 nucleotides in length. In embodiments, the RNA oligonucleotide is between about 3,200 nucleotides to about 10,000 nucleotides in length. In embodiments, the RNA oligonucleotide is between about 3,400 nucleotides to about 10,000 nucleotides in length. In embodiments, the RNA oligonucleotide is between about 3,600 nucleotides to about 10,000 nucleotides in length. In embodiments, the RNA oligonucleotide is between about 3,800 nucleotides to about 10,000 nucleotides in length. In embodiments, the RNA oligonucleotide is between about 4,000 nucleotides to about 10,000 nucleotides in length. In embodiments, the RNA oligonucleotide is between about 4,200 nucleotides to about 10,000 nucleotides in length. In embodiments, the RNA oligonucleotide is between about 4,400 nucleotides to about 10,000 nucleotides in length. In embodiments, the RNA oligonucleotide is between about 4,600 nucleotides to about 10,000 nucleotides in length. In embodiments, the RNA oligonucleotide is between about 4,800 nucleotides to about 10,000 nucleotides in length. In embodiments, the RNA oligonucleotide is between about 5,000 nucleotides to about 10,000 nucleotides in length. In embodiments, the RNA oligonucleotide is between about 5,200 nucleotides to about 10,000 nucleotides in length. In embodiments, the RNA oligonucleotide is between about 5,400 nucleotides to about 10,000 nucleotides in length. In embodiments, the RNA oligonucleotide is between about 5,600 nucleotides to about 10,000 nucleotides in length. In embodiments, the RNA oligonucleotide is between about 5,800 nucleotides to about 10,000 nucleotides in length. In embodiments, the RNA oligonucleotide is between about 6,000 nucleotides to about 10,000 nucleotides in length. In embodiments, the RNA oligonucleotide is between about 6,200 nucleotides to about 10,000 nucleotides in length. In embodiments, the RNA oligonucleotide is between about 6,400 nucleotides to about 10,000 nucleotides in length. In embodiments, the RNA oligonucleotide is between about 6,600 nucleotides to about 10,000 nucleotides in length. In embodiments, the RNA oligonucleotide is between about 6,800 nucleotides to about 10,000 nucleotides in length. In embodiments, the RNA oligonucleotide is between about 7,000 nucleotides to about 10,000 nucleotides in length. In embodiments, the RNA oligonucleotide is between about 7,200 nucleotides to about 10,000 nucleotides in length. In embodiments, the RNA oligonucleotide is between about 7,400 nucleotides to about 10,000 nucleotides in length. In embodiments, the RNA oligonucleotide is between about 7,600 nucleotides to about 10,000 nucleotides in length. In embodiments, the RNA oligonucleotide is between about 7,800 nucleotides to about 10,000 nucleotides in length. In embodiments, the RNA oligonucleotide is between about 8,000 nucleotides to about 10,000 nucleotides in length. In embodiments, the RNA oligonucleotide is between about 8,200 nucleotides to about 10,000 nucleotides in length. In embodiments, the RNA oligonucleotide is between about 8,400 nucleotides to about 10,000 nucleotides in length. In embodiments, the RNA oligonucleotide is between about 8,600 nucleotides to about 10,000 nucleotides in length. In embodiments, the RNA oligonucleotide is between about 8,800 nucleotides to about 10,000 nucleotides in length. In embodiments, the RNA oligonucleotide is between about 9,000 nucleotides to about 10,000 nucleotides in length. In embodiments, the RNA oligonucleotide is between about 9,200 nucleotides to about 10,000 nucleotides in length. In embodiments, the RNA oligonucleotide is between about 9,400 nucleotides to about 10,000 nucleotides in length. In embodiments, the RNA oligonucleotide is between about 9,600 nucleotides to about 10,000 nucleotides in length. In embodiments, the RNA oligonucleotide is between about 9,800 nucleotides to about 10,000 nucleotides in length.

In embodiments, the RNA oligonucleotide (e.g. RNA stem loop oligonucleotide) is between about 15 nucleotides to about 9,800 nucleotides in length. In embodiments, the RNA oligonucleotide is between about 15 nucleotides to about 9,600 nucleotides in length. In embodiments, the RNA oligonucleotide is between about 15 nucleotides to about 9,400 nucleotides in length. In embodiments, the RNA oligonucleotide is between about 15 nucleotides to about 9,200 nucleotides in length. In embodiments, the RNA oligonucleotide is between about 15 nucleotides to about 9,000 nucleotides in length. In embodiments, the RNA oligonucleotide is between about 15 nucleotides to about 8,800 nucleotides in length. In embodiments, the RNA oligonucleotide is between about 15 nucleotides to about 8,600 nucleotides in length. In embodiments, the RNA oligonucleotide is between about 15 nucleotides to about 8,400 nucleotides in length. In embodiments, the RNA oligonucleotide is between about 15 nucleotides to about 8,200 nucleotides in length. In embodiments, the RNA oligonucleotide is between about 15 nucleotides to about 8,000 nucleotides in length. In embodiments, the RNA oligonucleotide is between about 15 nucleotides to about 7,800 nucleotides in length. In embodiments, the RNA oligonucleotide is between about 15 nucleotides to about 7,600 nucleotides in length. In embodiments, the RNA oligonucleotide is between about 15 nucleotides to about 7,400 nucleotides in length. In embodiments, the RNA oligonucleotide is between about 15 nucleotides to about 7,200 nucleotides in length. In embodiments, the RNA oligonucleotide is between about 15 nucleotides to about 7,000 nucleotides in length. In embodiments, the RNA oligonucleotide is between about 15 nucleotides to about 6,800 nucleotides in length. In embodiments, the RNA oligonucleotide is between about 15 nucleotides to about 6,600 nucleotides in length. In embodiments, the RNA oligonucleotide is between about 15 nucleotides to about 6,400 nucleotides in length. In embodiments, the RNA oligonucleotide is between about 15 nucleotides to about 6,200 nucleotides in length. In embodiments, the RNA oligonucleotide is between about 15 nucleotides to about 6,000 nucleotides in length. In embodiments, the RNA oligonucleotide is between about 15 nucleotides to about 5,800 nucleotides in length. In embodiments, the RNA oligonucleotide is between about 15 nucleotides to about 5,600 nucleotides in length. In embodiments, the RNA oligonucleotide is between about 15 nucleotides to about 5,400 nucleotides in length. In embodiments, the RNA oligonucleotide is between about 15 nucleotides to about 5,200 nucleotides in length. In embodiments, the RNA oligonucleotide is between about 15 nucleotides to about 5,000 nucleotides in length. In embodiments, the RNA oligonucleotide is between about 15 nucleotides to about 4,800 nucleotides in length. In embodiments, the RNA oligonucleotide is between about 15 nucleotides to about 4,600 nucleotides in length. In embodiments, the RNA oligonucleotide is between about 15 nucleotides to about 4,400 nucleotides in length. In embodiments, the RNA oligonucleotide is between about 15 nucleotides to about 4,200 nucleotides in length. In embodiments, the RNA oligonucleotide is between about 15 nucleotides to about 4,000 nucleotides in length. In embodiments, the RNA oligonucleotide is between about 15 nucleotides to about 3,800 nucleotides in length. In embodiments, the RNA oligonucleotide is between about 15 nucleotides to about 3,600 nucleotides in length. In embodiments, the RNA oligonucleotide is between about 15 nucleotides to about 3,400 nucleotides in length. In embodiments, the RNA oligonucleotide is between about 15 nucleotides to about 3,200 nucleotides in length. In embodiments, the RNA oligonucleotide is between about 15 nucleotides to about 2,000 nucleotides in length. In embodiments, the RNA oligonucleotide is between about 15 nucleotides to about 1,800 nucleotides in length. In embodiments, the RNA oligonucleotide is between about 15 nucleotides to about 1,600 nucleotides in length. In embodiments, the RNA oligonucleotide is between about 15 nucleotides to about 1,400 nucleotides in length. In embodiments, the RNA oligonucleotide is between about 15 nucleotides to about 1,200 nucleotides in length. In embodiments, the RNA oligonucleotide is between about 15 nucleotides to about 1,000 nucleotides in length. In embodiments, the RNA oligonucleotide is between about 15 nucleotides to about 800 nucleotides in length. In embodiments, the RNA oligonucleotide is between about 15 nucleotides to about 600 nucleotides in length. In embodiments, the RNA oligonucleotide is between about 15 nucleotides to about 400 nucleotides in length. In embodiments, the RNA oligonucleotide is between about 15 nucleotides to about 200 nucleotides in length. In embodiments, the RNA oligonucleotide is 15 nucleotides, 200 nucleotides in length, 400 nucleotides in length, 600 nucleotides in length, 800 nucleotides in length, 1,000 nucleotides in length, 1200 nucleotides in length, 1400 nucleotides in length, 1600 nucleotides in length, 1800 nucleotides in length, 2000 nucleotides in length, 2200 nucleotides in length, 2400 nucleotides in length, 2600 nucleotides in length, 2800 nucleotides in length, 3000 nucleotides in length, 3200 nucleotides in length, 3400 nucleotides in length, 3600 nucleotides in length, 3800 nucleotides in length, 4000 nucleotides in length, 4200 nucleotides in length, 4400 nucleotides in length, 4600 nucleotides in length, 4800 nucleotides in length, 5000 nucleotides in length, 5200 nucleotides in length, 5400 nucleotides in length, 5600 nucleotides in length, 5800 nucleotides in length, 6000 nucleotides in length, 6200 nucleotides in length, 6400 nucleotides in length, 6600 nucleotides in length, 6800 nucleotides in length, 7000 nucleotides in length, 7200 nucleotides in length, 7400 nucleotides in length, 7600 nucleotides in length, 7800 nucleotides in length, 8000 nucleotides in length, 8200 nucleotides in length, 8400 nucleotides in length, 8600 nucleotides in length, 8800 nucleotides in length, 9000 nucleotides in length, 9200 nucleotides in length, 9400 nucleotides in length, 9600 nucleotides in length, 9800 nucleotides in length, or 10,000 nucleotides in length.

In embodiments, the RNA oligonucleotide (e.g. RNA stem loop oligonucleotide) is between about 20 nucleotides to about 300 nucleotides in length. In embodiments, the RNA oligonucleotide is between about 40 nucleotides to about 300 nucleotides in length. In embodiments, the RNA oligonucleotide is between about 60 nucleotides to about 300 nucleotides in length. In embodiments, the RNA oligonucleotide is between about 80 nucleotides to about 300 nucleotides in length. In embodiments, the RNA oligonucleotide is between about 100 nucleotides to about 300 nucleotides in length. In embodiments, the RNA oligonucleotide is between about 120 nucleotides to about 300 nucleotides in length. In embodiments, the RNA oligonucleotide is between about 140 nucleotides to about 300 nucleotides in length. In embodiments, the RNA oligonucleotide is between about 160 nucleotides to about 300 nucleotides in length. In embodiments, the RNA oligonucleotide is between about 180 nucleotides to about 300 nucleotides in length. In embodiments, the RNA oligonucleotide is between about 200 nucleotides to about 300 nucleotides in length. In embodiments, the RNA oligonucleotide is between about 220 nucleotides to about 300 nucleotides in length. In embodiments, the RNA oligonucleotide is between about 240 nucleotides to about 300 nucleotides in length. In embodiments, the RNA oligonucleotide is between about 260 nucleotides to about 300 nucleotides in length. In embodiments, the RNA oligonucleotide is between about 280 nucleotides to about 300 nucleotides in length.

In embodiments, the RNA oligonucleotide (e.g. RNA stem loop oligonucleotide) is between about 20 nucleotides to about 280 nucleotides in length. In embodiments, the RNA oligonucleotide is between about 20 nucleotides to about 260 nucleotides in length. In embodiments, the RNA oligonucleotide is between about 20 nucleotides to about 240 nucleotides in length. In embodiments, the RNA oligonucleotide is between about 20 nucleotides to about 220 nucleotides in length. In embodiments, the RNA oligonucleotide is between about 20 nucleotides to about 200 nucleotides in length. In embodiments, the RNA oligonucleotide is between about 20 nucleotides to about 180 nucleotides in length. In embodiments, the RNA oligonucleotide is between about 20 nucleotides to about 160 nucleotides in length. In embodiments, the RNA oligonucleotide is between about 20 nucleotides to about 140 nucleotides in length. In embodiments, the RNA oligonucleotide is between about 20 nucleotides to about 120 nucleotides in length. In embodiments, the RNA oligonucleotide is between about 20 nucleotides to about 100 nucleotides in length. In embodiments, the RNA oligonucleotide is between about 20 nucleotides to about 80 nucleotides in length. In embodiments, the RNA oligonucleotide is between about 20 nucleotides to about 60 nucleotides in length. In embodiments, the RNA oligonucleotide is between about 20 nucleotides to about 40 nucleotides in length. In embodiments, the RNA oligonucleotide is 20 nucleotides, 40 nucleotides, 60 nucleotides, 80 nucleotides, 100 nucleotides, 120 nucleotides, 140 nucleotides, 160 nucleotides, 180 nucleotides, 200 nucleotides, 220 nucleotides, 240 nucleotides, 260 nucleotides, 280 nucleotides, or 300 nucleotides in length.

For the RNA oligonucleotide (e.g. first RNA oligonucleotide, second RNA oligonucleotide, RNA stem loop oligonucleotide, first RNA stem loop oligonucleotide, second RNA stem loop oligonucleotide, etc.) provided herein, in embodiments, the RNA oligonucleotide is about 20 nucleotides, 40 nucleotides, 60 nucleotides, 80 nucleotides, 100 nucleotides, 150 nucleotides, 200 nucleotides, 250 nucleotides, 300 nucleotides, 350 nucleotides, 400 nucleotides, 450 nucleotides or 500 nucleotides in length. In embodiments, the RNA oligonucleotide is about 20 nucleotides in length. In embodiments, the RNA oligonucleotide is about 40 nucleotides in length. In embodiments, the RNA oligonucleotide is about 60 nucleotides in length. In embodiments, the RNA oligonucleotide is about 80 nucleotides in length. In embodiments, the RNA oligonucleotide is about 100 nucleotides in length. In embodiments, the RNA oligonucleotide is about 150 nucleotides nucleotides in length. In embodiments, the RNA oligonucleotide is about 200 nucleotides in length. In embodiments, the RNA oligonucleotide is about 250 nucleotides in length. In embodiments, the RNA oligonucleotide is about 300 nucleotides in length. In embodiments, the RNA oligonucleotide is about 350 nucleotides in length. In embodiments, the RNA oligonucleotide is about 400 nucleotides in length. In embodiments, the RNA oligonucleotide is about 450 nucleotides in length. In embodiments, the RNA oligonucleotide is about 500 nucleotides in length. In embodiments, the RNA oligonucleotide is 20 nucleotides in length. In embodiments, the RNA oligonucleotide is 40 nucleotides in length. In embodiments, the RNA oligonucleotide is 60 nucleotides in length. In embodiments, the RNA oligonucleotide is 80 nucleotides in length. In embodiments, the RNA oligonucleotide is 100 nucleotides in length. In embodiments, the RNA oligonucleotide is 150 nucleotides nucleotides in length. In embodiments, the RNA oligonucleotide is 200 nucleotides in length. In embodiments, the RNA oligonucleotide is 250 nucleotides in length. In embodiments, the RNA oligonucleotide is 300 nucleotides in length. In embodiments, the RNA oligonucleotide is 350 nucleotides in length. In embodiments, the RNA oligonucleotide is 400 nucleotides in length. In embodiments, the RNA oligonucleotide is 450 nucleotides in length. In embodiments, the RNA oligonucleotide is 500 nucleotides in length.

In embodiments, the RNA oligonucleotide (e.g. RNA stem loop oligonucleotide) is an mRNA, a gRNA, an sgRNA, an shRNA, a siRNA, a tRNA, a long non-coding RNA, an rRNA or a ribozyme. In embodiments, the RNA oligonucleotide is an mRNA. In embodiments, the RNA oligonucleotide is a gRNA. In embodiments, the RNA oligonucleotide is an sgRNA. In embodiments, the RNA oligonucleotide is an shRNA. In embodiments, the RNA oligonucleotide is an shRNA. In embodiments, the RNA oligonucleotide is a siRNA. In embodiments, the RNA oligonucleotide is a tRNA. In embodiments, the RNA oligonucleotide is a long non-coding RNA. In embodiments, the RNA oligonucleotide is an rRNA. In embodiments, the RNA oligonucleotide is a ribozyme.

In embodiments, the RNA oligonucleotide (e.g. RNA stem loop oligonucleotide) is an sgRNA. In embodiments, the sgRNA includes the sequence of SEQ ID NO:7, 8, 9, 10, 11, 12, 13, 14, 15, 16, 17, 18, 19, 20, 21, 22, 23, 24, 25, 26, 27, or 28. In embodiments, the sgRNA includes the sequence of SEQ ID NO:7. In embodiments, the sgRNA includes the sequence of SEQ ID NO:8. In embodiments, the sgRNA includes the sequence of SEQ ID NO:9. In embodiments, the sgRNA includes the sequence of SEQ ID NO:10. In embodiments, the sgRNA includes the sequence of SEQ ID NO:11. In embodiments, the sgRNA includes the sequence of SEQ ID NO:12. In embodiments, the sgRNA includes the sequence of SEQ ID NO:13. In embodiments, the sgRNA includes the sequence of SEQ ID NO: 14. In embodiments, the sgRNA includes the sequence of SEQ ID NO:15. In embodiments, the sgRNA includes the sequence of SEQ ID NO:16. In embodiments, the sgRNA includes the sequence of SEQ ID NO:17. In embodiments, the sgRNA includes the sequence of SEQ ID NO: 18. In embodiments, the sgRNA includes the sequence of SEQ ID NO:19. In embodiments, the sgRNA includes the sequence of SEQ ID NO:20. In embodiments, the sgRNA includes the sequence of SEQ ID NO:21. In embodiments, the sgRNA includes the sequence of SEQ ID NO:22. In embodiments, the sgRNA includes the sequence of SEQ ID NO:23. In embodiments, the sgRNA includes the sequence of SEQ ID NO:24. In embodiments, the sgRNA includes the sequence of SEQ ID NO:25. In embodiments, the sgRNA includes the sequence of SEQ ID NO:26. In embodiments, the sgRNA includes the sequence of SEQ ID NO:27. In embodiments, the sgRNA includes the sequence of SEQ ID NO:28. In embodiments, the sgRNA is the sequence of SEQ ID NO:7. In embodiments, the sgRNA is the sequence of SEQ ID NO:8. In embodiments, the sgRNA is the sequence of SEQ ID NO:9. In embodiments, the sgRNA is the sequence of SEQ ID NO:10. In embodiments, the sgRNA is the sequence of SEQ ID NO:11. In embodiments, the sgRNA is the sequence of SEQ ID NO:12. In embodiments, the sgRNA is the sequence of SEQ ID NO:13. In embodiments, the sgRNA is the sequence of SEQ ID NO:14. In embodiments, the sgRNA is the sequence of SEQ ID NO:15. In embodiments, the sgRNA is the sequence of SEQ ID NO:16. In embodiments, the sgRNA is the sequence of SEQ ID NO:17. In embodiments, the sgRNA is the sequence of SEQ ID NO:18. In embodiments, the sgRNA is the sequence of SEQ ID NO:19. In embodiments, the sgRNA is the sequence of SEQ ID NO:20. In embodiments, the sgRNA is the sequence of SEQ ID NO:21. In embodiments, the sgRNA is the sequence of SEQ ID NO:22. In embodiments, the sgRNA is the sequence of SEQ ID NO:23. In embodiments, the sgRNA is the sequence of SEQ ID NO:24. In embodiments, the sgRNA is the sequence of SEQ ID NO:25. In embodiments, the sgRNA is the sequence of SEQ ID NO:26. In embodiments, the sgRNA is the sequence of SEQ ID NO:27. In embodiments, the sgRNA is the sequence of SEQ ID NO:28.

In embodiments, the first RNA stem loop is the stem loop 2 of the sgRNA and the second RNA stem loop is the tetra-loop of the sgRNA. In embodiments, the first RNA stem loop is the tetra-loop of the sgRNA and the second RNA stem loop is the stem loop 2 of the sgRNA.

For the RNA compound provided herein, in embodiments, $L^1$ is $$-L^{101}-L^{102}-L^{103}-L^{104}-L^{105}-L^{106}-L^{107}-;$$

$L^{101}$ is a bond, —C(O)—, —C(O)O—, —OC(O)—, —O—, —S—, —$NR^{101}$—, —C(O)$NR^{101}$—, —$NR^{101}$C(O)—, —$NR^{101}$C(O)O—, —OC(O)$NR^{101}$—, —$NR^{101}$C(O)$NR^{101}$—, —$NR^{101}$C(NH)$NR^{101}$—, —$S(O)_2$—, —$NR^{101}S(O)_2$—, —$S(O)_2NR^{101}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{102}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{103}$ is a bond, —C(O)—, —C(O)O—, —OC(O)—, —O—, —S—, —$NR^{103}$—, —C(O)$NR^{103}$—, —$NR^{103}$C(O)—, —$NR^{103}$C(O)O—, —OC(O)$NR^{103}$—, —$NR^{103}$C(O)$NR^{103}$—, —$NR^{103}$C(NH)$NR^{103}$—, —$S(O)_2$—, —$NR^{103}S(O)_2$—, —$S(O)_2NR^{103}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{104}$ is a bond, —C(O)—, —C(O)O—, —OC(O)—, —O—, —S—, —$NR^{104}$—, —C(O)$NR^{104}$—, —$NR^{104}$C(O)—, —$NR^{104}$C(O)O—, —OC(O)$NR^{104}$—, —$NR^{104}$C(O)$NR^{104}$—, —$NR^{104}$C(NH)$NR^{104}$—, —$S(O)_2$—, —$NR^{104}S(O)_2$—, —$S(O)_2NR^{104}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{105}$ is a bond, —C(O)—, —C(O)O—, —OC(O)—, —O—, —S—, —$NR^{105}$—, —C(O)$NR^{105}$—, —$NR^{105}$C(O)—, —$NR^{105}$C(O)O—, —OC(O)$NR^{105}$—, —$NR^{105}$C(O)$NR^{105}$—, —$NR^{105}$C(NH)$NR^{105}$—, —$S(O)_2$—, —$NR^{105}S(O)_2$—, —$S(O)_2NR^{105}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{106}$ is a bond, —C(O)—, —C(O)O—, —OC(O)—, —O—, —S—, —$NR^{106}$—, —C(O)$NR^{106}$—, —$NR^{106}$C(O)—, —$NR^{106}$C(O)O—, —OC(O)$NR^{106}$—, —$NR^{106}$C(O)$NR^{106}$—, —$NR^{106}$C(NH)$NR^{106}$—, —$S(O)_2$—, —$NR^{106}S(O)_2$—, —$S(O)_2NR^{106}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker;

$L^{107}$ is a bond, —C(O)—, —C(O)O—, —OC(O)—, —O—, —S—, —$NR^{107}$—, —C(O)$NR^{107}$—, —$NR^{107}$C(O)—, —$NR^{107}$C(O)O—, —OC(O)$NR^{107}$—, —$NR^{107}$C(O)$NR^{107}$—, —$NR^{107}$C(NH)$NR^{107}$—, —$S(O)_2$—, —$NR^{107}S(O)_2$—, —$S(O)_2NR^{107}$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker; and each $R^{101}$, $R^{102}$, $R^{103}$, $R^{104}$, $R^{105}$, $R^{106}$, and $R^{107}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered).

In embodiments, a substituted $L^{101}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{101}$ is substituted with a plurality of groups selected from substituent groups, size-limited substituent groups, and lower substituent groups; each substituent group, size-limited substituent group, and/or lower substituent group may optionally be different. In embodiments, when $L^{101}$ is substituted, it is substituted with at least one substituent group. In embodiments, when $L^{101}$ is substituted, it is substituted with at least one size-limited substituent group. In embodiments, when $L^{101}$ is substituted, it is substituted with at least one lower substituent group.

In embodiments, $L^{101}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, —$S(O)_2$—, —$NHS(O)_2$—, —$S(O)_2NH$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{101}$ is a bond. In embodiments, $L^{101}$ is —C(O)—. In embodiments, $L^{101}$ is —C(O)O—. In embodiments, $L^{101}$ is —OC(O)—. In embodiments, $L^{101}$ is —O—. In embodiments, $L^{101}$ is —S—. In embodiments, $L^{101}$ is —$NR^{101}$—. In embodiments, $L^{101}$ is —NH—. In embodiments, $L^{101}$ is —$C(O)NR^{101}$—. In embodiments, $L^{101}$ is —C(O)NH—. In embodiments, $L^{101}$ is —$NR^1C(O)$—. In embodiments, $L^{101}$ is —NHC(O)—. In embodiments, $L^{101}$ is —$NR^{101}C(O)O$—. In embodiments, $L^{101}$ is —NHC(O)O—. In embodiments, $L^{101}$ is —$OC(O)NR^{101}$—. In embodiments, $L^{101}$ is —OC(O)NH—. In embodiments, $L^{101}$ is —$NR^{101}C(O)NR^{101}$—. In embodiments, $L^{101}$ is —NHC(O)NH—. In embodiments, $L^{101}$ is —$NR^{101}C(NH)NR^{101}$—. In embodiments, $L^{101}$ is —NHC(NH)NH—. In embodiments, $L^{101}$ is —$S(O)_2$—. In embodiments, $L^{101}$ is —$NR^{101}S(O)_2$—. In embodiments, $L^{101}$ is —$NHS(O)_2$—. In embodiments, $L^{101}$ is —$S(O)_2NR^{101}$—. In embodiments, $L^{101}$ is —$S(O)_2NH$—. In embodiments, $L^{101}$ is substituted or unsubstituted heteroalkylene. In embodiments, $L^{101}$ is substituted or unsubstituted 2 to 10 membered heteroalkylene. In embodiments, $L^{101}$ is unsubstituted 2 to 10 membered heteroalkylene. In embodiments, $L^{101}$ is unsubstituted 2 to 6 membered heteroalkylene. In embodiments, $L^{101}$ is —$CH_2NH$—.

In embodiments, a substituted $R^{101}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{101}$ is substituted with a plurality of groups selected from substituent groups, size-limited substituent groups, and lower substituent groups; each substituent group, size-limited substituent group, and/or lower substituent group may optionally be different. In embodiments, when $R^{101}$ is substituted, it is substituted with at least one substituent group. In embodiments, when $R^{101}$ is substituted, it is substituted with at least one size-limited substituent group. In embodiments, when $R^{101}$ is substituted, it is substituted with at least one lower substituent group.

In embodiments, $R^{101}$ is hydrogen or unsubstituted $C_1$-$C_4$ alkyl. In embodiments, $R^{101}$ is hydrogen. In embodiments, $R^{101}$ is unsubstituted $C_1$-$C_4$ alkyl. In embodiments, $R^{101}$ is unsubstituted methyl. In embodiments, $R^{101}$ is unsubstituted ethyl. In embodiments, $R^{101}$ is unsubstituted propyl. In embodiments, $R^{101}$ is unsubstituted n-propyl. In embodiments, $R^{101}$ is unsubstituted isopropyl. In embodiments, $R^{101}$ is unsubstituted butyl. In embodiments, $R^{101}$ is unsubstituted n-butyl. In embodiments, $R^{101}$ is unsubstituted isobutyl. In embodiments, $R^{101}$ is unsubstituted tert-butyl.

In embodiments, a substituted $L^{102}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{102}$ is substituted with a plurality of groups selected from substituent groups, size-limited substituent groups, and lower substituent groups; each substituent group, size-limited substituent group, and/or lower substituent group may optionally be different. In embodiments, when $L^{102}$ is substituted, it is substituted with at least one substituent group. In embodiments, when $L^{102}$ is substituted, it is substituted with at least one size-limited substituent group. In embodiments, when $L^{102}$ is substituted, it is substituted with at least one lower substituent group.

In embodiments, $L^{102}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, —$S(O)_2$—, —$NHS(O)_2$—, —$S(O)_2NH$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{102}$ is a bond. In embodiments, $L^{102}$ is —C(O)—. In embodiments, $L^{102}$ is —C(O)O—. In embodiments, $L^{102}$ is —OC(O)—. In embodiments, $L^{102}$ is —O—. In embodiments, $L^{102}$ is —S—. In embodiments, $L^{102}$ is —$NR^{102}$—. In embodiments, $L^{102}$ is —NH—. In embodiments, $L^{102}$ is —$C(O)NR^{102}$—. In embodiments, $L^{102}$ is —C(O)NH—. In embodiments, $L^{102}$ is —$NR^{102}C(O)$—. In embodiments, $L^{102}$ is —NHC(O)—. In embodiments, $L^{102}$ is —$NR^{102}C(O)O$—. In embodiments, $L^{102}$ is —NHC(O)O—. In embodiments, $L^{102}$ is —$OC(O)NR^{102}$—. In embodiments, $L^{102}$ is —OC(O)NH—. In embodiments, $L^{102}$ is —$NR^{1102}C(O)NR^{102}$—. In embodiments, $L^{102}$ is —NHC(O)NH—. In embodiments, $L^{102}$ is —$NR^{102}C(NH)NR^{102}$—. In embodiments, $L^{102}$ is —NHC(NH)NH—. In embodiments, $L^{102}$ is —$S(O)_2$—. In embodiments, $L^{102}$ is —$NR^{102}S(O)_2$—. In embodiments, $L^{102}$ is —$NHS(O)_2$—. In embodiments, $L^{102}$ is —$S(O)_2NR^{102}$—. In embodiments, $L^{102}$ is —$S(O)_2NH$—. In embodiments, $L^{102}$ is substituted or unsubstituted alkylene. In embodiments, $L^{102}$ is unsubstituted $C_1$-$C_{10}$ alkylene. In embodiments, $L^{102}$ is unsubstituted methylene. In embodiments, $L^{102}$ is unsubstituted ethylene. In embodiments, $L^{102}$ is unsubstituted propylene. In embodiments, $L^{102}$ is unsubstituted n-propylene. In embodiments, $L^{102}$ is unsubstituted butylene. In embodiments, $L^{102}$ is unsubstituted n-butylene. In embodiments, $L^{102}$ is substituted or unsubstituted heteroalkylene. In embodiments, $L^{102}$ is substituted or unsubstituted 2 to 16 membered heteroalkylene. In embodiments, $L^{102}$ is substituted or unsubstituted 2 to 10 membered heteroalkylene. In embodiments, $L^{102}$ is substituted (e.g., oxo-substituted) 2 to 16 membered heteroalkylene. In embodiments, $L^{102}$ is substituted (e.g., oxo-substituted) 2 to 10 membered heteroalkylene. In embodiments, $L^{102}$ is -(unsubstituted $C_1$-$C_{10}$ alkylene)-NHC(O)—. In embodiments, $L^{102}$ is —$(CH_2)$—NHC(O)—. In embodiments, $L^{102}$ is —$(CH_2)_2$—NHC(O)—. In embodiments, $L^{102}$ is —$(CH_2)_3$—NHC(O)—. In embodiments, $L^{102}$ is —$(CH_2)_4$—NHC(O)—. In embodiments, $L^{102}$ is —$(CH_2)_5$—NHC(O)—. In embodiments, $L^{102}$ is —$(CH_2)_6$—NHC(O)—. In embodiments, $L^{102}$ is —$(CH_2)_7$—NHC(O)—. In embodiments, $L^{102}$ is —$(CH_2)_8$—NHC(O)—. In embodiments, $L^{102}$ is —$(CH_2)_9$—NHC(O)—. In embodiments, $L^{102}$ is —$(CH_2)_{10}$—NHC(O)—. In embodiments, $L^{102}$ is -(unsubstituted $C_1$-$C_{10}$ alkylene)-NHC(O)O—. In embodiments, $L^{102}$ is —$(CH_2)$—NHC(O)O—. In embodiments, $L^{102}$ is —$(CH_2)_2$—NHC(O)O—. In embodiments, $L^{102}$ is —$(CH_2)_3$—NHC(O)O—. In embodiments, $L^{102}$ is —$(CH_2)_4$—NHC(O)O—. In embodiments, $L^{102}$ is —$(CH_2)_5$—NHC(O)O—. In embodiments, $L^{102}$ is —$(CH_2)_6$—NHC(O)O—. In embodiments, $L^{102}$ is —$(CH_2)_7$ —NHC(O)O—. In embodiments, $L^{102}$ is —$(CH_2)_8$ —NHC(O)O—. In embodiments, $L^{102}$ is —$(CH_2)_9$ —NHC(O)O—. In embodiments, $L^{102}$ is —$(CH_2)_{10}$—NHC(O)O—. In embodiments, $L^{102}$ is -(unsubstituted $C_1$-$C_{10}$ alkylene)-NHC(O)O-(unsubstituted $C_1$-$C_{10}$ alkylene)-. In embodiments, $L^{102}$ is —$(CH_2)$—NHC(O)O—$C(CH_3)$—. In embodiments, $L^{102}$ is —$(CH_2)_2$—NHC(O)O—$C(CH_3)$—. In embodiments, $L^{102}$ is —$(CH_2)_3$—NHC(O)O—$C(CH_3)$—. In embodiments, $L^{102}$ is —$(CH_2)_4$—NHC(O)O—$C(CH_3)$—. In embodiments, $L^{102}$ is —$(CH_2)_5$ —NHC(O)O—$C(CH_3)$—. In embodiments, $L^{102}$ is —$(CH_2)_6$ —NHC(O)O—$C(CH_3)$—. In embodiments, $L^{102}$ is —$(CH_2)_7$—NHC(O)O—$C(CH_3)$—. In embodiments, $L^{102}$ is —$(CH_2)_8$—NHC(O)O—$C(CH_3)$—. In embodiments, $L^{102}$ is —$(CH_2)_9$—NHC(O)O—$C(CH_3)$—. In embodiments, $L^{102}$ is —$(CH_2)_{10}$—NHC(O)O—$C(CH_3)$—.

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group.

In embodiments, $R^{102}$ is hydrogen or unsubstituted $C_1$-$C_4$ alkyl. In embodiments, $R^{102}$ is hydrogen. In embodiments, $R^{102}$ is unsubstituted $C_1$-$C_4$ alkyl. In embodiments, $R^{102}$ is unsubstituted methyl. In embodiments, $R^{102}$ is unsubstituted ethyl. In embodiments, $R^{102}$ is unsubstituted propyl. In embodiments, $R^{102}$ is unsubstituted n-propyl. In embodiments, $R^{102}$ is unsubstituted isopropyl. In embodiments, $R^{102}$ is unsubstituted butyl. In embodiments, $R^{102}$ is unsubstituted n-butyl. In embodiments, $R^{102}$ is unsubstituted isobutyl. In embodiments, $R^{102}$ is unsubstituted tert-butyl.

In embodiments, a substituted $L^{103}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{103}$ is substituted with a plurality of groups selected from substituent groups, size-limited substituent groups, and lower substituent groups; each substituent group, size-limited substituent group, and/or lower substituent group may optionally be different. In embodiments, when $L^{103}$ is substituted, it is substituted with at least one substituent group. In embodiments, when $L^{103}$ is substituted, it is substituted with at least one size-limited substituent group. In embodiments, when $L^{103}$ is substituted, it is substituted with at least one lower substituent group.

In embodiments, $L^{103}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, —$S(O)_2$—, —NHS$(O)_2$—, —$S(O)_2$NH—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{103}$ is a bond. In embodiments, $L^{103}$ is —C(O)—. In embodiments, $L^{103}$ is —C(O)O—. In embodiments, $L^{103}$ is —OC(O)—. In embodiments, $L^{103}$ is —O—. In embodiments, $L^{103}$ is —S—. In embodiments, $L^{103}$ is —$NR^{103}$—. In embodiments, $L^{103}$ is —NH—. In embodiments, $L^{103}$ is —C(O)$NR^{103}$—. In embodiments, $L^{103}$ is —C(O)NH—. In embodiments, $L^{103}$ is —$NR^{103}$C(O)—. In embodiments, $L^{103}$ is —NHC(O)—. In embodiments, $L^{103}$ is —$NR^{103}$C(O)O—. In embodiments, $L^{103}$ is —NHC(O)O—. In embodiments, $L^{103}$ is —OC(O)$NR^{103}$—. In embodiments, $L^{103}$ is —OC(O)NH—. In embodiments, $L^{103}$ is —$NR^{103}$C(O)$NR^{103}$—. In embodiments, $L^{103}$ is —NHC(O)NH—. In embodiments, $L^{103}$ is —$NR^{103}$C(NH)$NR^{103}$—. In embodiments, $L^{103}$ is —NHC(NH)NH—. In embodiments, $L^{103}$ is —$S(O)_2$—. In embodiments, $L^{103}$ is —$NR^{103}S(O)_2$—. In embodiments, $L^{103}$ is —NHS$(O)_2$—. In embodiments, $L^{103}$ is —$S(O)_2NR^{103}$—. In embodiments, $L^{103}$ is —$S(O)_2$NH—. In embodiments, $L^{103}$ is substituted or unsubstituted alkylene. In embodiments, $L^{103}$ is substituted $C_1$-$C_{10}$ alkylene. In embodiments, $L^{103}$ is a 7-(diethylamino)coumarin-4-yl)methyl (DEACM)-substituted $C_1$-$C_{10}$ alkylene. In embodiments, $L^{103}$ is substituted (e.g., DEACM-substituted) methylene. In embodiments, $L^{103}$ is substituted (e.g., DEACM-substituted) ethylene. In embodiments, $L^{103}$ is substituted (e.g., DEACM-substituted) propylene. In embodiments, $L^{103}$ is substituted (e.g., DEACM-substituted) n-propylene. In embodiments, $L^{103}$ is substituted (e.g., DEACM-substituted) butylene. In embodiments, $L^{103}$ is substituted (e.g., DEACM-substituted) n-butylene. In embodiments, $L^{103}$ is.

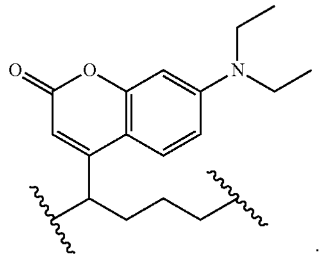 [SMILES: *CCCC(*)c1cc(=O)oc2cc(N(CC)CC)ccc12]

In embodiments, $L^{103}$ is substituted or unsubstituted heteroalkylene. In embodiments, $L^{103}$ is substituted or unsubstituted 2 to 16 membered heteroalkylene. In embodiments, $L^{103}$ is substituted or unsubstituted 2 to 10 membered heteroalkylene. In embodiments, $L^{103}$ is substituted (e.g., oxo-substituted) 2 to 16 membered heteroalkylene. In embodiments, $L^{103}$ is substituted (e.g., oxo-substituted) 2 to 10 membered heteroalkylene. In embodiments, $L^{103}$ is a substituted or unsubstituted phenylene. In embodiments, $L^{103}$ is a substituted phenylene. In embodiments $L^{103}$ is

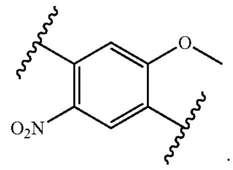 [SMILES: *c1cc([N+](=O)[O-])c(*)cc1OC]

In embodiments, a substituted $R^{103}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{103}$ is substituted with a plurality of groups selected from substituent groups, size-limited substituent groups, and lower substituent groups; each substituent group, size-limited substituent group, and/or lower substituent group may optionally be different. In embodiments, when $R^{103}$ is substituted, it is substituted with at least one substituent group. In embodiments, when $R^{103}$ is substituted, it is substituted with at least one size-limited substituent group. In embodiments, when $R^{103}$ is substituted, it is substituted with at least one lower substituent group.

In embodiments, $R^{103}$ is hydrogen or unsubstituted $C_1$-$C_4$ alkyl. In embodiments, $R^{103}$ is hydrogen. In embodiments, $R^{103}$ is unsubstituted $C_1$-$C_4$ alkyl. In embodiments, $R^{103}$ is unsubstituted methyl. In embodiments, $R^{103}$ is unsubstituted ethyl. In embodiments, $R^{103}$ is unsubstituted propyl. In embodiments, $R^{103}$ is unsubstituted n-propyl. In embodiments, $R^{103}$ is unsubstituted isopropyl. In embodiments, $R^{103}$ is unsubstituted butyl. In embodiments, $R^{103}$ is unsubstituted n-butyl. In embodiments, $R^{103}$ is unsubstituted isobutyl. In embodiments, $R^{103}$ is unsubstituted tert-butyl.

In embodiments, a substituted $L^{104}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{104}$ is substituted with a plurality of groups selected from substituent groups, size-limited substituent groups, and lower substituent groups; each substituent group, size-limited substituent group, and/or lower substituent group may optionally be different. In embodiments, when $L^{104}$ is substituted, it is substituted with at least one substituent group. In embodiments, when $L^{104}$ is substituted, it is substituted with at least one size-limited substituent group. In embodiments, when $L^{104}$ is substituted, it is substituted with at least one lower substituent group.

In embodiments, $L^{104}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, —$S(O)_2$—, —$NHS(O)_2$—, —$S(O)_2NH$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{104}$ is a bond. In embodiments, $L^{104}$ is —C(O)—. In embodiments, $L^{104}$ is —C(O)O—. In embodiments, $L^{104}$ is —OC(O)—. In embodiments, $L^{104}$ is —O—. In embodiments, $L^{104}$ is —S—. In embodiments, $L^{104}$ is —$NR^{104}$—. In embodiments, $L^{104}$ is —NH—. In embodiments, $L^{104}$ is —C(O)$NR^{104}$—. In embodiments, $L^{104}$ is —C(O)NH—. In embodiments, $L^{104}$ is —$NR^{104}$C(O)—. In embodiments, $L^{104}$ is —NHC(O)—. In embodiments, $L^{104}$ is —$NR^{104}$C(O)O—. In embodiments, $L^{104}$ is —NHC(O)O—. In embodiments, $L^{104}$ is —OC(O)$NR^{104}$—. In embodiments, $L^{104}$ is —OC(O)NH—. In embodiments, $L^{104}$ is —$NR^{104}$C(O)$NR^{104}$—. In embodiments, $L^{104}$ is —NHC(O)NH—. In embodiments, $L^{104}$ is —$NR^{104}$C(NH)$NR^{104}$—. In embodiments, $L^{104}$ is —NHC(NH)NH—. In embodiments, $L^{104}$ is —$S(O)_2$—. In embodiments, $L^{104}$ is —$NR^{104}S(O)_2$—. In embodiments, $L^{104}$ is —$NHS(O)_2$—. In embodiments, $L^{104}$ is —$S(O)_2NR^{104}$—. In embodiments, $L^{104}$ is —$S(O)_2NH$—. In embodiments, $L^{104}$ is substituted or unsubstituted heteroalkylene. In embodiments, $L^{104}$ is substituted or unsubstituted 2 to 16 membered heteroalkylene. In embodiments, $L^{104}$ is substituted or unsubstituted 2 to 10 membered heteroalkylene. In embodiments, $L^{104}$ is —$(CH_2CH_2O)_n$—, wherein n is as described herein, including in embodiments. In embodiments, $L^{104}$ is —$(CH_2CH_2O)_{10}$—. In embodiments, $L^{104}$ is —$(CH_2CH_2O)_5$—. In embodiments, $L^{104}$ is —$(CH_2CH_2O)_2$—. In embodiments, $L^{104}$ is substituted (e.g., oxo-substituted) 2 to 16 membered heteroalkylene. In embodiments, $L^{104}$ is substituted (e.g., oxo-substituted) 2 to 10 membered heteroalkylene. In embodiments, $L^{104}$ is —O-(unsubstituted $C_1$-$C_6$ alkylene)-C(O)NH—. In embodiments, $L^{104}$ is —$O(CH_2)$—C(O)NH—. In embodiments, $L^{104}$ is —$O(CH_2)_2$—C(O)NH—. In embodiments, $L^{104}$ is —$O(CH_2)_3$—C(O)NH—. In embodiments, $L^{104}$ is —$O(CH_2)_4$—C(O)NH—. In embodiments, $L^{104}$ is —$O(CH_2)_5$—C(O)NH—. In embodiments, $L^{104}$ is —$O(CH_2)_6$—C(O)NH—. In embodiments, $L^{104}$ is —O-(unsubstituted $C_1$-$C_6$ alkylene)-C(O)NH—$(CH_2CH_2O)_n$—$CH_2$—, wherein n is as described herein, including in embodiments. In embodiments, $L^{104}$ is —$O(CH_2)$—C(O)NH—$(CH_2CH_2O)_n$—$CH_2$—. In embodiments, $L^{104}$ is —$O(CH_2)_2$—C(O)NH—$(CH_2CH_2O)_n$—$CH_2$—. In embodiments, $L^{104}$ is —$O(CH_2)_3$—C(O)NH—$(CH_2CH_2O)_n$—$CH_2$—. In embodiments, $L^{104}$ is —$O(CH_2)_4$—C(O)NH—$(CH_2CH_2O)_n$—$CH_2$—. In embodiments, $L^{104}$ is substituted or unsubstituted heteroarylene. In embodiments, $L^{104}$ is unsubstituted 5 to 6 membered heteroarylene. In embodiments, $L^{104}$ is unsubstituted triazolylene. In embodiments, $L^{104}$ is

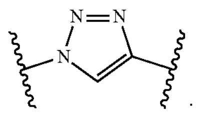 [SMILES: *c1cn(*)nn1]

In embodiments, a substituted $R^{104}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{104}$ is substituted with a plurality of groups selected from substituent groups, size-limited substituent groups, and lower substituent groups; each substituent group, size-limited substituent group, and/or lower substituent group may optionally be different. In embodiments, when $R^{104}$ is substituted, it is substituted with at least one substituent group. In embodiments, when $R^{104}$ is substituted, it is substituted with at least one size-limited substituent group. In embodiments, when $R^{104}$ is substituted, it is substituted with at least one lower substituent group.

In embodiments, $R^{104}$ is hydrogen or unsubstituted $C_1$-$C_4$ alkyl. In embodiments, $R^{104}$ is hydrogen. In embodiments, $R^{104}$ is unsubstituted $C_1$-$C_4$ alkyl. In embodiments, $R^{104}$ is unsubstituted methyl. In embodiments, $R^{104}$ is unsubstituted ethyl. In embodiments, $R^{104}$ is unsubstituted propyl. In embodiments, $R^{104}$ is unsubstituted n-propyl. In embodiments, $R^{104}$ is unsubstituted isopropyl. In embodiments, $R^{104}$ is unsubstituted butyl. In embodiments, $R^{104}$ is unsubstituted n-butyl. In embodiments, $R^{104}$ is unsubstituted isobutyl. In embodiments, $R^{104}$ is unsubstituted tert-butyl.

In embodiments, a substituted $L^{105}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{105}$ is substituted with a plurality of groups selected from substituent groups, size-limited substituent groups, and lower substituent groups; each substituent group, size-limited substituent group, and/or lower substituent group may optionally be different. In embodiments, when $L^{105}$ is substituted, it is substituted with at least one substituent group. In embodiments, when $L^{105}$ is substituted, it is substituted with at least one size-limited substituent group. In embodiments, when $L^{105}$ is substituted, it is substituted with at least one lower substituent group.

In embodiments, $L^{105}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, $—S(O)_2—$, $—NHS(O)_2—$, $—S(O)_2NH—$, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{105}$ is a bond. In embodiments, $L^{105}$ is —C(O)—. In embodiments, $L^{105}$ is —C(O)O—. In embodiments, $L^{105}$ is —OC(O)—. In embodiments, $L^{105}$ is —O—. In embodiments, $L^{105}$ is —S—. In embodiments, $L^{105}$ is $—NR^{105}—$. In embodiments, $L^{105}$ is —NH—. In embodiments, $L^{105}$ is $—C(O)NR^{105}—$. In embodiments, $L^{105}$ is —C(O)NH—. In embodiments, $L^{105}$ is $—NR^{105}C(O)—$. In embodiments, $L^{105}$ is —NHC(O)—. In embodiments, $L^{105}$ is $—NR^{105}C(O)O—$. In embodiments, $L^{105}$ is —NHC(O)O—. In embodiments, $L^{105}$ is $—OC(O)NR^{105}—$. In embodiments, $L^{105}$ is —OC(O)NH—. In embodiments, $L^{105}$ is $—NR^{105}C(O)NR^{105}—$. In embodiments, $L^{105}$ is —NHC(O)NH—. In embodiments, $L^{105}$ is $—NR^{105}C(NH)NR^{105}—$. In embodiments, $L^{105}$ is —NHC(NH)NH—. In embodiments, $L^{105}$ is $—S(O)_2—$. In embodiments, $L^{105}$ is $—NR^{105}S(O)_2—$. In embodiments, $L^{105}$ is $—NHS(O)_2—$. In embodiments, $L^{105}$ is $—S(O)_2NR^{105}—$. In embodiments, $L^{105}$ is $—S(O)_2NH—$. In embodiments, $L^{105}$ is substituted or unsubstituted heteroalkylene. In embodiments, $L^{105}$ is substituted or unsubstituted 2 to 16 membered heteroalkylene. In embodiments, $L^{105}$ is substituted or unsubstituted 2 to 10 membered heteroalkylene. In embodiments, $L^{105}$ is $—(CH_2CH_2O)_n—$, wherein n is as described herein, including in embodiments. In embodiments, $L^{105}$ is $—(CH_2CH_2O)_{10}—$. In embodiments, $L^{105}$ is $—(CH_2CH_2O)_5—$. In embodiments, $L^{105}$ is $—(CH_2CH_2O)_4—$. In embodiments, $L^{105}$ is substituted (e.g., oxo-substituted) 2 to 16 membered heteroalkylene. In embodiments, $L^{105}$ is substituted (e.g., oxo-substituted) 2 to 10 membered heteroalkylene. In embodiments, $L^{105}$ is -(unsubstituted $C_1$-$C_{10}$ alkylene)-NHC(O)—. In embodiments, $L^{105}$ is $—(CH_2)—NHC(O)—$. In embodiments, $L^{105}$ is $—(CH_2)_2—NHC(O)—$. In embodiments, $L^{105}$ is $—(CH_2)_3—NHC(O)—$. In embodiments, $L^{105}$ is $—(CH_2)_4—NHC(O)—$. In embodiments, $L^{105}$ is $—(CH_2)_5—NHC(O)—$. In embodiments, $L^{105}$ is $—(CH_2)_6—NHC(O)—$. In embodiments, $L^{105}$ is $—(CH_2)_7—NHC(O)—$. In embodiments, $L^{105}$ is $—(CH_2)_8—NHC(O)—$. In embodiments, $L^{105}$ is $—(CH_2)_9—NHC(O)—$. In embodiments, $L^{105}$ is $—(CH_2)_{10}—NHC(O)—$. In embodiments, $L^{105}$ is $—CH_2—$O-(unsubstituted $C_1$-$C_6$ alkylene)-C(O)NH—. In embodiments, $L^{105}$ is $—CH_2—O(CH_2)—C(O)NH—$. In embodiments, $L^{105}$ is $—CH_2—O(CH_2)_2—C(O)NH—$. In embodiments, $L^{105}$ is $—CH_2—O(CH_2)_3—C(O)NH—$. In embodiments, $L^{105}$ is $—CH_2—O(CH_2)_4—C(O)NH—$. In embodiments, $L^{105}$ is $—CH_2—O(CH_2)_5—C(O)NH—$. In embodiments, $L^{105}$ is $—CH_2—O(CH_2)_6—C(O)NH—$. In embodiments, $L^{105}$ is substituted or unsubstituted heteroarylene. In embodiments, $L^{105}$ is unsubstituted 5 to 6 membered heteroarylene. In embodiments, $L^{105}$ is unsubstituted triazolylene. In embodiments, $L^{105}$ is

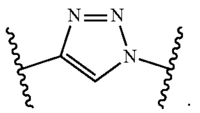 [SMILES: *c1cn(*)nn1]

In embodiments, a substituted $R^{105}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{105}$ is substituted with a plurality of groups selected from substituent groups, size-limited substituent groups, and lower substituent groups; each substituent group, size-limited substituent group, and/or lower substituent group may optionally be different. In embodiments, when $R^{105}$ is substituted, it is substituted with at least one substituent group. In embodiments, when $R^{105}$ is substituted, it is substituted with at least one size-limited substituent group. In embodiments, when $R^{105}$ is substituted, it is substituted with at least one lower substituent group.

In embodiments, $R^{105}$ is hydrogen or unsubstituted $C_1$-$C_4$ alkyl. In embodiments, $R^{105}$ is hydrogen. In embodiments, $R^{105}$ is unsubstituted $C_1$-$C_4$ alkyl. In embodiments, $R^{105}$ is unsubstituted methyl. In embodiments, $R^{105}$ is unsubstituted ethyl. In embodiments, $R^{105}$ is unsubstituted propyl. In embodiments, $R^{105}$ is unsubstituted n-propyl. In embodiments, $R^{105}$ is unsubstituted isopropyl. In embodiments, $R^{105}$ is unsubstituted butyl. In embodiments, $R^{105}$ is unsubstituted n-butyl. In embodiments, $R^{105}$ is unsubstituted isobutyl. In embodiments, $R^{105}$ is unsubstituted tert-butyl.

In embodiments, a substituted $L^{106}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{106}$ is substituted with a plurality of groups selected from substituent groups, size-limited substituent groups, and lower substituent groups; each substituent group, size-limited substituent group, and/or lower substituent group may optionally be different. In embodiments, when $L^{106}$ is substituted, it is substituted with at least one substituent group. In embodiments, when $L^{106}$ is substituted, it is substituted with at least one size-limited substituent group. In embodiments, when $L^{106}$ is substituted, it is substituted with at least one lower substituent group.

In embodiments, $L^{106}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, $—S(O)_2—$, $—NHS(O)_2—$, $—S(O)_2NH—$, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{106}$ is a bond. In embodiments, $L^{106}$ is —C(O)—. In embodiments, $L^{106}$ is —C(O)O—. In embodiments, $L^{106}$ is —OC(O)—. In embodiments, $L^{106}$ is —O—. In embodiments, $L^{106}$ is —S—. In embodiments, $L^{106}$ is $—NR^{106}—$. In embodiments, $L^{106}$ is —NH—. In embodiments, $L^{106}$ is $—C(O)NR^{106}—$. In embodiments, $L^{106}$ is —C(O)NH—. In embodiments, $L^{106}$ is $—NR^{106}C(O)—$. In embodiments, $L^{106}$ is —NHC(O)—. In embodiments, $L^{106}$ is $—NR^{106}C(O)O—$. In embodiments, $L^{106}$ is —NHC(O)O—. In embodiments, $L^{106}$ is $—OC(O)NR^{106}—$. In embodiments, $L^{106}$ is —OC(O)NH—. In embodiments, $L^{106}$ is $—NR^{106}C(O)NR^{106}—$. In embodiments, $L^{106}$ is —NHC(O)NH—. In embodiments, $L^{106}$ is $—NR^{106}C(NH)NR^{106}—$. In embodiments, $L^{106}$ is —NHC(NH)NH—. In embodiments, $L^{106}$ is $—S(O)_2—$. In embodiments, $L^{106}$ is $—NR^{106}S(O)_2—$. In embodiments, $L^{106}$ is $—NHS(O)_2—$. In embodiments, $L^{106}$ is $—S(O)_2NR^{106}—$. In embodiments, $L^{106}$ is $—S(O)_2NH—$. In embodiments, $L^{106}$ is substituted or unsubstituted alkylene. In embodiments, $L^{106}$ is unsubstituted $C_1$-$C_{10}$ alkylene. In embodiments, $L^{106}$ is unsubstituted $C_1$-$C_6$ alkylene. In embodiments, $L^{106}$ is unsubstituted methylene. In embodiments, $L^{106}$ is unsubstituted ethylene. In embodiments, $L^{106}$ is unsubstituted propylene. In embodiments, $L^{106}$ is unsubstituted n-propylene. In embodiments, $L^{106}$ is unsubstituted butylene. In embodiments, $L^{106}$ is unsubstituted n-butylene. In embodiments, $L^{106}$ is unsubstituted pentylene. In embodiments, $L^{106}$ is unsubstituted n-pentylene. In embodiments, $L^{106}$ is unsubstituted hexylene. In embodiments, $L^{106}$ is unsubstituted n-hexylene. In embodiments, $L^{106}$ is substituted or unsubstituted heteroalkylene. In embodiments, $L^{106}$ is substituted or unsubstituted 2 to 16 membered heteroalkylene. In embodiments, $L^{106}$ is substituted or unsubstituted 2 to 10 membered heteroalkylene. In embodiments, $L^{106}$ is substituted (e.g., oxo-substituted) 2 to 16 membered heteroalkylene. In embodiments, $L^{106}$ is substituted (e.g., oxo-substituted) 2 to 10 membered heteroalkylene. In embodiments, $L^{106}$ is $—CH_2—C(O)NH-$(unsubstituted $C_1$-$C_{10}$ alkylene)-. In embodiments, $L^{106}$ is $—CH_2—C(O)NH—(CH_2)—$. In embodiments, $L^{106}$ is $—CH_2—C(O)NH—(CH_2)_2—$. In embodiments, $L^{106}$ is $—CH_2—C(O)NH—(CH_2)_3—$. In embodiments, $L^{106}$ is $—CH_2—C(O)NH—(CH_2)_4—$. In embodiments, $L^{106}$ is $—CH_2—C(O)NH—(CH_2)_5—$. In embodiments, $L^{106}$ is $—CH_2—C(O)NH—(CH_2)_6—$. In embodiments, $L^{106}$ is $—CH_2—C(O)NH—(CH_2)_7—$. In embodiments, $L^{106}$ is $—CH_2—C(O)NH—(CH_2)_8—$. In embodiments, $L^{106}$ is $—CH_2—C(O)NH—(CH_2)_9—$. In embodiments, $L^{106}$ is $—CH_2—C(O)NH—(CH_2)_{10}—$.

In embodiments, a substituted $R^{106}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{106}$ is substituted with a plurality of groups selected from substituent groups, size-limited substituent groups, and lower substituent groups; each substituent group, size-limited substituent group, and/or lower substituent group may optionally be different. In embodiments, when $R^{106}$ is substituted, it is substituted with at least one substituent group. In embodiments, when $R^{106}$ is substituted, it is substituted with at least one size-limited substituent group. In embodiments, when $R^{106}$ is substituted, it is substituted with at least one lower substituent group.

In embodiments, $R^{106}$ is hydrogen or unsubstituted $C_1$-$C_4$ alkyl. In embodiments, $R^{106}$ is hydrogen. In embodiments, $R^{106}$ is unsubstituted $C_1$-$C_4$ alkyl. In embodiments, $R^{106}$ is unsubstituted methyl. In embodiments, $R^{106}$ is unsubstituted ethyl. In embodiments, $R^{106}$ is unsubstituted propyl. In embodiments, $R^{106}$ is unsubstituted n-propyl. In embodiments, $R^{106}$ is unsubstituted isopropyl. In embodiments, $R^{106}$ is unsubstituted butyl. In embodiments, $R^{106}$ is unsubstituted n-butyl. In embodiments, $R^{106}$ is unsubstituted isobutyl. In embodiments, $R^{106}$ is unsubstituted tert-butyl.

In embodiments, a substituted $L^{107}$ (e.g., substituted alkylene, substituted heteroalkylene, substituted cycloalkylene, substituted heterocycloalkylene, substituted arylene, and/or substituted heterarylene) is substituted with at least one substituent group, size-limited substituent group, or lower substituent group; wherein if the substituted $L^{107}$ is substituted with a plurality of groups selected from substituent groups, size-limited substituent groups, and lower substituent groups; each substituent group, size-limited substituent group, and/or lower substituent group may optionally be different. In embodiments, when $L^{107}$ is substituted, it is substituted with at least one substituent group. In embodiments, when $L^{107}$ is substituted, it is substituted with at least one size-limited substituent group. In embodiments, when $L^{107}$ is substituted, it is substituted with at least one lower substituent group.

In embodiments, $L^{107}$ is a bond, —C(O)—, —C(O)O—, —OC(O)—, —O—, —S—, —NH—, —C(O)NH—, —NHC(O)—, —NHC(O)O—, —OC(O)NH—, —NHC(O)NH—, —NHC(NH)NH—, —$S(O)_2$—, —$NHS(O)_2$—, —$S(O)_2NH$—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), substituted or unsubstituted heteroarylene (e.g., 5 to 10 membered, 5 to 9 membered, or 5 to 6 membered), a peptide linker, or a cleavable linker.

In embodiments, $L^{107}$ is a bond. In embodiments, $L^{107}$ is —C(O)—. In embodiments, $L^{107}$ is —C(O)O—. In embodiments, $L^{107}$ is —OC(O)—. In embodiments, $L^{107}$ is —O—. In embodiments, $L^{107}$ is —S—. In embodiments, $L^{107}$ is —$NR^{107}$—. In embodiments, $L^{107}$ is —NH—. In embodiments, $L^{107}$ is —C(O)$NR^{107}$—. In embodiments, $L^{107}$ is —C(O)NH—. In embodiments, $L^{107}$ is —$NR^{107}$C(O)—. In embodiments, $L^{107}$ is —NHC(O)—. In embodiments, $L^{107}$ is —$NR^{107}$C(O)O—. In embodiments, $L^{107}$ is —NHC(O)O—. In embodiments, $L^{107}$ is —OC(O)$NR^{107}$—. In embodiments, $L^{107}$ is —OC(O)NH—. In embodiments, $L^{107}$ is —$NR^{107}$C(O)$NR^{107}$—. In embodiments, $L^{107}$ is —NHC(O)NH—. In embodiments, $L^{107}$ is —$NR^{107}$C(NH)$NR^{107}$—. In embodiments, $L^{107}$ is —NHC(NH)NH—. In embodiments, $L^{107}$ is —$S(O)_2$—. In embodiments, $L^{107}$ is —$NR^{107}S(O)_2$—. In embodiments, $L^{107}$ is —$NHS(O)_2$—. In embodiments, $L^{107}$ is —$S(O)_2NR^{107}$—. In embodiments, $L^{107}$ is —$S(O)_2NH$—. In embodiments, $L^{107}$ is substituted or unsubstituted heteroalkylene. In embodiments, $L^{107}$ is substituted or unsubstituted 2 to 10 membered heteroalkylene. In embodiments, $L^{107}$ is unsubstituted 2 to 10 membered heteroalkylene. In embodiments, $L^{107}$ is unsubstituted 2 to 6 membered heteroalkylene. In embodiments, $L^{107}$ is —$NHCH_2$—.

In embodiments, a substituted $R^{107}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{107}$ is substituted with a plurality of groups selected from substituent groups, size-limited substituent groups, and lower substituent groups; each substituent group, size-limited substituent group, and/or lower substituent group may optionally be different. In embodiments, when $R^{107}$ is substituted, it is substituted with at least one substituent group. In embodiments, when $R^{107}$ is substituted, it is substituted with at least one size-limited substituent group. In embodiments, when $R^{107}$ is substituted, it is substituted with at least one lower substituent group.

In embodiments, $R^{107}$ is hydrogen or unsubstituted $C_1$-$C_4$ alkyl. In embodiments, $R^{107}$ is hydrogen. In embodiments, $R^{107}$ is unsubstituted $C_1$-$C_4$ alkyl. In embodiments, $R^{107}$ is unsubstituted methyl. In embodiments, $R^{107}$ is unsubstituted ethyl. In embodiments, $R^{107}$ is unsubstituted propyl. In embodiments, $R^{107}$ is unsubstituted n-propyl. In embodiments, $R^{107}$ is unsubstituted isopropyl. In embodiments, $R^{107}$ is unsubstituted butyl. In embodiments, $R^{107}$ is unsubstituted n-butyl. In embodiments, $R^{107}$ is unsubstituted isobutyl. In embodiments, $R^{107}$ is unsubstituted tert-butyl.

In embodiments, $L^1$ is -$L^{101}$-$L^{102}$-$L^{103}$-$(CH_2CH_2O)_n$-$L^{105}$-$L^{106}$-$L^{107}$-; and n is as described herein, including in embodiments. In embodiments, n is an integer from 1 to 20. In embodiments, n is an integer from 2 to 10.

In embodiments, $L^{101}$, $L^{102}$, $L^{103}$, $L^{105}$, $L^{106}$, and $L^{107}$ are independently substituted or unsubstituted 2 to 10 membered heteroalkylene.

In embodiments, $L^{101}$ is an unsubstituted 2 to 10 membered heteroalkylene; $L^{102}$ is a substituted 2 to 16 membered heteroalkylene; $L^{103}$ is a substituted $C_1$-$C_6$ alkylene; $L^{104}$ is an unsubstituted 5 to 6 membered heteroarylene; $L^{105}$ is a substituted 2 to 10 membered heteroalkylene; $L^{106}$ is an unsubstituted $C_1$-$C_6$ alkylene; and $L^{107}$ is an unsubstituted 2 to 10 membered heteroalkylene.

In embodiments, $L^{104}$ is an unsubstituted triazolylene.

In embodiments, $L^{101}$ is an unsubstituted 2 to 10 membered heteroalkylene; $L^{102}$ is a substituted 2 to 16 membered heteroalkylene; $L^{103}$ is a substituted phenylene; $L^{104}$ is a substituted 2 to 10 membered heteroalkylene; $L^{105}$ is —$(CH_2CH_2O)_n$—; $L^{106}$ is a substituted 2 to 10 membered heteroalkylene; $L^{107}$ is an unsubstituted 2 to 10 membered heteroalkylene; and n is as described herein, including in embodiments. In embodiments, n is an integer from 1 to 20. In embodiments, n is an integer from 2 to 10.

In embodiments, $L^{101}$ is an unsubstituted 2 to 10 membered heteroalkylene; $L^{102}$ is a substituted 2 to 16 membered heteroalkylene; $L^{103}$ is a substituted phenylene; $L^{104}$ is a substituted 2 to 25 membered heteroalkylene; $L^{105}$ is an unsubstituted 5 to 6 membered heteroarylene; $L^{106}$ is a substituted 2 to 16 membered heteroalkylene; $L^{107}$ is an unsubstituted 2 to 10 membered heteroalkylene.

In embodiments, $L^{101}$ is —$CH_2NH$— and $L^{107}$ is —$NHCH_2$—.

In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10. In embodiments, n is 11. In embodiments, n is 12. In embodiments, n is 13. In embodiments, n is 14. In embodiments, n is 15. In embodiments, n is 16. In embodiments, n is 17. In embodiments, n is 18. In embodiments, n is 19. In embodiments, n is 20.

In embodiments, when $R^{101}$ is substituted, $R^{101}$ is substituted with one or more first substituent groups denoted by $R^{101.1}$ as explained in the definitions section above in the description of "first substituent group(s)". In embodiments, when an $R^{101.1}$ substituent group is substituted, the $R^{101.1}$ substituent group is substituted with one or more second substituent groups denoted by $R^{101.2}$ as explained in the definitions section above in the description of "first substituent group(s)". In embodiments, when an $R^{101.2}$ substituent group is substituted, the $R^{101.2}$ substituent group is substituted with one or more third substituent groups denoted by $R^{101.3}$ as explained in the definitions section above in the description of "first substituent group(s)". In the above embodiments, $R^{101}$, $R^{101.1}$, $R^{101.2}$, and $R^{101.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{101}$, $R^{101.1}$, $R^{101.2}$, and $R^{101.3}$, respectively.

In embodiments, when $R^{102}$ is substituted, $R^{102}$ is substituted with one or more first substituent groups denoted by $R^{102.1}$ as explained in the definitions section above in the description of "first substituent group(s)". In embodiments, when an $R^{102.1}$ substituent group is substituted, the $R^{102.1}$ substituent group is substituted with one or more second substituent groups denoted by $R^{102.2}$ as explained in the definitions section above in the description of "first substituent group(s)". In embodiments, when an $R^{102.2}$ substituent group is substituted, the $R^{102.2}$ substituent group is substituted with one or more third substituent groups denoted by $R^{102.3}$ as explained in the definitions section above in the description of "first substituent group(s)". In the above embodiments, $R^{102}$, $R^{102.1}$, $R^{102.2}$, and $R^{102.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{102}$, $R^{102.1}$, $R^{102.2}$, and $R^{102.3}$, respectively.

In embodiments, when $R^{103}$ is substituted, $R^{103}$ is substituted with one or more first substituent groups denoted by $R^{103.1}$ as explained in the definitions section above in the description of "first substituent group(s)". In embodiments, when an $R^{103.1}$ substituent group is substituted, the $R^{103.1}$ substituent group is substituted with one or more second substituent groups denoted by $R^{103.2}$ as explained in the definitions section above in the description of "first substituent group(s)". In embodiments, when an $R^{103.2}$ substituent group is substituted, the $R^{10}3.2$ substituent group is substituted with one or more third substituent groups denoted by $R^{1033}$ as explained in the definitions section above in the description of "first substituent group(s)". In the above embodiments, $R^{103}$, $R^{103.1}$, $R^{103.2}$, and $R^{103.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{103}$, $R^{103.1}$, $R^{103.2}$, and $R^{103.3}$, respectively.

In embodiments, when $R^{104}$ is substituted, $R^{104}$ is substituted with one or more first substituent groups denoted by $R^{104.1}$ as explained in the definitions section above in the description of "first substituent group(s)". In embodiments, when an $R^{104.1}$ substituent group is substituted, the $R^{104.1}$ substituent group is substituted with one or more second substituent groups denoted by $R^{104.2}$ as explained in the definitions section above in the description of "first substituent group(s)". In embodiments, when an $R^{104.2}$ substituent group is substituted, the $R^{104.2}$ substituent group is substituted with one or more third substituent groups denoted by $R^{104.3}$ as explained in the definitions section above in the description of "first substituent group(s)". In the above embodiments, $R^{104}$, $R^{104.1}$, $R^{104.2}$, and $R^{104.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{104}$, $R^{104.1}$, $R^{104.2}$, and $R^{104.3}$, respectively.

In embodiments, when $R^{105}$ is substituted, $R^{105}$ is substituted with one or more first substituent groups denoted by $R^{105.1}$ as explained in the definitions section above in the description of "first substituent group(s)". In embodiments, when an $R^{105.1}$ substituent group is substituted, the $R^{105.1}$ substituent group is substituted with one or more second substituent groups denoted by $R^{105.2}$ as explained in the definitions section above in the description of "first substituent group(s)". In embodiments, when an $R^{105.2}$ substituent group is substituted, the $R^{105.2}$ substituent group is substituted with one or more third substituent groups denoted by $R^{105.3}$ as explained in the definitions section above in the description of "first substituent group(s)". In the above embodiments, $R^{105}$, $R^{105.1}$, $R^{105.2}$, and $R^{105.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{105}$, $R^{105.1}$, $R^{105.2}$, and $R^{105.3}$, respectively.

In embodiments, when $R^{106}$ is substituted, $R^{106}$ is substituted with one or more first substituent groups denoted by $R^{106.1}$ as explained in the definitions section above in the description of "first substituent group(s)". In embodiments, when an $R^{106.1}$ substituent group is substituted, the $R^{106.1}$ substituent group is substituted with one or more second substituent groups denoted by $R^{106.2}$ as explained in the definitions section above in the description of "first substituent group(s)". In embodiments, when an $R^{106.2}$ substituent group is substituted, the $R^{106.2}$ substituent group is substituted with one or more third substituent groups denoted by $R^{106.3}$ as explained in the definitions section above in the description of "first substituent group(s)". In the above embodiments, $R^{106}$, $R^{106.1}$, $R^{106.2}$, and $R^{106.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{106}$, $R^{106.1}$, $R^{106.2}$, and $R^{106.3}$, respectively.

In embodiments, when $R^{107}$ is substituted, $R^{107}$ is substituted with one or more first substituent groups denoted by $R^{107.1}$ as explained in the definitions section above in the description of "first substituent group(s)". In embodiments, when an $R^{107.1}$ substituent group is substituted, the $R^{107.1}$ substituent group is substituted with one or more second substituent groups denoted by $R^{107.2}$ as explained in the definitions section above in the description of "first substituent group(s)". In embodiments, when an $R^{107.2}$ substituent group is substituted, the $R^{107.2}$ substituent group is substituted with one or more third substituent groups denoted by $R^{1073}$ as explained in the definitions section above in the description of "first substituent group(s)". In the above embodiments, $R^{107}$, $R^{107.1}$, $R^{107.2}$, and $R^{107.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{107}$, $R^{107.1}$, $R^{107.2}$, and $R^{107.3}$, respectively.

In embodiments, when $L^{101}$ is substituted, $L^{101}$ is substituted with one or more first substituent groups denoted by $R^{L101.1}$ as explained in the definitions section above in the description of "first substituent group(s)". In embodiments, when an $R^{L101.1}$ substituent group is substituted, the $R^{L101.1}$ substituent group is substituted with one or more second substituent groups denoted by $R^{L101.2}$ as explained in the definitions section above in the description of "first substituent group(s)". In embodiments, when an $R^{L101.2}$ substituent group is substituted, the $R^{L101.2}$ substituent group is substituted with one or more third substituent groups denoted by $R^{L101.3}$ as explained in the definitions section above in the description of "first substituent group(s)". In the above embodiments, $L^{101}$, $R^{L101.1}$, $R^{L101.2}$, and $R^{L101.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{101}$, $R^{L101.1}$, $R^{L101.2}$, and $R^{L101.3}$, respectively.

In embodiments, when $L^{102}$ is substituted, $L^{102}$ is substituted with one or more first substituent groups denoted by $R^{L102.1}$ as explained in the definitions section above in the description of "first substituent group(s)". In embodiments, when an $R^{L102.1}$ substituent group is substituted, the $R^{L102.1}$ substituent group is substituted with one or more second substituent groups denoted by $R^{L102.2}$ as explained in the definitions section above in the description of "first substituent group(s)". In embodiments, when an $R^{L102.2}$ substituent group is substituted, the $R^{L102.2}$ substituent group is substituted with one or more third substituent groups denoted by $R^{L102.3}$ as explained in the definitions section above in the description of "first substituent group(s)". In the above embodiments, $L^{102}$, $R^{L102.1}$, $R^{L102.2}$, and $R^{L102.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{102}$, $R^{L102.1}$, $R^{L102.2}$, and $R^{L102.3}$, respectively.

In embodiments, when $L^{103}$ is substituted, $L^{103}$ is substituted with one or more first substituent groups denoted by $R^{L103.1}$ as explained in the definitions section above in the description of "first substituent group(s)". In embodiments, when an $R^{L103.1}$ substituent group is substituted, the $R^{L103.1}$ substituent group is substituted with one or more second substituent groups denoted by $R^{L103.2}$ as explained in the definitions section above in the description of "first substituent group(s)". In embodiments, when an $R^{L103.2}$ substituent group is substituted, the $R^{L103.2}$ substituent group is substituted with one or more third substituent groups denoted by $R^{L1033}$ as explained in the definitions section above in the description of "first substituent group(s)". In the above embodiments, $L^{103}$, $R^{L103.1}$, $R^{L103.2}$ and $R^{L103.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{103}$, $R^{L103.1}$, $R^{L103.2}$, and $R^{L103.3}$, respectively.

In embodiments, when $L^{104}$ is substituted, $L^{104}$ is substituted with one or more first substituent groups denoted by $R^{L104.1}$ as explained in the definitions section above in the description of "first substituent group(s)". In embodiments, when an $R^{L104.1}$ substituent group is substituted, the $R^{L104.1}$ substituent group is substituted with one or more second substituent groups denoted by $R^{L104.2}$ as explained in the definitions section above in the description of "first substituent group(s)". In embodiments, when an $R^{L104.2}$ substituent group is substituted, the $R^{L104.2}$ substituent group is substituted with one or more third substituent groups denoted by $R^{L104.3}$ as explained in the definitions section above in the description of "first substituent group(s)". In the above embodiments, $L^{104}$, $R^{L104.1}$, $R^{L104.2}$, and $R^{L104.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{104}$, $R^{L104.1}$, $R^{L104.2}$, and $R^{L104.3}$, respectively.

In embodiments, when $L^{105}$ is substituted, $L^{105}$ is substituted with one or more first substituent groups denoted by $R^{L105.1}$ as explained in the definitions section above in the description of "first substituent group(s)". In embodiments, when an $R^{L105.1}$ substituent group is substituted, the $R^{L105.1}$ substituent group is substituted with one or more second substituent groups denoted by $R^{L105.2}$ as explained in the definitions section above in the description of "first substituent group(s)". In embodiments, when an $R^{L105.2}$ substituent group is substituted, the $R^{L105.2}$ substituent group is substituted with one or more third substituent groups denoted by $R^{L105.3}$ as explained in the definitions section above in the description of "first substituent group(s)". In the above embodiments, $L^{105}$, $R^{L105.1}$, $R^{L105.2}$, and $R^{L105.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{105}$, $R^{L105.1}$, $R^{L105.2}$, and $R^{L105.3}$, respectively.

In embodiments, when $L^{106}$ is substituted, $L^{106}$ is substituted with one or more first substituent groups denoted by $R^{L106.1}$ as explained in the definitions section above in the description of "first substituent group(s)". In embodiments, when an $R^{L106.1}$ substituent group is substituted, the $R^{L106.1}$ substituent group is substituted with one or more second substituent groups denoted by $R^{L106.2}$ as explained in the definitions section above in the description of "first substituent group(s)". In embodiments, when an $R^{L106.2}$ substituent group is substituted, the $R^{L106.2}$ substituent group is substituted with one or more third substituent groups denoted by $R^{L106.3}$ as explained in the definitions section above in the description of "first substituent group(s)". In the above embodiments, $L^{106}$, $R^{L106.1}$, $R^{L106.2}$, and $R^{L106.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{106}$, $R^{L106.1}$, $R^{L106.2}$, and $R^{L106.3}$, respectively.

In embodiments, when $L^{107}$ is substituted, $L^{107}$ is substituted with one or more first substituent groups denoted by $R^{L107.1}$ as explained in the definitions section above in the description of "first substituent group(s)". In embodiments, when an $R^{L107.1}$ substituent group is substituted, the $R^{L107.1}$ substituent group is substituted with one or more second substituent groups denoted by $R^{L107.2}$ as explained in the definitions section above in the description of "first substituent group(s)". In embodiments, when an $R^{L107.2}$ substituent group is substituted, the $R^{L107.2}$ substituent group is substituted with one or more third substituent groups denoted by $R^{L107.3}$ as explained in the definitions section above in the description of "first substituent group(s)". In the above embodiments, $L^{107}$, $R^{L107.1}$, $R^{L107.2}$, and $R^{L107.3}$ have values corresponding to the values of $L^{WW}$, $R^{LWW.1}$, $R^{LWW.2}$, and $R^{LWW.3}$, respectively, as explained in the definitions section above in the description of "first substituent group(s)", wherein $L^{WW}$, $R^{LWW.1}$, $R^{LWW.2}$, and $R^{LWW.3}$ are $L^{107}$, $R^{L107.1}$, $R^{L170.2}$, and $R^{L107.3}$, respectively.

In embodiments, $L^1$ is

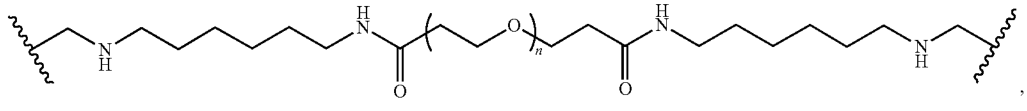

, wherein n is as described herein, including in embodiments.

In embodiments, $L^1$ is

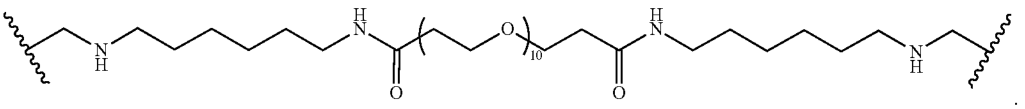

In embodiments, $L^1$ is

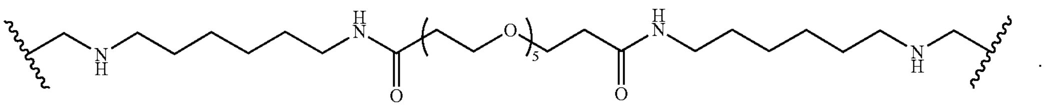

In embodiments, $L^1$ is

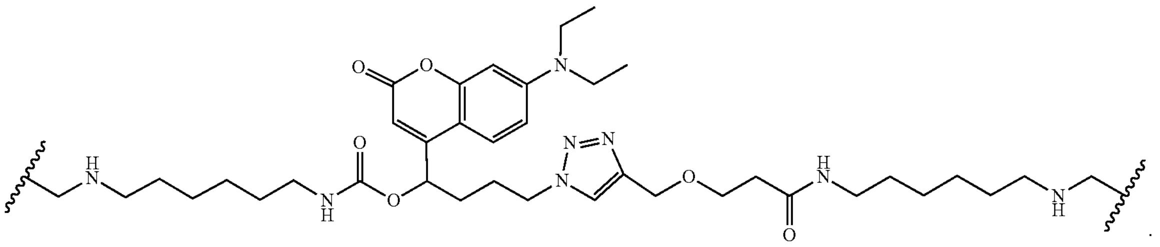 [SMILES: *CNCCCCCCNC(=O)CCOCc1cn(CCCC(OC(=O)NCCCCCCNC*)c2cc(=O)oc3cc(N(CC)CC)ccc23)nn1]

In embodiments, $L^1$ is

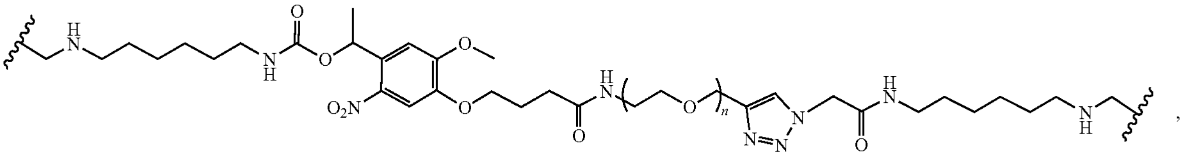

wherein n is as described herein, including in embodiments.

In embodiments, $L^1$ is

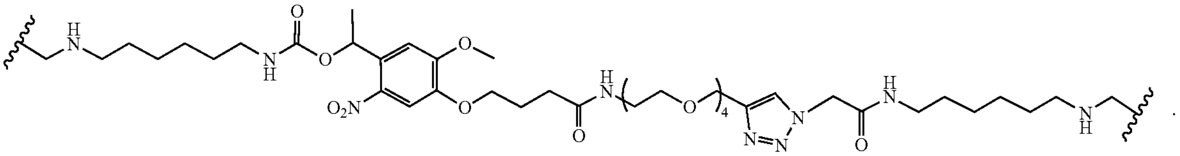

In embodiments, $L^1$ includes a photo-cleavable site. In embodiments, the photo-cleavable site is a monovalent form of an ortho-nitrobenzene, or derivative thereof. In embodiments, the photo-cleavable site is a divalent form of an ortho-nitrobenzene, or derivative thereof. In embodiments, the photo-cleavable site is

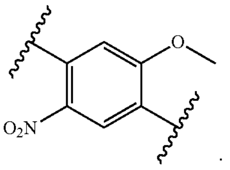 [SMILES: *c1cc([N+](=O)[O-])c(*)cc1OC]

In embodiments, the photo-cleavable site is a monovalent form of a coumarin, or derivative thereof. In embodiments, the photo-cleavable site is

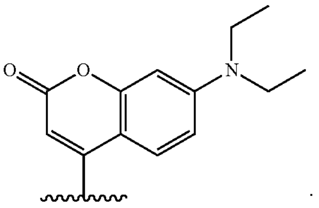 [SMILES: *c1cc(=O)oc2cc(N(CC)CC)ccc12]

In embodiments, the photo-cleavable site is a divalent form of a coumarin, or a derivative thereof. In embodiments, the photo-cleavable site is

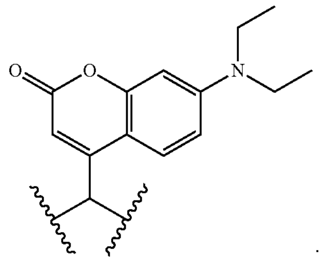 [SMILES: *C(*)c1cc(=O)oc2cc(N(CC)CC)ccc12]

In embodiments, the photo-cleavable site is a monovalent form of a salicyl-alcohol, or derivative thereof. In embodiments, the photo-cleavable site is a divalent form of a salicyl-alcohol, or derivative thereof.

In embodiments, $L^1$ includes a peptide linker. In embodiments, the peptide linker is about 3 to about 60 amino acid residues in length. In embodiments, the peptide linker is about 6 to about 60 amino acid residues in length. In embodiments, the peptide linker is about 9 to about 60 amino acid residues in length. In embodiments, the peptide linker is about 12 to about 60 amino acid residues in length. In embodiments, the peptide linker is about 15 to about 60 amino acid residues in length. In embodiments, the peptide linker is about 18 to about 60 amino acid residues in length. In embodiments, the peptide linker is about 21 to about 60 amino acid residues in length. In embodiments, the peptide linker is about 24 to about 60 amino acid residues in length. In embodiments, the peptide linker is about 27 to about 60 amino acid residues in length. In embodiments, the peptide linker is about 30 to about 60 amino acid residues in length. In embodiments, the peptide linker is about 33 to about 60 amino acid residues in length. In embodiments, the peptide linker is about 36 to about 60 amino acid residues in length. In embodiments, the peptide linker is about 39 to about 60 amino acid residues in length. In embodiments, the peptide linker is about 42 to about 60 amino acid residues in length. In embodiments, the peptide linker is about 45 to about 60 amino acid residues in length. In embodiments, the peptide linker is about 48 to about 60 amino acid residues in length. In embodiments, the peptide linker is about 51 to about 60 amino acid residues in length. In embodiments, the peptide linker is about 54 to about 60 amino acid residues in length. In embodiments, the peptide linker is about 57 to about 60 amino acid residues in length. In embodiments, the peptide linker is about 3 to about 57 amino acid residues in length. In embodiments, the peptide linker is about 3 to about 54 amino acid residues in length. In embodiments, the peptide linker is about 3 to about 51 amino acid residues in length. In embodiments, the peptide linker is about 3 to about 48 amino acid residues in length. In embodiments, the peptide linker is about 3 to about 45 amino acid residues in length. In embodiments, the peptide linker is about 3 to about 42 amino acid residues in length. In embodiments, the peptide linker is about 3 to about 39 amino acid residues in length. In embodiments, the peptide linker is about 3 to about 36 amino acid residues in length. In embodiments, the peptide linker is about 3 to about 33 amino acid residues in length. In embodiments, the peptide linker is about 3 to about 30 amino acid residues in length. In embodiments, the peptide linker is about 3 to about 27 amino acid residues in length. In embodiments, the peptide linker is about 3 to about 24 amino acid residues in length. In embodiments, the peptide linker is about 3 to about 21 amino acid residues in length. In embodiments, the peptide linker is about 3 to about 18 amino acid residues in length. In embodiments, the peptide linker is about 3 to about 15 amino acid residues in length. In embodiments, the peptide linker is about 3 to about 12 amino acid residues in length. In embodiments, the peptide linker is about 3 to about 9 amino acid residues in length. In embodiments, the peptide linker is about 3 to about 6 amino acid residues in length. In embodiments, the peptide linker is 3 amino acid residues, 6 amino acid residues, 9 amino acid residues, 12 amino acid residues, 15 amino acid residues, 18 amino acid residues, 21 amino acid residues, 24 amino acid residues, 27 amino acid residues, 30 amino acid residues, 33 amino acid residues, 36 amino acid residues, 39 amino acid residues, 42 amino acid residues, 45 amino acid residues, 48 amino acid residues, 51 amino acid residues, 54 amino acid residues, 57 amino acid residues, or 60 amino acid residues in length.

In embodiments, the peptide linker includes a protease cleavable site. In embodiments, the protease cleavable site is a matrix metalloprotease (MMP) cleavage site, a metalloprotease domain-containing (ADAM) metalloprotease cleavage site, a lysosomal cathepsin cleavage site (ALAL), or a legumain endopeptidase cleavage site (TANL). In embodiments, the protease cleavable site is a MMP cleavage site. In embodiments, the protease cleavable site is an ADAM metalloprotease cleavage site. In embodiments, the protease cleavable site is an ALAL cleavage site. In embodiments, the protease cleavable site is a TANL cleavage site.

Further exemplary cleavage sites include the cleavage site of ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMPP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, or TPSG1.

In embodiments, $L^1$ includes a pH sensitive cleavable site. In embodiments, the pH sensitive cleavable site is a divalent form of a phosphoramidyl hydroxypropylglycine. In embodiments, the pH sensitive cleavable site is a divalent form of a phosphoramidyl homoserine. In embodiments, the pH sensitive cleavable site is a divalent form of a phosphoramidyl serine. In embodiments, the pH cleavable site is cleaved at pH 6.5 or lower. In embodiments, the pH cleavable site is cleaved at pH 6 or lower. In embodiments, the pH cleavable site is cleaved at pH 5.5 or lower. In embodiments, the pH cleavable site is cleaved at pH 5 or lower. In embodiments, the pH cleavable site is cleaved at pH 4.5 or lower. In embodiments, the pH cleavable site is cleaved at pH 4 or lower. In embodiments, the pH cleavable site is cleaved at pH 3.5 or lower. In embodiments, the pH cleavable site is cleaved at pH 3 or lower.

In embodiments, the distance between $R^1$ and $R^2$ is from about 20 Å to about 200 Å. The distance between between $R^1$ and $R^2$ refers to the distance between the loop portion of the first RNA stem loop and the loop portion of the second RNA stem loop for the RNA compound provided herein including embodiments thereof. Thus, in embodiments, the distance between $R^1$ and $R^2$ includes the length of the linker $L^1$ and the two imidazoyl groups in the pre-Q1 portion of the pre-Q1 linking compound.

In embodiments, the distance between $R^1$ and $R^2$ is from about 40 Å to about 200 Å. In embodiments, the distance between $R^1$ and $R^2$ is from about 60 Å to about 200 Å. In embodiments, the distance between $R^1$ and $R^2$ is from about 80 Å to about 200 Å. In embodiments, the distance between $R^1$ and $R^2$ is from about 100 Å to about 200 Å. In embodiments, the distance between $R^1$ and $R^2$ is from about 120 Å to about 200 Å. In embodiments, the distance between $R^1$ and $R^2$ is from about 140 Å to about 200 Å. In embodiments, the distance between $R^1$ and $R^2$ is from about 160 Å to about 200 Å. In embodiments, the distance between $R^1$ and $R^2$ is from about 180 Å to about 200 Å.

In embodiments, the distance between $R^1$ and $R^2$ is from about 20 Å to about 180 Å. In embodiments, the distance between $R^1$ and $R^2$ is from about 20 Å to about 160 Å. In embodiments, the distance between $R^1$ and $R^2$ is from about 20 Å to about 140 Å. In embodiments, the distance between $R^1$ and $R^2$ is from about 20 Å to about 120 Å. In embodiments, the distance between $R^1$ and $R^2$ is from about 20 Å to about 100 Å. In embodiments, the distance between $R^1$ and $R^2$ is from about 20 Å to about 80 Å. In embodiments, the distance between $R^1$ and $R^2$ is from about 20 Å to about 60 Å. In embodiments, the distance between $R^1$ and $R^2$ is from about 20 Å to about 40 Å. In embodiments, the distance between $R^1$ and $R^2$ is about 20 Å, 40 Å, 60 Å, 80 Å, 100 Å, 120 Å, 140 Å, 160 Å, 180 Å, or 200 Å. In embodiments, the distance between $R^1$ and $R^2$ is about 71 Å. In embodiments, the distance between $R^1$ and $R^2$ is 71 Å. In embodiments, the distance between $R^1$ and $R^2$ is about 43 Å. In embodiments, the distance between $R^1$ and $R^2$ is 43 Å.

In embodiments, the compound (e.g., RNA compound or PreQ1 linking compound) is useful as a comparator compound. In embodiments, the comparator compound can be used to assess the activity of a test compound as set forth in an assay described herein (e.g., in the examples section, figures, or tables).

In embodiments, the compound (e.g., RNA compound or PreQ1 linking compound) is a compound as described herein, including in embodiments. In embodiments the compound (e.g., RNA compound or PreQ1 linking compound) is a compound described herein (e.g., in the examples section, figures, tables, or claims).

Methods

Methods provided herein are use are useful for attaching (e.g. linking) a first RNA stem loop and a second RNA stem loop by way of a preQ1 linking compound as provided herein including embodiments thereof. The first and second RNA stem loops may be in a single RNA oligonucleotide (e.g. RNA stem loop oligonucleotide) or in two RNA oligonucleotides. Attachment of the RNA stem loops may restrict the conformation or decrease the flexibility of the one or more RNA oligonucleotides. For example, the RNA oligonucleotide(s) may be restricted to a single conformation after attachment of the RNA stem loops. The RNA oligonucleotide(s) may be restricted to fewer conformations after attachment of the RNA stem loops, as compared to the RNA oligonucleotide(s) wherein the first RNA stem loop and the second RNA stem loop are not attached by the preQ1 linking compound (e.g. linking compound). Alternatively, attachment of the two stem loops may change the conformation of the one or more RNA oligonucleotides. In another instance, attachment of the two RNA stem loops may occlude binding of an RNA-binding enzyme (e.g. a nuclease, etc.). For example, enzyme binding to a RNA oligonucleotide(s) (e.g. a sgRNA, gRNA etc.) may be decreased or inhibited following linking of the stem loops by a preQ1 linking compound as provided herein. Thus, the changes in RNA structure/conformation induced by linking the RNA stem loops may modulate biological, enzymatic, and or signaling processes.

Methods provided herein generally involve contacting a PreQ1 linking compound provided herein including embodiments thereof, a tRNA-guanine transglycosylase (TGT) enzyme, and two RNA stem loops under conditions wherein a guanine from each of the RNA stem loops is removed and replaced with the preQ1 portion of the preQ1 linking compound provided herein. In embodiments, the preQ1 portion of the linking compound is an analog of preQ1. Thus, in an aspect is provided a method of linking a first RNA stem loop oligonucleotide and a second RNA stem loop oligonucleotide, the method including contacting the first RNA stem loop oligonucleotide and the second RNA stem loop oligonucleotide with a PreQ1 linking compound and a tRNA-guanine transglycosylase (TGT) enzyme, wherein the PreQ1 linking compound has the formula:

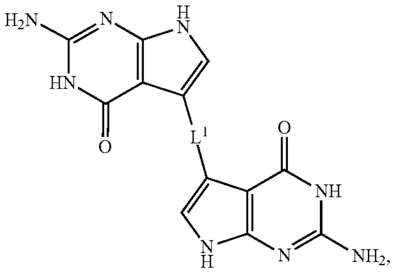

wherein $L^1$ is a covalent linker (e.g., as described herein, including in embodiments); wherein the first RNA stem loop oligonucleotide includes a first guanosine in a first RNA loop portion of a first RNA stem loop; and wherein the second RNA stem loop oligonucleotide includes a second guanosine in a second RNA loop portion of a second RNA stem loop.

The TGT enzyme is capable of replacing guanosine in a UGU sequence within the loop portion of an RNA stem loop with a preQ1 or an analog thereof. Thus, in embodiments, the first guanosine is in a first UGU sequence in the first RNA loop portion of the first RNA stem loop and the second guanosine is in a second UGU sequence in the second RNA loop portion of the second RNA stem loop.

In embodiments the first RNA stem loop includes the sequence of SEQ ID NO:1. In embodiments the first RNA stem loop is the sequence of SEQ ID NO:1. In embodiments the first RNA stem loop includes the sequence of SEQ ID NO:29. In embodiments the first RNA stem loop is the sequence of SEQ ID NO:29. In embodiments the first RNA stem loop includes the sequence of SEQ ID NO:30. In embodiments the first RNA stem loop is the sequence of SEQ ID NO:30. In embodiments the first RNA stem loop includes the sequence of SEQ ID NO:31. In embodiments the first RNA stem loop is the sequence of SEQ ID NO:31.

In embodiments the second RNA stem loop includes the sequence of SEQ ID NO:1. In embodiments the second RNA stem loop is the sequence of SEQ ID NO: 1. In embodiments the second RNA stem loop includes the sequence of SEQ ID NO:29. In embodiments the second RNA stem loop is the sequence of SEQ ID NO:29. In embodiments the second RNA stem loop includes the sequence of SEQ ID NO:30. In embodiments the second RNA stem loop is the sequence of SEQ ID NO:30. In embodiments the second RNA stem loop includes the sequence of SEQ ID NO:31. In embodiments the second RNA stem loop is the sequence of SEQ ID NO:31.

In embodiments, the loop portion of the first RNA stem loop includes the sequence of SEQ ID NO:32. In embodiments, the loop portion of the second RNA stem loop includes the sequence of SEQ ID NO:32. In embodiments, the loop portion of the first RNA stem loop is the sequence of SEQ ID NO:32. In embodiments, the loop portion of the second RNA stem loop is the sequence of SEQ ID NO:32.

In embodiments, the first RNA stem loop oligonucleotide and the second RNA stem loop oligonucleotide are independently between about 15 nucleotides to about 10,000 nucleotides in length. In embodiments, the first RNA oligonucleotide and the second RNA oligonucleotide are independently between about 20 nucleotides to about 280 nucleotides in length.

The methods provided herein may be used to link RNA stem loops in RNA oligonucleotides (e.g. RNA stem loop oligonucleotide) to modulate biological processes, enzyme activity and/or signaling pathways. For example, stem loops in transcript mRNA may be linked to inhibit or decrease gene expression. For example, linking stem loops in mRNA may inhibit mRNA processing or binding of proteins required for gene expression. In another example, stem loops in pre-miRNA may be linked to modulate gene silencing activity. In another example, stem loops in gRNA and/or sgRNA may be linked to modulate gene editing activity. Thus, in embodiments, the first RNA stem loop oligonucleotide and the second RNA stem loop oligonucleotide are independently a pre-miRNA. In embodiments, the first RNA stem loop oligonucleotide and the second RNA stem loop oligonucleotide are independently an mRNA, a gRNA, an sgRNA, an shRNA, a siRNA, a tRNA, a long non-coding RNA, an rRNA or a ribozyme.

For example, gene editing activity of a gRNA may be decreased when an RNA stem loop of the gRNA is linked to a second RNA stem loop, compared the gene editing activity of the an unlinked gRNA. In embodiments, the gene editing activity of the gRNA is decreased by 50%, 60%, 70%, 80%, 85%, 90%, 95% or 100%. Gene editing activity of an sgRNA may be decreased when a stem loop (e.g. stem loop 1, stem loop 2, stem loop 3, tetraloop) of the sgRNA is linked to a second RNA stem loop, compared to the gene editing activity of the unlinked sgRNA. The second RNA stem loop may be in the same sgRNA, or may be in a separate RNA oligonucleotide (e.g. RNA stem loop oligonucleotide). In embodiments, the gene editing activity of the sgRNA is decreased by 50%, 60%, 70%, 80%, 85%, 90%, 95% or 100%.

In embodiments, the first RNA stem loop oligonucleotide is a first sgRNA and the second RNA stem loop oligonucleotide is a second sgRNA. In embodiments, the first RNA stem loop is the stem loop 2 of the first sgRNA and the second RNA stem loop is the tetra-loop of the second sgRNA. In embodiments, the first RNA stem loop is the tetra-loop of the first sgRNA and the second RNA stem loop is the stem loop 2 of the second sgRNA.

In embodiments, the first RNA stem loop oligonucleotide, the second RNA stem loop oligonucleotide, the PreQ1 linking compound, and the TGT enzyme are added to a single reaction mixture simultaneously. In embodiments, simultaneously refers to addition of first RNA stem loop oligonucleotide, the second RNA stem loop oligonucleotide, the PreQ1 linking compound, and the TGT enzyme to a single reaction mixture within 1 second, 2 seconds, 5 seconds, 10 seconds, 20 seconds or 30 seconds of each other. In embodiments, simultaneously refers to adding the TGT enzyme to the single reaction mixture last, and within 1 second, 2 seconds, 5 seconds, 10 seconds, 20 seconds or 30 seconds of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 1 second of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 2 seconds of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 5 seconds of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 10 seconds of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 20 seconds of adding of the first RNA stem loop oligonucleotide, the second RNA stem loop oligonucleotide, and the PreQ1 linking compound to the reaction mixture. In embodiments, simultaneously refers to adding the TGT enzyme to the single reaction mixture last, and within 30 seconds of adding of the first RNA stem loop oligonucleotide, the second RNA stem loop oligonucleotide, and the PreQ1 linking compound to the reaction mixture.

In embodiments, the first RNA stem loop oligonucleotide, the PreQ1 linking compound, and the TGT enzyme are added to a single reaction mixture prior to adding the second RNA stem loop oligonucleotide to the reaction mixture. In embodiments, the second RNA stem loop oligonucleotide is added to the reaction mixture 1 minute after adding the the first RNA stem loop oligonucleotide, the PreQ1 linking compound, and the TGT enzyme to the reaction mixture. In embodiments, the second RNA stem loop oligonucleotide is added to the reaction mixture 1.5 minutes after adding the the first RNA stem loop oligonucleotide, the PreQ1 linking compound, and the TGT enzyme to the reaction mixture. In embodiments, the second RNA stem loop oligonucleotide is added to the reaction mixture 2 minutes after adding the the first RNA stem loop oligonucleotide, the PreQ1 linking compound, and the TGT enzyme to the reaction mixture. In embodiments, the second RNA stem loop oligonucleotide is added to the reaction mixture 5 minutes after adding the the first RNA stem loop oligonucleotide, the PreQ1 linking compound, and the TGT enzyme to the reaction mixture. In embodiments, the second RNA stem loop oligonucleotide is added to the reaction mixture 10 minutes after adding the the first RNA stem loop oligonucleotide, the PreQ1 linking compound, and the TGT enzyme to the reaction mixture. In embodiments, the second RNA stem loop oligonucleotide is added to the reaction mixture 15 minutes after adding the the first RNA stem loop oligonucleotide, the PreQ1 linking compound, and the TGT enzyme to the reaction mixture. In embodiments, the second RNA stem loop oligonucleotide is added to the reaction mixture 30 minutes after adding the the first RNA stem loop oligonucleotide, the PreQ1 linking compound, and the TGT enzyme to the reaction mixture.

In embodiments, the second RNA stem loop oligonucleotide, the PreQ1 linking compound, and the TGT enzyme are added to a single reaction mixture prior to adding the first RNA stem loop oligonucleotide to the reaction mixture. In embodiments, the first RNA stem loop oligonucleotide is added to the reaction mixture 1 minute after adding the the second RNA stem loop oligonucleotide, the PreQ1 linking compound, and the TGT enzyme to the reaction mixture. In embodiments, the first RNA stem loop oligonucleotide is added to the reaction mixture 1.5 minutes after adding the the second RNA stem loop oligonucleotide, the PreQ1 linking compound, and the TGT enzyme to the reaction mixture. In embodiments, the first RNA stem loop oligonucleotide is added to the reaction mixture 2 minutes after adding the the second RNA stem loop oligonucleotide, the PreQ1 linking compound, and the TGT enzyme to the reaction mixture. In embodiments, the first RNA stem loop oligonucleotide is added to the reaction mixture 5 minutes after adding the the second RNA stem loop oligonucleotide, the PreQ1 linking compound, and the TGT enzyme to the reaction mixture. In embodiments, the first RNA stem loop oligonucleotide is added to the reaction mixture 10 minutes after adding the the second RNA stem loop oligonucleotide, the PreQ1 linking compound, and the TGT enzyme to the reaction mixture. In embodiments, the first RNA stem loop oligonucleotide is added to the reaction mixture 15 minutes after adding the the second RNA stem loop oligonucleotide, the PreQ1 linking compound, and the TGT enzyme to the reaction mixture. In embodiments, the first RNA stem loop oligonucleotide is added to the reaction mixture 30 minutes after adding the the second RNA stem loop oligonucleotide, the PreQ1 linking compound, and the TGT enzyme to the reaction mixture.

In embodiments, the first RNA stem loop oligonucleotide, the PreQ1 linking compound, and the second RNA stem loop are added to a single reaction mixture prior to adding the the TGT enzyme to the reaction mixture.

For the methods provided herein, in embodiments, the two RNA stem loops may be in the same RNA stem loop oligonucleotide (e.g. RNA oligonucleotide). For example, two stem loops within a sgRNA oligonucleotide may be linked. In another example, two stem loops within a gRNA oligonucleotide may be linked. Thus, in an aspect is provided a method of linking a first RNA stem loop of an RNA stem loop oligonucleotide and a second RNA stem loop of the RNA stem loop oligonucleotide, the method including contacting the RNA stem loop oligonucleotide with a PreQ1 linking compound and a tRNA-guanine transglycosylase (TGT) enzyme, wherein the PreQ1 linking compound has the formula:

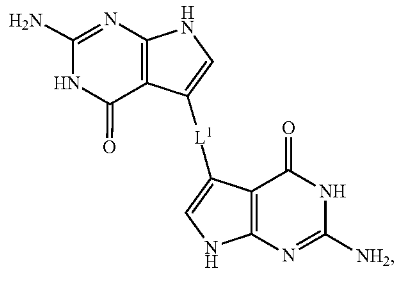

wherein $L^1$ is a covalent linker; and wherein the first RNA stem loop includes a first guanosine in a first RNA loop portion of the first RNA stem loop, and wherein the second RNA stem loop includes a second guanosine in a second RNA loop portion of the second RNA stem loop.

For the methods provided herein, in embodiments, the first guanosine is in a first UGU sequence in the first RNA loop portion of the first RNA stem loop and the second guanosine is in a second UGU sequence in the second RNA loop portion of the second RNA stem loop.

For the methods provided herein, in embodiments, the RNA stem loop oligonucleotide is between about 15 nucleotides to about 10,000 nucleotides in length. In embodiments, the RNA stem loop oligonucleotide is between about 20 nucleotides to about 300 nucleotides in length.

In embodiments, the RNA stem loop oligonucleotide is a pre-miRNA. In embodiments, the RNA stem loop oligonucleotide is an mRNA, a gRNA, an sgRNA, an shRNA, a siRNA, a tRNA, a long non-coding RNA, an rRNA or a ribozyme. In embodiments, the RNA stem loop oligonucleotide is an sgRNA. In embodiments, the first RNA stem loop is the stem loop 2 of the sgRNA and the second RNA stem loop is the tetra-loop of the sgRNA. In embodiments, the first RNA stem loop is the tetra-loop of the sgRNA and the second RNA stem loop is the stem loop 2 of said sgRNA.

For the methods provided herein, in embodiments, the RNA stem loop oligonucleotide, PreQ1 linking compound, and TGT enzyme are added to a single reaction mixture simultaneously. In embodiments, simultaneously refers to addition of RNA stem loop oligonucleotide, the PreQ1 linking compound, and the TGT enzyme to a single reaction mixture within 1 second, 2 seconds, 5 seconds, 10 seconds, 20 seconds or 30 seconds of each other. In embodiments, simultaneously refers to adding the TGT enzyme to the single reaction mixture last, and within 1 second, 2 seconds, 5 seconds, 10 seconds, 20 seconds or 30 seconds of adding the the RNA stem loop oligonucleotide and the PreQ1 linking compound to the reaction mixture.

For the methods provided herein, in embodiments, the TGT enzyme is a bacterial TGT enzyme. In embodiments the bacterial TGT enzyme is *Escherichia coli* TGT. In embodiments, the TGT enzyme is *Zymomonas mobilis* TGT.

For the methods provided herein, in embodiments, $L^1$ is $-L^{101}-L^{102}-L^{103}-L^{104}-L^{105}-L^{106}-L^{107}$; $L^{101}$ is a bond, —C(O)—, —C(O)O—, —OC(O)—, —O—, —S—, $—NR^{101}—$, $—C(O)NR^{101}—$, $—NR^{101}C(O)—$, $—NR^{101}C(O)O—$, $—OC(O)NR^{101}—$, $—NR^{101}C(O)NR^{101}—$, $—NR^{101}C(NH)NR^{101}—$, $—S(O)_2—$, $—NR^{101}S(O)_2—$, $—S(O)_2NR^{01}—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{102}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{103}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{104}$ is a bond, —C(O)—, —C(O)O—, —OC(O)—, —O—, —S—, —$NR^{104}$—, —C(O)$NR^{104}$—, —$NR^{104}$C(O)—, —$NR^{104}$C(O)O—, —OC(O)$NR^{104}$—, —$NR^{104}$C(O)$NR^{104}$—, —$NR^{104}$C(NH)$NR^{104}$—, —$S(O)_2$—, —$NR^{104}S(O)_2$—, —$S(O)_2NR^{104}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{105}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{106}$ is a bond, —C(O)—, —C(O)O—, —OC(O)—, —O—, —S—, —$NR^{106}$—, —C(O)$NR^{106}$—, —$NR^{106}$C(O)—, —$NR^{106}$C(O)O—, —OC(O)$NR^{106}$—, —$NR^{106}$C(O)$NR^{106}$—, —$NR^{106}$C(NH)$NR^{106}$—, —$S(O)_2$—, —$NR^{106}S(O)_2$—, —$S(O)_2NR^{106}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{107}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(N)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker; and each $R^{101}$, $R^{102}$, $R^{103}$, $R^{104}$, $R^{105}$, $R^{106}$, and $R^{107}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^1$ is -$L^{101}$-$L^{102}$-$L^{103}$-$(CH_2CH_2O)_n$-$L^{105}$-$L^{106}$-$L^{107}$-; and n is an integer from 1 to 20.

In embodiments, $L^{101}$, $L^{102}$, $L^{103}$, $L^{105}$, $L^{106}$, and $L^{107}$ are independently substituted or unsubstituted 2 to 10 membered heteroalkylene.

In embodiments, n is an integer from 2 to 10.

In embodiments, $L^{101}$ is an unsubstituted 2 to 10 membered heteroalkylene; $L^{102}$ is a substituted 2 to 16 membered heteroalkylene; $L^{103}$ is a substituted $C_1$-$C_6$ alkylene; $L^{104}$ is an unsubstituted 5 to 6 membered heteroarylene; $L^{105}$ is a substituted 2 to 10 membered heteroalkylene; $L^{106}$ is an unsubstituted $C_1$-$C_6$ alkylene; and $L^{107}$ is an unsubstituted 2 to 10 membered heteroalkylene. In embodiments, $L^{104}$ is an unsubstituted triazolylene.

In embodiments, $L^{101}$ is an unsubstituted 2 to 10 membered heteroalkylene; $L^{102}$ is a substituted 2 to 16 membered heteroalkylene; $L^{103}$ is a substituted phenylene; $L^{104}$ is a substituted 2 to 10 membered heteroalkylene; $L^{105}$ is —$(CH_2CH_2O)_n$—; $L^{106}$ is a substituted 2 to 10 membered heteroalkylene; $L^{107}$ is an unsubstituted 2 to 10 membered heteroalkylene; and n is an integer from 1 to 20.

In embodiments, n is an integer from 2 to 10.

In embodiments, $L^{101}$ is an unsubstituted 2 to 10 membered heteroalkylene; $L^{102}$ is a substituted 2 to 16 membered heteroalkylene; $L^{103}$ is a substituted phenylene; $L^{104}$ is a substituted 2 to 25 membered heteroalkylene; $L^{105}$ is an unsubstituted 5 to 6 membered heteroarylene; $L^{106}$ is a substituted 2 to 16 membered heteroalkylene; and $L^{107}$ is an unsubstituted 2 to 10 membered heteroalkylene. In embodiments, $L^{105}$ is an unsubstituted triazolylene.

In embodiments, $L^{101}$ is —$CH_2N$— and $L^{107}$ is —$NCH_2$—.

For the methods provided herein, in embodiments, the PreQ1 linking compound has the formula:

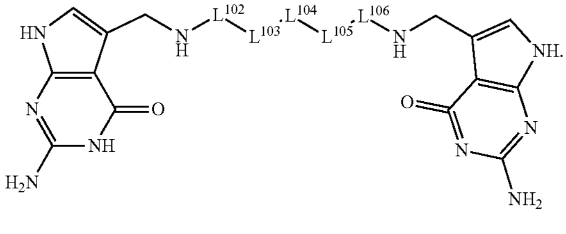

$L^{102}$, $L^{103}$, $L^{104}$, $L^{105}$, and $L^{106}$ are as described herein, including in embodiments.

For the methods provided herein, in embodiments, the PreQ1 linking compound has the formula:
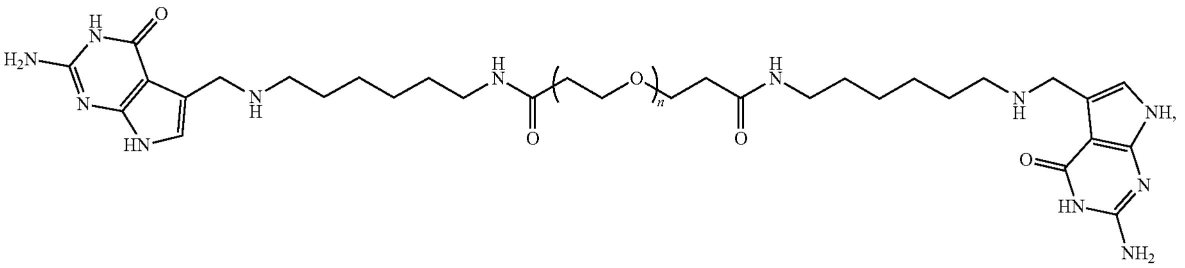
wherein n is as described herein, including in embodiments.
In embodiments, the PreQ1 linking compound has the formula:
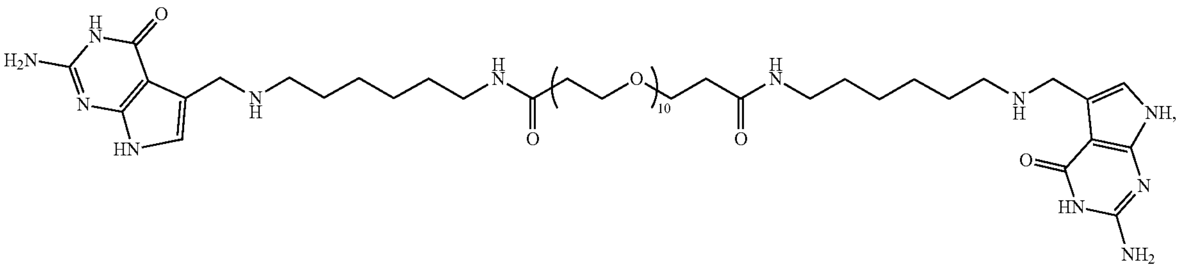
In embodiments, the PreQ1 linking compound has the formula:
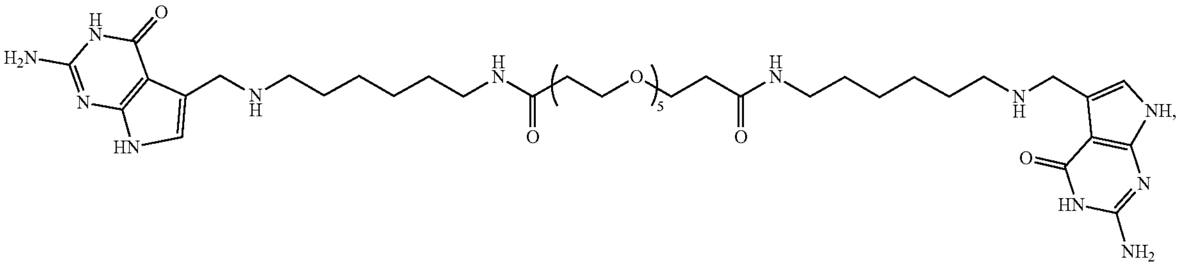
In embodiments, the PreQ1 linking compound has the formula:
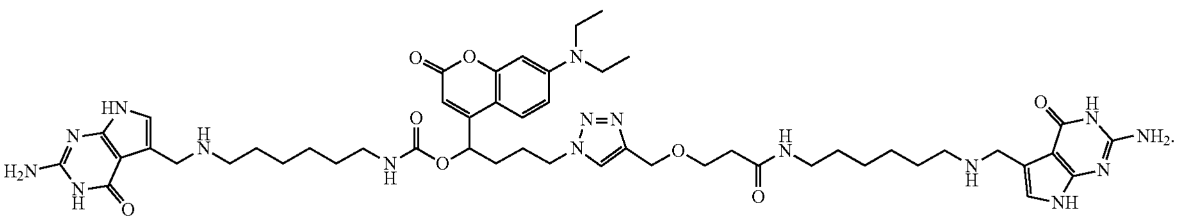 [SMILES: CCN(CC)c1ccc2c(C(CCCn3cc(COCCC(=O)NCCCCCCNCc4c[nH]c5nc(N)[nH]c(=O)c45)nn3)OC(=O)NCCCCCCNCc3c[nH]c4nc(N)[nH]c(=O)c34)cc(=O)oc2c1]

In embodiments, the PreQ1 linking compound has the formula:

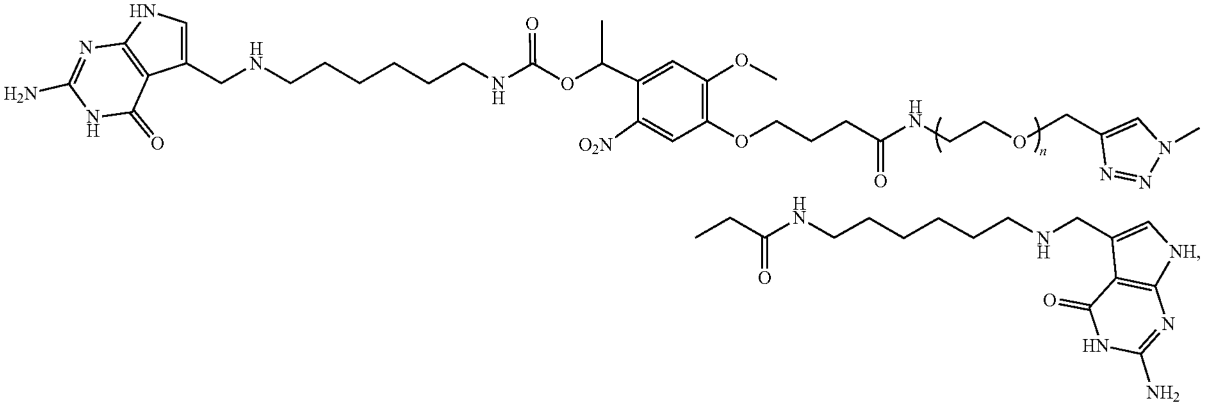

wherein n is as described herein, including in embodiments.

In embodiments, the PreQ1 linking compound has the formula:

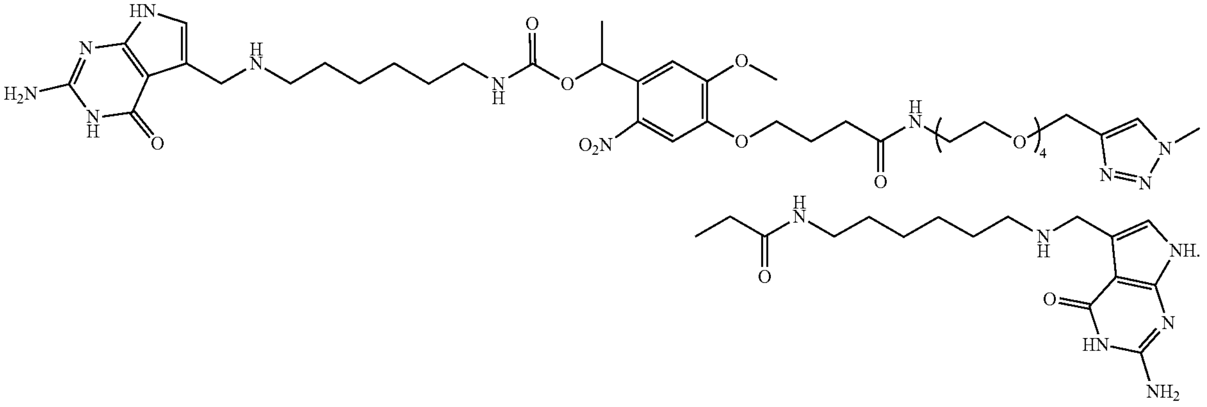

For the methods provided herein, in embodiments, $L^1$ includes a cleavable linker. Thus, the linked RNA stem loops may be unlinked by cleavage of $L^1$ at one or more cleavage sites. Freeing the RNA stem loops from their linked conformation may allow the RNA stem loop oligonucleotide(s) to exert its intended activity (e.g. gene expression, gene editing, gene silencing, etc.). In one example, $L^1$ may include a disease-specific cleavage site. A disease specific linker may be cleaved by an enzyme or protease that is only expressed at or expressed at high levels at a disease site (e.g. a tumor) or in a specific organ. In other example, $L^1$ may include a pH sensitive cleavage site that is cleaved at lower pH, for example in a tumor. $L^1$ may include any cleavable linker known in the art and described herein.

$L^1$ may include a cleavable site that can be with specific wavelengths of light. For example, photoactive compounds (e.g. coumarin) can be cleaved by visible light, thereby minimizing photo-toxicity. In another example, multiplexing of various RNA stem loop oligonucleotides can be achieved by selecting L1 linkers that can be cleaved at different wavelengths. Thus, in embodiments, $L^1$ includes a photo-cleavable site. The photo-cleavable site may include any photoactive compound known in the art and described herein. Photo-cleavable linkers are well-known in the art and are described in more detail in Shen, W. et al. Approaches for the synthesis of o-nitrobenzyl and coumarin linkers for use in photocleavable biomaterials and bioconjugates and their biomedical applications; Acta Biomaterialia, Volume 115, 1 Oct. 2020, Pages 75-91; doi.org/10.1016/j.actbio.2020.08.024; and Lerich, G. et al. Cleavable linkers in chemical biology; Bioorganic & Medicinal Chemistry, Volume 20, Issue 2, 15 Jan. 2012, Pages 571-582; doi.org/10.1016/j.bmc.2011.07.048; which are incorporated by reference herein in their entirety and for all purposes.

In embodiments, the photo-cleavable site is cleaved at by visible light. In embodiments, the photo-cleavable site is cleaved at a wavelength from about 380 to about 490 nm. In embodiments, the photo-cleavable site is cleaved at about 405-456 nm. In embodiments, the photo-cleavable site is cleaved at about 356-390 nm. In embodiments, the photo-cleavable site is cleaved at about 390 nm. In embodiments, the photo-cleavable site is cleaved at about 405 nm. In embodiments, the photo-cleavable site is cleaved at about 456 nm.

In embodiments, $L^1$ includes a peptide linker. In embodiments, the peptide linker includes a protease cleavable site.

In embodiments, the protease cleavable site is a matrix metalloprotease (MMP) cleavage site, a metalloprotease domain-containing (ADAM) metalloprotease cleavage site, a lysosomal cathepsin cleavage site (ALAL), or a legumain endopeptidase cleavage site (TANL). In embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP 9 cleavage site, a MMP 13 cleavage site or a MMP 2 cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site.

For the methods provided herein, $L^1$ may include a pH sensitive site, thereby allowing separation of the linked RNA stem loops in an acidic environment (e.g. in a tumor). In embodiments, $L^1$ comprises a pH sensitive cleavable site. The pH sensitive cleavable site may be cleaved at a pH below 7. The pH sensitive cleavable site may be cleaved at a pH below 6. The pH sensitive cleavable site may be cleaved at a pH below 5. The pH sensitive cleavable site may be cleaved at a pH below 4. The pH sensitive cleavable site may be cleaved at a pH below 3. In embodiments, the pH sensitive cleavable site includes phosphoramidyl hydroxypropylglycine. In embodiments, the pH sensitive cleavable site includes phosphoramidyl homoserine linker. In embodiments, the pH sensitive cleavable site includes phosphoramidyl serine.

Cells

The compositions provided herein, including the RNA compound and preQ1 linking compound, may be introduced into cells. Thus, in an aspect a cell including an RNA compound provided herein including embodiments thereof is provided.

In another aspect a cell including a preQ1 linking compound (e.g. linking compound) provided herein including embodiments thereof is provided. In embodiments, the cell includes a tRNA-guanine transglycosylase (TGT) enzyme.

In embodiments, the cell includes a RNA-guided DNA endonuclease. In embodiments, the endonuclease is Cas9. In embodiments, the endonuclease is Cpf1.

Embodiments

Embodiment 1. A method of modifying a single guide RNA (sgRNA) molecule comprising: a) contacting the sgRNA molecule with a tRNA guanine transglycosylase (TGT) enzyme or functional fragment thereof and 7-(aminomethyl)-7-deazaguanine (preQ1) or a derivative thereof, wherein i) the sgRNA molecule comprises a stem loop comprising a TGT recognition site; and ii) wherein the preQ1 is attached to a functional molecule by a chemical linker; and allowing the preQ1 to replace a guanine base in said TGT recognition site.

Embodiment 2. The method of embodiment 1, wherein the TGT recognition site is at a tetra-loop or a stem-loop 2 of said sgRNA.

Embodiment 3. A method of dimerizing two sgRNA molecules comprising: a) contacting a first sgRNA molecule and a second sgRNA molecule with a TGT enzyme or functional fragment thereof and a first preQ1 and a second preQ1 or a derivative thereof, wherein i) said first sgRNA comprises a first TGT recognition site; ii) said second sgRNA comprises a second TGT recognition site; and iii) said first preQ1 and said second preQ1 are attached by a chemical linker; and allowing said first preQ1 to replace a guanine base in said first TGT recognition site and allowing said second preQ1 to replace a guanine base in said second TGT recognition site.

Embodiment 4. A method of cyclizing an sgRNA molecule comprising: a) contacting the sgRNA molecule with tRNA guanine transglycosylase (TGT) enzyme or functional fragment thereof and a first preQ1 and a second preQ1 or derivative thereof, wherein i) the sgRNA molecule comprises a first TGT recognition site and a second TGT recognition site; and ii) wherein the first preQ1 and second preQ1 or derivative thereof are attached by a chemical linker; and allowing the first preQ1 to replace a guanine base in said first TGT recognition site and allowing the second preQ1 to replace a guanine base in said second TGT recognition site.

Embodiment 5. The method of embodiment 3 or 4, wherein said first TGT recognition site is at a tetra-loop and said second TGT recognition site is at a stem-loop 2 of the sgRNA.

Embodiment 6. The method of embodiment 3 or 4, wherein said first TGT recognition site is at a stem-loop 2 and said second TGT recognition site is at a tetra-loop of the sgRNA.

Embodiment 7. The method of any one of embodiments 1-6, wherein said chemical linker comprises a cleavable site.

Embodiment 8. An sgRNA molecule comprising a first stem loop comprising a first preQ1 or derivative thereof and a second step loop comprising a second preQ1 or derivative thereof, wherein said first preQ1 and second preQ1 are attached by a chemical linker, and wherein said chemical linker comprises a cleavable site.

Embodiment 9. A method of modulating expression of a target gene, comprising a) delivering to a cell comprising said target gene an oligonucleotide encoding a CRISPR associated endonuclease and the sgRNA of embodiment 8; and b) cleaving said chemical linker in said sgRNA; thereby modulating expression of said target gene.

P Embodiments

Embodiment P1. A method of linking a first RNA stem loop oligonucleotide and a second RNA stem loop oligonucleotide, the method comprising contacting the first RNA stem loop oligonucleotide and the second RNA stem loop oligonucleotide with a PreQ1 linking compound and a tRNA-guanine transglycosylase (TGT) enzyme, wherein the PreQ1 linking compound has the formula:

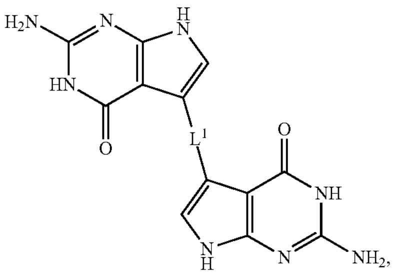

wherein $L^1$ is a covalent linker; wherein said first RNA stem loop oligonucleotide comprises a first guanosine in a first RNA loop portion of a first RNA stem loop; and wherein said second RNA stem loop oligonucleotide comprises a second guanosine in a second RNA loop portion of a second RNA stem loop.

Embodiment P2. The method of embodiment 1, wherein said first guanosine is in a first UGU sequence in the first RNA loop portion of the first RNA stem loop and said second guanosine is in a second UGU sequence in the second RNA loop portion of the second RNA stem loop.

Embodiment P3. The method of embodiment 1 or 2, wherein said first RNA stem loop oligonucleotide and said second RNA stem loop oligonucleotide are independently between about 15 nucleotides to about 10,000 nucleotides in length.

Embodiment P4. The method of any one of embodiments 1-3, wherein said first RNA stem loop oligonucleotide and said second RNA stem loop oligonucleotide are independently an mRNA, a gRNA, an sgRNA, an shRNA, a siRNA, a tRNA, a long non-coding RNA, an rRNA or a ribozyme.

Embodiment P5. The method of embodiment 4, wherein said first RNA stem loop oligonucleotide is a first sgRNA and said second RNA stem loop oligonucleotide is a second sgRNA.

Embodiment P6. The method of embodiment 5, wherein the first RNA stem loop is the stem loop 2 of the first sgRNA and the second RNA stem loop is the tetra-loop of the second sgRNA.

Embodiment P7. The method of embodiment 5, wherein the first RNA stem loop is the tetra-loop of the first sgRNA and the second RNA stem loop is the stem loop 2 of the second sgRNA.

Embodiment P8. The method of any one of embodiments 1-7, wherein the first RNA stem loop oligonucleotide, the second RNA stem loop oligonucleotide, the PreQ1 linking compound, and the TGT enzyme are added to a single reaction mixture simultaneously.

Embodiment P9. The method of any one of embodiments 1-7, wherein the first RNA stem loop oligonucleotide, the PreQ1 linking compound, and the TGT enzyme are added to a single reaction mixture prior to adding the second RNA stem loop oligonucleotide to said reaction mixture.

Embodiment P10. The method of any one of embodiments 1-7, wherein the second RNA stem loop oligonucleotide, the PreQ1 linking compound, and the TGT enzyme are added to a single reaction mixture prior to adding the first RNA stem loop oligonucleotide to said reaction mixture.

Embodiment P11. A method of linking a first RNA stem loop of an RNA stem loop oligonucleotide and a second RNA stem loop of said RNA stem loop oligonucleotide, the method comprising contacting said RNA stem loop oligonucleotide with a PreQ1 linking compound and a tRNA-guanine transglycosylase (TGT) enzyme, wherein said PreQ1 linking compound has the formula:

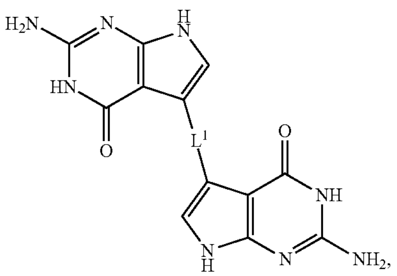

wherein $L^1$ is a covalent linker; and wherein said first RNA stem loop comprises a first guanosine in a first RNA loop portion of the first RNA stem loop, and wherein said second RNA stem loop comprises a second guanosine in a second RNA loop portion of the second RNA stem loop.

Embodiment P12. The method of embodiment 11, wherein said first guanosine is in a first UGU sequence in the first RNA loop portion of the first RNA stem loop and said second guanosine is in a second UGU sequence in the second RNA loop portion of the second RNA stem loop.

Embodiment P13. The method of embodiment 11 or 12, wherein said RNA stem loop oligonucleotide is between about about 15 nucleotides to about 10,000 nucleotides in length.

Embodiment P14. The method of any one of embodiments 11-13, wherein said RNA stem loop oligonucleotide is an mRNA, a gRNA, an sgRNA, an shRNA, a siRNA, a tRNA, a long non-coding RNA, an rRNA or a ribozyme.

Embodiment P15. The method of embodiment 14, wherein said RNA stem loop oligonucleotide is an sgRNA.

Embodiment P16. The method of embodiment 15, wherein said first RNA stem loop is the stem loop 2 of the sgRNA and the second RNA stem loop is the tetra-loop of said sgRNA.

Embodiment P17. The method of embodiment 15, wherein said first RNA stem loop is the tetra-loop of the sgRNA and the second RNA stem loop is the stem loop 2 of said sgRNA.

Embodiment P18. The method of any one of embodiments 11-17, wherein said RNA stem loop oligonucleotide, PreQ1 linking compound, and TGT enzyme are added to a single reaction mixture simultaneously.

Embodiment P19. The method of any one of embodiments 11-17, wherein said RNA stem loop oligonucleotide, PreQ1 linking compound, and TGT enzyme are added to a single reaction mixture sequentially.

Embodiment P20. The method of any one of embodiments 1-19, wherein said TGT enzyme is a bacterial TGT enzyme.

Embodiment P21. The method of any one of claims 1-20, wherein $L^1$ is $-L^{101}-L^{102}-L^{103}-L^{104}-L^{105}-L^{106}-L^{107}-$;

$L^{101}$ is a bond, —C(O)—, —C(O)O—, —OC(O)—, —O—, —S—, —$NR^{101}$—, —C(O)$NR^{101}$—, —$NR^{101}$C(O)—, —$NR^{101}$C(O)O—, —OC(O)$NR^{101}$—, —$NR^{101}$C(O)$NR^{101}$—, —$NR^{101}$C(NH)$NR^{101}$—, —$S(O)_2$—, —$NR^{101}S(O)_2$—, —$S(O)_2NR^{101}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{102}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{103}$ is a bond, —C(O)—, —C(O)O—, —OC(O)—, —O—, —S—, —$NR^{103}$—, —C(O)$NR^{103}$—, —$NR^{103}$C(O)—, —$NR^{103}$C(O)O—, —OC(O)$NR^{103}$—, —$NR^{103}$C(O)$NR^{103}$—, —$NR^{103}$C(NH)$NR^{103}$—, —$S(O)_2$—, —$NR^{103}S(O)_2$—, —$S(O)_2NR^{103}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{104}$ is a bond, —C(O)—, —C(O)O—, —OC(O)—, —O—, —S—, —$NR^{104}$—, —C(O)$NR^{104}$—, —$NR^{104}$C(O)—, —$NR^{104}$C(O)O—, —OC(O)$NR^{104}$—, —$NR^{104}$C(O)$NR^{104}$—, —$NR^{104}$C(NH)$NR^{104}$—, —$S(O)_2$—, —$NR^{104}S(O)_2$—, —$S(O)_2NR^{104}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{105}$ is a bond, —C(O)—, —C(O)O—, —OC(O)—, —O—, —S—, —$NR^{105}$—, —C(O)$NR^{105}$—, —$NR^{105}$C(O)—, —$NR^{105}$C(O)O—, —OC(O)$NR^{105}$—, —$NR^{105}$C(O)$NR^{105}$—, —$NR^{105}$C(NH)$NR^{105}$—, —$S(O)_2$—, —$NR^{105}S(O)_2$—, —$S(O)_2NR^{105}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{106}$ is a bond, —C(O)—, —C(O)O—, —OC(O)—, —O—, —S—, —$NR^{106}$—, —C(O)$NR^{106}$—, —$NR^{106}$C(O)—, —$NR^{106}$C(O)O—, —OC(O)$NR^{106}$—, —$NR^{106}$C(O)$NR^{106}$—, —$NR^{106}$C(NH)$NR^{106}$—, —$S(O)_2$—, —$NR^{106}S(O)_2$—, —$S(O)_2NR^{106}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{107}$ is a bond, —C(O)—, —C(O)O—, —OC(O)—, —O—, —S—, —$NR^{107}$—, —C(O)$NR^{107}$—, —$NR^{107}$C(O)—, —$NR^{107}$C(O)O—, —OC(O)$NR^{107}$—, —$NR^{107}$C(O)$NR^{107}$—, —$NR^{107}$C(NH)$NR^{107}$—, —$S(O)_2$—, —$NR^{107}S(O)_2$—, —$S(O)_2NR^{107}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker; and each $R^{101}$, $R^{102}$, $R^{103}$, $R^{104}$, $R^{105}$, $R^{106}$, and $R^{107}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P22. The method of embodiment 21, wherein $L^1$ is $-L^{101}-L^{102}-L^{103}-(CH_2CH_2O)_n-L^{105}-L^{106}-L^{107}-$; and n is an integer from 1 to 20.

Embodiment P23. The method of embodiment 22, wherein $L^{101}$, $L^{102}$, $L^{103}$, $L^{105}$, $L^{106}$, and $L^{107}$ are independently substituted or unsubstituted 2 to 10 membered heteroalkylene.

Embodiment P24. The method of embodiment 22 or 23, wherein n is an integer from 2 to 10.

Embodiment P25. The method of embodiment 21, wherein $L^{101}$ is an unsubstituted 2 to 10 membered heteroalkylene;

$L^{102}$ is a substituted 2 to 16 membered heteroalkylene;

$L^{103}$ is a substituted $C_1$-$C_6$ alkylene;

$L^{104}$ is an unsubstituted 5 to 6 membered heteroarylene;

$L^{105}$ is a substituted 2 to 10 membered heteroalkylene;

$L^{106}$ is an unsubstituted $C_1$-$C_6$ alkylene; and $L^{107}$ is an unsubstituted 2 to 10 membered heteroalkylene.

Embodiment P26. The method of embodiment 25, wherein $L^{104}$ is an unsubstituted triazolylene.

Embodiment P27. The method of embodiment 21, wherein $L^{101}$ is an unsubstituted 2 to 10 membered heteroalkylene;

$L^{102}$ is a substituted 2 to 16 membered heteroalkylene;

$L^{103}$ is a substituted phenylene;

$L^{104}$ is a substituted 2 to 10 membered heteroalkylene;

$L^{105}$ is —$(CH_2CH_2O)_n$—;

$L^{106}$ is a substituted 2 to 10 membered heteroalkylene;

$L^{107}$ is an unsubstituted 2 to 10 membered heteroalkylene; and n is an integer from 1 to 20.

Embodiment P28. The method of embodiment 27, wherein n is an integer from 2 to 10.

Embodiment P29. The method of embodiment 21, wherein $L^{101}$ is an unsubstituted 2 to 10 membered heteroalkylene;

$L^{102}$ is a substituted 2 to 16 membered heteroalkylene;

$L^{103}$ is a substituted phenylene;

$L^{104}$ is a substituted 2 to 25 membered heteroalkylene;

$L^{105}$ is an unsubstituted 5 to 6 membered heteroarylene;

$L^{106}$ is a substituted 2 to 16 membered heteroalkylene; and $L^{107}$ is an unsubstituted 2 to 10 membered heteroalkylene.

Embodiment P30. The method of embodiment 29, wherein $L^{105}$ is an unsubstituted triazolylene.

Embodiment P31. The method of any one of embodiments 21-30, wherein $L^{101}$ is —$CH_2NH$— and $L^{107}$ is —$NHCH_2$—.

Embodiment P32. The method of embodiment 21, wherein the PreQ1 linking compound has the formula:

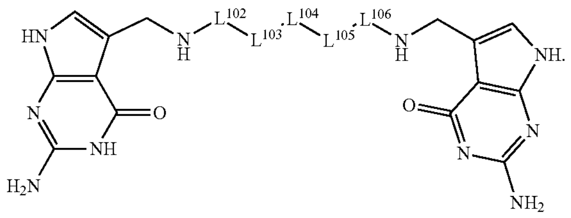

Embodiment P33. The method of any one of embodiments 1-32, wherein $L^1$ comprises a photo-cleavable site.

Embodiment P34. The method of embodiment 33, wherein said photo-cleavable site is cleaved at a wavelength from about 380 to about 490 nm.

Embodiment P35. The method of any one of embodiments 1-21, wherein $L^1$ comprises a peptide linker.

Embodiment P36. The method of any embodiment 35, wherein said peptide linker comprises a protease cleavable site.

Embodiment P37. The method of embodiment 36, wherein said protease cleavable site is a matrix metalloprotease (MMP) cleavage site, a metalloprotease domain-containing (ADAM) metalloprotease cleavage site, a lysosomal cathepsin cleavage site (ALAL), or a legumain endopeptidase cleavage site (TANL).

Embodiment P38. The method of any one of embodiments 1-21, wherein $L^1$ comprises a pH sensitive cleavable site.

Embodiment P39. An RNA compound having the formula:

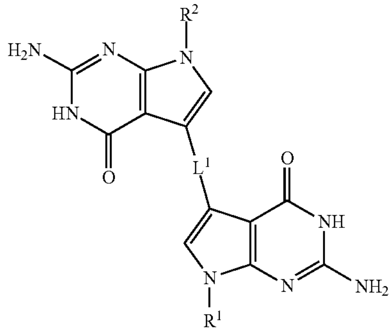

wherein $L^1$ is a covalent linker;

$R^1$ is a first RNA loop portion of a first RNA stem loop; and $R^2$ is a second RNA loop portion of a second RNA stem loop.

Embodiment P40. The RNA compound of embodiment 39, wherein said first RNA stem loop is in a first RNA oligonucleotide and said second RNA stem loop is in a second RNA oligonucleotide.

Embodiment P41. The RNA compound of embodiment 40, wherein said first RNA oligonucleotide and said second RNA oligonucleotide are independently between about 15 nucleotides to about 10,000 nucleotides in length.

Embodiment P42. The RNA compound of embodiment 40 or 41, wherein said first RNA oligonucleotide and said second RNA oligonucleotide are independently an mRNA, a gRNA, an sgRNA, an shRNA, a siRNA, a tRNA, a long non-coding RNA, an rRNA or a ribozyme.

Embodiment P43. The RNA compound of embodiment 42, wherein said first RNA oligonucleotide is a first sgRNA and said second RNA oligonucleotide is a second sgRNA.

Embodiment P44. The RNA compound of embodiment 43, wherein the first RNA stem loop is the stem loop 2 of the first sgRNA and the second RNA stem loop is the tetra-loop of the second sgRNA.

Embodiment P45. The RNA compound of embodiment 43, wherein the first RNA stem loop is the tetra-loop of the first sgRNA and the second RNA stem loop is the stem loop 2 of the second sgRNA.

Embodiment P46. The RNA compound of embodiment 39, wherein said first RNA stem loop and said second RNA stem loop are in the same RNA oligonucleotide.

Embodiment P47. The RNA compound of embodiment 46, wherein said RNA oligonucleotide is between about 15 nucleotides to about 10,000 nucleotides in length.

Embodiment P48. The RNA compound of embodiment 46 or 47, wherein said RNA oligonucleotide is an mRNA, a gRNA, an sgRNA, an shRNA, a siRNA, a tRNA, a long non-coding RNA, an rRNA or a ribozyme.

Embodiment P49. The RNA compound of embodiment 48, wherein said RNA oligonucleotide is an sgRNA.

Embodiment P50. The method of embodiment 49, wherein said first RNA stem loop is the stem loop 2 of the sgRNA and the second RNA stem loop is the tetra-loop of the sgRNA.

Embodiment P51. The method of embodiment 49, wherein said first RNA stem loop is the tetra-loop of the sgRNA and the second RNA stem loop is the stem loop 2 of the sgRNA.

Embodiment P52. The RNA compound of any one of embodiments 39-51, wherein $L^1$ is $-L^{101}-L^{102}-L^{103}-L^{104}-L^{105}-L^{106}-L^{107}-$;

$L^{101}$ is a bond, —C(O)—, —C(O)O—, —OC(O)—, —O—, —S—, —$NR^{101}$—, —C(O)$NR^{101}$—, —$NR^{101}$C(O)—, —$NR^{101}$C(O)O—, —OC(O)$NR^{101}$—, —$NR^{101}$C(O)$NR^{101}$—, —$NR^{101}$C(NH)$NR^{101}$—, —$S(O)_2$—, —$NR^{101}S(O)_2$—, —$S(O)_2NR^{101}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{102}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{103}$ is a bond, —C(O)—, —C(O)O—, —OC(O)—, —O—, —S—, —$NR^{103}$—, —C(O)$NR^{103}$—, —$NR^{103}$C(O)—, —$NR^{103}$C(O)O—, —OC(O)$NR^{103}$—, —$NR^{103}$C(O)$NR^{103}$—, —$NR^{103}$C(NH)$NR^{103}$—, —$S(O)_2$—, —$NR^{103}S(O)_2$—, —$S(O)_2NR^{103}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{104}$ is a bond, —C(O)—, —C(O)O—, —OC(O)—, —O—, —S—, —$NR^{104}$—, —C(O)$NR^{104}$—, —$NR^{104}$C(O)—, —$NR^{104}$C(O)O—, —OC(O)$NR^{104}$—, —$NR^{104}$C(O)$NR^{104}$—, —$NR^{104}$C(NH)$NR^{104}$—, —$S(O)_2$—, —$NR^{104}S(O)_2$—, —$S(O)_2NR^{104}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{105}$ is a bond, —C(O)—, —C(O)O—, —OC(O)—, —O—, —S—, —$NR^{105}$—, —C(O)$NR^{105}$—, —$NR^{105}$C(O)—, —$NR^{105}$C(O)O—, —OC(O)$NR^{105}$—, —$NR^{105}$C(O)$NR^{105}$—, —$NR^{105}$C(NH)$NR^{105}$—, —$S(O)_2$—, —$NR^{105}S(O)_2$—, —$S(O)_2NR^{105}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{106}$ is a bond, —C(O)—, —C(O)O—, —OC(O)—, —O—, —S—, $—NR^{106}—$, $—C(O)NR^{106}—$, $—NR^{106}C(O)—$, $—NR^{106}C(O)O—$, $—OC(O)NR^{106}—$, $—NR^{106}C(O)NR^{106}—$, $—NR^{106}C(NH)NR^{106}—$, $—S(O)_2—$, $—NR^{106}S(O)_2—$, $—S(O)_2NR^{106}—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{107}$ is a bond, —C(O)—, —C(O)O—, —OC(O)—, —O—, —S—, $—NR^{107}—$, $—C(O)NR^{107}—$, $—NR^{107}C(O)—$, $—NR^{107}C(O)O—$, $—OC(O)NR^{107}—$, $—NR^{107}C(O)NR^{107}—$, $—NR^{107}C(NH)NR^{107}—$, $—S(O)_2—$, $—NR^{107}S(O)_2—$, $—S(O)_2NR^{107}—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker; and each $R^{101}$, $R^{102}$, $R^{103}$, $R^{104}$, $R^{105}$, $R^{106}$, and $R^{107}$ is independently hydrogen, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P53. The RNA compound of embodiment 52, wherein $L^1$ is $-L^{101}-L^{102}-L^{103}-(CH_2CH_2O)_n-L^{105}-L^{106}-L^{107}-$; and n is an integer from 1 to 20.

Embodiment P54. The RNA compound of embodiment 53, wherein $L^{101}$, $L^{102}$, $L^{103}$, $L^{105}$, $L^{106}$, and $L^{107}$ are independently substituted or unsubstituted 2 to 10 membered heteroalkylene.

Embodiment P55. The RNA compound of embodiment 53 or 53, wherein n is an integer from 2 to 10.

Embodiment P56. The RNA compound of embodiment 52, wherein $L^{101}$ is an unsubstituted 2 to 10 membered heteroalkylene;

$L^{102}$ is a substituted 2 to 16 membered heteroalkylene;

$L^{103}$ is a substituted $C_1$-$C_6$ alkylene;

$L^{104}$ is an unsubstituted 5 to 6 membered heteroarylene;

$L^{105}$ is a substituted 2 to 10 membered heteroalkylene;

$L^{106}$ is an unsubstituted $C_1$-$C_6$ alkylene; and $L^{107}$ is an unsubstituted 2 to 10 membered heteroalkylene.

Embodiment P57. The RNA compound of embodiment 56, wherein $L^{104}$ is an unsubstituted triazolylene.

Embodiment P58. The RNA compound of embodiment 52, wherein $L^{101}$ is an unsubstituted 2 to 10 membered heteroalkylene;

$L^{102}$ is a substituted 2 to 16 membered heteroalkylene;

$L^{103}$ is a substituted phenylene;

$L^{104}$ is a substituted 2 to 10 membered heteroalkylene;

$L^{105}$ is $—(CH_2CH_2O)_1—$;

$L^{106}$ is a substituted 2 to 10 membered heteroalkylene;

$L^{107}$ is an unsubstituted 2 to 10 membered heteroalkylene; and n is an integer from 1 to 20.

Embodiment P59. The RNA compound of embodiment 58, wherein n is an integer from 2 to 10.

Embodiment P60. The RNA compound of embodiment 52, wherein $L^{101}$ is an unsubstituted 2 to 10 membered heteroalkylene;

$L^{102}$ is a substituted 2 to 16 membered heteroalkylene;

$L^{103}$ is a substituted phenylene;

$L^{104}$ is a substituted 2 to 25 membered heteroalkylene;

$L^{105}$ is an unsubstituted 5 to 6 membered heteroarylene;

$L^{106}$ is a substituted 2 to 16 membered heteroalkylene; and $L^{107}$ is an unsubstituted 2 to 10 membered heteroalkylene.

Embodiment P61. The RNA compound of embodiment 60, wherein $L^{105}$ is an unsubstituted triazolylene.

Embodiment P62. The RNA compound of any one of embodiments 52-61, wherein $L^{101}$ is $—CH_2NH—$ and $L^{107}$ is $—NHCH_2—$.

Embodiment P63. The RNA compound of any one of embodiments 39-62, wherein $L^1$ comprises a photo-cleavable site.

Embodiment P64. The RNA compound of any one of embodiments 39-52, wherein $L^1$ comprises a peptide linker.

Embodiment P65. The RNA compound of any one of embodiment 64, wherein said peptide linker comprises a protease cleavable site.

Embodiment P66. The RNA compound of embodiment 65, wherein said protease cleavable site is a matrix metalloprotease (MMP) cleavage site, a metalloprotease domain-containing (ADAM) metalloprotease cleavage site, a lysosomal cathepsin cleavage site (ALAL), or a legumain endopeptidase cleavage site (TANL).

Embodiment P67. The RNA compound of any one of embodiments 39-52, wherein $L^1$ comprises a pH sensitive cleavable site.

Embodiment P68. The RNA compound of any one of embodiments 39-67, wherein the distance between $R^1$ and $R^2$ is from about 20 Å to about 200 Å.

Embodiment P69. The RNA compound of embodiment 68, wherein the distance between $R^1$ and $R^2$ is from about 40 Å to 80 Å.

Embodiment P70. A cell comprising the RNA compound of any one of embodiments 39-69.

EXAMPLES

Example 1: Introduction to Exemplary Experiments

Chemical cross-linking enables rapid identification of RNA-protein and RNA-nucleic acid inter- and intramolecular interactions. However, no method exists to site-specifically and covalently cross-link two user-defined sites within an RNA. Here, we develop RNA-CLAMP, which enables site-specific and enzymatic cross-linking (clamping) of two selected guanine residues within an RNA. Intramolecular clamping can disrupt normal RNA function, whereas subsequent photo-cleavage of the crosslinker restores activity. We used RNA-CLAMP to clamp two stem loops within the single-guide RNA (sgRNA) of the CRISPR-Cas9 gene editing system via a photo-cleavable cross-linker, completely inhibiting editing. Visible light irradiation cleaved the cross-linker and restored gene editing with high spatiotemporal resolution. Design of two photo-cleavable linkers responsive to different wavelengths of light allowed multiplexed photo-activation of gene editing in mammalian cells. This photo-activated CRISPR-Cas9 gene editing platform benefits from undetectable background activity, provides a choice of activation wavelengths, and has multiplexing capabilities.

To the best of our knowledge, these techniques are the only CRISPR-Cas9 gene editing photo-regulation technique to date which avoids the use of toxic UV light and offers multiplexing capability with no background gene editing activity. Moreover, it is believed that this 'RNA-CLAMP' technique will serve as an extremely powerful and versatile technology in controlling the functions of other types of RNAs, for example, mRNA, shRNA, and ribozymes. The further development of the 'RNA-CLAMP' will greatly expand the RNA modifying toolbox.

Example 2: Multiplexed Photo-Activation of CRISPR/Cas9 Gene Editing by RNA-CLAMP Abstract We developed a versatile and powerful RNA modifying technique, named 'RNA-CLAMP', which enables site-specific and enzymatic cross-linking of two selected guanine residues within an RNA of interest. This covalent 'clamp' rigidifies the RNA, resulting in loss-of-function. By utilizing a photo-cleavable crosslinker, we are able to use light irradiation to release the 'clamped' RNA, resulting in gain-of-function. We applied the 'RNA-CLAMP' technique to the single guide RNA (sgRNA) of the CRISPR-Cas9 system. Upon intramolecular 'clamping' of the tetra-loop and the stemloop-2 of the sgRNA, the CRISPR/Cas9 gene editing activity was completely quenched. Visible light irradiation cleaves the photo-cleavable linker, restoring CRISPR-Cas9 gene editing activity with high spatiotemporal (single cell) resolution. Notably, by using two photo-cleavable cross-linkers which are responsive to two different wavelength of lights, we achieved multiplexed photo-activation of gene editing. Our technique offers great dynamic range of manipulation with no background at the caged stage and high activation rate.

Introduction

Numerous approaches have been developed to study and control RNA function. RNA probes often rely on non-covalent interactions, as in anti-sense DNA oligos, MS2-tagging, or RNA aptamers.[1-2] Covalent RNA modification strategies offer an additional level of robustness, which can be critical for analyzing or manipulating less abundant RNAs, especially in harsh cellular conditions. However, due to the complex structure and relative instability of RNA, site-specific and covalent modification of RNA remains challenging.[3-5] Chemical cross-linking enables rapid identification of RNA-protein and RNA-nucleic acid inter- and intramolecular interactions, as well as structural studies of complex RNAs.[6-8] However, to date, no method exists to achieve site-specific and covalent cross-linking of two user-defined sites within an RNA of interest. Many RNAs, such as the single-guide RNA (sgRNA) of the CRISPR gene editing system, require secondary and tertiary structure for function, indicating that site-specific cross-linking of two internal nucleotides within an RNA of interest would be useful for studying and manipulating RNA function. Here, we report an RNA-modifying technique, termed RNA-CLAMP, which allows for post-transcriptional and site-specific cross-linking of two guanine nucleotides within a single RNA of interest through a one-step enzymatic process. We applied the RNA-CLAMP technique to the sgRNA of CRISPR-Cas9 and achieved optical control of gene editing in mammalian cells with high spatiotemporal resolution and multiplexing capability.

Conditionally activated CRISPR-Cas9 gene editing systems allow for greater gene editing precision by limiting Cas9-mediated DNA cleavage to a specific time and location.[9-13] Optical control of CRISPR-Cas9 offers non-invasive manipulation of gene editing with high spatiotemporal resolution. Several approaches have been developed to optically control CRISPR-Cas9 gene editing by modifying either the Cas9 protein or the gRNA. For example, a genetically encoded light-activated Cas9 has caged lysine amino acids encoded within the Cas9 protein,[14] and split Cas9 proteins have been fused to a pair of photo-dimerizing proteins to allow optical control of CRISPR-Cas9 gene editing.[15] However, these approaches can suffer from incomplete caging and compromised activity when uncaged. Optical control via the gRNA includes, for example, using photo-cleavable DNA oligonucleotides that are complementary to the 20-nt target region of the gRNA to block binding to the target DNA.[16] The caged gRNA can be released upon photo-cleavage of the protector DNA oligo, resulting in activation of gene editing.[16] However, toxic UV light had to be applied to cells during activation to release the chemical linker used to synthesize the protector DNA oligo. Caged gRNA has been generated by substituting four nucleobases within the 5'-protospacer region with caged nucleobases during solid-state RNA synthesis.[17] This approach achieves high activation rates and low background at the caged stage. However, it requires solid-state synthesis, which is not widely accessible, and each gRNA needs to be individually designed and optimized for its DNA target. UV light was also used to activate the gRNA.

Currently, no optically-modulated CRISPR editing system is capable of using multiple wavelengths of light to achieve multiplex editing, possibly due to the reliance of UV-activated photoprotecting groups. To develop a robust, versatile, photo-activated CRISPR-Cas9 editing system capable of using visible light we asked whether RNA-CLAMP could be adapted to control gRNA activity via site-specifically cross-linking the gRNA with photocleavable linkers. Cas9's endonuclease activity requires the binding of gRNA, following by the formation of the Cas9-gRNA ribonucleoprotein (RNP). After interacting with the protospacer adjacent motif near the target DNA, the RNP complex goes through a conformational change, which is critical to its nuclease activity.[18-22] Thus, we reasoned that cross-linking the internal loops of the gRNA would reduce the conformational flexibility of the Cas9-gRNA RNP, resulting in loss-of-function. Subsequent cleavage of the cross-linker would remove the conformational restraint on the gRNA and activate gene editing. Here, we used RNA-CLAMP to cross-link two internal stem loops within the sgRNA. Upon clamping of the sgRNA, the Cas9-sgRNA RNP completely loses its DNA cleavage activity. Photo-cleavage of the crosslinker releases the gRNA and fully restores gene editing activity. Notably, cross-linkers that are responsive to different wavelengths of light can be used, allowing selection of the gene editing activation wavelength. We demonstrate multiplexed photo-activation of gene editing at two different genomic loci. The high efficiency of photo-activation enables spatiotemporal control, and we show that our technique allows gene editing within a single cell among a population of cells, which can be traced by time-lapse microscopy.

Site-Specific Cross-Linking of RNA by RNA-CLAMP

We previously developed a technique, RNA transglycosylation at guanosine (RNA-TAG), which enables site-specific and covalent conjugation of small molecule effectors, such as fluorophores, affinity tags, or translational regulators, onto an RNA of interest.[23] RNA-TAG utilizes a bacterial tRNA guanine transglycosylase (TGT) to exchange a guanine nucleobase within a specific 17-nucleotide RNA stem loop structure (Tag) with a modified analog of the natural substrate preqeuosine1 (preQ1). The RNA-TAG is carried out by a bacterial (*E. coli*) tRNA guanine transglycosylase (TGT), whose natural substrate is the nitrogenous base preQ1. Remarkably, we have successfully incorporated large functional groups including biotin, BODIPY, thiazole orange, and Cy7 through a polyethylene glycol linker attached to the exocyclic amine of preQ1. Larger RNAs, such as mRNA transcripts, can be site-specifically labeled if they possess the 17-nucleotide hairpin recognition motif. The RNA-TAG methodology could facilitate the detection and manipulation of RNA molecules by enabling the direct incorporation of functional artificial nucleobases using a simple hairpin recognition element (FIG. 1).

Figure 8A:
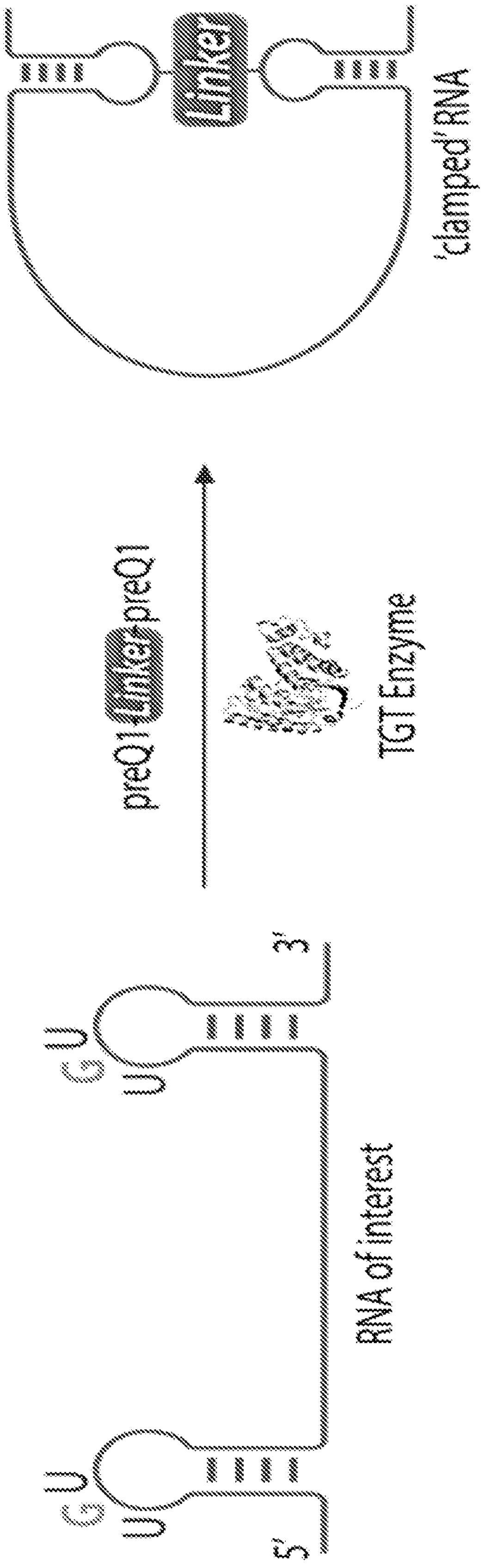
FIGS. 8A-8B.
Figure 8B:
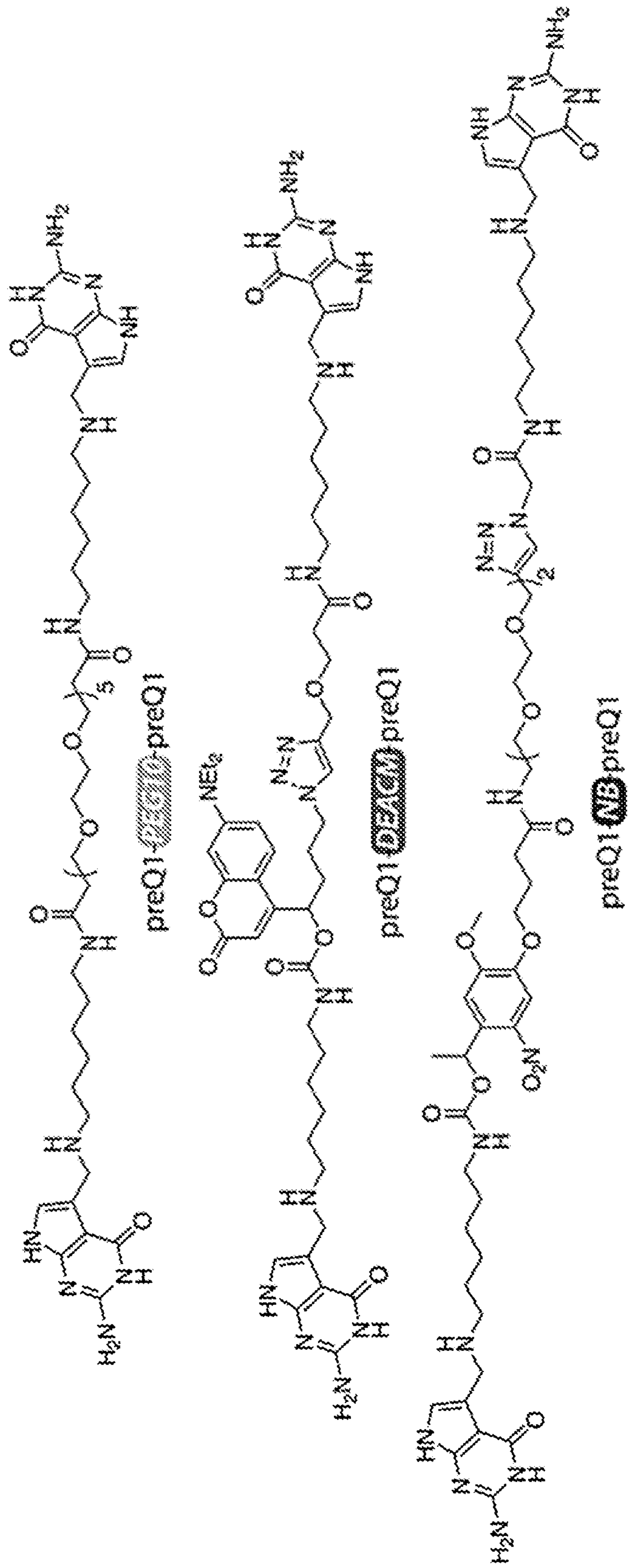

Covalent modification is site-specific, robust, and irreversible, and RNA-TAG technology has been adapted to image cellular RNA in fixed cells, regulate mRNA translation, and study RNA-protein interactions.[23-28] RNA-TAG could, in principle, be used to cyclize RNA targets with synthetic linkers, achieved by introducing two recognition sites on a single RNA, and then creating an internal cross-link using a bivalent linker (FIG. 8). Crosslinking would likely affect the structure of the RNA, thus interfering with its normal function, whereas the cleavage of the cross-linker would release the RNA, resulting in restoration of function.

CRISPR/Cas9 genome editing has become an extremely active topic in both biological sciences and gene therapeutic applications. Tools that allow researchers to spatiotemporally control gene editing may promote study of gene functions with a high precision and reduce off-targeting mutations by activating gene editing at a certain time and location.[9,10] We have seen a fast development of CRISPR/Cas9 gene editing techniques since 2012, when Martin Jinek, etc., discovered that Cas9 can act as a programmable RNA-guided DNA endonuclease.[11] Since then, many techniques have been developed to achieve chemical control of the CRISPR/Cas9 gene editing. For example, small-molecule inducers, such as doxycycline and rapamycin were used to induce gene editing in cells.[12,13] Also, conditional activation of CRISPR/Cas9 gene editing can also be achieved via transient delivery of purified Cas9:sgRNA complex.[14,15] These chemical methods have been used for generating conditional gene knockins/knockouts and reducing off-target gene editing. However, these approaches have limitations. [1] some small-molecule inducers, for example rapamycin, have undesirable biological effects and toxicity; [2] the slow diffusion rate of small-molecule inducers makes the regulation of gene editing less responsive and precise.

On the other hand, optical control of gene editing can overcome these challenges. First, a high spatiotemporal resolution can be achieved by the use of light. Second, by controlling the irradiation time period and light intensity, toxic effects can be minimized. Third, different wavelength of lights can be used to regulation different cellular process, enabling multiplexed manipulation of certain cellular processes. To date, there has been several approaches developed to achieve optical control of CRISPR/Cas9 gene editing. These techniques can be classified into two categories: the protein (Cas9) centric approaches and the guide RNA centric approaches.

Protein centric approaches aim to modify some key amino acid residues on the Cas9 in order to control the protein functions. Some alternative strategies use a split version of Cas9 that are fused to a pair of photo-dimerizing proteins, to achieve photo-control of CRISPR/Cas9. For example, James Hemphill, etc. developed a genetically encoded light-activated Cas9 by engineering a caged lysine amino acid within the Cas9 protein.[16] In this manner, several lysine residues were identified as possible caging sites. By irradiation with 365 nm UV light, the activity of the caged Cas9 can be restored up to wild-type level. For another example, Yuta Nihongaki and the co-workers engineered a photo-activatable Cas9 which consists of split Cas9 fragments and photoinducible dimerization domains.[17] The blue light irradiation brings together the photoinducible dimerization domains, activating the Cas9. In contrast, the function of Cas9 was deactivated without light irradiation. Note that these approaches either uses toxic UV light or the dynamic range of activation/deactivation was not great.

Figure 2:
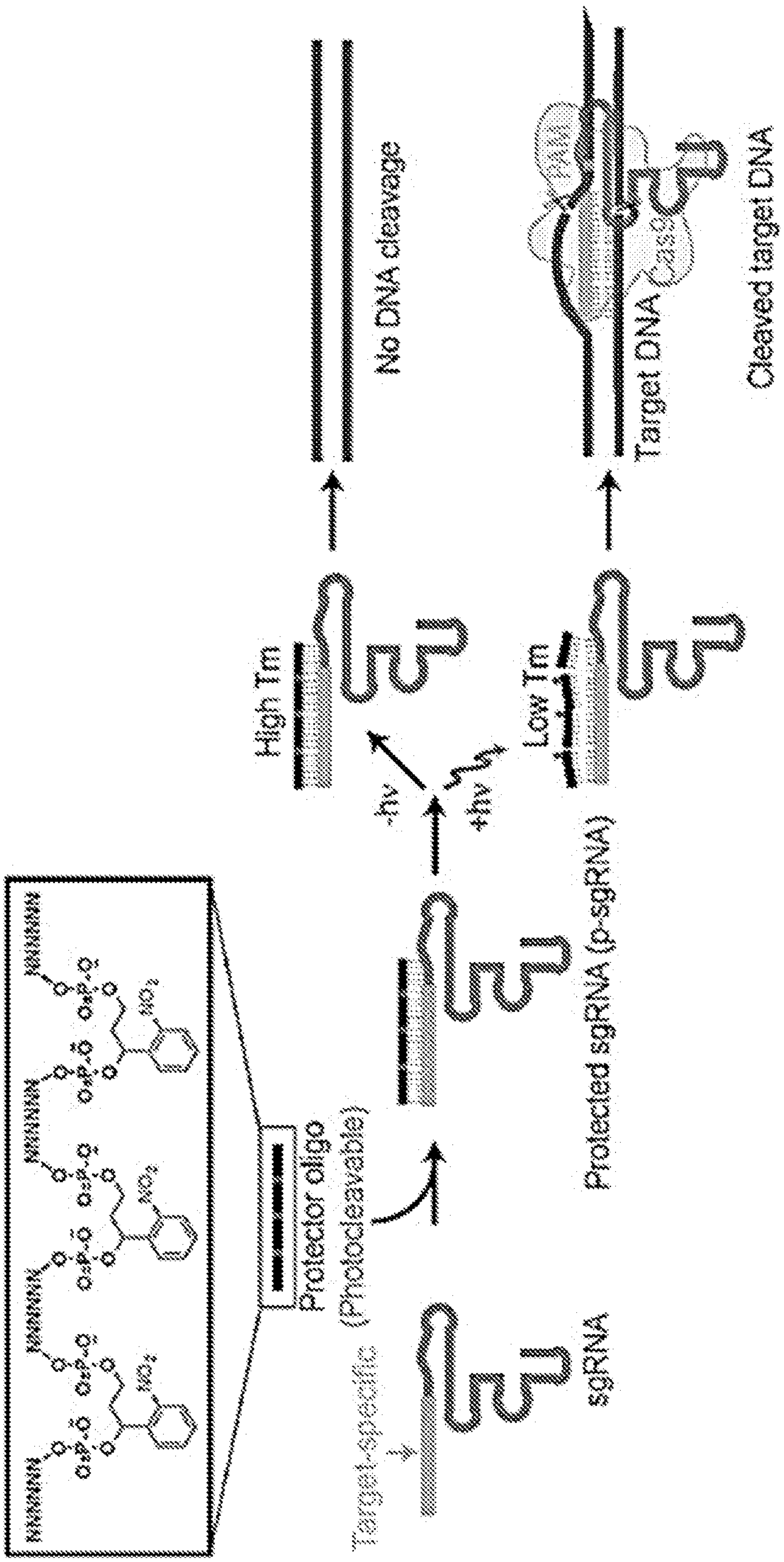
FIG. 2. Light-Activated CRISPR Using Guide RNAs with Photocleavable Protectors.[18]

Guide RNA centric approaches, in contrast, focus on modifying the single guide RNA or the trans-acting RNA/crispr RNA pair to control the function of gene editing. A typical strategy uses photocleavable DNA oligonucleotides that are complement to the target regions of the sgRNA to quench the activity of gene editing. Upon on photo-irradiation, the lower melting temperature of the shorter DNA oligos lose their ability to bind to the sgRNA, activating the gene editing (FIG. 2).[18] More recent study engineered caged gRNAs by substituting four nucleobases evenly distributed throughout the 5'-protospacer region with caged nucleobases during solid-state RNA synthesis.[19] This approach has achieved better dynamic range. However, it still required solid-state synthesis and each sgRNA has to be individually designed for different DNA targets. Again, a toxic UV light has to be used for the activation of sgRNA.

Photo-regulation offers rapid and non-invasive manipulation of cellular processes. There have been many approaches developed for the photo-regulation of CRISPR-Cas9 gene editing. Most of the current methods suffer from major drop backs as discussed above. Therefore, a method that enables photo-regulation of gene editing using visible light with high dynamic range will be highly desired. Most current methods use bulky groups to hinder the binding between the Cas9 with sgRNA or the binding between sgRNA with target DNA, in order to block the gene editing process.[16,17,19] Because of the lack of robustness of such non-covalent interactions, it is challenging to achieve a complete inhibition of gene editing. Besides, different blocking molecules, incuding anti-sense blocking oligonucleotides, have to by synthesized for each sgRNA. This process is expensive and time-consuming. The inhibition efficacy could also vary between targets, making such approaches less robust.

Figure 3A:
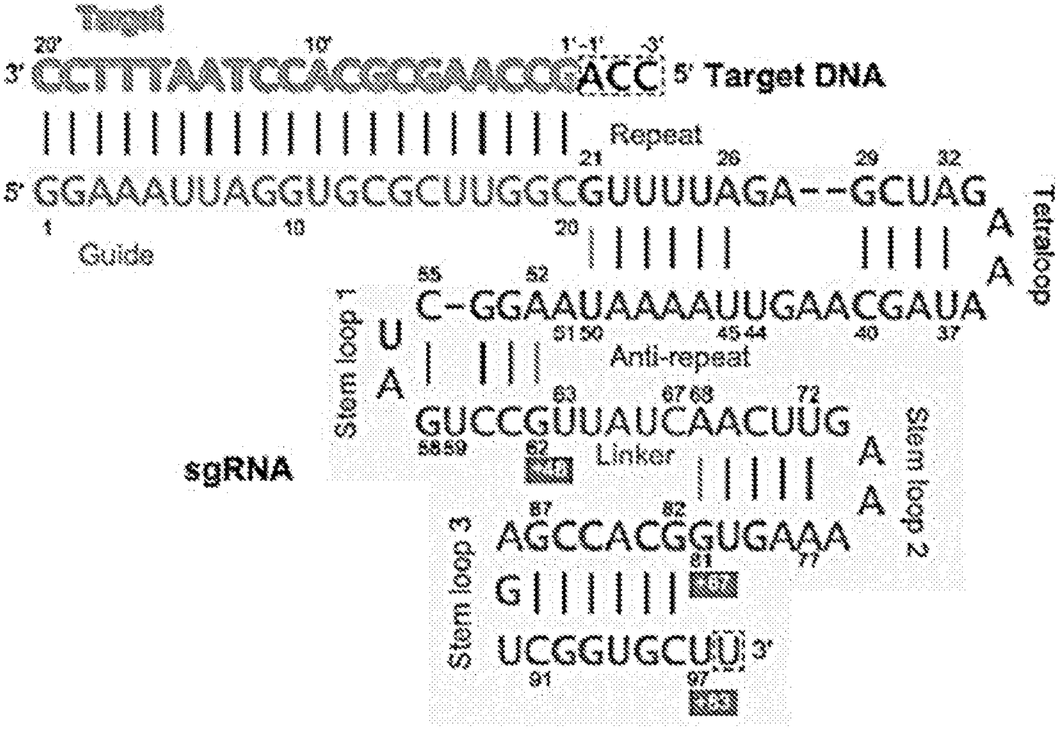
FIGS. 3A and 3B. Structure of the FIG. 3A. sgRNA in CRISPR/Cas9 system and the FIG. 3B sgRNA.[20] The crystal structure of dCas9 in complex with sgRNA (SEQ ID NO:4) and target DNA (SEQ ID NO:3) has been solved.
Figure 3B:
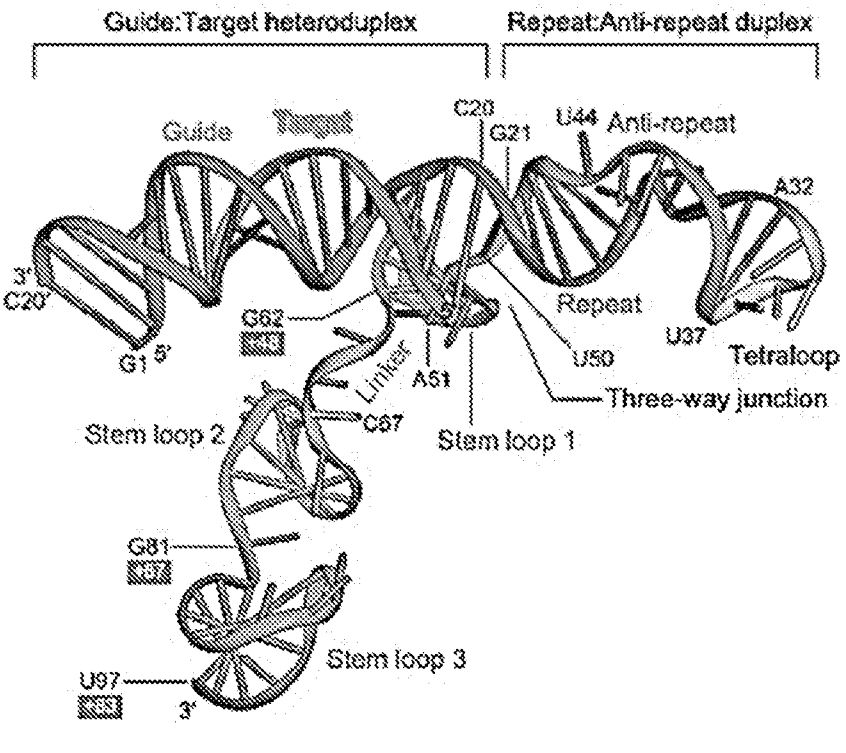
Figure 4:
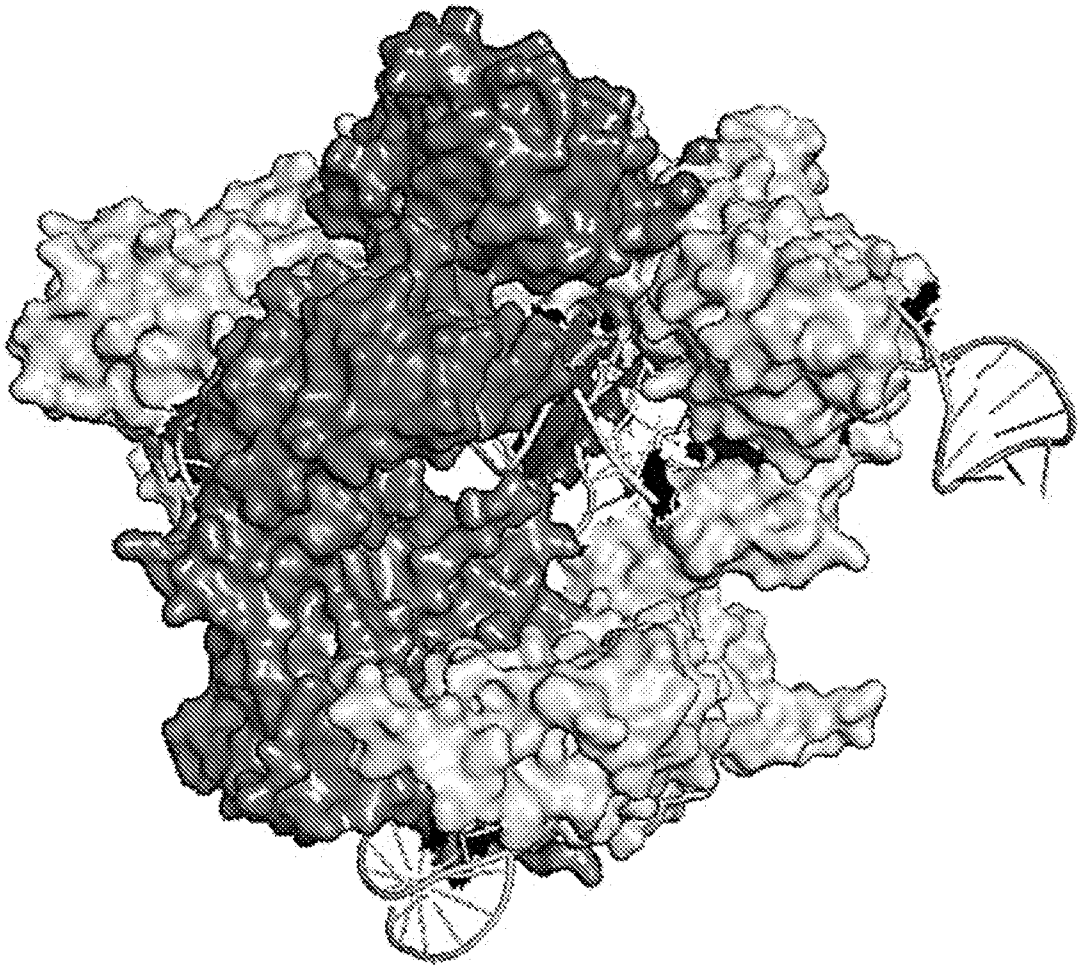
FIG. 4. The crystal structure of dCas9 in complex with sgRNA and target DNA.[20]

Fortunately, the crystal structure of dCas9 in complex with sgRNA and the target DNA provides insight into how the gene editing system works in the living system.[20] The sgRNA is a chimeric version of the wild-type trans-acting RNA and crRNA hybrid (FIGS. 3A and 3B). By inserting an artificial loop, the tetra-loop between the trans-acting RNA and the crRNA, the RNA hybrid can be stabilized, resulting easy-of-use and greater editing efficiency. In total, there are four stem-loops within the sgRNA, including the tetra-loop. As shown in the crystal structure (FIG. 4), Cas9 consists of two lobes: a recognition (REC) lobe and a nuclease (NUC) lobe (FIG. 4). The REC lobe can be divided into three regions, a long a helix referred to as the bridge helix (residues 60-93), the REC1 (residues 94-179 and 308-713)

domain, and the REC2 (residues 180-307) domain. This lobe is primarily interacting with the repeat:anti-Repeat duplex of the sgRNA. The NUC lobe consists of the RuvC (residues 1-59, 718-769, and 909-1098), HNH (residues 775-908), and PAM-interacting (PI) (residues 1099-1368) domains. This lobe is responsible for cleaving the target DNA under proper conformation. And the negatively charged sgRNA: target DNA heteroduplex is placed in the positively charged groove at the interface between the REC and NUC lobes.

Figure 5:
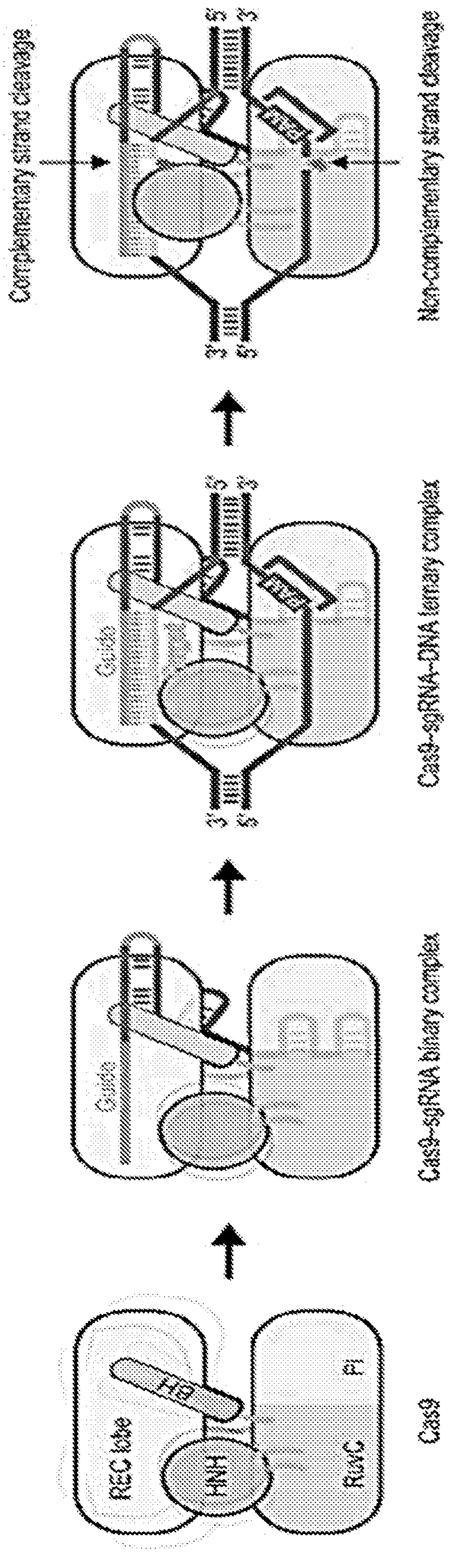
FIG. 5. A cartoon showing the proposed Model of RNA-guided DNA cleavage by Cas9.[20]

The sgRNA can be divided into two parts, the REC-interacting sequences and the RuvC interacting sequences. These two parts are connected flexible linker (UUAUC) (SEQ ID NO:42) (FIGS. 3A and 3B). The guide:target and repeat:anti-repeat duplexes are deeply buried in a positively charged groove at the interface of the two lobes, whereas the rest of the sgRNA extensively interacts with the positively charged surface on the back side of the protein. It is also found that the sgRNA:DNA Complex adopts a T-Shaped architecture, which is critical for the Cas9 to be in a functional conformation to perform the DNA cleavage. Based on the crystal structure, we hypothesize the flexible of Cas9 and sgRNA is likely to play a role in the assembly of the Cas9-sgRNA-DNA ternary complex. In summary, the CRISPR/Cas9 system may cleave the target DNA in the following three steps (FIG. 5).

1. Cas9 alone is complete inactive and unable to cleave DNA. The REC and RuvC lobes are not in a functional conformation. The addition of the sgRNA stabilizes the Cas9 protein by binding to the Bridge Helix. The stem-loop of the sgRNA also interacts with different domains of the Cas9, reinforcing the interactions.

2. The sgRNA then guides the Cas9-sgRNA complex to the genome target, where the PAM interacting domain of the Cas9 interacts the PAM sequencing, forcing the Cas9 into a functional conformation.

3. After the conformational activation, the DNA cleavage occurs at both the complementary and non-complementary strands.

Since the flexibility of the Cas9-sgRNA complex is critical to the function of the DNA cleavage, we may be able to structurally hinder this process by destroying this flexibility. RNA-TAG is a versatile and powerful RNA labeling tool. And sgRNA contains multiple stem-loop, which can be potentially labeled by TGT enzyme with sequence modifications. Thus, we tested the RNA-TAG technique to modify these stem-loop within the sgRNA sequence in order to hinder the Cas9 DNA cleavage activity. Since we were able to incorporate a photo-sensitive cage onto the RNA of interest, in this case, the sgRNA, we could use external light to release the 'photo-cage', therefore activating CRISPR/Cas9 gene editing upon light irradiation.

RNA-CLAMP: A Powerful Technique to Manipulate RNA

Figure 6:
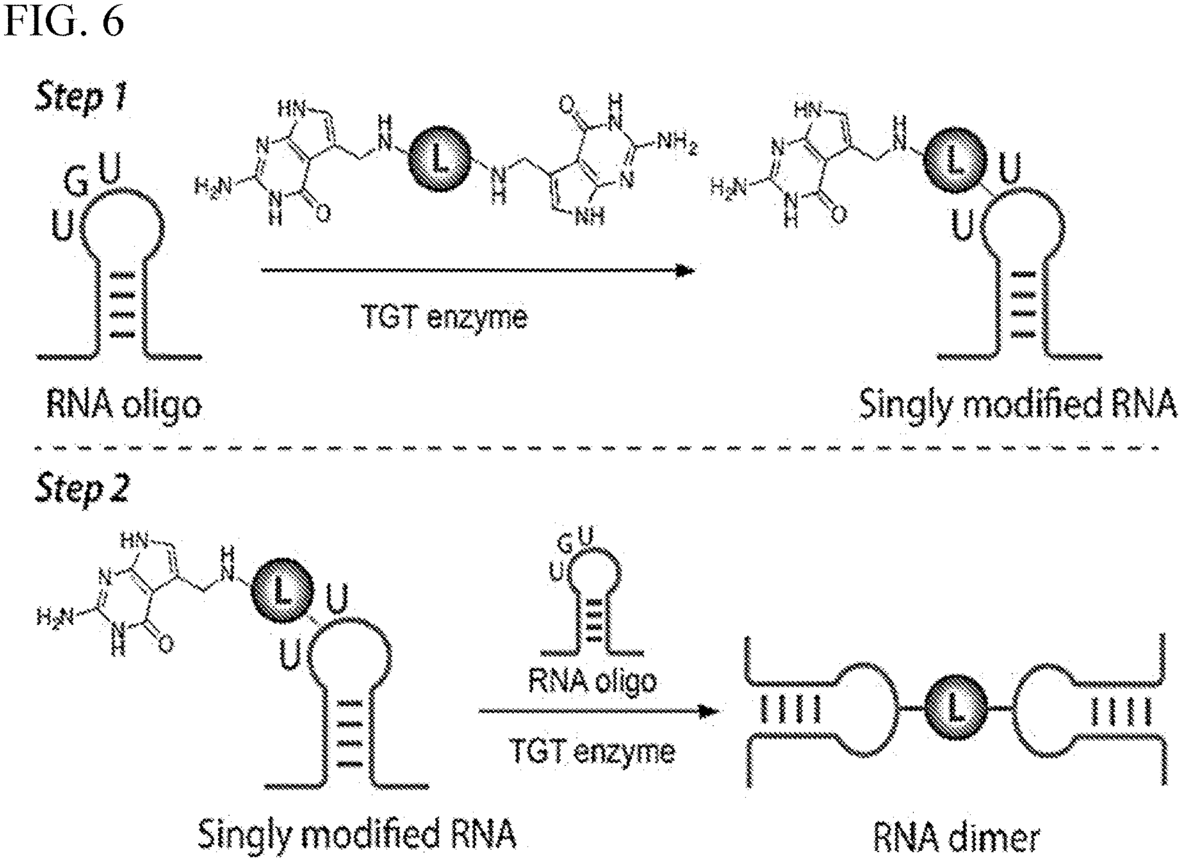
FIG. 6. A schematic of the two-step RNA oligo dimerization.
Figure 7:
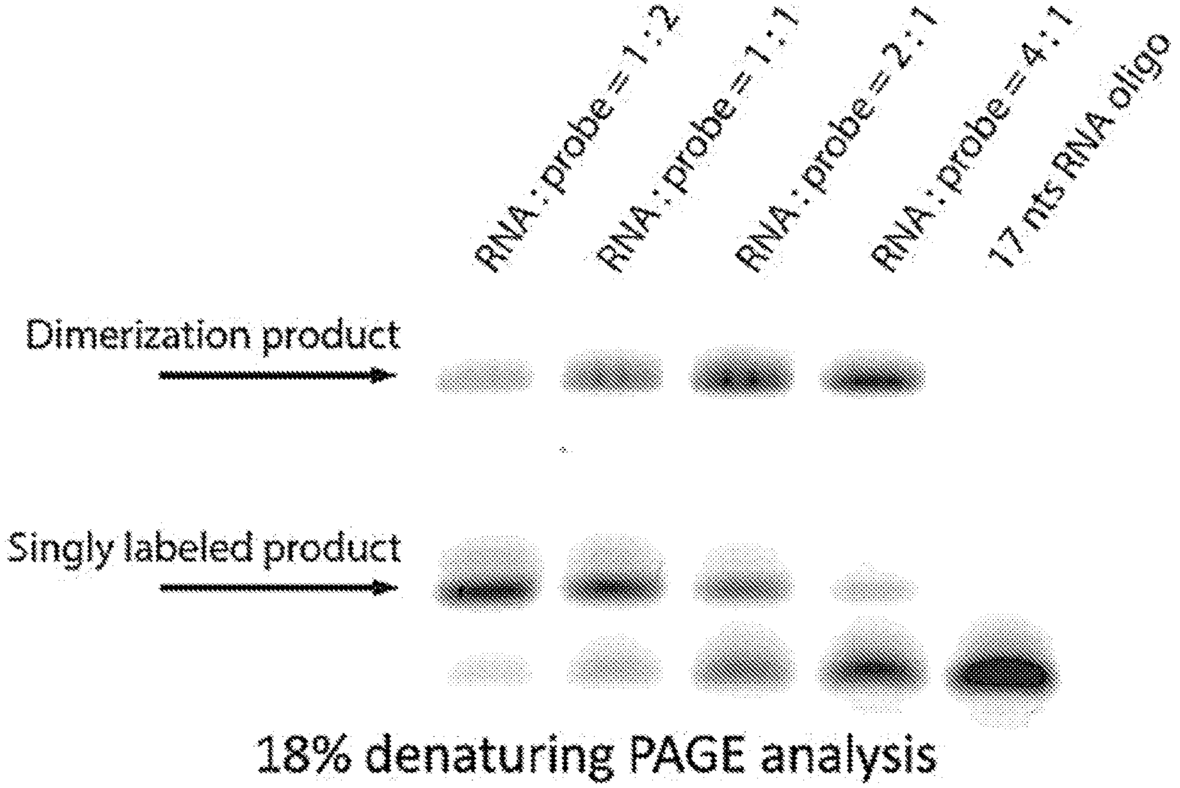
FIG. 7. 18% denaturing PAGE analysis of RNA dimerization. The bottom RNA bands represent the starting material, which is the 17-nt RNA oligo. The middle bands represent the singly labeled RNA oligo. The top bands represents the RNA dimer. By altering the RNA:preQ1-PEG10-preQ1 ratio, different conversions for the singly labeled product and dimer product were observed. The results demonstrated that the TGT enzyme can accept a preQ1 moiety bearing a large biomacromolecule, in this case a RNA oligo, and incorporated it onto an RNA of interest.

The enzymatic TGT approach has not been examined for dimerization/cyclization of RNA. The dimerization/cyclization process is different than traditional RNA labeling using the RNA-TAG technique. For instance, the RNA dimerization process as a two-step process (FIG. 6). The RNA enzyme substrates are the 17-nt RNA oligos. The small-molecule substrate is the synthesized preQ1-PEG10-preQ1, bearing two preQ1 moieties to facilitate dual-modification. Thus, the first step of the dimerization process is the traditional TGT labeling process, which involves the incorporation of the preQ1-PEG-preQ1 on the RNA oligo. The product is a singly labeled RNA. For the second labeling, however, the traditional small-molecule substrate is now a conjugated RNA oligo, which is much bulkier than a small-molecule substrate.

Figure 28A:
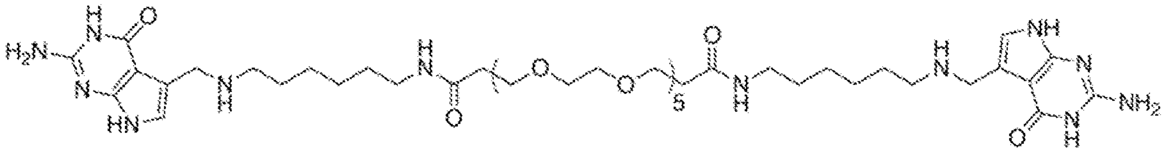
FIGS. 28A-28B. TGT labeling of the 17-nt RNA 'Tag' oligo using the FIG. 27A. PreQ1-PEG10-preQ1 small-molecule substrate (used without purification in this experiment).
Figure 28B:
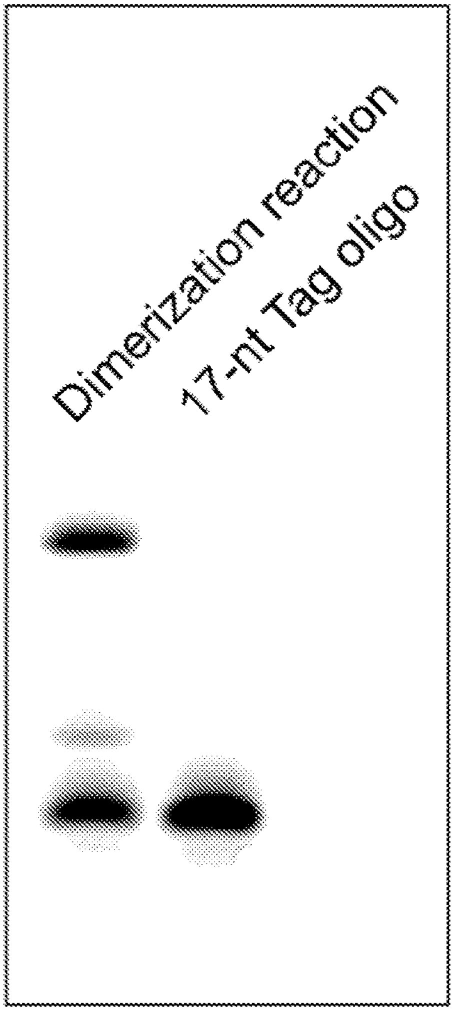

To determine whether RNA-TAG can be used for RNA intramolecular cross-linking (or clamping) we first verified that TGT enzymes accepted a bivalent linker (preQ1-PEG10-preQ1) and were able to dimerize small model RNA hairpins (FIGS. 28A-28B). To enable intramolecular cross-linking, an RNA substrate must have two TGT recognition motifs. Therefore, we designed a 74-nt long RNA molecule (RNA-1) with two Tag sequences and performed TGT enzymatic labeling using the preQ1-PEG10-preQ1 linker (FIG. 8A). To distinguish between the various RNA products (FIG. 9, 10A), we designed an RNAse-H digestion assay (FIG. 10B), which specifically cleaves DNA-RNA hybrids.[29-31]

Figure 10A:
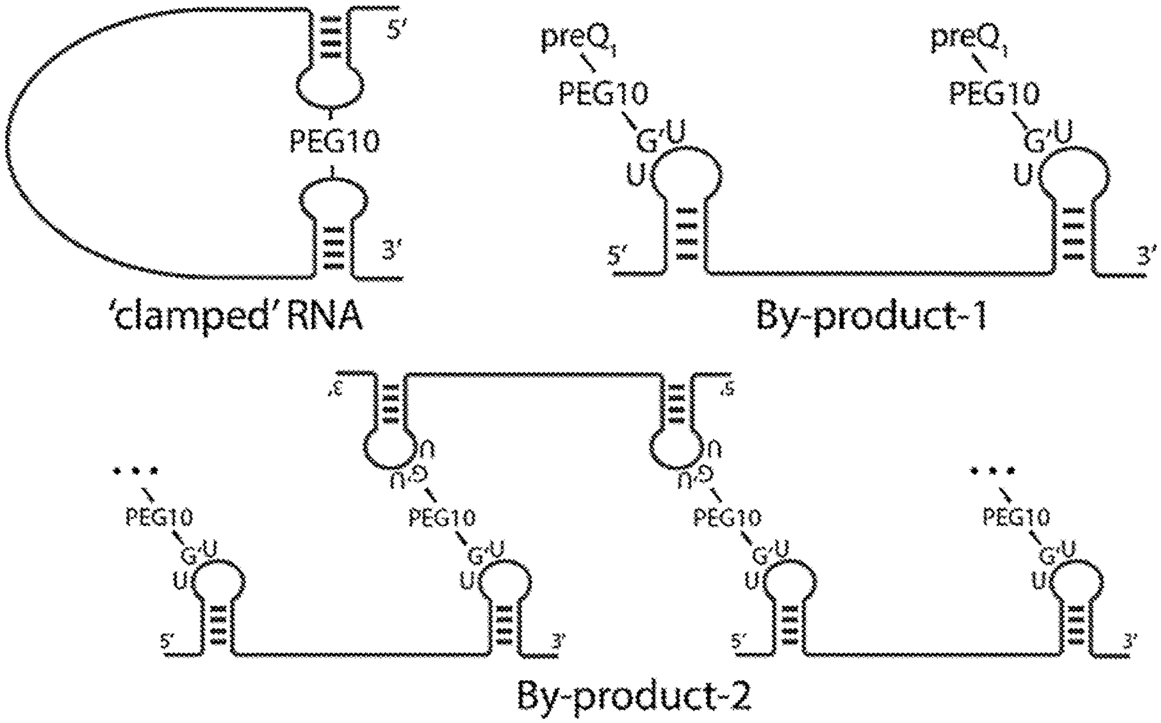
FIGS. 10A-10B.

Products from the RNA 'clamping' reaction are as described (FIG. 10A).

1. Both of the two hairpins within the RNA molecule get singly labeled by the TGT enzyme, generating a linear RNA molecule.

2. As desired, the preQ1-PEG10-preQ1 connects two hairpins, forming a 'clamped' RNA molecule. It should be noted that this RNA molecule still have two free ends. Thus, this is not a circular RNA molecule.

3. Because each RNA substrate has two potential modification sites, the reaction can generate a polymer containing different numbers of RNA molecules.

RNAse-H catalyzes the cleavage of RNA in an RNA/DNA substrate via a hydrolytic mechanism.[24] By designing a DNA template which is complementary to the RNA sequence along the RNA molecule, we can use RNAse-H to selectively cleave the RNA molecule. Through the DNA-templated RNAse-H digestion assay, the linear RNA product should be cleaved and generates two RNA fragments. The 'clamped' RNA products can also be cleaved. However, only one RNA fragment should be detected after the cleavage because the two ends of the 'clamped' RNA are covalently connected by a PEG10 linker. The cleavage of the polymer RNA construct should generate multiple RNA fragments as digestion products. This RNAse-H digestion model is shown in FIG. 10. The denaturing PAGE analysis of the RNAse-H assay proves our hypothesis.

Figure 11:
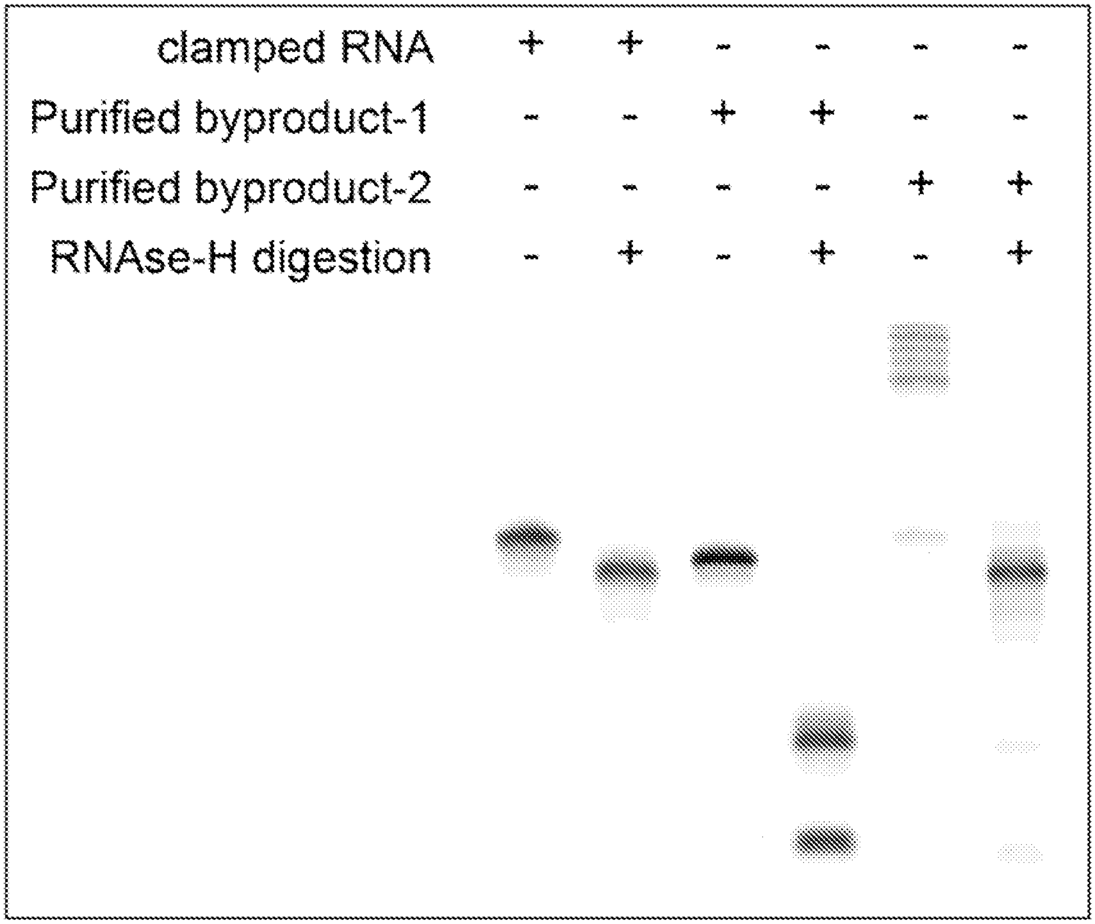
FIG. 11. RNAse-H digestion assay on the different RNA products after TGT clamping reaction. As expected, the 'clamped' RNA product resulted in a single RNA product after RNAse-H digestion. Other RNA by-products resulted in more than on RNA products after RNAse-H digestion.

Thus, using the DNA oligo which hybridizes to the RNA, we observed that clamped RNA showed a single-band RNAse-H digestion pattern, which is expected for an RNA that has been crosslinked intramolecularly. In contrast, all byproducts showed multi-band RNAse-H digestion patterns (FIG. 11). Thus, RNA-TAG can be used for site-specific and enzymatic cross-linking of two stem loops within an RNA of interest.

Figure 9:
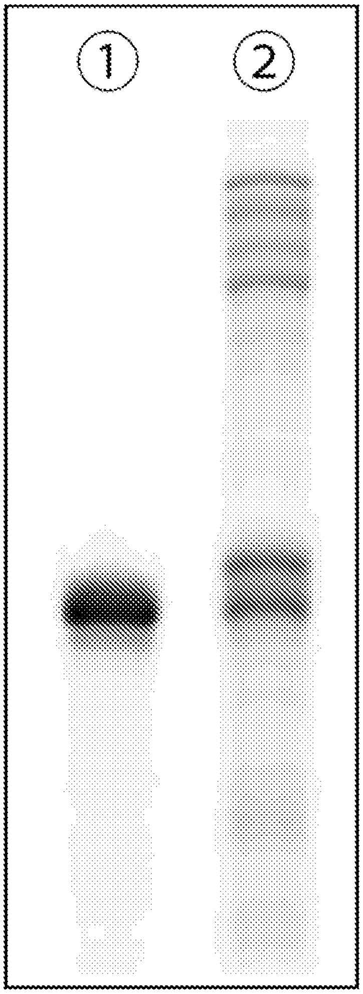
FIG. 9. 7% denaturing TBE PAGE analysis of the RNA clamping reaction. A) Line1: RNA-1 starting material. The purified RNA starting material (RNA-1) was presented as a single major band. Line2: multiple RNA products were observed after the TGT labeling reaction. RNA degradation was also observed shown as the smear bands below the RNA starting material.

Having demonstrated that RNA oligos can be dimerized by TGT labeling, we next examined whether the RNA-TAG technique can be used for RNA cyclization. To facilitate intramolecular cyclization, a RNA substrate needs to have two TGT enzymatic recognition sites. By using the small-molecule substrate, preQ1-PEG10-preQ1, a proposed RNA intramolecular cyclization reaction is shown in FIG. 8A. In this proposed reaction, two TGT enzymes bind to each RNA hairpin within the longer RNA. Next, the small-molecule substrate, preQ1-PEG10-preQ1 comes and connect the two RNA hairpins together, forming a open-ended circular RNA structure. It should be noted that unlike regular circular RNA, this 'clamped' RNA still have two free ends. Additionally, the sequence between these two hairpins should be flexible enough to enable the RNA 'clamping reaction. As a proof of concept, we designed a 100-nt RNA molecule with two Tags located at the ends. To ensure the flexibility of this RNA molecule, we designed the RNA sequence using m-fold to avoid strong secondary structures between these to hairpins.[21-23] The TGT labeling reaction was performed using the preQ1-PEG10-preQ1 linker to test whether an internal 'clamping' reaction can occur (FIG. 9).

sgRNA Crosslinking by RNA-CLAMP

Figure 12:
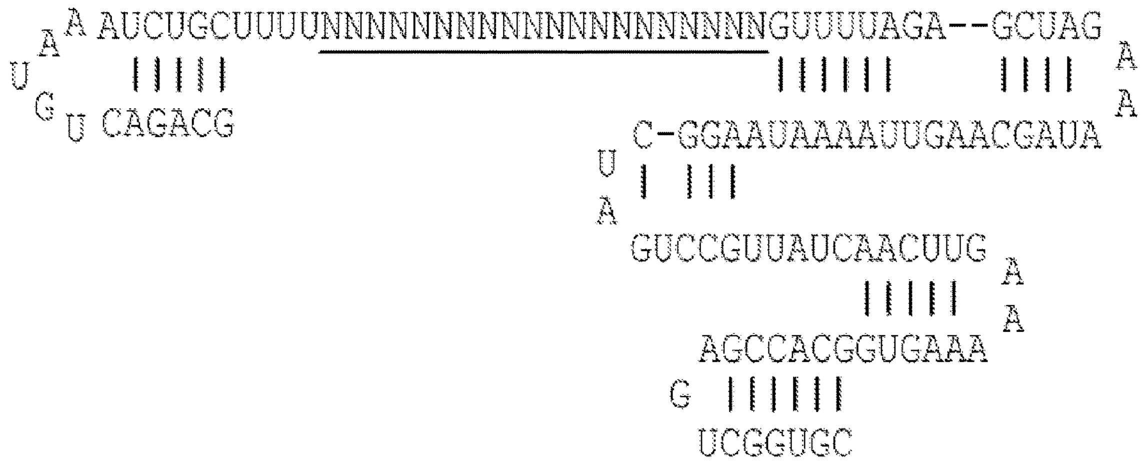
FIG. 12. Sequences of the wt-sgRNA (SEQ ID NO:8) and sgRNA-1 to sgRNA-10 (SEQ ID NO:9-18).
Figure 12:
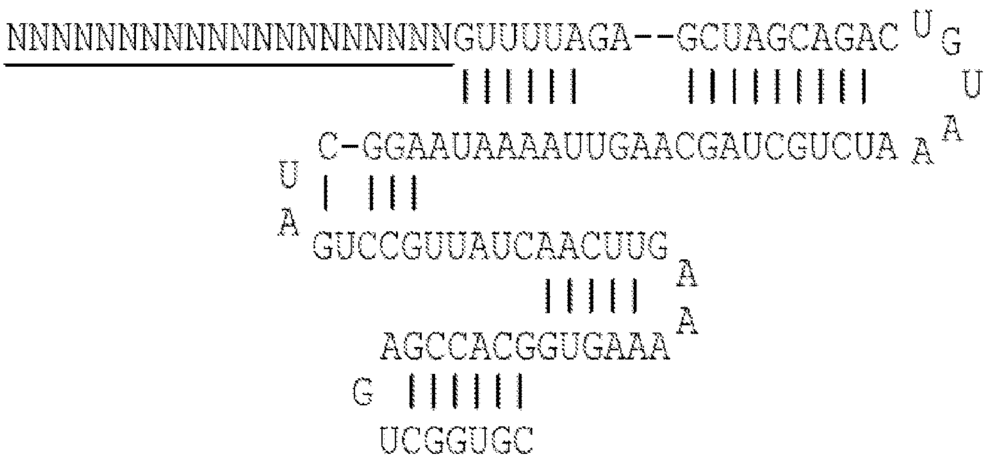
Figure 12:
Figure 12:
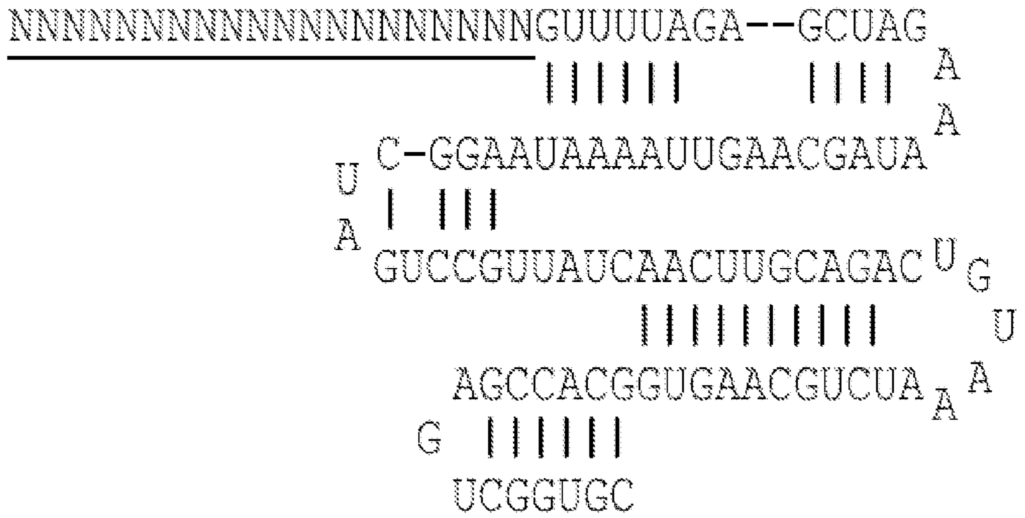
Figure 12:
Figure 12:
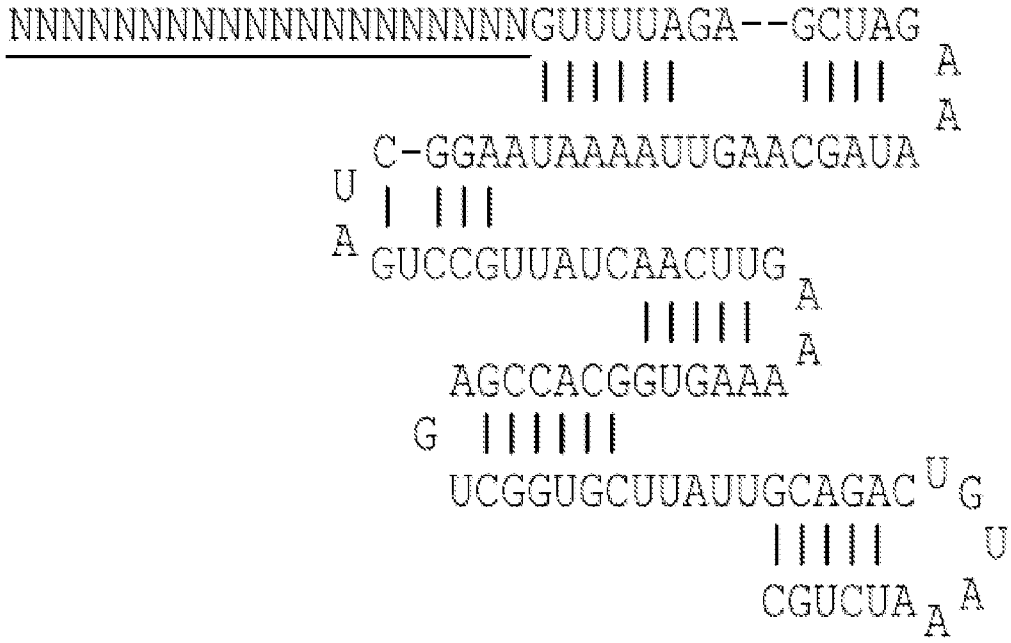
Figure 12:
Figure 12:
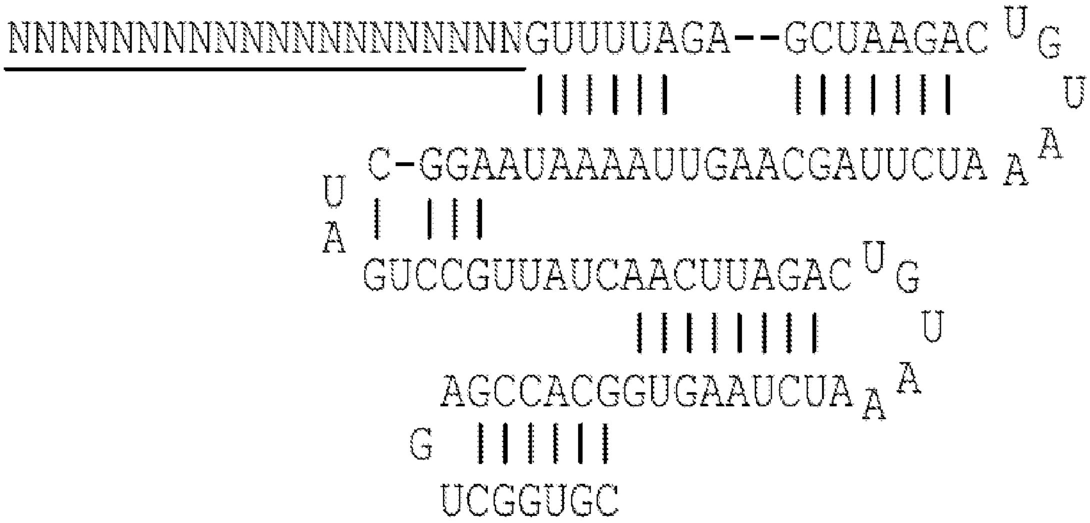
Figure 12:
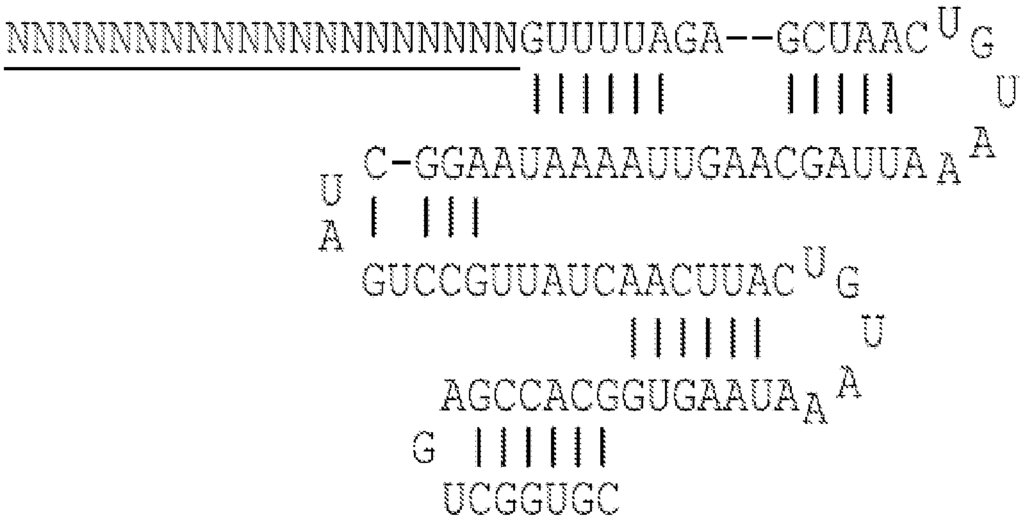
Figure 12:
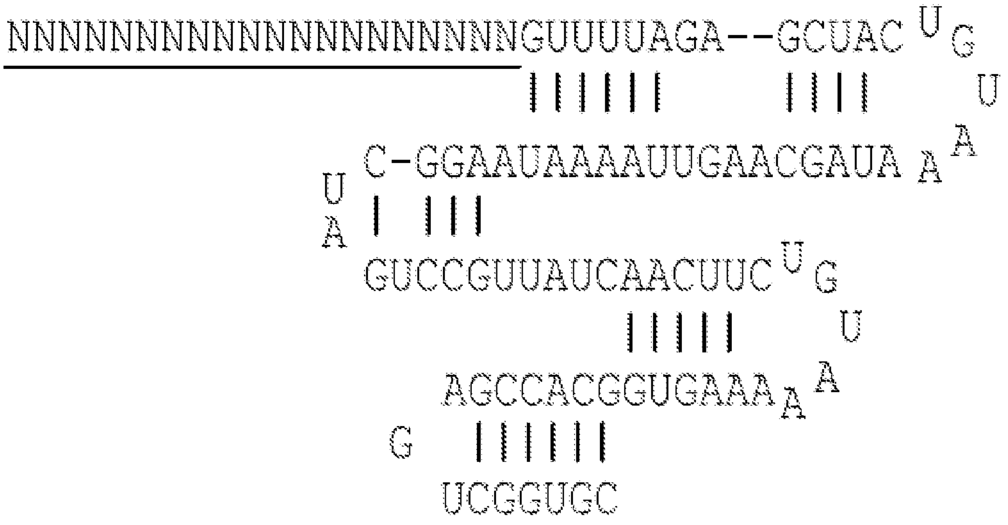
Figure 12:
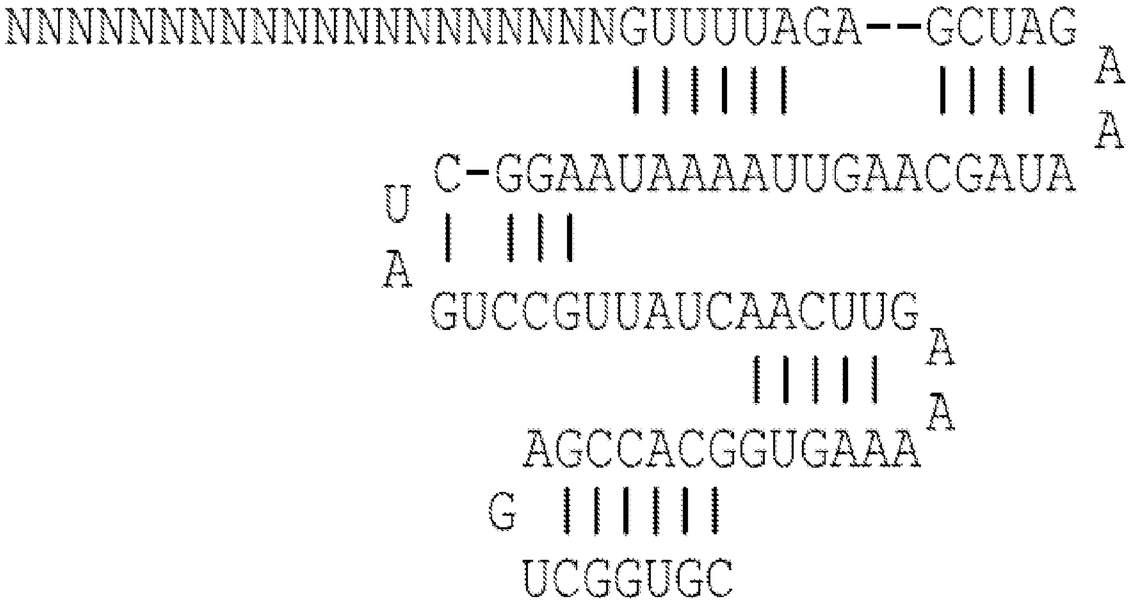
Figure 13:
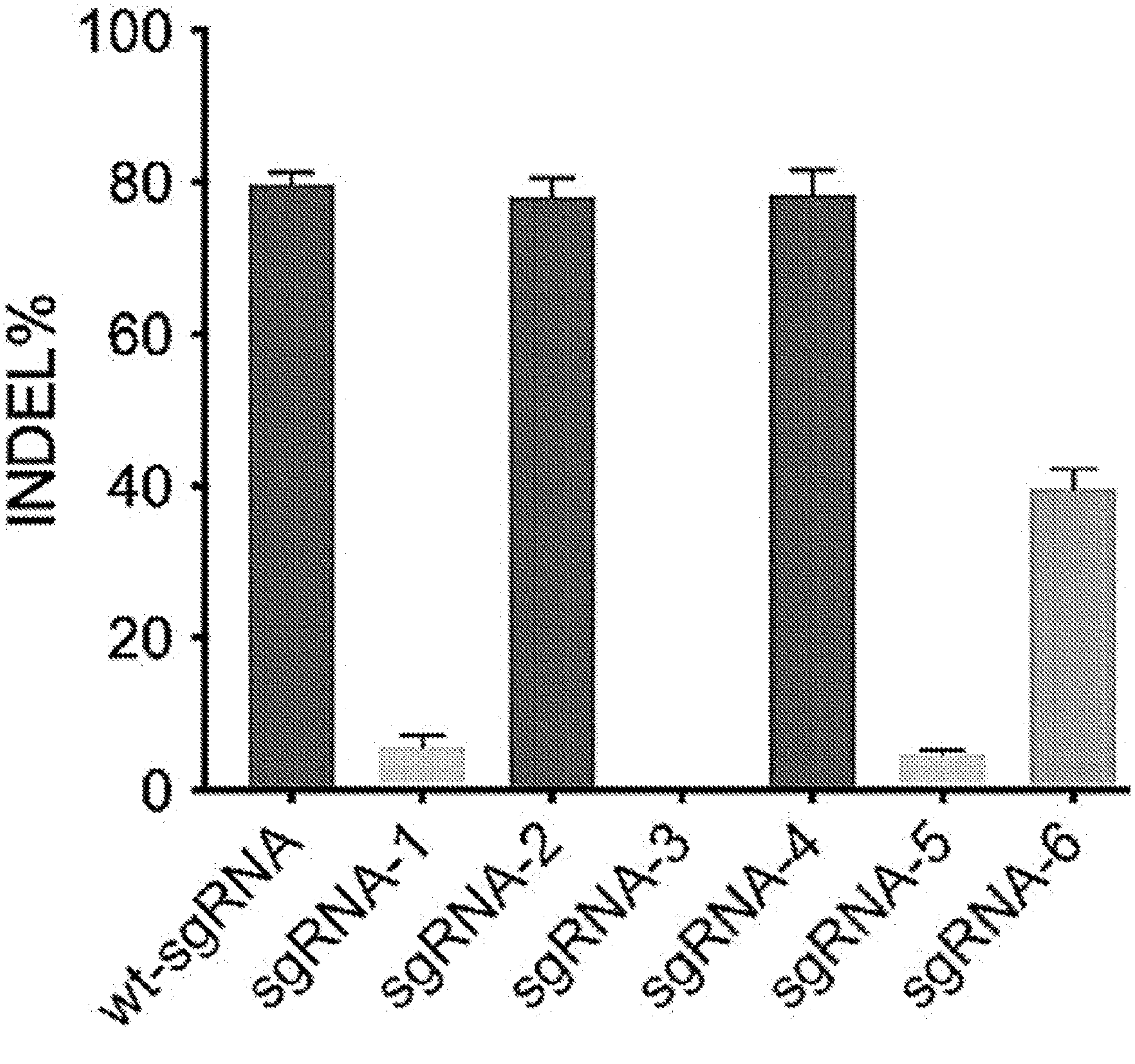
FIG. 13. INDEL rate at the DYRK1A genome site generated by different sgRNAs after being delivered into Cas9-expressing HEK-293 cells. sgRNA-2, sgRNA-4 and sgRNA-7 had wild-type level gene editing activity.
Figure 14:
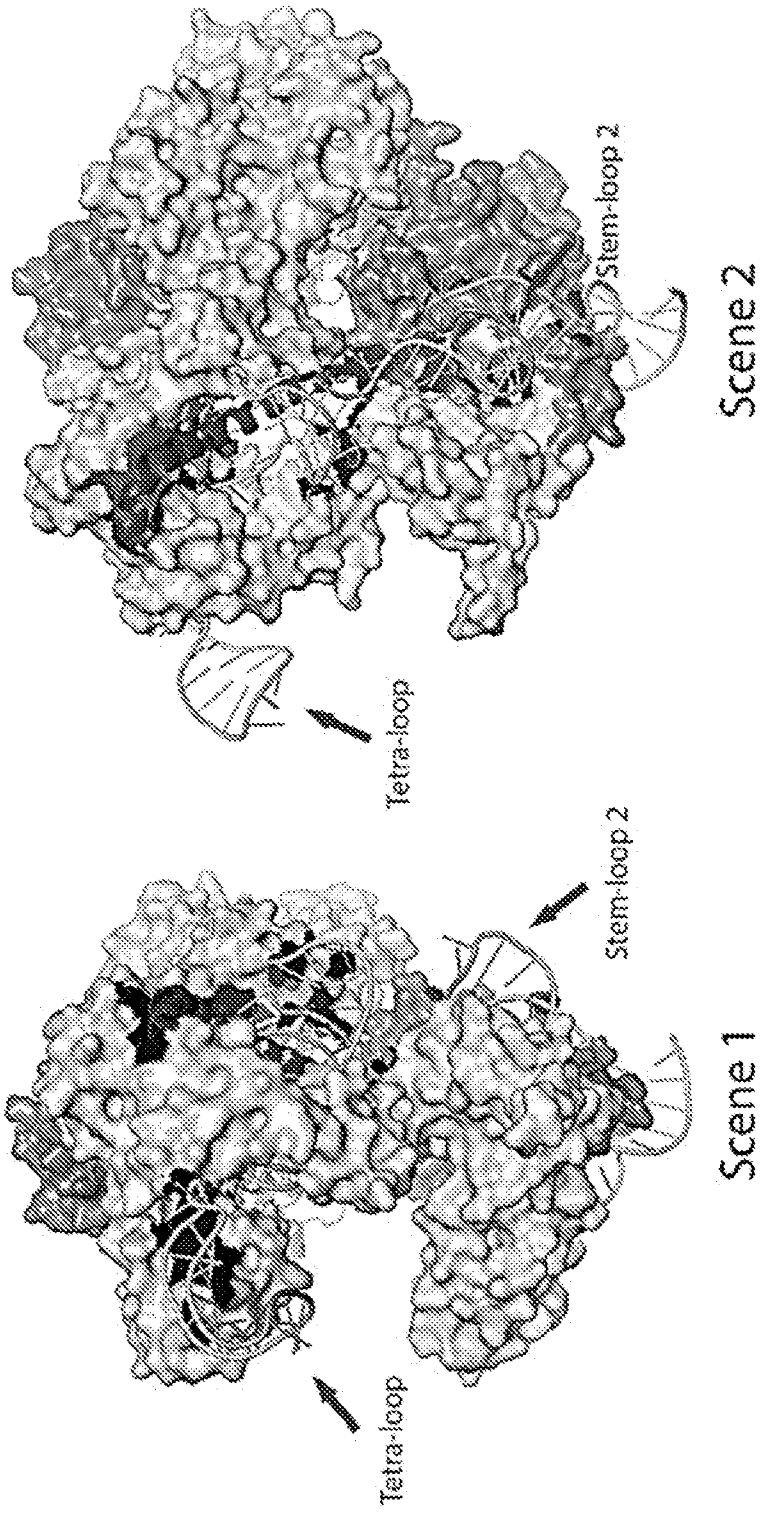
FIG. 14. Tetra-loop and Stem-loop 2 of the Cas9. Side view of the dCas9-sgRNA-DNA ternary complex with the tetra-loop and stem-loop 2 highlighted. Both of the two loops are solvent accessible.
Figure 16A:
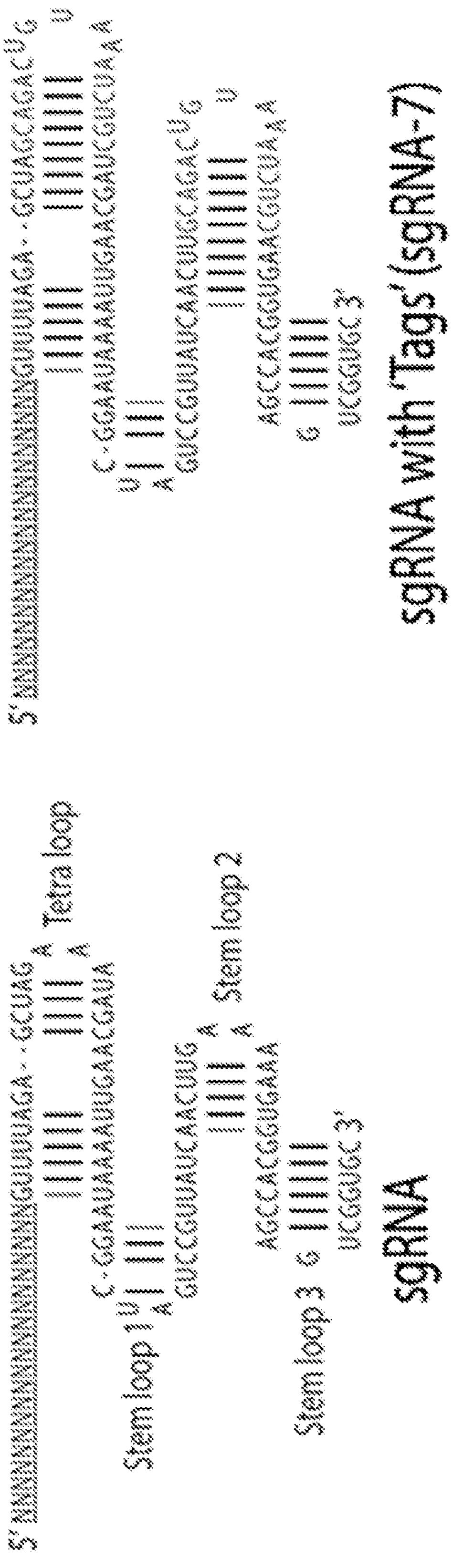
FIGS. 16A-16B. sgRNA crosslinking by RNA-CLAMP.
Figure 16B:
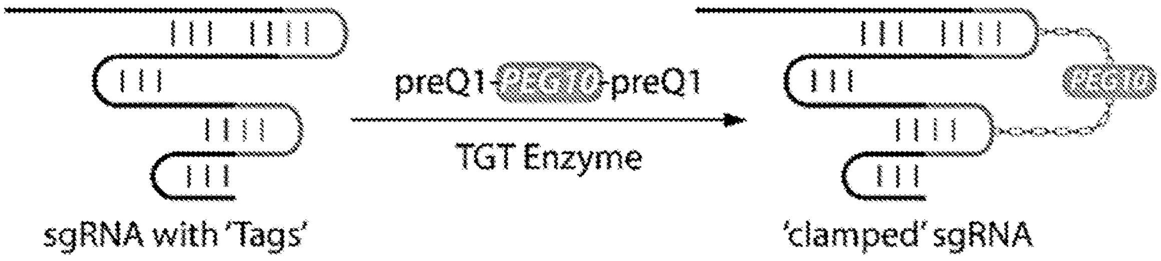

We asked whether RNA-CLAMP could be used to control CRISPR-Cas9 editing via cyclization of the sgRNA. The sgRNA is highly structured when in complex with dCas9 and target DNA, forming three stem loops and one tetraloop, with some of the stem loops being tolerant to mutations.[18] A sgRNA contains four stem-loops and two free ends (FIGS. 3A and 3B). We screened the 17-nt Tag recognition sequence (GCAGACUGUAAAUCUGC) (SEQ ID NO:1) at all 6 potential labeling sites within the sgRNA: insertion at the 5'-end (sgRNA-1) or 3'-end (sgRNA-6) and substituting the 17-nt Tag stem loop for either the tetra loop (sgRNA-2), stem loop 1 (sgRNA-3), stem loop 2 (sgRNA-4) or stem loop 3 (sgRNA-5) (FIG. 12). All the sgRNAs target the DYRK1A genome locus.[32] To screen for activity, we transiently transfected the sgRNAs into HEK-293 cells stably expressing Cas9 protein. Three days after transfection, genomic DNA was harvested and the sgRNA targeted region was amplified by PCR. Sanger sequencing results were analyzed using the ICE tool to determine the INDEL rate, which is representative of the gene editing efficiency of the sgRNA.[33] We found that sgRNA-1, sgRNA-3, and sgRNA-5 had significantly reduced activity (FIG. 13). For sgRNA-1, the 5' insertion of the Tag sequence might inhibit DNA strand invasion of the sgRNA, interfering with DNA cleavage. sgRNA-3 was less active, likely because the RNA three-way-junction structure formed near stem loop 1 plays a role in binding the Cas9 arginine-rich bridge helix and seems not to tolerate sequence modification.[18] sgRNA-5 likely has reduced activity because stem loop 3 interacts extensively with the Cas9 protein. However, sgRNA-2 and sgRNA-4 retained wild-type level activity (FIG. 13), likely because the modified stem loops are solvent exposed and have been shown to tolerate sequence mutations (FIGS. 3A, 3B, 4, and 14).[18] Based on these findings, we constructed sgRNA-7, where two Tag sequences are inserted at both the tetraloop and stem loop 2 (FIGS. 16A-16B). sgRNA-7 had wild-type level gene editing activity, making it the best candidate for cyclization using RNA CLAMP.

To obtain optimal gene editing efficiency, we examined different Cas9 delivery approaches, including transfection or electroporation of Cas9 vector or mRNA, electroporation of Cas9-sgRNA RNP complex and sequential transfection of Cas9-mRNA and sgRNA. The gene editing efficiency varies from 20% INDEL to 80% INDEL with different delivery strategies. We constructed an engineered mammalian single-colony HEK-293 cell line that stably expresses Cas9 enzyme using the lentiviral approach. To quantify the activity of sgRNA, we delivered sgRNA1 to sgRNA6 into the HEK-293-Cas9 cells using lipofectamine RNAiMAX. One day after transfection, culturing medium was exchanged with fresh full-growth medium (DMEM with 10% FBS). Three days after transfection, genomic DNA was extracted from the cells, following by PCR amplification of the sgRNA targeted region. The PCR amplified DNA fragments were further analyzed by either the T7E1 nuclease digestion assay or by Sanger sequencing to quantify gene knockouts efficiency of the targeted region.[25,26]

sgRNA Caging Strategies

Figure 15:
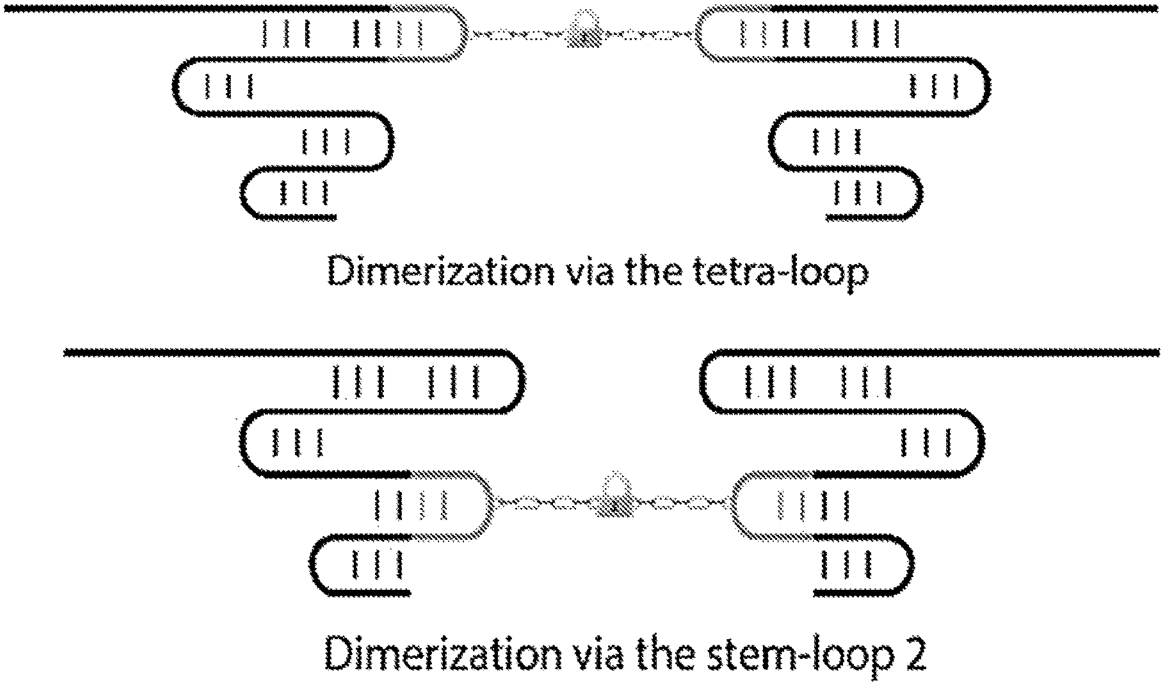
FIG. 15. Caging of sgRNA by dimierization.

The ability to dimerize or 'clamp' the RNA provides potential to cage the sgRNA by altering its ternary structure. The first strategy is to dimerize the sgRNA by covalently linking the tetra-loop or the stem-loop 2 between two sgRNAs (FIG. 15). It had been previously discovered that dimerization of the Cas9-sgRNA complex may lead to reduction in activity.[27] In this study, the researcher showed that a small bacteriophage-encoded anti-CRISPR protein blocks activity of a single Cas9 ortholog and induces Cas9 dimerization while preventing binding to the target DNA. Thus, it is possible that we can also inhibit the Cas9 activity by dimerizing the Cas9-sgRNA complexing through our TGT enzymatic dimerization of the sgRNAs (FIG. 15). Interestingly, we found that instead of inhibiting the Cas9 activity, the dimerization of the sgRNA only reduced the Cas9 activity by about 50%.

To determine the effect of intramolecular clamping on gene editing efficiency, we clamped sgRNA-7 using preQ1-PEG10-preQ1 and gel purified the clamped sgRNA-7. We observed a higher yield (78.5% conversion) of the cyclized clamped sgRNA after TGT labeling, compared to cross-linking of the RNA-1 (27.9% conversion, FIG. 9), likely due to the sgRNA being highly structured the tetra loop and the stem loop 2 are close to each other in space.[18] The clamped sgRNA-7 gave rise to 12.3% INDELs when used for gene editing in HEK-293 cells, compared to 80.7% INDELs when using the unmodified (linear) sgRNA-7, the loss in activity likely being due to clamping decreasing the conformational flexibility of the sgRNA.

Figure 17:
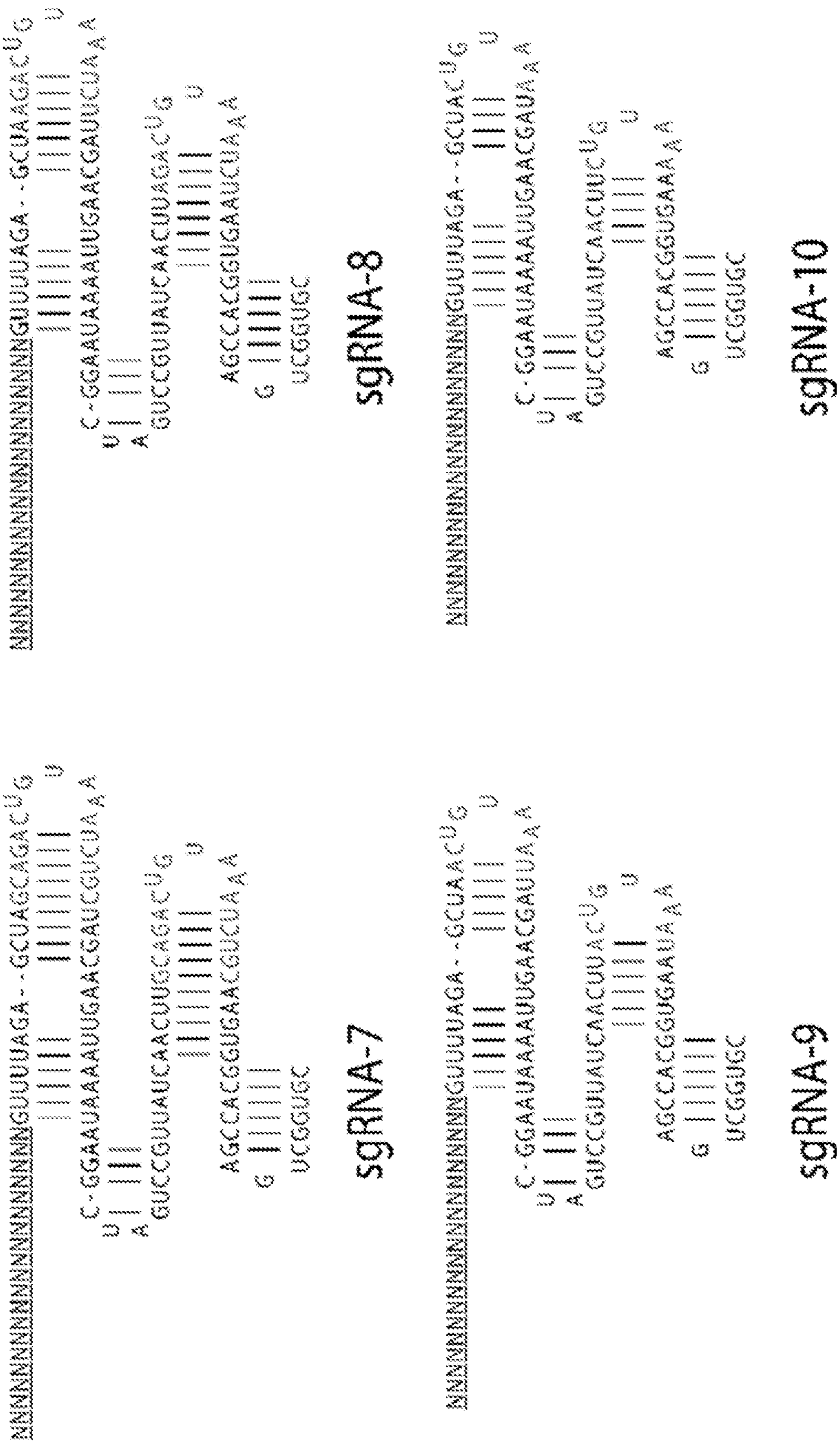
FIG. 17. Sequences of sgRNA7 to sgRNA10 (SEQ ID NO:15-18).
Figure 18:
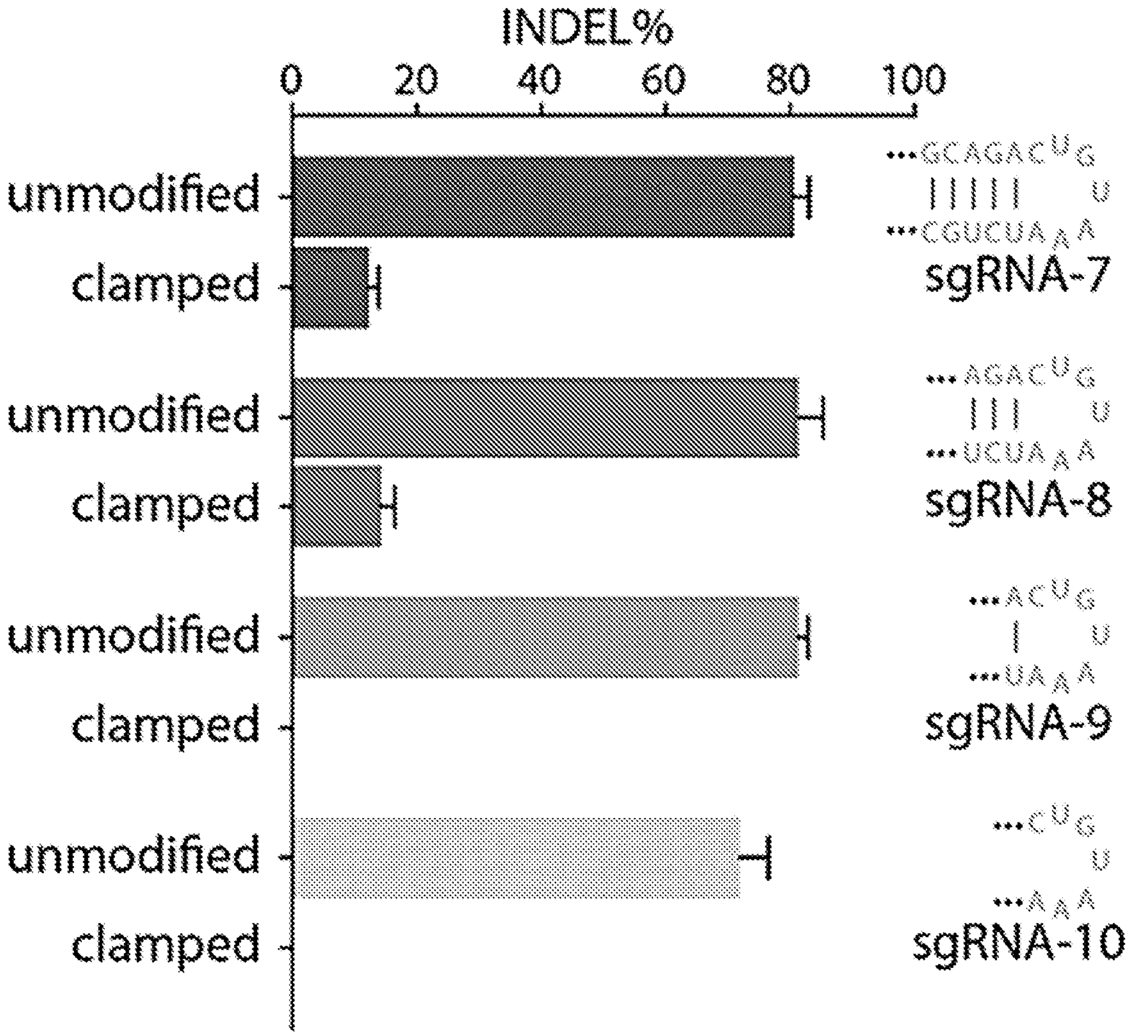
FIG. 18. Gene editing efficiency of truncated sgRNA-8 to sgRNA-10 compared to nontruncated sgRNA-7. Truncating 2 or 4 base pairs within the 'Tag' sequences of the sgRNA had little effect on gene editing efficiency, as shown in the figure that the unmodified sgRNA-7 (no truncation) (SEQ ID NO:29), sgRNA-8 (truncate 2 base pairs) (SEQ ID NO:30), and sgRNA-9 (truncate 4 base pairs) (SEQ ID NO:31) has similar gene editing activity. However, truncating 4 or 5 base pairs within the 'Tag' sequences of the sgRNA completely deactivated gene editing when the sgRNAs were at the 'clamped' form. As shown in the figure, the 'clamped' sgRNA-9 (truncate 4 base pairs) and sgRNA-10 (truncate 5 base pairs) (SEQ ID NO:32) had no detectable gene editing activity. Error bar represented standard deviation.
Figure 19:
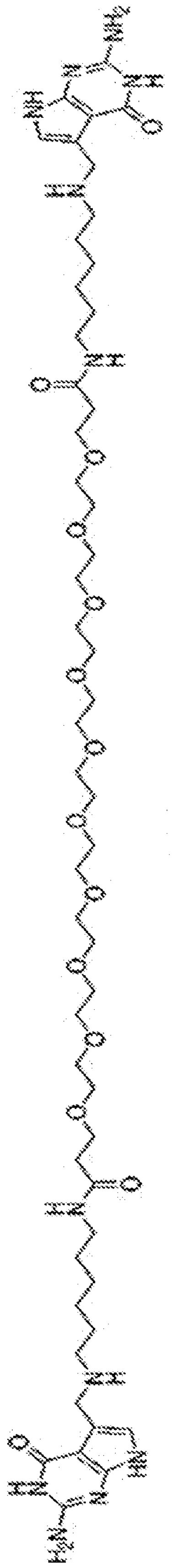
FIG. 19. Structures of preQ1-PEG10-preQ1 and preQ1-DEACM-preQ1.
Figure 19:
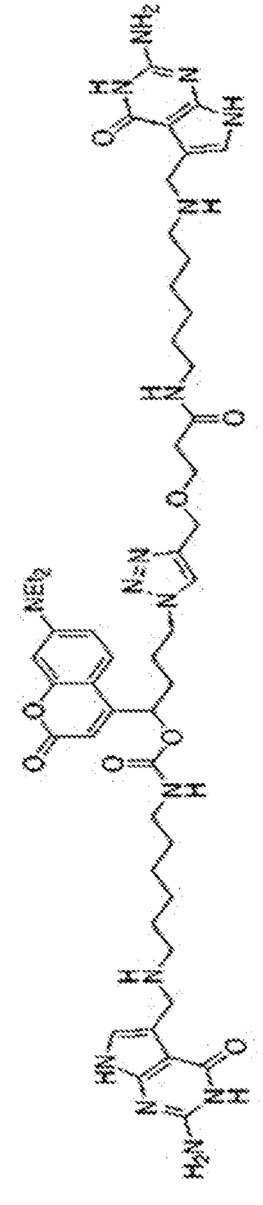

To test this idea, we shortened the distance between the two cross-linked guanines to further rigidify the sgRNA, with the aim of completely silencing gene editing. TGT does not require the full 17-nt Tag sequence to label the RNA: A 7-nt (CUGUAAA) (SEQ ID NO:32) loop within a stable RNA stem structure (in this case, provided by the sgRNA backbone) is sufficient to promote TGT labeling. We constructed sgRNA-8, sgRNA-9, and sgRNA-10 (FIG. 17), which contained truncated stems of the Tag sequence (FIG. 12), thereby shortening the distance between the substituted guanines. sgRNA8 and sgRNA10 have similar gene editing activity compared to sgRNA-7 in their linear form (FIG. 18). We clamped sgRNA-8, sgRNA-9, and sgRNA-10, and tested their gene editing activity (FIG. 13). While clamped sgRNA-8 had 17.6% gene editing activity, compared to its unmodified form, clamped sgRNA-9 and sgRNA-10 had no detectable gene editing activity, demonstrating that reducing the distance between the two cross-linked guanine residues reduces or eliminates editing activity.

Photo-Activation of CRISPR-Cas9 Gene Editing

Figure 20A:
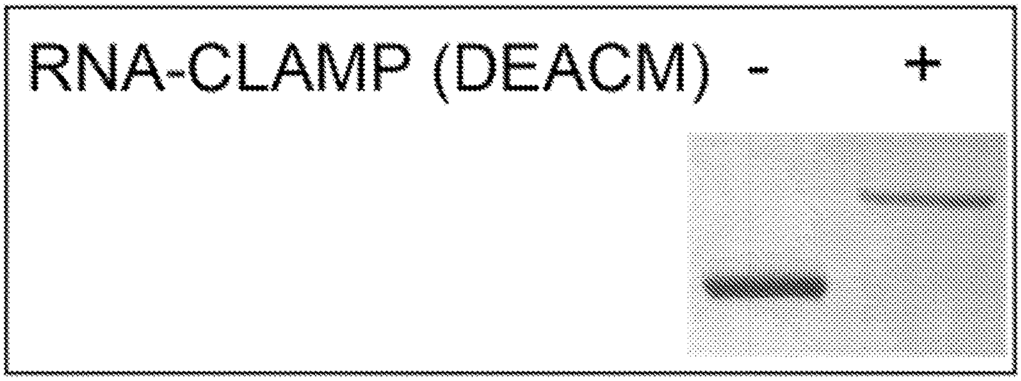
FIGS. 20A-20B. 'Clamping' of the sgRNA-9 using preQ1-DEACM-preQ1.
Figure 20B:
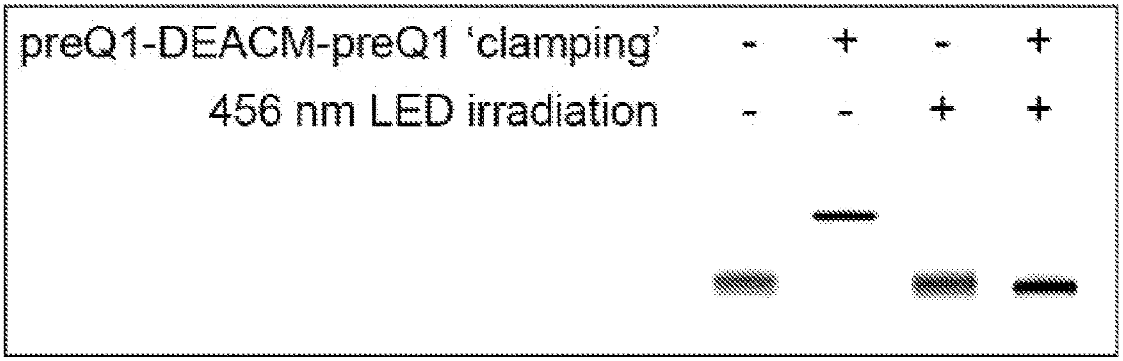

We then tested the reactivity of the newly synthesized preQ1-DEACM-preQ1 probe using sgRNA7 under a standard TGT labeling condition. The 'clamped' sgRNA7 was further gel purified to get rid of undesired RNA products. To test the photo-cleavage activity of the DEACM linker, a 456 nm wavelength of LED light was used to irradiate the 'clamped' sgRNA (water solution) for 3 minutes, following by denaturing PAGE analysis (FIG. 20B). As shown in the PAGE analysis, irradiation with 456 nm wavelength of light was harmless to the integrity of the unlabeled sgRNA. However, three minutes of irradiation completely cleaved the DEACM linker, resulting in a significant gel shift of the photo-linearized sgRNA compared to the 'clamped' sgRNA.

It should be noted that the head-to-head distance of the preQ1-PEG10-preQ1 is around 71 Å, while the head-to-head distance of preQ1-DEACM-preQ1 is only about 43 Å. We purposely designed a shorter probe to reduce the distance between the two guanine residues after the internal 'clamping' reaction, which should result in a greater inhibition effect. We observed that the new preQ1-DEACM-preQ1 substrate was able to inhibit all sgRNAs with different stem length (sgRNA7-10), upon TGT enzymatic 'clamping'.

Figure 21:
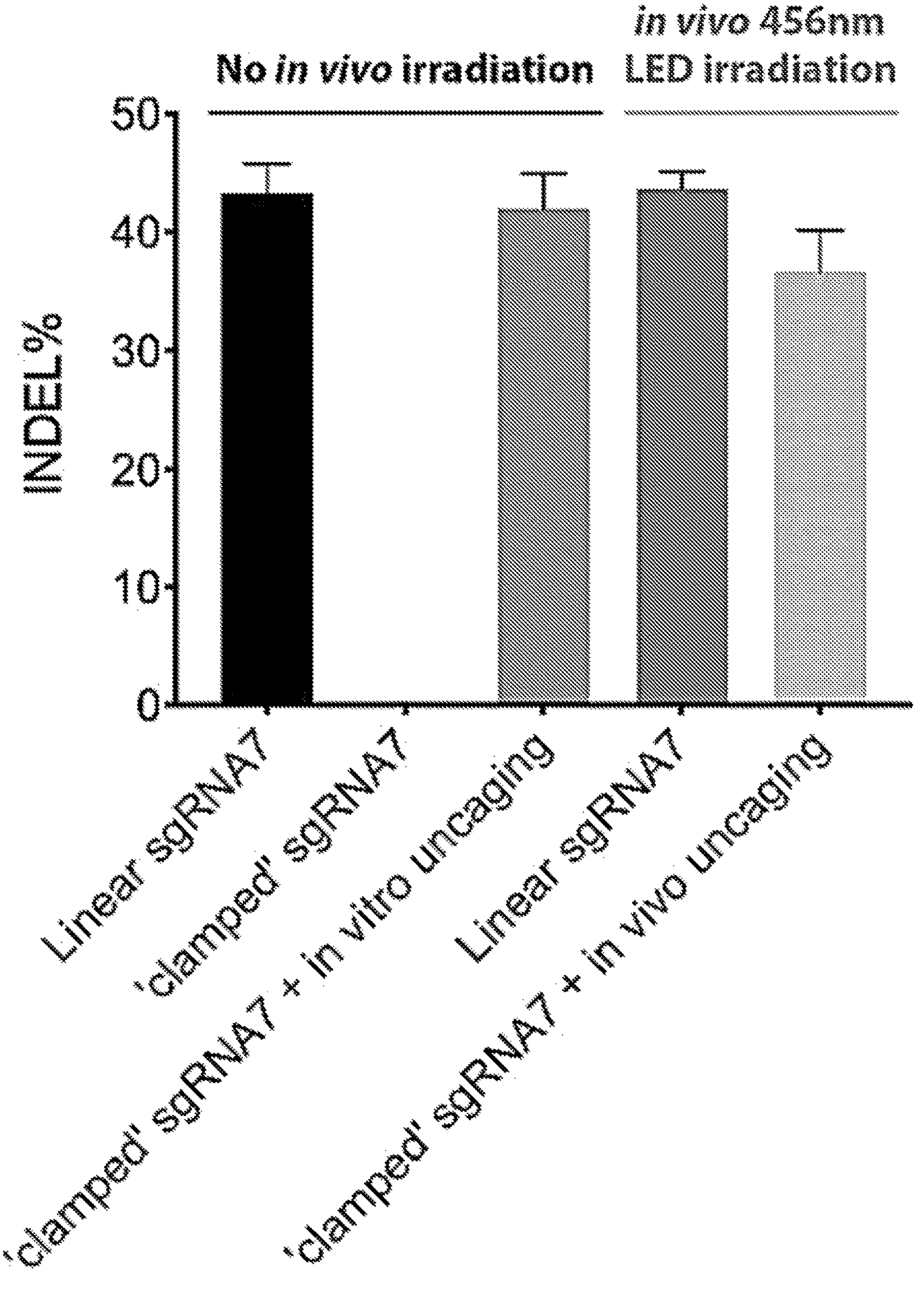
FIG. 21. In vivo photo-activation of Cas9 gene editing by 456 nm LED.
Figure 27A:
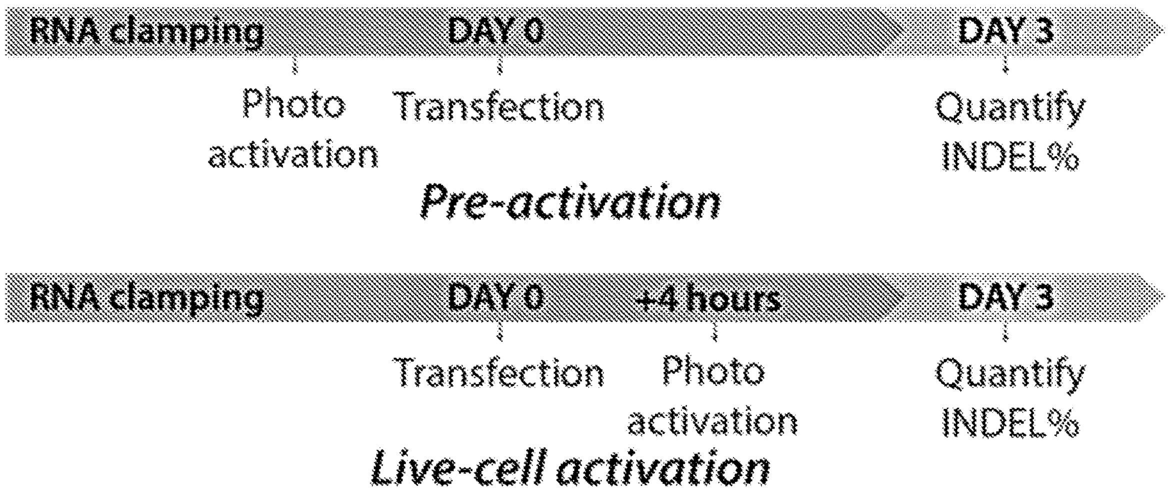
FIG. 27A-27D. Photo-activation of CRISPR-Cas9 gene editing.
Figure 27B:
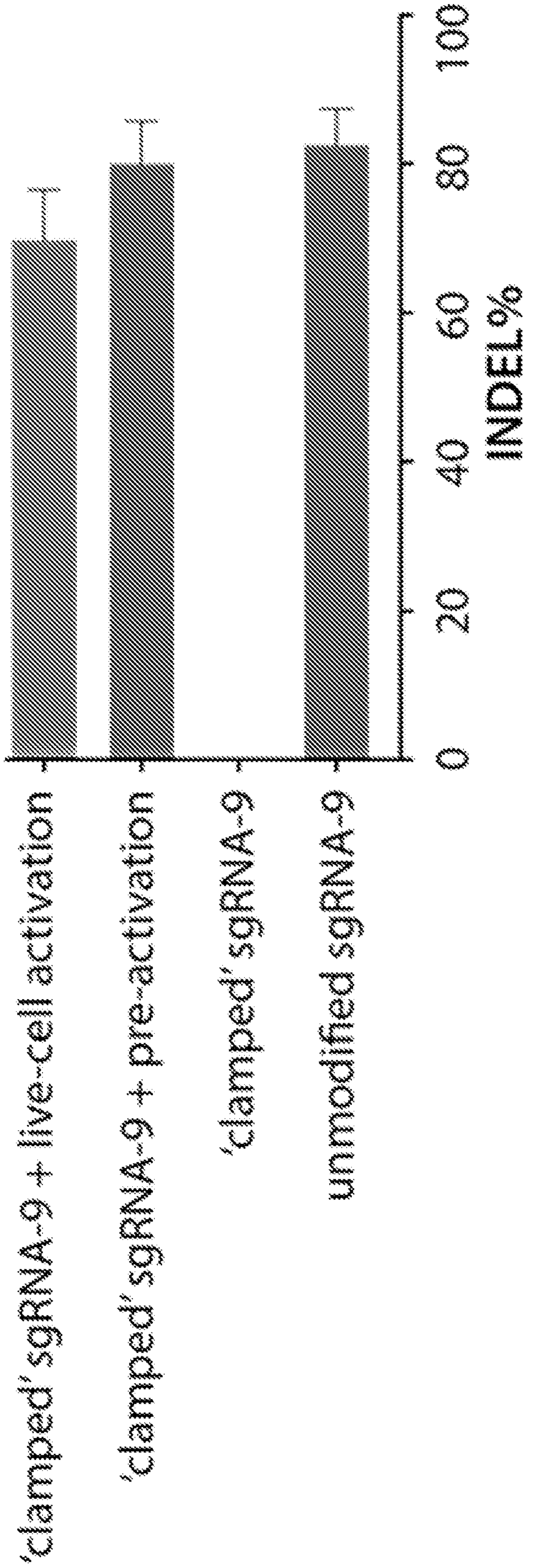
Figure 27C:
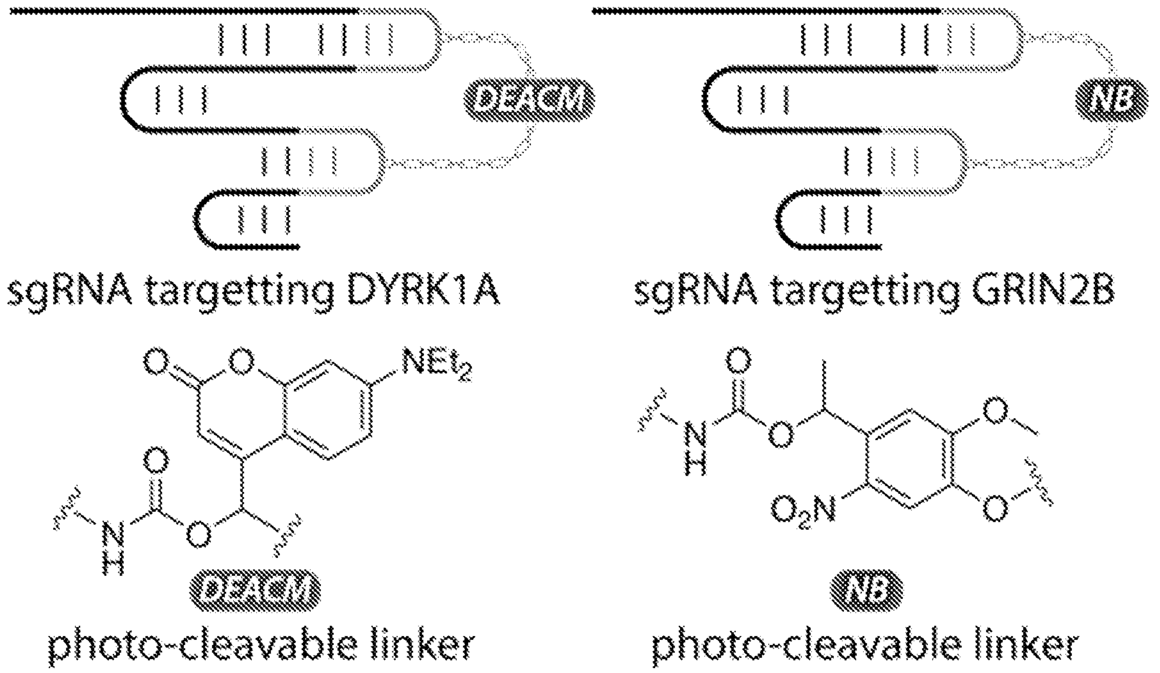

To test whether photo-cleavage of the crosslinker could activate the sgRNA in live mammalian cells, we delivered the linear, clamped, or pre-activated sgRNA-9 into a Cas9-expressing HEK293 cell line (FIG. 27A). For pre-activation, clamped sgRNA-9 was irradiated with 456 nm light (LED) for 3 minutes prior to transfection. For live-cell photo-activation, sgRNA transfected cells were irradiated with 456 nm light for 3 minutes, 4 hours after transfection. Three days later, INDEL rates were analyzed to quantify gene editing efficiency. Pre-activation completely restored the activity of the clamped sgRNA to the wild-type level (FIGS. 21, 27B). Live-cell photo-activation restored the clamped sgRNA-9's activity to 84.6% compared to wild-type. The slightly lower live-cell photo-activation might be due to degradation of the clamped sgRNA within the 4-hour transfection window. The clamped sgRNA completely blocked editing.

Figure 22:
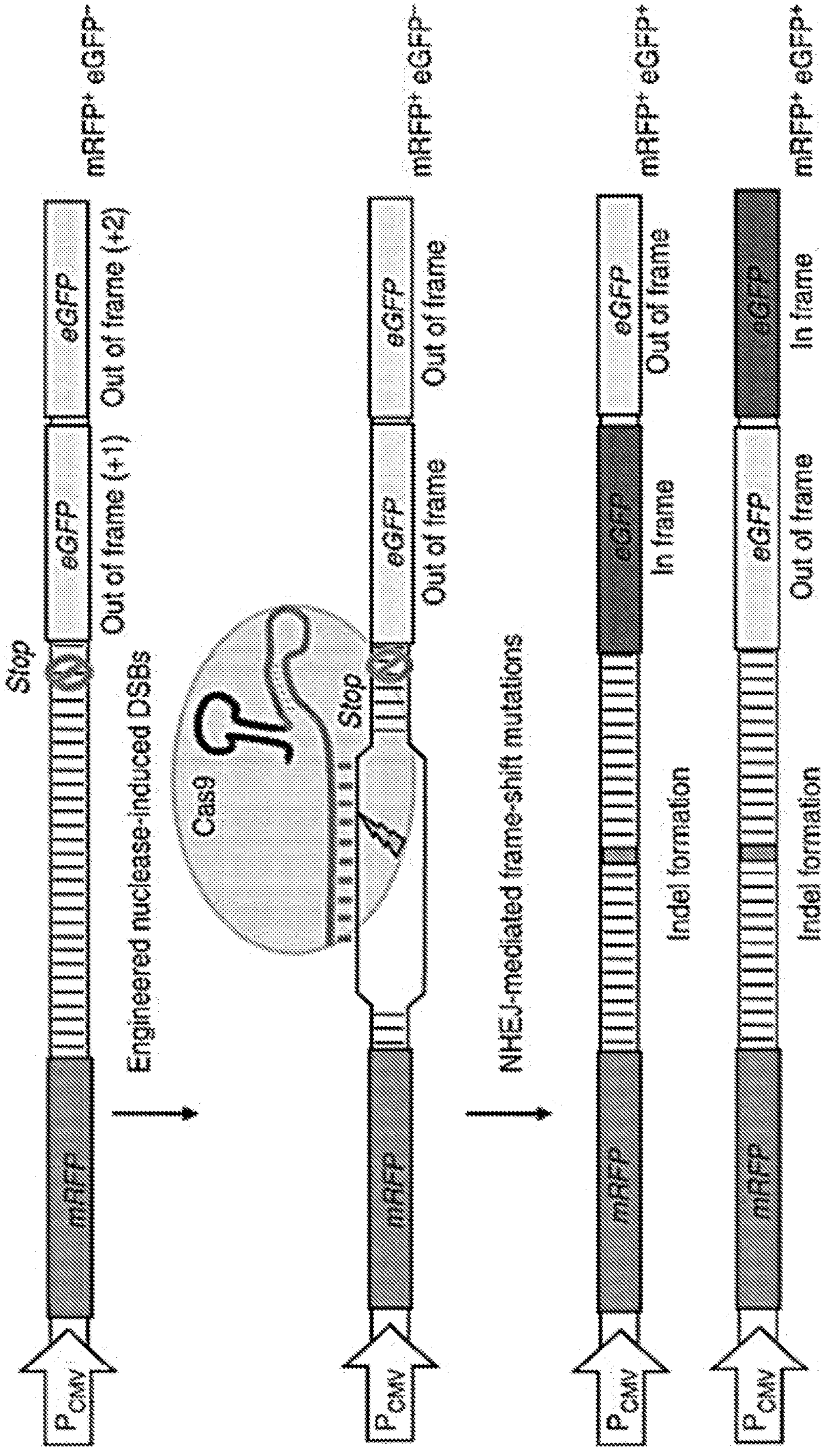
FIG. 22. Demonstration of the mechanism of the surrogate GFP reporter.

To analyze the spatiotemporal resolution of our CRISPR-Cas9 photo-activation technology, we constructed a GFP reporter stable cell line which expresses GFP only when CRISPR-Cas9 gene editing occurs at the specific genome locus targeted by sgRNA-12.[35] In the absence of gene editing, the cells only expressed mCherry while edited cells expressed both mCherry and GFP (FIG. 22). Once a double-strand brake is generated by Cas9 nuclease, error-prone nonhomologous end joining will occur which often results in INDEL mutations. This indel formation may cause frame shifts, making either of the downstream GFP genes in frame and expresses. Theoretically, if a frameshift is randomly generated, the expression activation rate of the downstream GFP is 66.6%. To deliver this surrogate fluorescence reporter genes into the genome of the HEK-293 cells, we applied a 'sleeping beauty' (SB) transposon system.[33,34] First, the three fluorescence protein genes were cloned into a SB vector containing blasticidin resistance genes. A Cas9 targeting site (SURR) was inserted between the RFP and the first GFP genes. Then, the constructed SB vector and the SB100X transposase vector were co-delivered into HEK-293 cells by lipofectamine transfection. Three days after transfection, blasticidin selection (10 μg/mL) was performed. During the 14-day selection, cells were frequently propagated to increase blasticidin selection efficacy.

Figure 23:
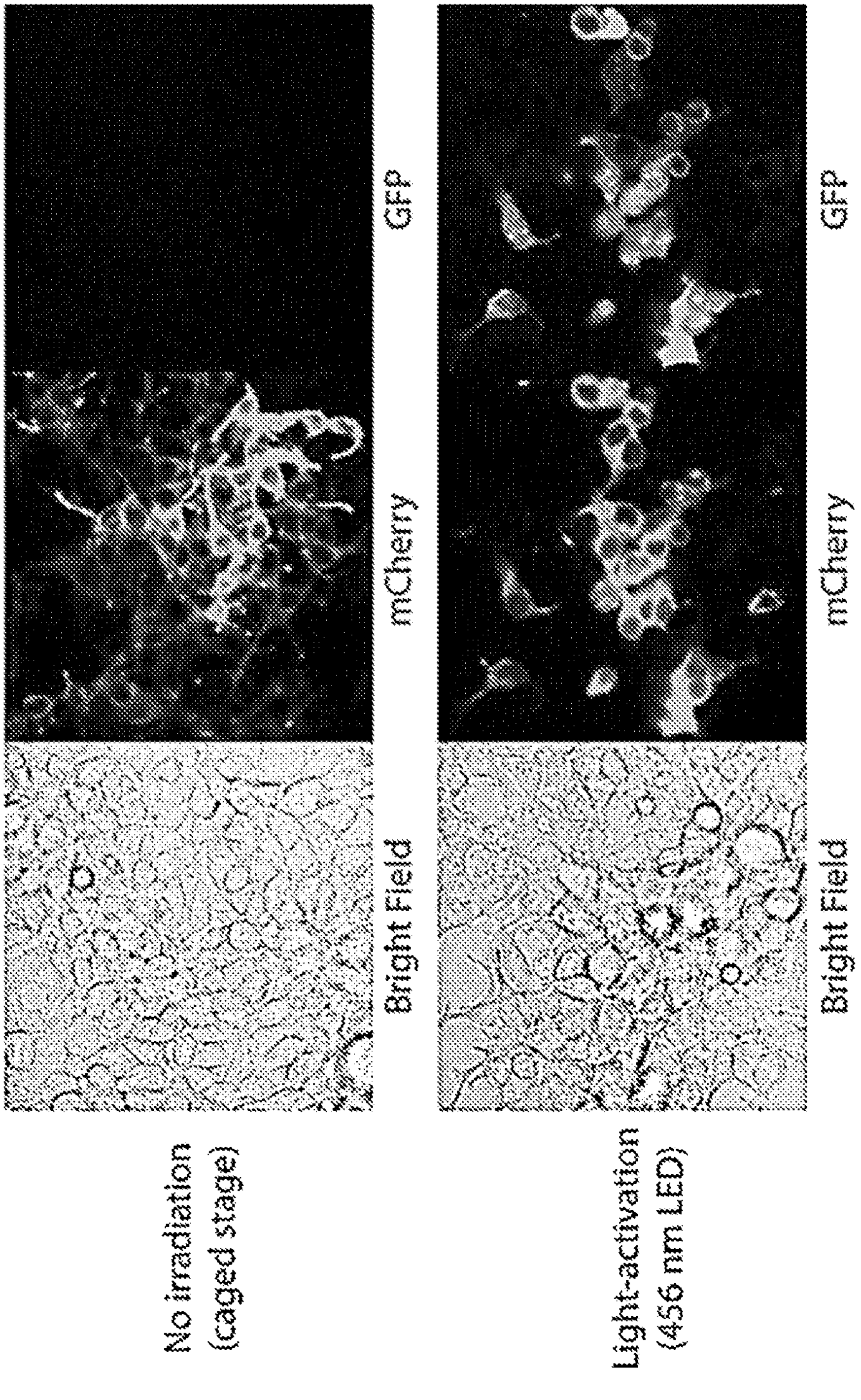
FIG. 23. 456 nm LED photo-activation of gene editing using the surrogate EGFP reporter cell line. Without gene editing at the locus between the mCherry and GFP open reading frames, cells only expressed mCherry protein, not the GFP protein. Once Cas9-mediated gene editing happened at the designed locus, followed by the cellular NHEJ DNA repair pathway, the expression of the GFP protein was activated.
Figure 24:
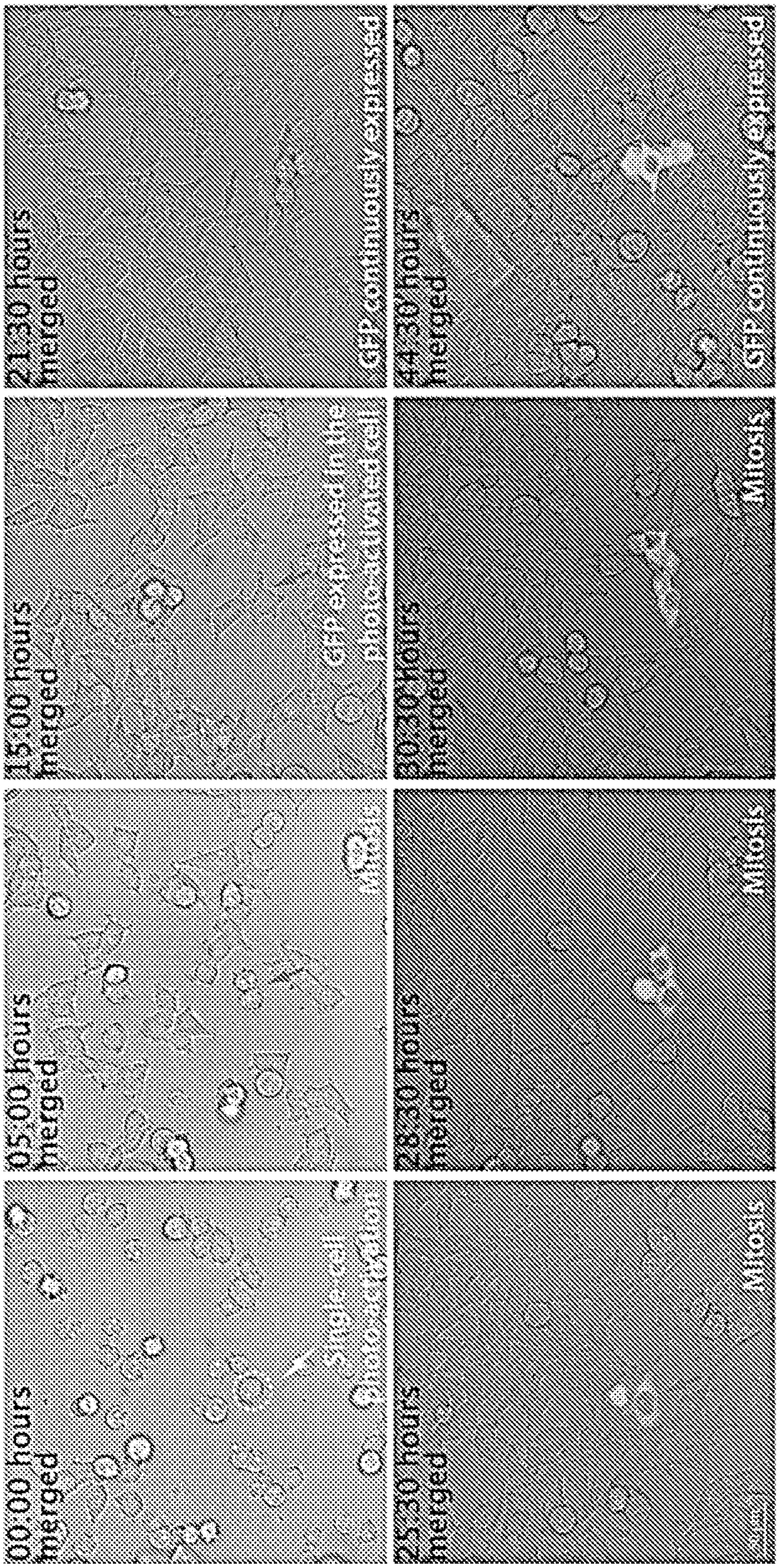
FIG. 24. Single-cell photo-activation of CRISPR-Cas9 gene editing using a GFP reporter stable cell line. At the 0 hour time point, one single cell was irradiated with a 405 nm laser for 10 seconds. After 5 hours, the laser irradiated cell went through mitosis (red arrow). After 15 hours, one daughter cell started expressing GFP. The other daughter cell expressed GFP after 21.5 hours. Cells were continuously imaged for 44.5 hours to observe GFP expression. Notably, only the laser irradiated cell and its daughter cells expressed GFP, but not the surrounding cells, demonstrating single-cell resolution of photo-activated gene editing. Scale bar=50 μm.

We delivered clamped sgRNA-12 into the reporter HEK-293 cells by transient transfection. 4 hours later, selected cells were irradiated with a 405 nm wavelength laser, and imaged continuously to observe cell growth and GFP expression. For example, a single cell was laser irradiated for 10 seconds to activate the clamped sgRNA (FIG. 24). 15 hours later, the cell went through mitosis and GFP expression was observed in one of the daughter cells, indicating INDEL formation by CRISPR-Cas9 editing. (FIG. 23). As expected, most cells expressed RFP. However, the cells transfected with 'clamped' sgRNA did not express GFP, meaning that the 'clamped' sgRNA has no activity, which was in line with our previous observation (FIG. 21). At 21.5 hours, GFP was continuously expressed in both of the daughter cells, and at 28.5 hours, one of the daughter cells went through mitosis, followed by mitosis in the other daughter cell, such that we ended up with a total of 4 cells expressing GFP as a result of single-cell light guided CRISPR-Cas9 gene editing (FIG. 24).

Multiplex Photo-Activation of Gene Editing

Figure 25:
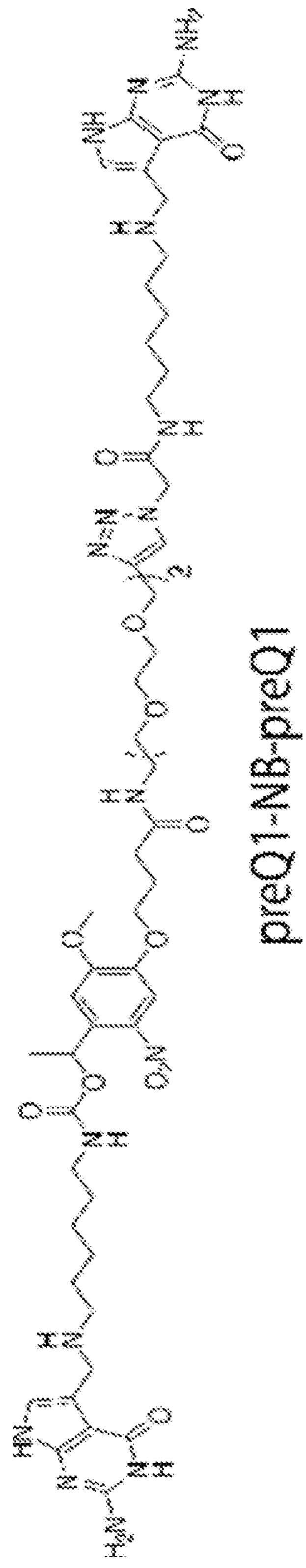
FIG. 25. Structure of the small-molecule substrate preQ1-NB-preQ1.
Figure 26:
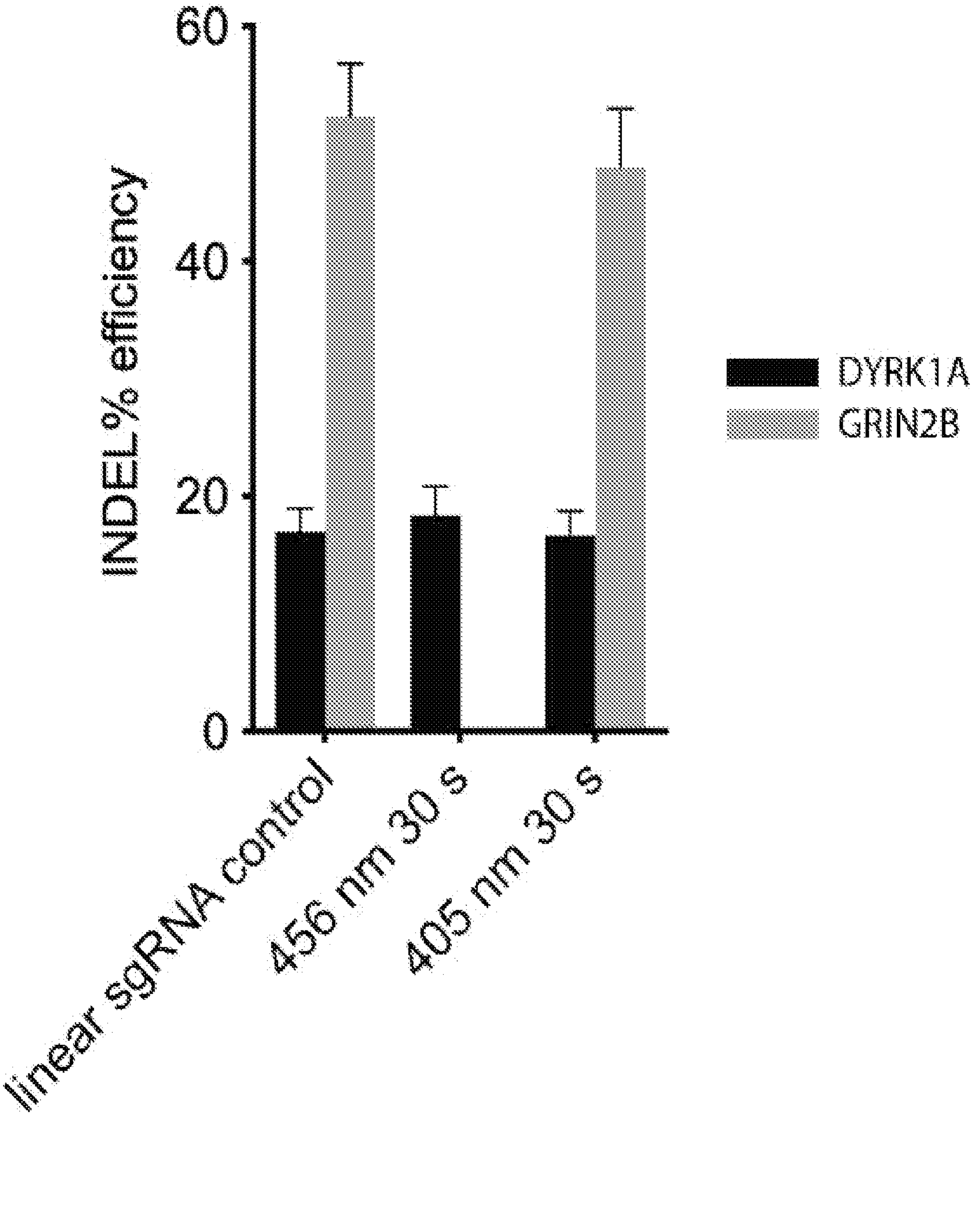
FIG. 26. Multiplexed photo-activation of gene editing.
Figure 27D:
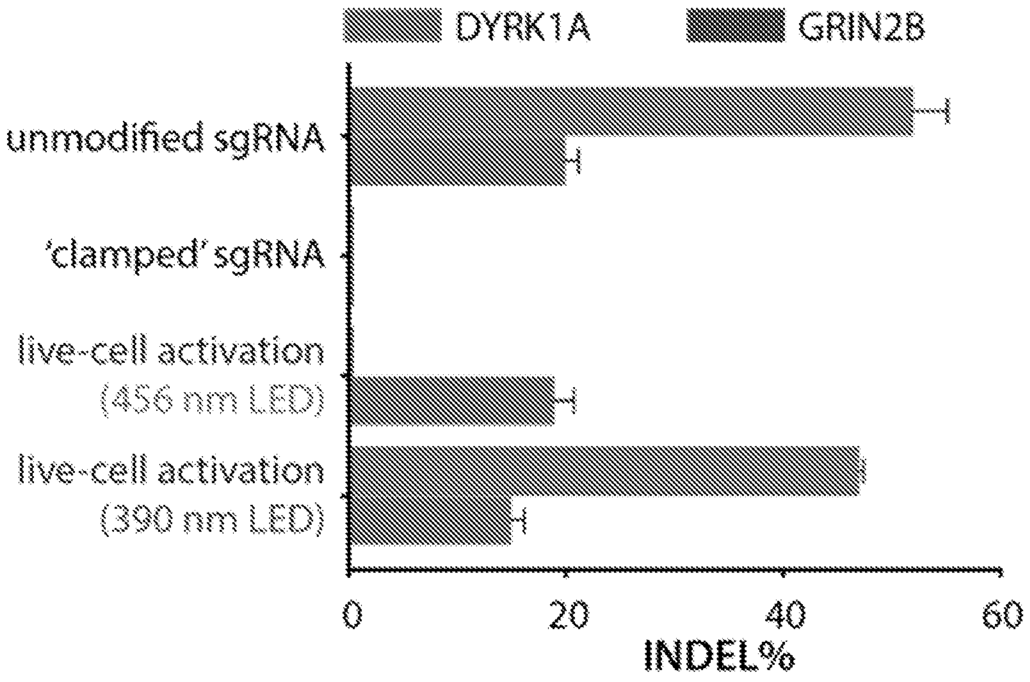

By using guide RNAs with different 20 nt guide sequences, multiple genomic locations can be targeted at the same time using CRISPR-Cas9. Compared to light activation of Cas9 activity, light activation of the guide RNA should allow multiplexed photo-activated gene editing since RNA-CLAMP technology works with a range of photo-cleavable linkers. To test whether multiplexed photo-activation of gene editing is feasible, we synthesized a nitrobenzyl (NB) based photo-cleavable linker, preQ1-NB-preQ1, which can be cleaved by irradiation with 390 nm (UV) light (FIG. 25). The NB linker is not cleaved by the 456 nm light which is used to cleave the DEACM linker, whereas 390 nm light cleaves both linkers. Thus, it is possible to control photocleavage and gene editing of two genes in a wavelength specific manner. We used the preQ1-NB-preQ1 to clamp sgRNA-11, which targets the GRIN2B genome locus. sgRNA-11 has the same guide RNA backbone as the sgRNA-9. Clamped sgRNA-9 and clamped sgRNA-11 were transfected into Cas9-expressing HEK-293 cells. Cells were irradiated with either 456 nm light (3 minutes) or 390 nm LED light (30 seconds) to trigger the photo-activation of gene editing, as per previously established photo-activation protocols (FIG. 27A). Gene editing efficiency was quantified by Sanger sequencing as INDEL %. Irradiation with the 456 nm light only triggered gene editing at the DYRK1A genome locus, while irradiation with the 390 nm wavelength of light triggered gene editing at both loci (FIG. 27D). Thus, RNA-CLAMP photo-activated gene editing is compatible with different wavelengths of light enabling multiplexed photo-activation of editing (FIG. 26).

Clamped sgRNA Forms Cas9-sgRNA RNPs and Binds to Target DNA

We asked whether clamped sgRNA maintains the capability to form the Cas9 RNP and bind to target DNA. We designed a 60 bp DNA substrate containing the sgRNA-9 target sequence with the NGG PAM, based on previous studies of sgRNA binding to Cas9 and target DNA.[36] We confirmed the DNA substrate bound to the Cas9-sgRNA RNP (FIG. 30) using a non-targeting sgRNA-11 as the negative control. Formation of Cas9-sgRNA RNP was observed, using gel shift analysis, by mixing Cas9 protein with all three sgRNAs: linear sgRNA-9, clamped sgRNA-9, and linear sgRNA-11. We also observed the formation of the Cas9-sgRNA-DNA ternary complex by mixing Cas9 protein, the unmodified or 'clamped' sgRNA-9, and the DNA substrate. However, the Cas9-sgRNA-DNA ternary complex was not observed for sgRNA-11 (the non-targeting sgRNA), demonstrating the specificity of the CRISPR-Cas9 system. These results suggest that although the RNA clamping completely quenches the DNA cleavage activity, the clamped RNP is still able to specifically recognize and bind to its DNA target. Further work will be required to decipher the precise mechanism by which clamping the sgRNA prevents Cas9 function. These data suggest that light activation of clamped sgRNA could trigger rapid gene editing. Photo-activation of a caged crRNA, which retains the ability to form a DNA binding Cas9 RNP, has been shown to display fast activation dynamics, enables the study of DNA damage responses and DNA repair.[37]

Conclusion

We have developed an RNA crosslinking approach, RNA-CLAMP, which allows site-specific and enzymatic crosslinking of two internal stem loops within an RNA of interest. By incorporating a photo-cleavable linker, the clamped RNA can be released by irradiation with a user-selected wavelength of light. Given the simplicity of the activation mechanism, RNA-CLAMP offers considerable flexibility through, for example, use of two photo-activatable crosslinkers that can be cleaved using different wavelengths of light. In principle, a variety of alternative photo-cleavable linkers can be used.[38] Multiplexed light activated gene editing should facilitate the study of complex gene networks with high spatiotemporal precision. Beyond photo-cleavable linkers, different conditionally cleavable linkers could also be used for clamping the RNA. For example, redox sensitive disulfide bonds, pH-sensitive linkers, and enzymatically cleavable peptides.[39-42] Furthermore, the RNA-CLAMP technique can also be used to intermolecularly cross-link two RNA molecules. The versatility of our RNA-CLAMP technology will promote the development of a wide-range of biotechnologies when site-specific cross-linking of RNAs is desired.

We applied the RNA-CLAMP technique to the CRISPR-Cas9 sgRNA. By swapping the 4-nt sequence (GAAA) within the sgRNA tetra loop and stem loop 2 for the 7-nt TGT recognition motif (CUGUAAA) (SEQ ID NO:32), we were able to site-specifically cross-link the two guanine residues within the TGT recognition motifs, resulting in the Cas9-sgRNA RNP complex completely losing its DNA cleavage activity while maintaining the ability to bind its DNA target. Live-cell photo-irradiation triggered cleavage of the crosslinker and activated CRISPR-Cas9 gene editing. This photo-activated gene editing platform has nondetectable gene editing background at the caged stage and a high cellular activation rate (84.6%). Photo-activation also offers high spatiotemporal precision. We were able to photo-activate CRISPR-Cas9 editing within a single cell in a population of cells. Furthermore, by using photo-cleavable linkers which are responsive to different wavelengths of light, we achieved multiplexed photo-activation of gene editing. Thus, this approach of photo-activated gene editing technologies is capable of deciphering complex gene networks, as well as stimuli responsive CRISPR-based gene therapies

Example 3: Materials and Methods

Reagents and Instruments

Commercially available methanesulfonyl chloride, sodium azide, tetra-n-butylammonium fluoride in THE (1M), N-succinimidyl carbonate, 4-dimethylaminopyridine, N,N-diisopropylethylamine, copper(I) bromide and common organic solvents were obtained from Sigma-Aldrich. Deuterated chloroform ($CDCl_3$) was obtained from Cambridge Isotope Laboratories. All reagents obtained from commercial suppliers were used without further purification. Analytical thin-layer chromatography was performed on E. Merck silica gel 60 $F_{254}$ plates. Silica gel flash chromatography was performed using E. Merck silica gel (type 60SDS, 230-400 mesh). Solvent mixtures for chromatography are reported as v/v ratios. HPLC analysis was carried out on an Eclipse Plus C8 analytical column with Phase A/Phase B gradients [Phase A: $H_2O$ with 0.1% formic acid; Phase B: MeOH with 0.1% formic acid]. HPLC purification was carried out on a Zorbax SB-C18 semipreparative column with Phase A/Phase B gradients [Phase A: $H_2O$ with 0.1% formic acid; Phase B: MeOH with 0.1% formic acid]. Proton nuclear magnetic resonance (H NMR) spectra were recorded on a VarianVX-500 MHz spectrometer, and were referenced relative to residual proton resonances in $CDCl_3$ (at 7.24 ppm). Chemical shifts were reported in parts per million (ppm, 6) relative to tetramethylsilane (at 0.00 ppm). $^1$H NMR splitting patterns are assigned as singlet (s), doublet (d), triplet (t), quartet (q) or pentuplet (p). All first-order splitting patterns were designated on the basis of the appearance of the multiplet. Splitting patterns that could not be readily interpreted are designated as multiplet (m) or broad (br). Electrospray Ionization-Time of Flight (ESI-TOF) spectra were obtained on an Agilent 6230 Accurate-Mass TOF mass spectrometer.

DNA oligonucleotides were purchased from Integrated DNA Technologies (Coralville, IA). Molecular biology reagents such as restriction digestion enzymes, Q5 HF-DNA polymerase, T7 RNA polymerase, nucleotide stains and competent bacterial strains were purchased from New England Biolabs (Ipswitch, MA), Promega (Madison, WI), or Life Technologies (Carlsbad, CA).

Spinning-disk confocal microscopy images were acquired on a Yokagawa spinning-disk system (Yokagawa, Japan) built around an Axio Observer Z1 motorized inverted microscope (Carl Zeiss S-3 Microscopy GmbH, Germany) with a with a 20×0.8 NA objective to an ORCA-Flash4.0 V2 Digital CMOS camera (Hamamatsu, Japan) using ZEN Blue imaging software (Carl Zeiss Microscopy GmbH, Germany). The fluorophores were excited with diode lasers (405 nm-20 mW, 488 nm-30 mW, and 561 nm-20 mW). Images were processed using ImageJ (Fiji).

LED Light Sources for Photo-Activation

- 456 nm LED (50 W max) light source was purchased from KESSIL.
- 390 nm LED (52 W max) light source was purchased from KESSIL.

Reaction Buffers

- TGT Storage Buffer: 25 mM HEPES, pH 7.3, 2 mM DTT, 1 mM EDTA, and 100 μM PMSF.
- TGT Reaction Buffer: 100 mM HEPES, pH 7.3, 5 mM DTT, and 20 mM $MgCl_2$.
- T7 Reaction Buffer: 40 mM Tris pH 7.5, 5 mM DTT, 25 mM $MgCl_2$, 2 mM spermidine.

Synthesis

Synthesis of preQ1-PEG10-preQ1

Scheme S1. Synthesis of preQ1-PEG10-preQ1.

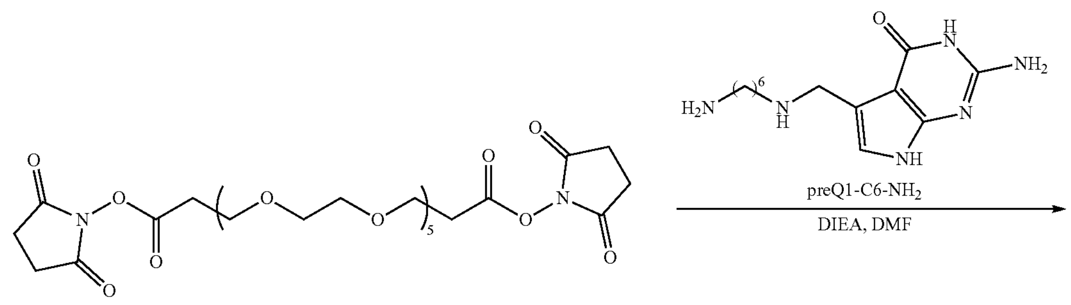

Bis-PEG10-NHS ester

-continued

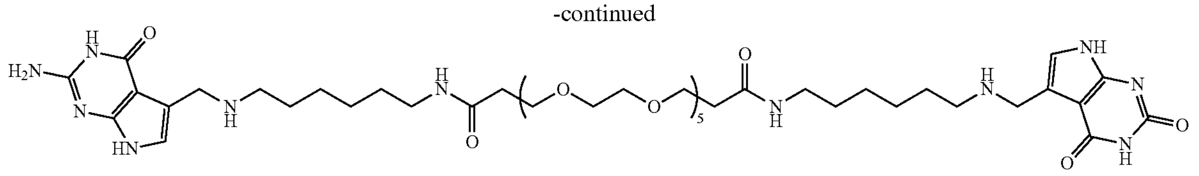

preQ1-PEG10-preQ1

The bis-PEG10-NHS ester was purchased from BROADPHARM (San Diego, CA). The synthesis of preQ1-C6-$NH_2$ was followed as previously described.[1] Bis-PEG10-NHS ester (6.8 mg, 9 µmol) was dissolved in 0.5 mL DMF followed by slow addition of the preQ1-C6-$NH_2$ (5.0 mg, 18 µmol in 0.5 mL DMF) and DIEA (5.8 mg, 45 µmol). The reaction solution was stirred for 1 hour at room temperature. The crude product was directly subjected to semipreparative HPLC purification, using a C18 column [gradient of $H_2O$ with 0.1% formic acid and MeOH with 0.1% formic acid 95:5 (0 min) to 5:95 (10 min to 18 min)]. The semipreparative HPLC fractions containing product preQ1-PEG10-preQ1 were dried in vacuo, yielding 6.6 mg (6.1 µmol, 68% yield) purified product as a white residue. HRMS (M+H$^+$) calcd for $[C_{50}H_{87}N_{12}O_{14}]^+$ 1079.6459, found 1079.6460.

$^1$H NMR (500 MHz, $CD_3OD$): δ 8.55 (s, 1H), 7.21-7.16 (m, 1H), 6.84-6.83 (m, 1H), 4.64 (s, 1H), 4.24-4.23 (m, 1H), 3.74-3.72 (m, 17H), 3.62-3.61 (m, 10H), 3.18 (t, J=5.0 Hz, 1H), 3.04 (t, J=5.0 Hz, 1H), 2.42 (t, J=5.0 Hz, 1H), 2.32-2.28 (m, 1H), 2.17-2.15 (m, 14H), 2.05-2.03 (m, 16H), 1.89-1.87 (m, 16H), 1.72 (t, J=5.0 Hz, 1H), 1.52 (t, J=5.0 Hz, 1H), 1.44 (t, J=5.0 Hz, 1H), 1.35 (t, J=5.0 Hz, 1H).

$^{13}$C NMR (126 MHz, $CD_3OD$): δ 210.14, 173.94, 162.70, 154.57, 118.15, 110.25, 99.70, 71.98, 71.51, 71.43, 71.29, 71.03, 68.87, 68.56, 67.69, 47.60, 44.89, 40.03, 37.68, 30.82, 30.74, 30.65, 30.12, 26.99, 26.65, 26.50, 26.42, 26.36.

Synthesis of preQ1-NB-preQ1

Scheme S2. Synthesis of the preQ1-NB-preQ1.

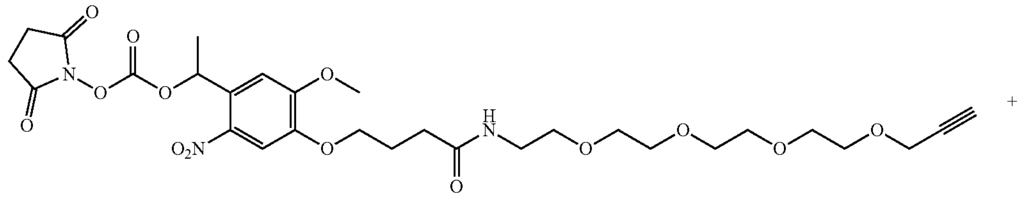

Alkyne-NB-NHS ester

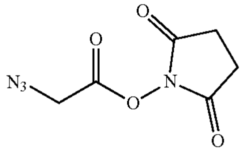

Azido-NHS ester

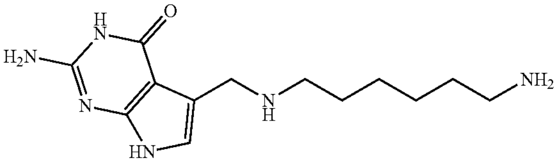

preQ1-C6-$NH_2$

1. DMF (12 mM), DIPEA (16 eq), r.t. for 1 hour
2. CuI (2 eq), solium L-ascorbate (1 eq)
$CH_3CN/H_2O$ (2/1) (10 mM), r.t. for 4 hours

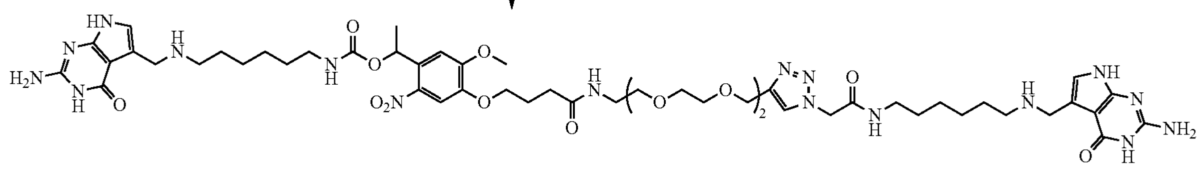

preQ1-C6-$NH_2$ was dissolved in 2 mL of anhydrous DMF Anhydrous DIPEA (20 µL, 125 µmol) was added to the mixture. Alkyne-NB—NHS ester (8 mg, 12 µmol) and Azido-NHS ester (5 mg, 25 µmol) was added to the stirred mixture and the reaction proceeded at room temperature for 1 hour. Then the reaction solvent was removed under reduced pressure and the residue was dried in vacuo. Next, 1.2 mL of $CH_3CN$:$H_2O$ (0.6 mL:0.6 mL), CuI (6 mg, 32 mol), and sodium L-ascorbate (2.4 mg, 12 µmol) were added to the reaction residue. The reaction mixture was stirred at room temperature for 4 hours. Upon completion, the reaction solvent was removed under reduced pressure and the residue was dried over high vacuum. Then $CH_2Cl_2$ was added, followed by filtration. The filtrate was concentrated by reduced pressure and the residue was purified by HPLC yielding the title compound preQ1-NB-preQ1 as a pale-yellow solid (8.9 mg, 62%). HRMS (M+H$^+$) calcd for $[C_{53}H_{80}N_{17}O_{14}]^+$ 1178.6065, found 1178.6071.

Synthesis of preQ1-alkyne

Scheme 3. Synthesis of the preQ1-alkyne

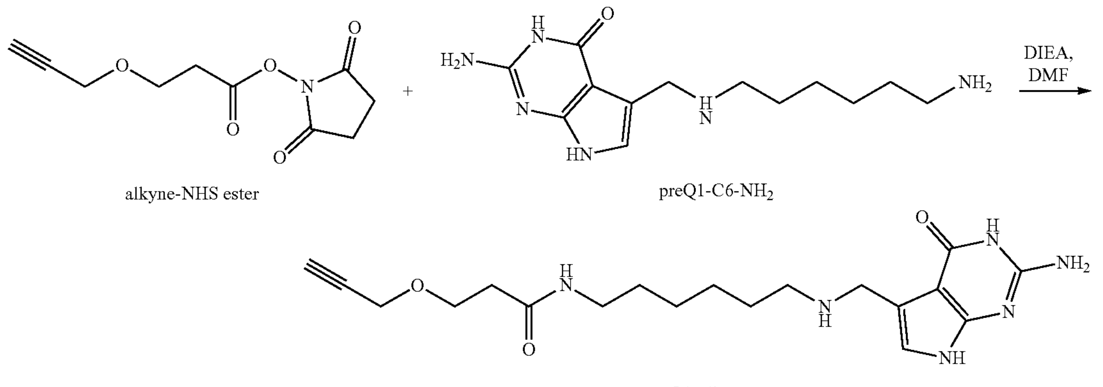

alkyne-NHS ester $preQ1-C6-NH_2$ preQ1-alkyne

To the solution of alkyne-NHS ester (30.0 mg, 0.13 mmol, commercially available from BroadPharm, San Diego, USA; CAS #: 1174157-65-3) in DMF (3 mL) was added previously reported $preQ1-C6-NH_2$ (41.9 mg, 0.13 mmol) and DIEA (38.7 mg, 0.30 mmol). The resulting solution was 152.92, 152.39, 117.49, 108.24, 98.06, 78.87, 74.52, 74.25, 65.43, 57.27, 45.99, 43.22, 38.44, 35.92, 28.48, 25.67, 15.71. HRMS ($M+H^+$) calcd for $[C_{19}H_{29}N_6O_3]^+$ 389.2298, found 389.2296.

Synthesis of preQ1-DEACM-preQ1

Scheme 4. Synthesis of preQ1-DEACM-preQ1

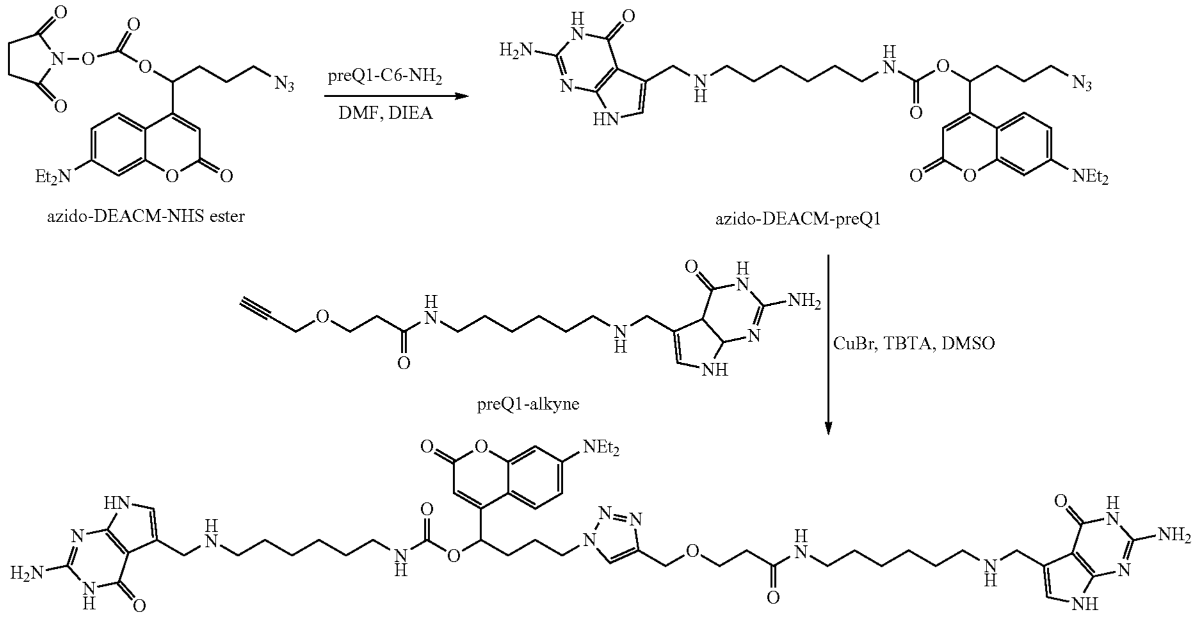

azido-DEACM-NHS ester azido-DEACM-preQ1 preQ1-alkyne preQ1-DEACM-preQ1 stirred overnight. After the substitution reaction completed, the solution was directly dried in vacuo. Then the mixture was purified by flash chromatography (0-50% EtOAc in hexanes) to afford the product preQ1-alkyne as pale white solid (45.9 mg, 91%). $^1H$ NMR (500 MHz, Methanol-d4) δ 6.87 (s, 1H), 4.28 (s, 2H), 4.17 (d, J=2.4 Hz, 2H), 3.79 (t, J=6.1 Hz, 2H), 3.38 (s, 1H), 3.24-3.18 (m, 2H), 3.08 (t, J=7.5 Hz, 2H), 2.89 (t, J=2.4 Hz, 1H), 2.46 (t, J=6.1 Hz, 2H), 1.76 (p, J=7.5 Hz, 2H), 1.56 (p, J=7.1 Hz, 2H), 1.51-1.36 (m, 4H). $^{13}C$ NMR (126 MHz, Methanol-d4, δ): δ 172.09, 161.06, The preparation of the azido-DEACM-HNS ester is described in previous report.[5] $preQ1-C6-NH_2$ (8.8 mg, 0.032 mmol) and DIEA (7.1 mg, 0.055 mmol) in DMF (0.5 mL) was added to azido-DEACM-NHS ester (5.0 mg, 0.011 mmol) in DMF (0.5 mL). The resulting solution was stirred for 1 hour. After the substitution completed, the solution was directly subjected to semipreparative HPLC purification, using a C18 column [gradient of $H_2O$ with 0.14% formic acid and MeOH with 0.1% formic acid 95:5 (0 min) to 5:95 (10 min to 18 min)]. Shielded from light, the fractions containing the product azido-DEACM-preQ1 [confirmed by low resolution MS, LRMS ($M+H^+$) calcd for $[C_{31}H_{43}N_{10}O_5]^+$ 635.3, found 635.3] from semipreparative HPLC purification were dried in vacuo with ice bath. Otherwise, the product azido-DEACM-preQ1 is prone to decompose. After drying in vacuo with ice bath, there is a little amount of water left in the vial, due to the low temperature, which was directly applied to the next step without further processing.

Shielded from light, CuBr [0.8 mg, 0.0055 mmol in DMSO:$H_2O$ (0.3 ml:0.3 mL)] was added to the vial, followed by the addition of preQ1-alkyne (4.3 mg, 0.011 mmol) in DMSO (0.4 mL). The resulting solution was stirred for about 2 hours. After the click reaction completed, the solution was directly subjected to semipreparative HPLC purification, using a $C_{18}$ column [gradient of $H_2O$ with 0.1% formic acid and MeOH with 0.1% formic acid 95:5 (0 min) to 5:95 (10 min to 18 min)]. Shielded from light, the fractions containing the product preQ1-DEACM-preQ1 from semipreparative HPLC purification were dried in vacuo at room temperature. After drying in vacuo with ice bath, there was a little amount of water left in the vial, due to the low temperature. Then, a solvent mixture of $H_2O$: MeCN (0.3 ml:0.3 mL) was added to the vial. After freezing lyophilization, preQ1-DEACM-preQ1 (0.5 mg, 4.4% for 2 steps) was obtained, confirmed by HRMS. HRMS ($M+2H^+$) calcd for $[C_{50}H_{72}N_{16}O_8]^+$ 512.2850, found 512.2854.

RNA Labeling Using the RNA-CLAMP Technology

Dimerization of the 17-Nt Tag RNA Oligo by RNA-CLAMP 17-nt RNA Tag oligo (GCAGACUGUAAAUCUGC) (SEQ ID NO:1) was purchased from IDT. TGT labeling reaction was assembled with the following components in 1×TGT reaction buffer: 10 μM of 17-nt RNA oligo, 5 μM of TGT enzyme, 5 μM of small-molecule substrate (preQ1-PEG10-preQ1, FIG. 28A), and 5 mM DTT. The reaction mixture was incubated at 37° C. for 4 hours. 1 μL of proteinase K was added into reaction mixture and incubated at 37° C. for 30 minutes to terminate the labeling reaction. The reaction was analyzed on 18% denaturing PAGE (FIG. 28A). In FIG. 28A, we can see that after the TGT labeling reaction, two new RNA products were produced. The top RNA band is the dimerized 17-nt Tag oligo. The middle band is the singly labeled Tag oligo. This experiment demonstrated the capability of the TGT enzyme to form a covalent bond between two RNA hairpins and builds the foundation for our RNA-CLAMP technology.

Intramolecular Cross-Link of the RNA

Sequence of the RNA-1 (the Tag Sequences are Underlined)

```
                                    (SEQ ID NO: 6)
GCAGACTGTAAATCTGCCACTAGTAACGGCCGCCAGT

GTGCTGGAATTCTGCAGATAGCAGACTGTAAATCTGC
```

The in vitro transcription reaction was performed following previous established protocols [1]. PAGE gel purified RNA-1 was subjected to TGT labeling reaction using the preQ1-PEG10-preQ1 small-molecule substrate. TGT labeling reaction was assembled with the following components in 1×TGT reaction buffer: 1 μM of RNA-1, 2 μM of TGT enzyme, 1 μM of small-molecule substrate (preQ1-PEG10-preQ1, FIG. 28A), 1 unit/μL of Super RNase Inhibitor (Invitrogen, catalog number AM2694), and 5 mM DTT. The reaction mixture was incubated at 37° C. for 4 hours. Next, 1 μL of proteinase K was added into the reaction mixture and incubated at 37° C. for 30 minutes to terminate the labeling reaction and get rid of potential RNAse contamination. Note: adding the small-molecule substrate last should promote higher 'clamping' conversion. The reason is that the TGT enzyme forms a covalent bound with the RNA substrate, resulting in a TGT-RNA intermediate. Adding the small-molecule substrate last ensured that two TGT molecules were covalently tethered to the RNA. In this manner, intermolecular cross-linking of RNA can be reduced. The crude TGT labeling products were analyzed by 7% denaturing TBE PAGE (FIG. 9). As shown in FIG. 9, we observed multiple RNA products. First, we observed unlabeled RNA starting material, shown as the bottom band with the same migration distance as Line 1. We also observed RNA degradation shown as smear bands below the RNA starting material. We hypothesize that, apart from the desired 'clamped' RNA product, the TGT labeling reaction should at least generate two kinds of by-products: by-product 1 was generated by attaching one small-molecule substrate at each Tag sequence without forming intermolecular or intramolecular cross-linking; by-product 2 was formed through intermolecular cross-linking, which were shown as multiple top bands in Line 2.

Figure 10B:
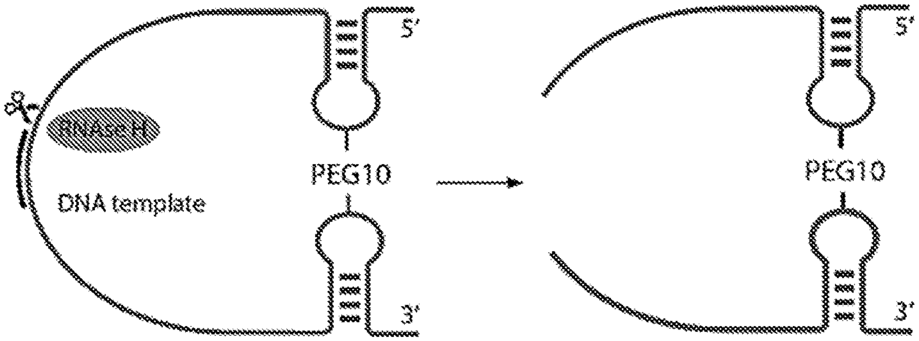
Figure 10B:
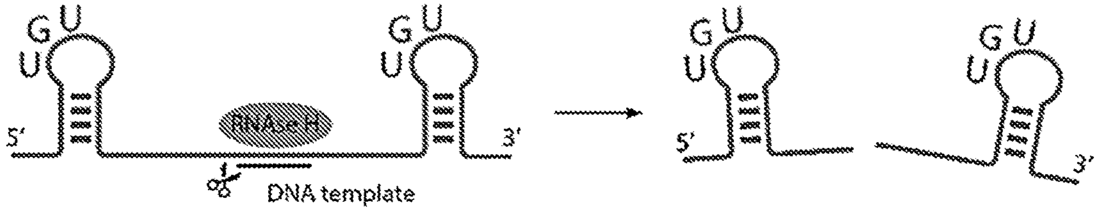

To distinguish between multiple RNA products after the TGT reaction, we designed an RNAse-H digestion assay (FIG. 10B). RNAse-H only digests RNA-DNA hybrids. We designed a DNA oligo which was complementary to the internal sequence of RNA-1 and use RNAse-H to specifically cut the internal sequence of RNA-1. As illustrated in FIG. 10B, after the RNAse-H digestion (DNA oligo used for the RNAse-H digestion assay on RNA-1: CCAGCACACTGGCGGCCG) (SEQ ID NO:41), linear RNA products would generate two RNA fragments whereas the 'clamped' RNA product would only generate one RNA digestion product. We separated the product bands observed on (FIG. 9) (Line 2) and ran each RNA product through the RNAse-H digestion assay (FIG. 11). As expected, both the RNA byproduct-1 and byproduct-2 generated two or multiple bands after the RNAse-H digestion assay. Only the 'clamped' RNA product generated one single band after the RNAse-H digestion assay. Therefore, we verified that TGT can successfully form an intramolecular cross-link (or 'clamp') on the RNA of interest using the preQ1-PEG10-preQ1 small-molecule substrate.

Synthesis of the Single-Guide RNA (sgRNA)

In Vitro Transcription Reaction Template

In vitro transcription template was purchased from IDT as ssDNA and used directly for in vitro transcription reactions.

In vitro transcription template (ssDNA, 20 nt targeting sequence was shown as $N^{20}$)

TABLE 1

| | |
|---|---|
| DYRKIA targeting sequence | GCTGCTGGCCTTCAGATGGC (SEQ ID NO: 33) |
| GRIN2B targeting sequence | GGAGAACAGCACTCCGCTCT (SEQ ID NO: 34) |

In Vitro Transcription Reaction

Each IVT reaction was set up with 50 nM of linearized DNA template, 5 mM of each ATP, CTP, UTP, 9 mM of GTP (NEB, Ipswitch, MA), 0.004 unit/μL of thermostable inorganic pyrophosphatase (NEB, Ipswitch, MA), 0.25 μg/μL T7 RNA polymerase, 0.05% Triton X-100 (Sigma, St. Louis, MO) and 1 unit/μL RNase Inhibitor, Murine (NEB, Ipswitch, MA). The IVT reaction was carried out at 37° C. for 4 hours to allow for sufficient RNA synthesis. To remove DNA template, 2 μL of 100 mM $CaCl_2$ and 20 units of Turbo DNase (Life Technologies, Carlsbad, CA) were added to the mixture and incubated at 37° C. for 1 hour. The mixture was then centrifuged at 10,000 RCF for 5 minutes at room temperature to pellet any remaining magnesium pyrophosphate. The supernatant was resuspended in 50 μL RNase free water, followed by 12% denaturing PAGE purification. Purified IVT products were stored at −80° C. until used.

Intramolecular Cross-Link of the sgRNA by RNA-CLAMP

RNA-CLAMP Using preQ1-DEACM-preQ1

To 'clamp' the sgRNA-9, 1 μM of sgRNA transcript, 1 μM of TGT enzyme, 1 μM of small-molecule substrate, 5 mM of DTT, 1 unit/μL of RNAse Inhibitor was assembled in 1×TGT buffer. The reaction mixture was incubated at 37° C. for 4 hours, followed by the addition of 1 μL of proteinase K. The crude labeling products were analyzed by 12% denaturing TBE-PAGE (FIG. 20A). As shown in FIG. 20A, the conversion rate to the 'clamped' sgRNA was 79.4%, which is much higher than the conversion rate of the RNA-1. We reasoned that this was due to the stable ternary structure of the sgRNA. The first Tag sequence was located at the tetra-loop of the sgRNA and the second Tag sequence was located at the stem loop 2 of the sgRNA. These two loops are well-structured and close to each other, promoting higher intramolecular cross-linking conversion. To get rid of undesired RNA product and reduce background gene editing activity, 'clamped' sgRNA-9 was purified by denaturing TBE-PAGE. The purified 'clamped' sgRNA-9 was shown as a single band on a 12% denaturing PAGE gel (FIG. 20B). To uncage the 'clamped' sgRNA-9, a 456 nm LED light (50 W max) was used to irradiate the 'clamped' sgRNA in water for 3 minutes. LED irradiation completely photo-cleaved the DEACM linker, transforming the 'clamped' sgRNA to its linear form (FIG. 20B).

RNA-CLAMP Using preQ1-NB-preQ1

Figure 29:
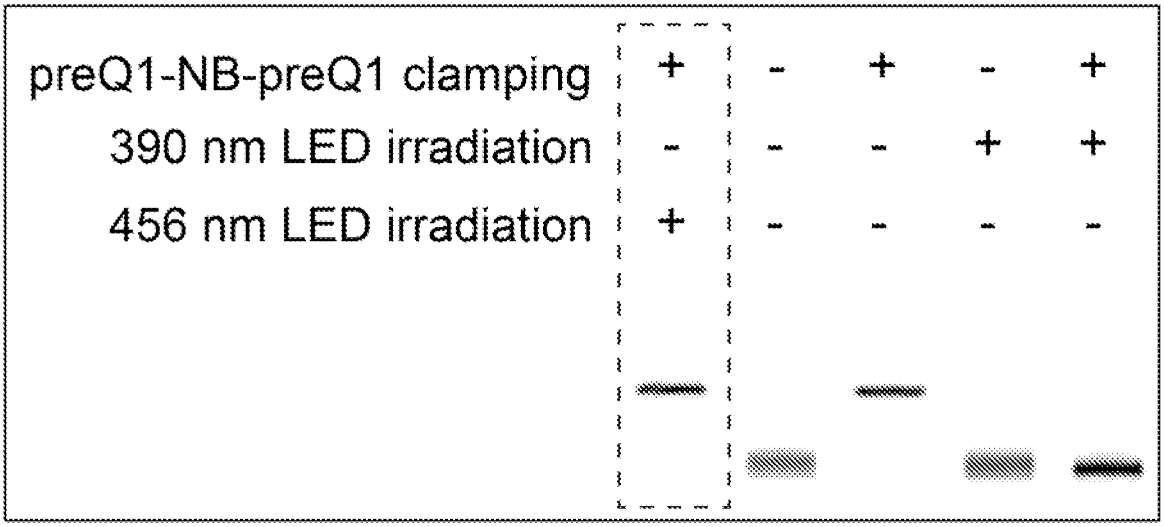
FIG. 29. 'Clamping' of the sgRNA-11 using preQ1-NB-preQ1 substrate and the in vitro photo-uncaging. 12% denaturing PAGE analysis of the in vitro photo-cleavage of 'clamped' sgRNA-11. The NB linker was responsive to 390 nm wavelength of light. Irradiation with 390 nm LED light (52 W) for 30 seconds completely cleaved the NB linker, transforming the 'clamped' sgRNA-1 to its linear form. However, only minimal cleavage of the NB linker was observed under 456 nm LED irradiation (0.09% as measured by RNA band intensities).

Similarly, we performed RNA-CLAMP reaction on sgRNA-11 using the preQ1-NB-preQ1 small molecule substrate. As shown in FIG. 29, the 'clamped' sgRNA-11 can be completely photo-uncaged by irradiation with a 390 nm LED light (52 W max) for 30 seconds. As a control experiment, we irradiated the 'clamped' sgRNA-11 using the 456 nm LED light for 3 minutes. Only minimal photo-cleavage of the NB linker was observed (0.09%), demonstrating that the NB linker can be efficiently cleaved by a 390 nm LED, but not a 456 nm LED.

CRISPR-Cas9 Gene Editing

Gene Editing in HEK-293-Cas9 Cell Line

Gene editing experiments were performed following previously reported protocols.[2] For gene editing experiments using HEK-293-Cas9 cell line, 250 ng sgRNA and 0.5 μL Lipofectamine RNAiMAX were used to form the Lipo-RNA complex. The formed complex was added with 150 μL DMEM (10% FBS) containing 40K HEK-293-Cas9 cells. The transfection was performed in a 96-well plate format. 24 hours after transfection, cell medium was changed to complete DMEM medium. At day 4, genomic DNA was extracted using 80 μL QuickExtract™ DNA Extraction Solution (Lucigen, catalog number: QE09050). Following the manufacturer's protocol, the extraction solution was heated at 65° C. for 15 minutes and then at 95° C. for another 15 minutes. The resulting solution was diluted using water at a 1:10 ratio. The diluted product was directly used as a template for PCR amplification of the genomic region. For PCR amplification of the genomic region, Q5 HOTSTART HIFI DNA polymerase 2× master mix was used following the manufacturer's protocol without further optimization. The primers used for amplifying the DYRK1A and GRIN2B genome locus are listed below.

TABLE 2

| | |
|---|---|
| DYRKIA_fwd | GGAGCTGGTCTGTTGGAGAA (SEQ ID NO: 35) |
| DYRKIA_rvs | TCCCAATCCATAATCCCACGTT (SEQ ID NO: 36) |
| GRIN2B_fwd | CAGGAGGGCCAGGAGATTTG (SEQ ID NO: 37) |
| GRIN2B_rvs | TGAAATCGAGGATCTGGGCG (SEQ ID NO: 38) |

Crude PCR products were column purified using a Zymo DNA purification kit. The purified PCR amplicon was analyzed by Sanger sequencing to estimate INDEL % using the ICE tool.[3] The wt-sgRNA gene editing INDEL % was usually around 70-80% following this protocol.

Gene Editing in HEK-293 Cell Line

For gene editing experiments performed using a HEK-293 wild-type cell line, mRNA encoding the Cas9 protein (Trilink, catalog number L-7206-20) was transfected into HEK-293 cells one day prior to sgRNA transfection. For mRNA transfection, Lipo-RNA complex was formed by using 500 ng mRNA, 0.9 μL Lipofectamine RNAiMAX in 50 μL total volume, combined with 150 μL DMEM complete medium containing 40K HEK-293 cells. At day 2, sgRNA transfection was performed following the protocol described in the previous section. The wt-sgRNA gene editing INDEL % was usually around 40-50% following this protocol.

Surrogate EGFP Reporter

The surrogate EGFP reported was adopted from a previously reported method.[4] In brief, an mCherry transgene is constitutively expressed by a CMV promoter, whereas the expression of downstream GFP genes are disrupted by an in-frame stop codon as well as a frame shift (+1 or +2 shift). Without INDEL formation, the cell will express mCherry but not GFP. However, when an INDEL is formed by CRISPR-Cas9 mediated gene editing and the cellular NHEJ pathway, the frame shift of the downstream GFP gene can be corrected, resulting in GFP expression.

To test the surrogate reporter in HEK-293 cells. The preQ1-DEACM-preQ1 'clamped' sgRNA-12 targeting the sequence between the mCherry and the GFP genes was introduced into the surrogate EGFP reporter cells by transient transfection (sgRNA targeting sequence: GTTCAGGGCTTGACCAACAC) (SEQ ID NO:40). 4 hours later, the transfection medium was replaced with complete cell-growth medium and cells were irradiated with a 456 nm LED (50 W max) for 3 minutes. Cell images were taken 48 hours after the LED irradiation event. As shown in FIG. 23, cells only express the mCherry protein, not the GFP protein without light-irradiation. This is because the 'clamped' sgRNA-12 has no gene editing activity and the expression of GFP was completely quenched by the stop codon and the frame shift. However, 456 nm photo-irradiation cleaved the DEACM linker, activating the sgRNA-12. The Cas9 enzyme was therefore able to bind and cleave the designed DNA target sequence between the mCherry open reading frame and the GFP open reading frame. The cellular NHEJ pathway then generated random insertion or deletion which may destroy the stop-codon and correct the frame shift, resulting in the activation of the GFP expression. Notably, the 'clamping' of the sgRNA completely deactivated its gene editing activity. Therefore, we observed no leakiness of GFP expression in the non-irradiated cells.

In Vitro Binding Assay of the 'Clamped' sgRNA

We investigated the binding of the unmodified or 'clamped' sgRNA with the Cas9 protein (NEB, catalog number M0646T) in vitro. First, we designed a double-stranded 60 bp DNA substrate which contains the sgRNA-9 target sequence with the required NGG PAM. We used sgRNA-11 as the negative control non-targeting sgRNA, since sgRNA-11 did not target the 60 bp DNA substrate.

Figure 30:
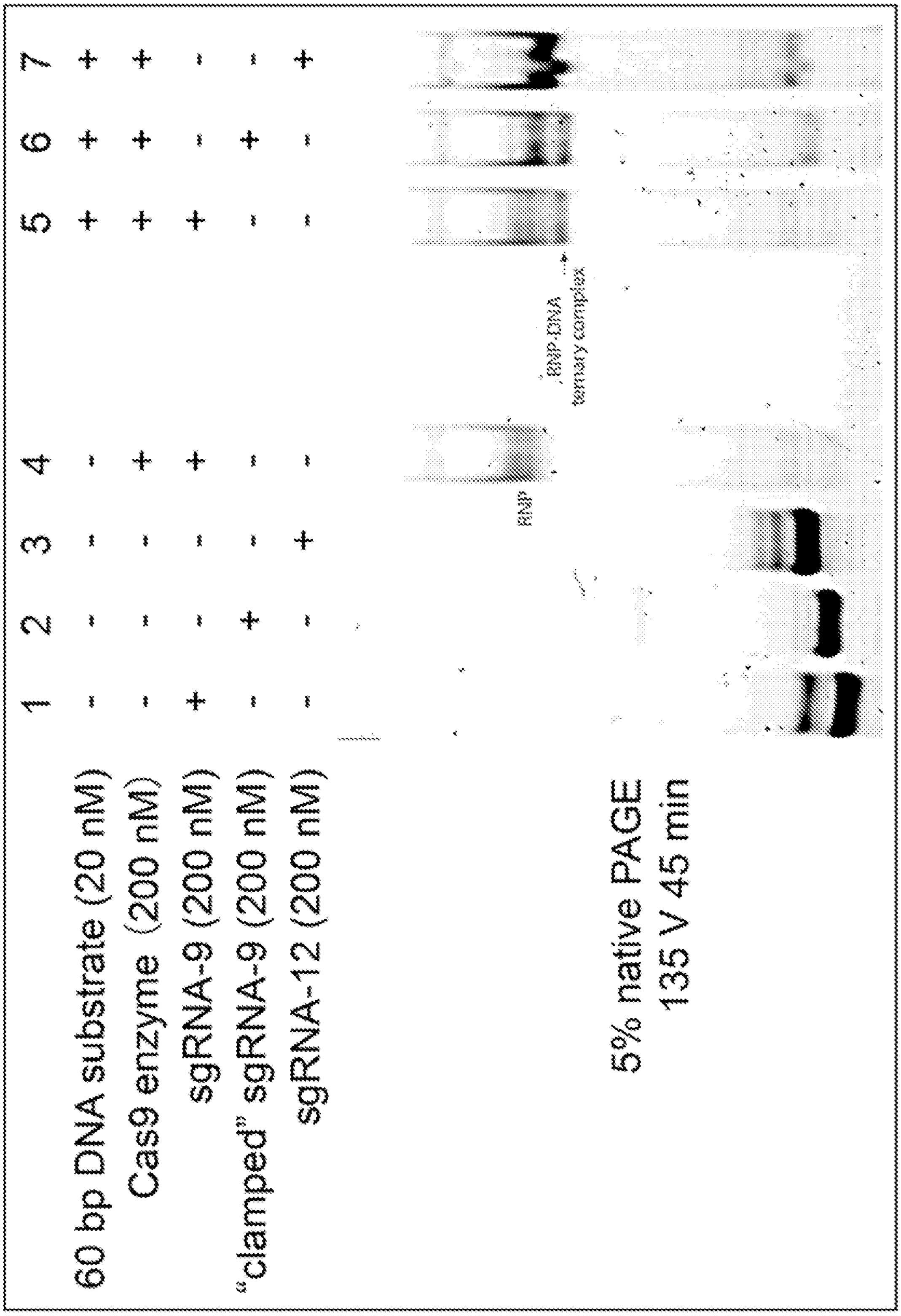
FIG. 30. In vitro binding assay of unmodified or 'clamped' sgRNA and the DNA substrate. Line 1 and line 3 represented unmodified sgRNAs. Because native PAGE analysis was used, we observed multiple RNA bands in line 1 and line 3, which is expected. RNA band in line 2 represented 'clamped' sgRNA-9. Here, we only observed a single band. We reasoned that this was because the intramolecular crosslinking of sgRNA-9 rigidified its ternary structure. Cas9-sgRNA-DNA ternary complexes (pointed with a red arrow) were observed in both line 5 and line 6, demonstrating that the 'clamped' sgRNA-9 can also bind to the DNA target. Since the sgRNA-12 did not target the DNA substrate, no Cas9-sgRNA-DNA complex was observed in line 7, demonstrating the specificity of the Cas9-sgRNA ribonucleoprotein.

To test the binding the sgRNA and the 60 bp DNA substrate in vitro, 200 nM of Cas9 enzyme and 200 nM of sgRNA were incubated in 1×NEB buffer 3.1 for 15 minutes at room temperature. Next, 20 nM of DNA substrate was added into the pre-formed Cas9-sgRNA RNP and incubated at 37° C. for 90 seconds. After the incubation, the reaction mixture was immediately placed on ice with the addition of 50% reaction volume of 50% glycerol to stop the reaction (Note: it is important to quench the reaction as quickly as possible). Finally, the reaction was analyzed on 5% native TBE-PAGE (FIG. 30). In FIG. 30, lane 1 to lane 3 are the loading control of the sgRNA. The unmodified sgRNA-9 and sgRNA-11 were shown as multiple bands in the native TBE gel due to their secondary/ternary structures. Interestingly, the 'clamped' sgRNA-9 was shown as a single major band on the native gel. We reasoned it was because the intramolecular clamping rigidified the structure of the sgRNA. The formation of the sgRNA-9 Cas9 RNP was detected in lane 4. The formation of the Cas9-sgRNA-DNA ternary complex was only detected in lane 5 (unmodified sgRNA-9) and lane 6 ('clamped' sgRNA-9), but not in lane 7 (non-targeting sgRNA-11), demonstrating that the 'clamped' sgRNA-9 was also able to bind to the Cas9 as well as the target DNA in vitro.

REFERENCES FOR EXAMPLES 1-2

[1] Nihongaki, Y., Kawano, F., Nakajima, T. & Sato, M. Photoactivatable CRISPR-Cas9 for optogenetic genome editing. *Nat. Biotechnol.* 33, 755-760 (2015).

[2] Alexander, S. C. & Devaraj, N. K. Developing a Fluorescent Toolbox to Shed Light on the Mysteries of RNA. *Biochemistry* 56, 5185-5193 (2017).

[3] Velema, W. A., Park, H. S., Kadina, A., Orbai, L. & Kool, E. T. Trapping Transient RNA Complexes by Chemically Reversible Acylation. *Angew. Chem. Int. Ed.* 132, 22201-22206 (2020).

[4] Velema, W. A. & Kool, E. T. The chemistry and applications of RNA 2'-OH acylation. *Nat Rev Chem* 4, 22-37 (2019).

[5] Holstein, J. M. & Rentmeister, A. Current covalent modification methods for detecting RNA in fixed and living cells. *Methods* 98, 18-25 (2016).

[6] Kaewsapsak, P., Shechner, D. M., Mallard, W., Rinn, J. L. & Ting, A. Y. Live-cell mapping of organelle-associated RNAs via proximity biotinylation combined with protein-RNA crosslinking. *eLife* 6, (2017).

[7] Dorn, G. et al. Structural modeling of protein-RNA complexes using crosslinking of segmentally isotope-labeled RNA and MS/MS. *Nat Methods* 14, 487-490 (2017).

[8] Hentze, M. W., Castello, A., Schwarzl, T. & Preiss, T. A brave new world of RNA-binding proteins. *Nat. Rev. Mol. Cell. Biol.* 19, 327-341 (2018).

[9] Dow, L. E. et al. Inducible in vivo genome editing with CRISPR-Cas9. *Nat. Biotechnol.* 33, 390-394 (2015).

[10] Zetsche, B., Volz, S. E. & Zhang, F. A split-Cas9 architecture for inducible genome editing and transcription modulation. *Nat. Biotechnol.* 33, 139-142 (2015).

[11] Kim, S., Kim, D., Cho, S. W., Kim, J. & Kim, J.-S. Highly efficient RNA-guided genome editing in human cells via delivery of purified Cas9 ribonucleoproteins. *Genome Research* 24, 1012-1019 (2014).

[12] Zuris, J. A. et al. Cationic lipid-mediated delivery of proteins enables efficient protein-based genome editing in vitro and in vivo. *Nat. Biotechnol.* 33, 73-80 (2014).

[13] Ramakrishna, S. et al. Gene disruption by cell-penetrating peptide-mediated delivery of Cas9 protein and guide RNA. *Genome Research* 24, 1020-1027 (2014).

[14] Hemphill, J., Borchardt, E. K., Brown, K., Asokan, A. & Deiters, A. Optical Control of CRISPR/Cas9 Gene Editing. *J. Am. Chem. Soc.* 137, 5642-5645 (2015).

[15] Nihongaki, Y., Kawano, F., Nakajima, T. & Sato, M. Photoactivatable CRISPR-Cas9 for optogenetic genome editing. *Nat. Biotechnol.* 33, 755-760 (2015).

[16] Jain, P. K. et al. Development of Light-Activated CRISPR Using Guide RNAs with Photocleavable Protectors. *Angew. Chem. Int. Ed.* 55, 12440-12444 (2016).

[17] Zhou, W. et al. Spatiotemporal Control of CRISPR/Cas9 Function in Cells and Zebrafish using Light-Activated Guide RNA. *Angew. Chem. Int. Ed.* 132, 9083-9088 (2020).

[18] Nishimasu, H. et al. Crystal Structure of Cas9 in Complex with Guide RNA and Target DNA. *Cell* 156, 935-949 (2014).

[19] Jiang, F. & Doudna, J. A. CRISPR-Cas9 Structures and Mechanisms. *Annu. Rev. Biophys.* 46, 505-529 (2017).

[20] Doudna, J. A. & Charpentier, E. The new frontier of genome engineering with CRISPR-Cas9. *Science* 346, 1258096 (2014).

[21] Hsu, P. D., Lander, E. S. & Zhang, F. Development and Applications of CRISPR-Cas9 for Genome Engineering. *Cell* 157, 1262-1278 (2014).

[22] Harrington, L. B. et al. A Broad-Spectrum Inhibitor of CRISPR-Cas9. *Cell* 170, 1224-1233.e15 (2017).

[23] Alexander, S. C., Busby, K. N., Cole, C. M., Zhou, C. Y. & Devaraj, N. K. Site-Specific Covalent Labeling of RNA by Enzymatic Transglycosylation. *J. Am. Chem. Soc.* 137, 12756-12759 (2015).

[24] Ehret, F., Zhou, C. Y., Alexander, S. C., Zhang, D. & Devaraj, N. K. Site-Specific Covalent Conjugation of Modified mRNA by tRNA Guanine Transglycosylase. *Mol. Pharmaceutics* 15, 737-742 (2017).

[25] Zhou, C. Y., Alexander, S. C. & Devaraj, N. K. Fluorescent turn-on probes for wash-free mRNA imaging via covalent site-specific enzymatic labeling. *Chem. Sci.* 8, 7169-7173 (2017).

[26] Zhang, D., Zhou, C. Y., Busby, K. N., Alexander, S. C. & Devaraj, N. K. Light-Activated Control of Translation by Enzymatic Covalent mRNA Labeling. *Angew. Chem. Int. Ed* 130, 2872-2876 (2018).

[27] Zhang, D., Jin, S., Piao, X. & Devaraj, N. K. Multiplexed Photoactivation of mRNA with Single-Cell Resolution. *ACS Chem. Biol.* 15, 1773-1779 (2020).

[28] Busby, K. N., Fulzele, A., Zhang, D., Bennett, E. J. & Devaraj, N. K. Enzymatic RNA Biotinylation for Affinity Purification and Identification of RNA-Protein Interactions. *ACS Chem. Biol.* 15, 2247-2258 (2020).

[29] Nakamura, H. et al. How does RNase H recognize a DNA.RNA hybrid? *Proc. Natl Acad. Sci.* 88, 11535-11539 (1991).

[30] Klumpp, K. Two-metal ion mechanism of RNA cleavage by HIV RNase H and mechanism-based design of selective HIV RNase H inhibitors. *Nucleic Acids Res.* 31, 6852-6859 (2003).

[31] Nowotny, M., Gaidamakov, S. A., Crouch, R. J. & Yang, W. Crystal Structures of RNase H Bound to an RNA/DNA Hybrid: Substrate Specificity and Metal-Dependent Catalysis. *Cell* 121, 1005-1016 (2005).

[32] Ran, F. A. et al. Genome engineering using the CRISPR-Cas9 system. *Nat. Protoc.* 8, 2281-2308 (2013).

[33] Hsiau, T. et al. Inference of CRISPR Edits from Sanger Trace Data. *BioRxiv* (2018)

[34] Goguen, B. N., Aemissegger, A. & Imperiali, B. Sequential Activation and Deactivation of Protein Function Using Spectrally Differentiated Caged Phosphoamino Acids. *J. Am. Chem. Soc.* 133, 11038-11041 (2011).

[35] Kim, H. et al. Surrogate reporters for enrichment of cells with nuclease-induced mutations. *Nat. Methods* 8, 941-943 (2011).

[36] Wu, X. et al. Genome-wide binding of the CRISPR endonuclease Cas9 in mammalian cells. *Nat. Biotechnol.* 32, 670-676 (2014).

[37] Liu, Y. et al. Very fast CRISPR on demand. *Science* 368, 1265-1269 (2020).

[38] Luciano, M. P. et al. A near-infrared light-mediated cleavable linker strategy using the heptamethine cyanine chromophore. in *Methods in Enzymology* 245-275 (2020).

[39] Antelmann, H. & Helmann, J. D. Thiol-Based Redox Switches and Gene Regulation. *Antioxidants & Redox Signaling* 14, 1049-1063 (2011).

[40] Choy, C. J., Geruntho, J. J., Davis, A. L. & Berkman, C. E. Tunable pH-Sensitive Linker for Controlled Release. *Bioconjugate Chem.* 27, 824-830 (2016).

[41] Leriche, G., Chisholm, L. & Wagner, A. Cleavable linkers in chemical biology. *Bioorganic & Medicinal Chemistry* 20, 571-582 (2012).

[42] Bargh, J. D., Isidro-Llobet, A., Parker, J. S. & Spring, D. R. Cleavable linkers in antibody-drug conjugates. *Chem. Soc. Rev.* 48, 4361-4374 (2019).

REFERENCES FOR EXAMPLE 3

[1] Zhang, D., Zhou, C. Y., Busby, K. N., Alexander, S. C. & Devaraj, N. K. Light-Activated Control of Translation by Enzymatic Covalent mRNA Labeling. *Angew. Chem. Int. Ed.* 130, 2872-2876 (2018).

[2] Ran, F. A. et al. Genome engineering using the CRISPR-Cas9 system. *Nat. Protoc.* 8, 2281-2308 (2013).

[3] Hsiau, T. et al. Inference of CRISPR Edits from Sanger Trace Data. *BioRxiv* (2018)

[4] Kim, H. et al. Surrogate reporters for enrichment of cells with nuclease-induced mutations. *Nat. Methods* 8, 941-943 (2011).

[5] Zhang, D., Jin, S., Piao, X. & Devaraj, N. K. Multiplexed Photoactivation of mRNA with Single-Cell Resolution. *ACS Chem. Biol.* 15, 1773-1779 (2020).

```
INFORMAL SEQUENCE LISTING
RNA Stem Loop
                                                        (SEQ ID NO: 1)
GCAGACUGUAAAUCUGC

RNA Stem Loop (preQ1)
                                                        (SEQ ID NO: 2)
GCAGACU(pQ1)UAAAUCUGC

Target DNA
                                                        (SEQ ID NO: 3)
CCTTTAATCCACGCGAACCGACC

Example sgRNA
                                                        (SEQ ID NO: 4)
GGAAAUUAGGUGCGCUUGGCGUUUUAGAGCUAGAAAUAGCAAGUUAAAAUAAGG

CUAGUCCGUUAUCAACUUGAAAAAGUGGCACCGAGUCGGUGCUU

Codon
                                                        (SEQ ID NO: 5)
UGU

Sequence of the RNA-1 (the Tag sequences are underlined)
                                                        (SEQ ID NO: 6)
GCAGACTGTAAATCTGCCACTAGTAACGGCCGCCAGTGTGCTGGAATTCTGCAGATA

GCAGACTGTAAATCTGC

sgRNA:
                                                        (SEQ ID NO: 7)
NNNNNNNNNNNNNNNNNNNNGTTTTAGAGCTAGAAATAGCAAGTTAAAATAAGGC

TAGTCCGTTATCAACTTGAAAAAGTGGCACCGAGTCGGTGC

wt-sgRNA:
                                                        (SEQ ID NO: 8)
CTAATACGACTCACTATANNNNNNNNNNNNNNNNNNNNGTTTTAGAGCTAGAAATA

GCAAGTTAAAATAAGGCTAGTCCGTTATCAACTTGAAAAAGTGGCACCGAGTCGGT

GCTTTTTT
```

-continued sgRNA-1:
(SEQ ID NO: 9)
GCAGACTGTAAATCTGCTTTTNNNNNNNNNNNNNNNNNNNNGTTTTAGAGCTAGAA

ATAGCAAGTTAAAATAAGGCTAGTCCGTTATCAACTTGAAAAAGTGGCACCGAGTC

GGTGC sgRNA-2:
(SEQ ID NO: 10)
NNNNNNNNNNNNNNNNNNNNGTTTTAGAGCTAGCAGACTGTAAATCTGCTAGCAA

GTTAAAATAAGGCTAGTCCGTTATCAACTTGAAAAAGTGGCACCGAGTCGGTGC sgRNA-3:
(SEQ ID NO: 11)
NNNNNNNNNNNNNNNNNNNNGTTTTAGAGCTAGAAATAGCAAGTTAAAATAAGGC

GCAGACTGTAAATCTGCGTCCGTTATCAACTTGAAAAAGTGGCACCGAGTCGGTGC sgRNA-4:
(SEQ ID NO: 12)
NNNNNNNNNNNNNNNNNNNNGTTTTAGAGCTAGAAATAGCAAGTTAAAATAAGGC

TAGTCCGTTATCAACTTGCAGACTGTAAATCTGCAAGTGGCACCGAGTCGGTGC sgRNA-5:
(SEQ ID NO: 13)
NNNNNNNNNNNNNNNNNNNNGTTTTAGAGCTAGAAATAGCAAGTTAAAATAAGGC

TAGTCCGTTATCAACTTGAAAAAGTGGCACCGAGCAGACTGTAAATCTGCTCGGTGC sgRNA-6:
(SEQ ID NO: 14)
NNNNNNNNNNNNNNNNNNNNGTTTTAGAGCTAGAAATAGCAAGTTAAAATAAGGC

TAGTCCGTTATCAACTTGAAAAAGTGGCACCGAGTCGGTGCTTATTGCAGACTGTAA

ATCTGC sgRNA-7:
(SEQ ID NO: 15)
NNNNNNNNNNNNNNNNNNNNGTTTTAGAGCTAGCAGACTGTAAATCTGCTAGCAA

GTTAAAATAAGGCTAGTCCGTTATCAACTTGCAGACTGTAAATCTGCAAGTGGCACC

GAGTCGGTGC sgRNA-8:
(SEQ ID NO: 16)
NNNNNNNNNNNNNNNNNNNNGTTTTAGAGCTAAGACTGTAAATCTTAGCAAGTTAA

AATAAGGCTAGTCCGTTATCAACTTAGACTGTAAATCTAAGTGGCACCGAGTCGGTG

C sgRNA-9:
(SEQ ID NO: 17)
NNNNNNNNNNNNNNNNNNNNGTTTTAGAGCTAACTGTAAATTAGCAAGTTAAAATA

AGGCTAGTCCGTTATCAACTTACTGTAAATAAGTGGCACCGAGTCGGTGC sgRNA-10:
(SEQ ID NO: 18)
NNNNNNNNNNNNNNNNNNNNGTTTTAGAGCTACTGTAAATAGCAAGTTAAAATAA

GGCTAGTCCGTTATCAACTTCTGTAAAAAGTGGCACCGAGTCGGTGC sgRNA-1:
(SEQ ID NO: 19)
CTAATACGACTCACTATAGCAGACTGTAAATCTGCTTTTNNNNNNNNNNNNNNNNN

NNNGTTTTAGAGCTAGAAATAGCAAGTTAAAATAAGGCTAGTCCGTTATCAACTTG

AAAAAGTGGCACCGAGTCGGTGCTTTTTT

-continued sgRNA-2:
(SEQ ID NO: 20)
CTAATACGACTCACTATANNNNNNNNNNNNNNNNNNNNGTTTTAGAGCTAGCAGAC
TGTAAATCTGCTAGCAAGTTAAAATAAGGCTAGTCCGTTATCAACTTGAAAAAGTGG
CACCGAGTCGGTGCTTTTTT sgRNA-3:
(SEQ ID NO: 21)
CTAATACGACTCACTATANNNNNNNNNNNNNNNNNNNNGTTTTAGAGCTAGAAATA
GCAAGTTAAAATAAGGCGCAGACTGTAAATCTGCGTCCGTTATCAACTTGAAAAAG
TGGCACCGAGTCGGTGCTTTTTTT sgRNA-4:
(SEQ ID NO: 22)
CTAATACGACTCACTATANNNNNNNNNNNNNNNNNNNNGTTTTAGAGCTAGAAATA
GCAAGTTAAAATAAGGCTAGTCCGTTATCAACTTGCAGACTGTAAATCTGCAAGTGG
CACCGAGTCGGTGCTTTTTT sgRNA-5:
(SEQ ID NO: 23)
CTAATACGACTCACTATANNNNNNNNNNNNNNNNNNNNGTTTTAGAGCTAGAAATA
GCAAGTTAAAATAAGGCTAGTCCGTTATCAACTTGAAAAAGTGGCACCGAGCAGAC
TGTAAATCTGCTCGGTGCTTTTTT sgRNA-6:
(SEQ ID NO: 24)
CTAATACGACTCACTATANNNNNNNNNNNNNNNNNNNNGTTTTAGAGCTAGAAATA
GCAAGTTAAAATAAGGCTAGTCCGTTATCAACTTGAAAAAGTGGCACCGAGTCGGT
GCTTATTGCAGACTGTAAATCTGCTTTTTT sgRNA-7:
(SEQ ID NO: 25)
CTAATACGACTCACTATANNNNNNNNNNNNNNNNNNNNGTTTTAGAGCTAGCAGAC
TGTAAATCTGCTAGCAAGTTAAAATAAGGCTAGTCCGTTATCAACTTGCAGACTGTA
AATCTGCAAGTGGCACCGAGTCGGTGCTTTTTT sgRNA-8:
(SEQ ID NO: 26)
CTAATACGACTCACTATANNNNNNNNNNNNNNNNNNNNGTTTTAGAGCTAAGACTG
TAAATCTTAGCAAGTTAAAATAAGGCTAGTCCGTTATCAACTTAGACTGTAAATCTA
AGTGGCACCGAGTCGGTGCTTTTTT sgRNA-9:
(SEQ ID NO: 27)
CTAATACGACTCACTATANNNNNNNNNNNNNNNNNNNNGTTTTAGAGCTAACTGTA
AATTAGCAAGTTAAAATAAGGCTAGTCCGTTATCAACTTACTGTAAATAAGTGGCAC
CGAGTCGGTGCTTTTTT sgRNA-10:
(SEQ ID NO: 28)
CTAATACGACTCACTATANNNNNNNNNNNNNNNNNNNNGTTTTAGAGCTACTGTAA
ATAGCAAGTTAAAATAAGGCTAGTCCGTTATCAACTTCTGTAAAAAGTGGCACCGA
GTCGGTGCTTTTTT sgRNA-7 stem loop:
(SEQ ID NO: 29)
GCAGACUGUAAAUCUGC sgRNA-8 stem loop:
(SEQ ID NO: 30)
AGACUGUAAAUCU -continued sgRNA-9 stem loop:
(SEQ ID NO: 31)
ACUGUAAAU sgRNA-10 stem loop:
(SEQ ID NO: 32)
CUGUAAA DYRKIA targeting sequence
(SEQ ID NO: 33)
GCTGCTGGCCTTCAGATGGC GRIN2B targeting sequence
(SEQ ID NO: 34)
GGAGAACAGCACTCCGCTCT DYRKIA_fwd
(SEQ ID NO: 35)
GGAGCTGGTCTGTTGGAGAA DYRKIA_rvs
(SEQ ID NO: 36)
TCCCAATCCATAATCCCACGTT GRIN2B_fwd
(SEQ ID NO: 37)
CAGGAGGGCCAGGAGATTTG GRIN2B_rvs
(SEQ ID NO: 38)
TGAAATCGAGGATCTGGGCG Sequence of the EGFP surrogate reporter
(SEQ ID NO: 39)
ATGGTGAGCAAGGGCGAGGAGGATAACATGGCCATCATCAAGGAG
TTCATGCGCTTCAAGGTGCACATGGAGGGCTCCGTGAACGGCCAC
GAGTTCGAGATCGAGGGCGAGGGCGAGGGCCGCCCCTACGAGGGC
ACCCAGACCGCCAAGCTGAAGGTGACCAAGGGTGGCCCCCTGCCC
TTCGCCTGGGACATCCTGTCCCCTCAGTTCATGTACGGCTCCAAG
GCCTACGTGAAGCACCCCGCCGACATCCCCGACTACTTGAAGCTG
TCCTTCCCCGAGGGCTTCAAGTGGGAGCGCGTGATGAACTTCGAG
GACGGCGGCGTGGTGACCGTGACCCAGGACTCCTCCCTGCAAGAC
GGCGAGTTCATCTACAAGGTGAAGCTGCGCGGCACCAACTTCCCC
TCCGACGGCCCCGTAATGCAGAAGAAGACGATGGGCTGGGAGGCC
TCCTCCGAGCGGATGTACCCCGAGGACGGCGCCCTGAAGGGCGAG
ATCAAGCAGAGGCTGAAGCTGAAGGACGGCGGCCACTACGACGCT
GAGGTCAAGACCACCTACAAGGCCAAGAAGCCCGTGCAGCTGCCC
GGCGCCTACAACGTGAACATCAAGTTGGACATCACCTCCCACAAC
GAGGACTACACCATCGTGGAACAGTACGAACGCGCCGAGGGCCGC
CACTCCACCGGCGGCATGGACGAGCTGTACAAGGaGCTAGCATTG
TTCAGGGCTTGACCAACACTGGGTCCCTGCAGGatccagtgaGCA
AGGGCGAGGAGCTGTTCACCGGGGTGGTGCCCATCCTGGTCGAGC
TGGACGGCGACGTAAACGGCCACAAGTTCAGCGTGTCCGGCGAGG
GCGAGGGCGATGCCACCTACGGCAAGCTGACCCTGAAGTTCATCT
GCACCACCGGCAAGCTGCCCGTGCCCTGGCCCACCCTCGTGACCA
CCCTGACCTACGGCGTGCAGTGCTTCAGCCGCTACCCCGACCACA
TGAAGCAGCACGACTTCTTCAAGTCCGCCATGCCCGAAGGCTACG
TCCAGGAGCGCACCATCTTCTTCAAGGACGACGGCAACTACAAGA -continued

CCCGCGCCGAGGTGAAGTTCGAGGGCGACACCCTGGTGAACCGCA

TCGAGCTGAAGGGCATCGACTTCAAGGAGGACGGCAACATCCTGG

GGCACAAGCTGGAGTACAACTACAACAGCCACAACGTCTATATCA

TGGCCGACAAGCAGAAGAACGGCATCAAGGTGAACTTCAAGATCC

GCCACAACATCGAGGACGGCAGCGTGCAGCTCGCCGACCACTACC

AGCAGAACACCCCCATCGGCGACGGCCCCGTGCTGCTGCCCGACA

ACCACTACCTGAGCACCCAGTCCGCCCTGAGCAAAGACCCCAACG

AGAAGCGCGATCACATGGTCCTGCTGGAGTTCGTGACCGCCGCCG

GGATCACTCTCGGCATGGACGAGCTGTACAAGgttataacatggg taacctctacgtgagcaagggcgaggAGCTGTTCACCGGGGTGGT

GCCCATCCTGGTCGAGCTGGACGGCGACGTAAACGGCCACAAGTT

CAGCGTGTCCGGCGAGGGCGAGGGCGATGCCACCTACGGCAAGCT

GACCCTGAAGTTCATCTGCACCACCGGCAAGCTGCCCGTGCCCTG

GCCCACCCTCGTGACCACCCTGACCTACGGCGTGCAGTGCTTCAG

CCGCTACCCCGACCACATGAAGCAGCACGACTTCTTCAAGTCCGC

CATGCCCGAAGGCTACGTCCAGGAGCGCACCATCTTCTTCAAGGA

CGACGGCAACTACAAGACCCGCGCCGAGGTGAAGTTCGAGGGCGA

CACCCTGGTGAACCGCATCGAGCTGAAGGGCATCGACTTCAAGGA

GGACGGCAACATCCTGGGGCACAAGCTGGAGTACAACTACAACAG

CCACAACGTCTATATCATGGCCGACAAGCAGAAGAACGGCATCAA

GGTGAACTTCAAGATCCGCCACAACATCGAGGACGGCAGCGTGCA

GCTCGCCGACCACTACCAGCAGAACACCCCCATCGGCGACGGCCC

CGTGCTGCTGCCCGACAACCACTACCTGAGCACCCAGTCCGCCCT

GAGCAAAGACCCCAACGAGAAGCGCGATCACATGGTCCTGCTGGA

GTTCGTGACCGCCGCCGGGATCACTCTCGGCATGGACGAGCTGTA

CAAGTAA sgRNA targeting sequence (SEQ ID NO: 40)

GTTCAGGGCTTGACCAACAC

DNA oligo used for the RNAse-H digestion assay on RNA-1:

(SEQ ID NO: 41)

CCAGCACACTGGCGGCCG

Linker (SEQ ID NO: 42)

UUAUC

What is claimed is:

1. A method of linking a first RNA stem loop oligonucleotide and a second RNA stem loop oligonucleotide, the method comprising contacting the first RNA stem loop oligonucleotide and the second RNA stem loop oligonucleotide with a PreQ1 linking compound and a tRNA-guanine transglycosylase (TGT) enzyme, wherein the PreQ1 linking compound has the formula:

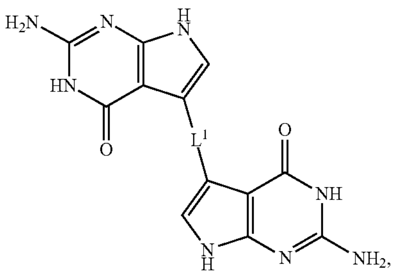

wherein $L^1$ is a covalent linker;

wherein said first RNA stem loop oligonucleotide comprises a first guanosine in a first RNA loop portion of a first RNA stem loop; and wherein said second RNA stem loop oligonucleotide comprises a second guanosine in a second RNA loop portion of a second RNA stem loop.

2. The method of claim 1, wherein said first guanosine is in a first UGU sequence in the first RNA loop portion of the first RNA stem loop and said second guanosine is in a second UGU sequence in the second RNA loop portion of the second RNA stem loop.

3. The method of claim 1, wherein said first RNA stem loop oligonucleotide and said second RNA stem loop oligonucleotide are independently an mRNA, a gRNA, an sgRNA, an shRNA, a siRNA, a tRNA, a long non-coding RNA, an rRNA or a ribozyme.

4. The method of claim 1, wherein said TGT enzyme is a bacterial TGT enzyme.

5. The method of claim 1, wherein $L^1$ is $-L^{101}-L^{102}-L^{103}-L^{104}-L^{105}-L^{106}-L^{107}-$;

$L^{101}$ is a bond, —C(O)—, —C(O)O—, —OC(O)—, —O—, —S—, —NR$^{101}$—, —C(O)NR$^{101}$—, —NR$^{101}$C(O)—, —NR$^{101}$C(O)O—, —OC(O)NR$^{101}$—, —NR$^{101}$C(O)NR$^{101}$—, —NR$^{101}$C(NH)NR$^{101}$—, —S(O)$_2$—, —NR$^{101}$S(O)$_2$—, —S(O)$_2$NR$^{101}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{102}$ is a bond, —C(O)—, —C(O)O—, —OC(O)—, —O—, —S—, —NR$^{102}$—, —C(O)NR$^{102}$—, —NR$^{102}$C(O)—, —NR$^{102}$C(O)O—, —OC(O)NR$^{102}$—, —NR$^{102}$C(O)NR$^{102}$—, —NR$^{102}$C(NH)NR$^{102}$—, —S(O)$_2$—, —NR$^{102}$S(O)$_2$—, —S(O)$_2$NR$^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{103}$ is a bond, —C(O)—, —C(O)O—, —OC(O)—, —O—, —S—, —NR$^{103}$—, —C(O)NR$^{103}$—, —NR$^{103}$C(O)—, —NR$^{103}$C(O)O—, —OC(O)NR$^{103}$—, —NR$^{103}$C(O)NR$^{103}$—, —NR$^{103}$C(NH)NR$^{103}$—, —S(O)$_2$—, —NR$^{103}$S(O)$_2$—, —S(O)$_2$NR$^{103}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{104}$ is a bond, —C(O)—, —C(O)O—, —OC(O)—, —O—, —S—, —NR$^{104}$—, —C(O)NR$^{104}$—, —NR$^{104}$C(O)—, —NR$^{104}$C(O)O—, —OC(O)NR$^{104}$—, —NR$^{104}$C(O)NR$^{104}$—, —NR$^{104}$C(NH)NR$^{104}$—, —S(O)$_2$—, —NR$^{104}$S(O)$_2$—, —S(O)$_2$NR$^{104}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{105}$ is a bond, —C(O)—, —C(O)O—, —OC(O)—, —O—, —S—, —NR$^{105}$—, —C(O)NR$^{105}$—, —NR$^{105}$C(O)—, —NR$^{105}$C(O)O—, —OC(O)

$NR^{105}$—, —$NR^{105}C(O)NR^{105}$—, —$NR^{105}C(NH)NR^{105}$—, —$S(O)_2$—, —$NR^{105}S(O)_2$—, —$S(O)_2NR^{105}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{106}$ is a bond, —C(O)—, —C(O)O—, —OC(O)—, —O—, —S—, —$NR^{106}$—, —$C(O)NR^{106}$—, —$NR^{106}C(O)$—, —$NR^{106}C(O)O$—, —$OC(O)NR^{106}$—, —$NR^{106}C(O)NR^{106}$—, —$NR^{106}C(NH)NR^{106}$—, —$S(O)_2$—, —$NR^{106}S(O)_2$—, —$S(O)_2NR^{106}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{107}$ is a bond, —C(O)—, —C(O)O—, —OC(O)—, —O—, —S—, —$NR^{107}$—, —$C(O)NR^{107}$—, —$NR^{107}C(O)$—, —$NR^{107}C(O)O$—, —$OC(O)NR^{107}$—, —$NR^{107}C(O)NR^{107}$—, —$NR^{107}C(NH)NR^{107}$—, —$S(O)_2$—, —$NR^{107}S(O)_2$—, —$S(O)_2NR^{107}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker; and each $R^{101}$, $R^{102}$, $R^{103}$, $R^{104}$, $R^{105}$, $R^{106}$, and $R^{107}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

6. The method of claim 5, wherein the PreQ1 linking compound has the formula:

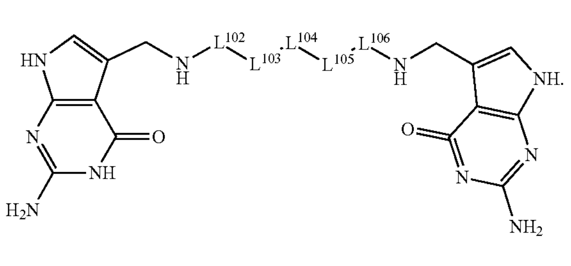

7. The method of claim 1, wherein $L^1$ comprises a photo-cleavable site.

8. The method of claim 1, wherein $L^1$ comprises a peptide linker.

9. A method of linking a first RNA stem loop of an RNA stem loop oligonucleotide and a second RNA stem loop of said RNA stem loop oligonucleotide, the method comprising contacting said RNA stem loop oligonucleotide with a PreQ1 linking compound and a tRNA-guanine transglycosylase (TGT) enzyme, wherein said PreQ1 linking compound has the formula:

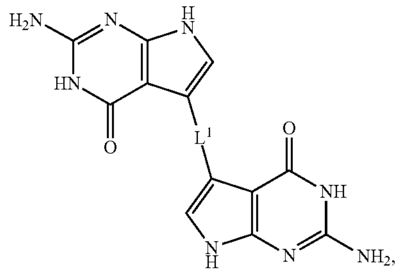

wherein $L^1$ is a covalent linker; and wherein said first RNA stem loop comprises a first guanosine in a first RNA loop portion of the first RNA stem loop, and wherein said second RNA stem loop comprises a second guanosine in a second RNA loop portion of the second RNA stem loop.

10. The method of claim 9, wherein said first guanosine is in a first UGU sequence in the first RNA loop portion of the first RNA stem loop and said second guanosine is in a second UGU sequence in the second RNA loop portion of the second RNA stem loop.

11. The method of claim 9, wherein said RNA stem loop oligonucleotide is an mRNA, a gRNA, an sgRNA, an shRNA, a siRNA, a tRNA, a long non-coding RNA, an rRNA or a ribozyme.

12. The method of claim 11, wherein said RNA stem loop oligonucleotide is an sgRNA.

13. The method of claim 12, wherein said first RNA stem loop is the stem loop 2 of the sgRNA and the second RNA stem loop is the tetra-loop of said sgRNA.

14. An RNA compound having the formula:

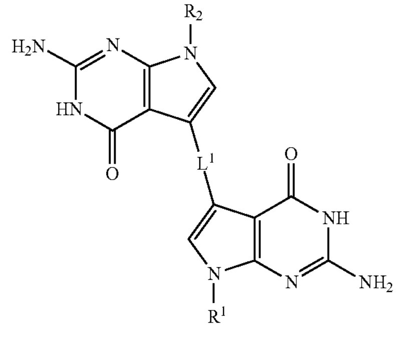

wherein $L^1$ is a covalent linker;

$R^1$ is a first RNA loop portion of a first RNA stem loop; and $R^2$ is a second RNA loop portion of a second RNA stem loop.

15. The RNA compound of claim 14, wherein said first RNA stem loop is in a first RNA oligonucleotide and said second RNA stem loop is in a second RNA oligonucleotide.

16. The RNA compound of claim 15, wherein said first RNA oligonucleotide and said second RNA oligonucleotide are independently an mRNA, a gRNA, an sgRNA, an shRNA, a siRNA, a tRNA, a long non-coding RNA, an rRNA or a ribozyme.

17. The RNA compound of claim 14, wherein said first RNA stem loop and said second RNA stem loop are in the same RNA oligonucleotide.

18. The RNA compound of claim 14, wherein $L^1$ is $-L^{101}-L^{102}-L^{103}-L^{104}-L^{105}-L^{106}-L^{107}-$;

$L^{101}$ is a bond, —C(O)—, —C(O)O—, —OC(O)—, —O—, —S—, —$NR^{101}$—, —C(O)$NR^{101}$—, —$NR^{101}$C(O)—, —$NR^{101}$C(O)O—, —OC(O)$NR^{101}$—, —$NR^{101}$C(O)$NR^{101}$—, —$NR^{101}$C(NH)$NR^{101}$—, —$S(O)_2$—, —$NR^{101}S(O)_2$—, —$S(O)_2NR^{101}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{102}$ is a bond, —C(O)—, —C(O)O—, —OC(O)—, —O—, —S—, —$NR^{102}$—, —C(O)$NR^{102}$—, —$NR^{102}$C(O)—, —$NR^{102}$C(O)O—, —OC(O)$NR^{102}$—, —$NR^{102}$C(O)$NR^{102}$—, —$NR^{102}$C(NH)$NR^{102}$—, —$S(O)_2$—, —$NR^{102}S(O)_2$—, —$S(O)_2NR^{102}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{103}$ is a bond, —C(O)—, —C(O)O—, —OC(O)—, —O—, —S—, —$NR^{103}$—, —C(O)$NR^{103}$—, —$NR^{103}$C(O)—, —$NR^{103}$C(O)O—, —OC(O)$NR^{103}$—, —$NR^{103}$C(O)$NR^{103}$—, —$NR^{103}$C(NH)$NR^{103}$—, —$S(O)_2$—, —$NR^{103}S(O)_2$—, —$S(O)_2NR^{103}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{104}$ is a bond, —C(O)—, —C(O)O—, —OC(O)—, —O—, —S—, —$NR^{104}$—, —C(O)$NR^{104}$—, —$NR^{104}$C(O)—, —$NR^{104}$C(O)O—, —OC(O)$NR^{104}$—, —$NR^{104}$C(O)$NR^{104}$—, —$NR^{104}$C(NH)$NR^{104}$—, —$S(O)_2$—, —$NR^{104}S(O)_2$—, —$S(O)_2NR^{104}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{105}$ is a bond, —C(O)—, —C(O)O—, —OC(O)—, —O—, —S—, —$NR^{105}$—, —C(O)$NR^{105}$—, —$NR^{105}$C(O)—, —$NR^{105}$C(O)O—, —OC(O)$NR^{105}$—, —$NR^{105}$C(O)$NR^{105}$—, —$NR^{105}$C(NH)$NR^{105}$—, —$S(O)_2$—, —$NR^{105}S(O)_2$—, —$S(O)_2NR^{105}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{106}$ is a bond, —C(O)—, —C(O)O—, —OC(O)—, —O—, —S—, —$NR^{106}$—, —C(O)$NR^{106}$—, —$NR^{106}$C(O)—, —$NR^{106}$C(O)O—, —OC(O)$NR^{106}$—, —$NR^{106}$C(O)$NR^{106}$—, —$NR^{106}$C(NH)$NR^{106}$—, —$S(O)_2$—, —$NR^{106}S(O)_2$—, —$S(O)_2NR^{106}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker;

$L^{107}$ is a bond, —C(O)—, —C(O)O—, —OC(O)—, —O—, —S—, —$NR^{107}$—, —C(O)$NR^{107}$—, —$NR^{107}$C(O)—, —$NR^{107}$C(O)O—, —OC(O)$NR^{107}$—, —$NR^{107}$C(O)$NR^{107}$—, —$NR^{107}$C(NH)$NR^{107}$—, —$S(O)_2$—, —$NR^{107}S(O)_2$—, —$S(O)_2NR^{107}$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a peptide linker, or a cleavable linker; and each $R^{101}$, $R^{102}$, $R^{103}$, $R^{104}$, $R^{105}$, $R^{106}$, and $R^{107}$ is independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

19. The RNA compound of claim 14, wherein $L^1$ comprises a photo-cleavable site.

20. A cell comprising the RNA compound of claim 14.

* * * * *